United States Patent
Takoh

(10) Patent No.: US 9,657,333 B2
(45) Date of Patent: May 23, 2017

(54) METHOD FOR DETECTING TARGET SUBSTANCE, ASSAY KIT, AND DETECTION APPARATUS

(71) Applicant: Kimiyasu Takoh, Tokyo (JP)

(72) Inventor: Kimiyasu Takoh, Tokyo (JP)

(73) Assignee: NEC Coporation, Tokyo (JP)

( * ) Notice: Subject to any disclaimer, the term of this patent is extended or adjusted under 35 U.S.C. 154(b) by 86 days.

(21) Appl. No.: 14/388,075

(22) PCT Filed: Feb. 19, 2013

(86) PCT No.: PCT/JP2013/053956
§ 371 (c)(1),
(2) Date: Sep. 25, 2014

(87) PCT Pub. No.: WO2013/145939
PCT Pub. Date: Oct. 3, 2013

(65) Prior Publication Data
US 2015/0064696 A1    Mar. 5, 2015

(30) Foreign Application Priority Data

Mar. 28, 2012  (JP) .................................. 2012-073255

(51) Int. Cl.
*C07H 21/04*  (2006.01)
*C12Q 1/68*   (2006.01)
(Continued)

(52) U.S. Cl.
CPC .......... *C12Q 1/6825* (2013.01); *C12N 15/111* (2013.01); *C12N 15/115* (2013.01);
(Continued)

(58) Field of Classification Search
CPC . C12N 15/111; C12N 15/115; C12N 2310/16; C12N 2310/3519;
(Continued)

(56) References Cited

U.S. PATENT DOCUMENTS

2008/0287666 A1    11/2008    Watanabe et al.

FOREIGN PATENT DOCUMENTS

| EP | 1 992705 A1 | 11/2008 |
| JP | 2008-278837 A | 11/2008 |
| WO | WO-2013/014843 A1 | 1/2013 |

OTHER PUBLICATIONS

Liang, X. et al. (J. Am. Chem. Soc., vol. 124, pp. 1877-1883 (2002).*

(Continued)

*Primary Examiner* — Teresa Strzelecka
(74) *Attorney, Agent, or Firm* — Wilmer Cutler Pickering Hale and Dorr LLP

(57) ABSTRACT

The present invention provides a method for detecting a target substance, including the steps of: preparing a complex (hybrid) comprising an aptamer which binds to the target substance, a first nucleic acid fragment comprising a nucleotide sequence complementary to the aptamer and a photoisomerizable molecule bound to a portion of the complementary nucleotide sequence, wherein the aptamer and the first nucleic acid fragment bound with the photoisomerizable molecule form double-stranded nucleotides binding; subjecting the photoisomerizable molecule to a first photoisomerization treatment to destabilize the double-stranded nucleotides binding; forming a complex of the target substance and the aptamer so as to dissolve the destabilized double-stranded nucleotides binding; subjecting the photoisomerizable molecule to a second photoisomerization treatment to restabilize double-stranded nucleotides binding; and detecting dissolution of double-stranded nucleotides binding wherein the first nucleic acid fragment bound with the photoisomerizable molecule separates from the aptamer.

10 Claims, 6 Drawing Sheets

(51) Int. Cl.
*C12N 15/115* (2010.01)
*C12N 15/11* (2006.01)
*G01N 33/53* (2006.01)
*G01N 33/542* (2006.01)

(52) U.S. Cl.
CPC ....... *C12Q 1/6834* (2013.01); *G01N 33/5308* (2013.01); *G01N 33/542* (2013.01); *C12N 2310/16* (2013.01); *C12N 2310/3519* (2013.01); *C12N 2320/10* (2013.01)

(58) Field of Classification Search
CPC  C12N 2320/10; C12Q 1/6825; C12Q 1/6834; G01N 33/5308; G01N 33/542
See application file for complete search history.

(56) References Cited

OTHER PUBLICATIONS

Y. Kim et al., Using Photons to Manipulate Enzyme Inhibition by an Azobenzene-modified Nucleic Acid Probe, Proc. Natl. Acad. Science, USA, 2009, vol. 106, pp. 6489-6494, (6 pages).
M. Liu, et. al., In Vitro Selection of a Photoresponsive RNA Aptamer to Hemin, Bioorganic & Medicinal Chemistry Letters, 2010, vol. 20, pp. 2964-2967, (4 pages).
R. Nutiu and Y. Li, Structure-Switching Signaling Aptamers, Journal American Chemical Society, 2003, vol. 125, pp. 4771-4778 (8 pages).
International Search Report, Corresponding to PCT/JP2013/053956, dated May 21, 2013, 2 pages.

* cited by examiner (a)

(b)

(c)

METHOD FOR DETECTING TARGET SUBSTANCE, ASSAY KIT, AND DETECTION APPARATUS

CROSS-REFERENCE TO RELATED APPLICATIONS

The present application is a national stage application of International Application No. PCT/JP2013/053956 entitled "Method for Detecting Target Substance, Assay Kit, and Detection Apparatus," filed on Feb. 19, 2013, which claims the benefit of priority from Japanese Patent Application No. JP2012-073255, filed on Mar. 28, 2012, the disclosures of which are incorporated herein in their entirety by reference thereto.

TECHNICAL FIELD

The present invention relates to a method for detecting a target substance, an assay kit for a target substance, and an apparatus for detecting a target substance.

BACKGROUND ART

Aptamers are referred to nucleic acids (DNA, RNA, and PNA) having binding affinity to specific substances. The substances to be specifically bound by the aptamers (hereinafter, referred to as target substances) are known to cover a wide spectrum of substances including biomolecules such as proteins, hormones, and peptides, artificial molecules such as agricultural chemicals, and small molecules such as potassium ions. Thus, level of the target substance contained in a sample can be quantified by detection of the binding of each aptamer to its target substance. Also, a sensor specifically responding to the target substance can be constructed by means of outputting the binding of the aptamer to the target substance as electric signals.

In the case when the detection of the target substance is carried out by using such an aptamer, such approach in which the formation and dissolution of a double-stranded nucleic acid portion between the aptamer and its complementary nucleic acid sequence is used as a measure for detection, because of advantages such as the applicability of this approach to aptamers having various steric structures (see e.g., Non Patent Document 1 and Patent Document 1).

For example, Non Patent Document 1 describes a method for detecting ATP in which an ATP aptamer 101 labeled with a fluorescent material 103 and a complementary strand 102 labeled with a quencher 104 for the fluorescence of the fluorescent material 103 are used for detection (FIGS. 1(a) to 1(c)). In the absence of ATP, the ATP aptamer 101 and its complementary strand 102 form a double-stranded nucleic acid portion 105 through their nucleotide sequences complementary to each other (FIG. 1(a)). When an ATP 107 is added to this double-stranded nucleic acid portion 105 (double-strand formation region), the complementary base pairs composing the double-strand formation region are dissociated in association with the binding of the ATP 107 to the ATP aptamer 101, resulting in the dissolution of the double-stranded nucleic acid portion 105 (double-strand formation region) (FIGS. 1(b) and 1(c)). When the double-stranded nucleic acid portion 105 is formed, the fluorescent material 103 is located in proximity to the quencher 104. When the double-stranded nucleic acid portion 105 is dissolved, the quencher 104 is placed distant from the fluorescent material 103. In such a case, the presence or absence of the double-stranded nucleic acid portion 105 can be detected by use of fluorescence resonance energy transfer (FRET). Thus, the presence or absence of the double-stranded nucleic acid portion 105 can be detected, as described therein, to thereby detect the presence or absence of the target substance ATP 107.

Alternatively, Patent Document 1 describes a sensor for detecting the presence or absence of a target substance by detecting the presence or absence of a double-stranded nucleic acid portion constituted by an aptamer immobilized on a substrate and its complementary strand. For example, as shown in FIG. 2, an aptamer 101 is immobilized on a substrate 108, and a complementary strand 102 having a labeling material 106 is hybridized thereto to form a double-stranded nucleic acid portion 105 (FIG. 2(a)). When a target substance 110 is added thereto, the double-stranded nucleic acid portion 105 is dissolved in association with the binding between the target substance 110 and the aptamer 101 to dissociate therefrom the complementary strand 102 having the labeling material 106 (FIG. 2(b)). The change in physical or chemical properties caused by the dissociation of the complementary strand 102 having the labeling material 106 is detected to thereby detect the formation of the binding between the target substance 110 and the aptamer 101. As a result of, for example, forming the binding of an aptamer 101 to a target substance 110, the separation of a complementary strand 102 having a metal particle 106 from a surface plasmon resonance sensor substrate 108 can be detected, as described therein, to thereby detect the presence of the target substance 110.

PRIOR ART DOCUMENT

Patent Document

Patent Document 1: JP2008-278837A

Non Patent Document

Non Patent Document 1: Razvan Nutiu, et al., Journal of American Chemical Society, 2003, 125, p. 4771-4778

Non Patent Document 2: Youngmi Kim, et al., Proceedings of the National Academy of Sciences of the United States of America, 2009, 106, p. 6489-6494.

DISCLOSURE OF INVENTION

Problem to be Solved by the Invention

The approach disclosed in Patent Document 1 and the approach disclosed in Non Patent Document 1 utilize the phenomenon where, when an aptamer binds to a target substance to form a "target substance/aptamer complex", the aptamer comprised in the complex loses its "ability to maintain a double strand" to compose a "complementary strand/aptamer hybrid" by forming a double strand with its complementary strand. Particularly, the forms shown in FIGS. 1 and 2 utilize the "ability to dissolve a double strand" by which the double-stranded nucleic acid portion in the "complementary strand/aptamer hybrid" is dissolved upon action of a target substance on the aptamer comprised in the "complementary strand/aptamer hybrid" to promote the formation of a "target substance/aptamer complex".

As a result of conducting studies, the present inventor has found that, in the techniques of Patent Document 1 and Non Patent Document 1, the structure of the double-stranded nucleic acid portion in the "complementary strand/aptamer hybrid" is to be further improved in order to achieve best trade-off between following "reciprocal features", i.e., the "ability to dissolve a double strand" which is used in "binding to a target substance" and the "ability to maintain a double strand" which is exerted in "non-binding to a target substance".

Specifically, for the purpose of rapid detection of a target substance in a sampled specimen, the double-stranded nucleic acid portion needs to be immediately dissolved by the action of the target substance on the "complementary strand/aptamer hybrid" to promote the formation of a "target substance/aptamer complex". However, if the double-stranded nucleic acid portion comprised in the "complementary strand/aptamer hybrid" has excessive intermolecular force for binding, the double-stranded nucleic acid portion is difficult to dissolve by the action of a target substance. Consequently, this might inhibit the detection of the target substance based on the measurement of the decreased amount of the "complementary strand/aptamer hybrid".

On the other hand, a possible approach for reducing the intermolecular force for binding of the double-stranded nucleic acid portion comprised in the "complementary strand/aptamer hybrid" to promote double strand dissolution is to decrease in the number of nucleobases to be hybridized in the double-stranded nucleic acid portion. However, if the number of nucleobases in the double-strand formation region (double-stranded nucleic acid portion) is excessively reduced, it causes drastical increase in the dissociation constant $K_{Dhybrid}(T_L)$ of the "complementary strand/aptamer hybrid"=[Complementary strand]*[Aptamer]/[Hybrid]. For this reason, the addition of a sampled specimen to a liquid phase decreases the complementary strand concentration [Complementary strand] and the aptamer concentration [Aptamer] in the liquid phase, even if the target substance is absent in the sampled specimen. In such a case, the dissociation of the hybrid occurs according to the dissociation constant $K_{Dhybrid}(T_L)$. Accordingly, the hybrid concentration [Hybrid] is relatively decreased. This event might inhibit the detection of the target substance based on the measurement of the decreased amount of the "complementary strand/aptamer hybrid".

For achieving best trade-off between the following "contrary features", i.e., the "ability to dissolve a double strand" and the "ability to maintain a double strand", it is thus required to optimize the intermolecular force for binding of the double-stranded nucleic acid portion comprised in the "complementary strand/aptamer hybrid". Previously, the double-strand formation site of the "complementary strand/aptamer hybrid" has been very difficult to design on the basis of the adjustment of the number of nucleobases in the double-strand formation region (double-stranded nucleic acid portion).

Non Patent Document 1 states that the temperature $T_L$ of a mixed solution of a sampled specimen mixed with a "complementary strand/aptamer hybrid" (aptamer that has formed a nucleic acid double strand) can be temporarily raised to thereby increase a dissociation constant $K_{D1}(T_L)$ by use of the temperature dependence of the dissociation constant $K_{Dhybrid}(T_L)$, resulting in the promoted dissolution of the double strand. Such a rise in solution temperature T, however, also destabilizes the steric structure of the aptamer comprised in the "target substance/aptamer complex". A rise in solution temperature $T_L$ therefore also increases the dissociation constant $K_{Dcomplex}(T_L)$ of the "target substance/aptamer complex"=[Target substance]*[Aptamer]/[Complex]. Consequently, this might reduce the ability of the target substance to bind to the aptamer, and thereby inhibit the detection of the target substance based on the measurement of the decreased amount of the "complementary strand/aptamer hybrid".

When the target substance contained in the sample for detection is, for example, a heat-labile protein or the like, a rise in solution temperature $T_L$ might cause thermal denaturation or coagulation. Consequently, this might hinder the accurate measurement of the concentration of the target substance contained in the sample for detection.

The present invention has been made in consideration of these situations, and an object of the present invention is to provide a method for detecting a target substance which is excellent in precision of detection by use of an aptamer and a nucleic acid fragment which are improved in terms of trade-off between their reciprocal features.

Means for Solving the Problems

The present invention provides a method for detecting a target substance, characterized in that the method comprising the steps of:

preparing a complex comprising:

an aptamer which is capable of binding to the target substance in a sampled specimen;

a first nucleic acid fragment comprising a nucleotide sequence complementary to the aptamer; and a photoisomerizable molecule bound to both of or only any one of the aptamer and the first nucleic acid fragment, wherein the photoisomerizable molecule is bound to a double-strand formation site where the aptamer and the first nucleic acid fragment hybridize with each other;

isomerizing the photoisomerizable molecule in the complex to reduce the stability of the double-strand formation site;

allowing the target substance to bind to the aptamer so as to separate the first nucleic acid fragment from the double-strand formation site of the aptamer;

isomerizing the photoisomerizable molecule in the complex to increase the stability of the double-strand formation site; and detecting dissolution of double strand wherein the first nucleic acid fragment separates from the aptamer.

In this context, an aptamer which can specifically bind to the target substance is preferably used. Desirably, the photoisomerizable molecule is bound only to the first nucleic acid fragment.

The present invention also provides an assay kit for use in the detection of a target substance, characterized in that the kit comprising a complex comprising:

an aptamer which can bind to the target substance in a sampled specimen;

a first nucleic acid fragment comprising a nucleotide sequence complementary to the aptamer; and a photoisomerizable molecule bound to both of or only any one of the aptamer and the first nucleic acid fragment, wherein the photoisomerizable molecule is bound to a double-strand formation site where the aptamer and the first nucleic acid fragment hybridize with each other.

In this context, an aptamer which can specifically bind to the target substance is preferably used. Desirably, the photoisomerizable molecule is bound only to the first nucleic acid fragment.

The present invention further provides an apparatus for detecting a target substance, characterized in that the apparatus comprising:

the assay kit mentioned above;

a region for binding on which the target substance is bound to the aptamer;

a region for detection on which dissolution of double strand is detected; and a light source for the isomerization of the photoisomerizable molecule provided in the assay kit.

Effects of Invention

The present invention provides a method for detecting a target substance with excellent reliability.

BRIEF DESCRIPTION OF DRAWINGS

FIG. 4(a) shows a structure in which one first nucleic acid fragment is linked to the aptamer via a spacer. FIG. 4(b) shows a structure in which two first nucleic acid fragments are linked to the aptamer via a branched spacer.

Figure 1:
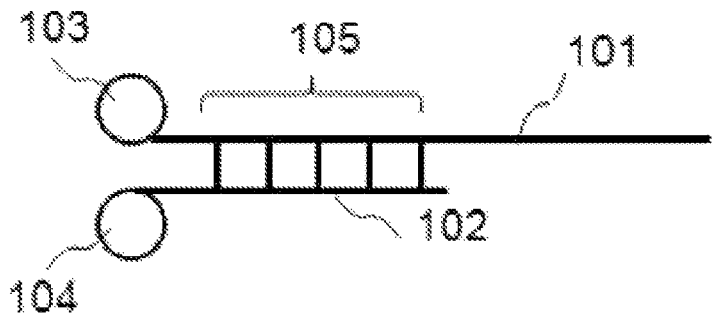
FIG. 1 is a diagram schematically showing the procedures of a conventional method for detecting a target substance using an aptamer labeled with a fluorescent material.
Figure 1:
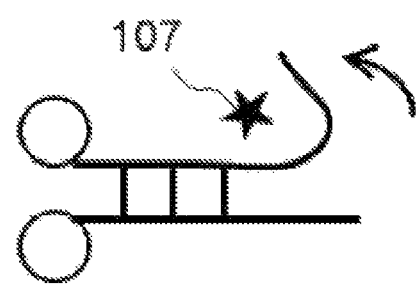
Figure 1:
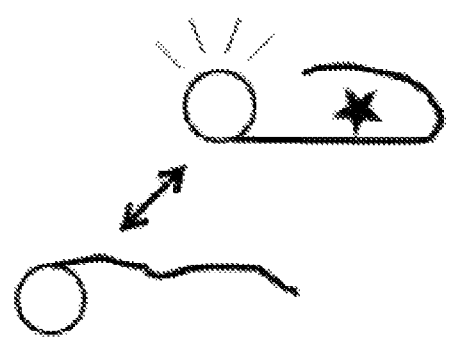
Figure 2:
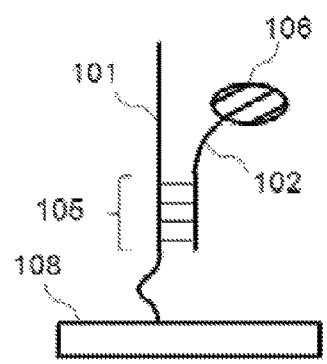
FIG. 2 is a diagram schematically showing the procedures of a conventional method for detecting a target substance using an aptamer immobilized on a substrate.
Figure 2:
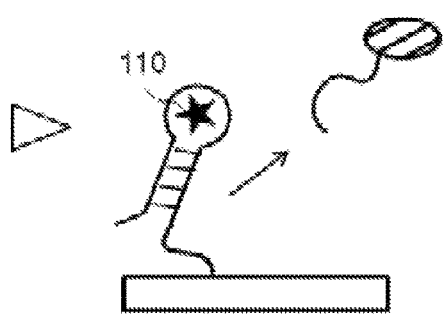

Each symbol shown in the drawings represents the following meaning:

DESCRIPTION OF SYMBOLS

1. Aptamer
2. First nucleic acid fragment
3. Photoisomerizable molecule
4. Basal material for immobilization
5. Double-strand formation site
6. Labeling material
7. Target substance
9. Spacer
10. Second nucleic acid fragment
11. Complex (hybrid)
12 Linking portion
13. Region for detection
14. Region for capture
21. Solvent-philic basal material
101. Aptamer
102. Complementary strand
103. Fluorescent material
104. Quencher
105. Double-stranded nucleic acid portion
106. Labeling material
107. ATP
108. Substrate
110. Target substance
131. Thrombin aptamer
132. Complementary strand
133. Photoisomerizable molecule
134. Thrombin

BEST MODE FOR CARRYING OUT THE INVENTION

Embodiments of the method for detecting a target substance according to the present invention will be explained in detail with reference to the drawings. In all the drawings, the same symbols will be used to designate the corresponding components, so that unnecessary description therefor will be appropriately omitted.

First Embodiment

The method for detecting a target substance according to the first embodiment will be explained in detail with reference to FIG. 3.

The first embodiment exemplifies the method for detecting a target substance and the assay kit for target substance detection according to the present invention.

The method for detecting a target substance 7 according to the first embodiment comprises steps described below. First, a complex (hybrid) 11 is prepared. The complex (hybrid) 11 comprises an aptamer 1, a first nucleic acid fragment 2, and a photoisomerizable molecule 3. The aptamer 1 comprises a nucleotide sequence which specifically binds to the target substance 7 in a sampled specimen (subject to be assayed). The first nucleic acid fragment 2 comprises a nucleotide sequence complementary to the aptamer 1. The aptamer 1 and the first nucleic acid fragment 2 have double-strand formation sites 5 at which their complementary nucleotide sequences compose a double strand. The photoisomerizable molecule 3 is reversibly isomerized by irradiation with light energy. Also, the photoisomerizable molecule 3 is bound to one or both of a part of the double-strand formation site 5 in the first nucleic acid fragment 2 and a part of the double-strand formation site 5 in the aptamer 1. Subsequently, the photoisomerizable molecule 3 is isomerized by irradiation with light energy to destabilize the double-stranded nucleotides binding. Subsequently, the target substance 7 is allowed to bind to the aptamer 1 to form a target substance/aptamer complex composed of the target substance 7 and the aptamer 1. Then, the first nucleic acid fragment 2 is separated from the aptamer 1 comprised in the target substance/aptamer complex to dissolve the double strand. Subsequently, the photoisomerization reaction of the photoisomerizable molecule 3 is caused again to stabilize the double-stranded nucleotides binding in the complex (hybrid) 11. Then, the dissolution of the double strand is detected.

In the first embodiment, the term "dissolution of the double strand" means that, for example, the double-stranded nucleotides binding disappears by the separation of the first nucleic acid fragment 2 from the aptamer 1.

The term "photoisomerization of the photoisomerizable molecule 3 to destabilize the double-stranded nucleotides binding" means that, for example, the structural change of the photoisomerizable molecule 3 caused by the photoisomerization increases the distortion of the double strand structure. Due to the "increased distortion of the double strand structure", the melting temperature $T_{melting}$ of the double-stranded nucleotides binding is lowered to a first melting temperature $T_{melting-1}$. The term "photoisomerization of the photoisomerizable molecule 3 to stabilize the double-stranded nucleotides binding" means that, for example, the structural change of the photoisomerizable molecule 3 caused by the photoisomerization decreases the distortion of the double strand structure. Due to the "decreased distortion of the double strand structure", the melting temperature $T_{melting}$ of the double-stranded nucleotides binding is raised to a second melting temperature $T_{melting-2}$.

Various techniques known in the art can be used for detecting the dissolution of the double strand and will be specifically described later.

In the first embodiment, the aptamer 1 and the first nucleic acid fragment 2 composing the complex (hybrid) 11 forms double-stranded nucleotides binding through the hybridization of their double-strand formation sites 5. The "stability of this double-stranded nucleotides binding" can be reversibly changed by the photoisomerization of the photoisomerizable molecule 3 bound to the double-strand formation site 5. Specifically, the melting temperature $T_{melting}$ of the double-stranded nucleotides binding can be reversibly changed between the first melting temperature $T_{melting-1}$ and the second melting temperature $T_{melting-2}$ by the reversible photoisomerization of the photoisomerizable molecule 3.

In this state of the "stability of the double-stranded nucleotides binding" reduced by the photoisomerization reaction of the photoisomerizable molecule 3, the target substance 7 can be allowed to bind to the aptamer 1 to thereby form a target substance 7/aptamer 1 complex. As a result, the double strand can be efficiently dissolved. This eliminates the previous need of decreasing the number of nucleobases in the double-strand formation sites 5 in order to lower the melting temperature $T_{melting}$ of the complex (hybrid) 11 for the purpose of "improving the ability to dissolve a double strand". Thus, the design of the double-strand formation site 5 of the aptamer 1 can be adapted to the "ability to maintain a double strand".

Prior to the detection of the dissolution of the double strand, the melting temperature $T_{melting}$ of the double-stranded nucleotides binding can be changed from the first melting temperature $T_{melting-1}$ to the second melting temperature $T_{melting-2}$ improve the "stability of double-stranded nucleotides binding". In such a case when the target substance 7 is not contained in the sample, the double strand can therefore be efficiently maintained as to the complex (hybrid) 11. Accordingly, this permits accurate detection of the "dissolution of the double strand" caused by the formation of the target substance 7/aptamer 1 complex.

In addition, the influence of steric hindrance attributed to the photoisomerizable molecule 3 structurally changed by the isomerization thereof is confined to the proximity of the double-strand formation site 5 where the photoisomerizable molecule 3 is positioned. Thus, the isomerization of the photoisomerizable molecule 3 destabilizes the double strand, but does not deform the whole steric structure of the aptamer 1. Particularly, when the solution temperature $T_L$ used for the detection process is significantly higher than the first melting temperature $T_{melting-1}$ ($T_L \gg T_{melting-1}$), the dissolution between the aptamer 1 and the first nucleic acid fragment 2 caused by the "destabilization of the double-stranded nucleotides binding" occurs at this solution temperature $T_L$ used for the detection process. In this case, the isomerization of the photoisomerizable molecule 3 bound to the double-strand formation site 5 of the first nucleic acid fragment 2 has no influence on a steric structure formed by the single-stranded nucleic acid molecule of the dissociated aptamer 1. This can reduce the adverse effect of the change in the dissociation constant $K_{Dcomplex}(T_L)$ of the target substance 7/aptamer 1 complex on detection sensitivity. As compared with the conventional method using the operation of raising the solution temperature $T_L$, this approach can reduce the amount of a rise in the solution temperature $T_L$ and thus does less damage to the sample (i.e. the target substance 7), which is induced by thermal denaturation or coagulation, even if the target substance 7 contained in the sample for detection is, for example, a heat-labile protein. As a result, in the case where the target substance 7 is, for example, a heat-labile protein, the adverse effect on detection sensitivity, which is caused by the thermal denaturation or coagulation, can be suppressed, which enables accurate detection.

As described above, in the first embodiment, without use of the "selection of the number of nucleobases and the nucleotide sequence" of the double-strand formation site 5 which the aptamer 1 and the first nucleic acid fragment 2 have, the "ability to dissolve a double strand" is achieved by employing the photoisomerization of the photoisomerizable molecule 3 bound to a part of the aptamer 1 and/or a part of the nucleic acid fragment 2 to lower the melting temperature $T_{melting}$ of the complex (hybrid) 11 to the first melting temperature $T_{melting-1}$. In other words, in order to attain both of the following "reciprocal features", i.e., the "ability to dissolve a double strand" and the "ability to maintain a double strand", in place of the technique depending only on the "selection of the number of nucleobases and the nucleotide sequence" of the double-strand formation site 5, such approach is used in which the "ability to dissolve a double strand" is achieved by lowering the melting temperature $T_{melting}$ of the complex (hybrid) 11 to the first melting temperature $T_{melting-1}$, in association with the isomerization of the photoisomerizable molecule 3, while the "ability to maintain a double strand" is achieved by the "selection of the number of nucleobases and the nucleotide sequence" of the double-strand formation site 5. As a result, the optimization of two functions, the "ability to dissolve a double strand" and the "ability to maintain a double strand", can be dealt separately by the selection of the "number and site of the photoisomerizable molecule 3" to be bound to the double-strand formation site 5 and by the selection of the "number of nucleobases and the nucleotide sequence" of the double-strand formation site 5. Further, as the steric hindrance attributed to the structural change of the photoisomerizable molecule 3 has influence only on the proximity of the double-strand formation site 5, the adverse effect of the imparting of the "ability to dissolve a double strand" on the steric structure of the aptamer 1, which is involved directly in binding to the target substance 7 can be reduced. Thus, use of the structure of the complex (hybrid) 11 according to the first embodiment can achieve both of the following "receiprocal features", i.e., the "ability to dissolve a double strand" and the "ability to maintain a double strand", in a much easier way than the conventional technique which requires the difficult design of the "number of nucleobases and the nucleotide sequence" of the double-strand formation site 5. Use of the complex (hybrid) 11 in which both of the "ability to dissolve a double strand" and the "ability to maintain a double strand" are attained can achieve the detection of the target substance 7 with excellent detection sensitivity.

The method for detecting a target substance according to the first embodiment is comprised of the following steps:

(Step 1):
a complex (hybrid) preparation step of preparing a complex (hybrid) 11 in which an aptamer 1 which specifically binds to the target substance 7 and a first nucleic acid fragment 2 comprising a nucleotide sequence complementary to the aptamer 1 have a double-strand formation site 5, and a photoisomerizable molecule 3 disposed on the double-strand formation site 5;

(Step 2):
a first photoisomerization step of subjecting the photoisomerizable molecule 3 to photoisomerization reaction by irradiation with a first irradiation light having a first wavelength ($\lambda_1$) to destabilize the double-stranded nucleotides binding of the aptamer 1 and the first nucleic acid fragment 2, thereby converting the complex to a first photoisomerization-treated complex (hybrid) having a first melting temperature $T_{melting\text{-}1}$;

(Step 3):
a contact step of contacting the first photoisomerization-treated complex (hybrid) with a sample in a liquid phase having a solution temperature $T_{L1}$;

(Step 4):
a binding step of allowing the target substance 7 to bind to the aptamer 1 by the action of the target substance 7 in the sample on the aptamer 1 comprised in the first photoisomerization-treated complex (hybrid) in a liquid phase having a solution temperature $T_{L2}$ to form a target substance 7/aptamer 1 complex;

(Step 5):
a dissolution step of dissolving the double-stranded nucleic acid portions in the complex of the aptamer 1 and the first nucleic acid fragment 2, in association with the formation of the target substance 7/aptamer 1 complex, in a liquid phase having a solution temperature $T_{L3}$, to separate the first nucleic acid fragment 2 from the target substance 7/aptamer 1 complex;

(Step 6):
a second photoisomerization step of subjecting the photoisomerizable molecule 3 to photoisomerization reaction by irradiation with a second irradiation light having a second wavelength ($\lambda 2$) to stabilize the double-stranded nucleotides binding of the aptamer 1 and the first nucleic acid fragment 2 composing the first photoisomerization-treated complex (hybrid), thereby converting the complex to a second photoisomerization-treated complex (hybrid) having a second melting temperature $T_{melting\text{-}2}$; and (Step 7):
a detection step of detecting the double-stranded nucleic acid portions of the aptamer 1 and the first nucleic acid fragment 2 composing the second photoisomerization-treated complex (hybrid) to detect the second photoisomerization-treated complex (hybrid).

Hereinafter, each of steps of which the method for detecting a target substance according to the first embodiment is comprised will be explained in more detail with reference to the first embodiment illustrated in FIG. 3.

"Step of Preparation of Complex (Hybrid)"

First, a complex (hybrid) 11 is prepared. This complex (hybrid) comprises an aptamer 1, a first nucleic acid fragment 2, and a photoisomerizable molecule 3 (FIG. 3(a)).

In the first embodiment, at least a part of the nucleotide sequence of the aptamer 1 that participates in the formation of the steric structure of a target substance 7/aptamer 1 complex through binding to the target substance 7 is contained in the double-strand formation site 5 that participates in the formation of double-stranded nucleotides binding with the first nucleic acid fragment 2. The first nucleic acid fragment 2 has a double-strand formation site 5 capable of forming double-stranded nucleotides binding with the aptamer 1. In addition, the photoisomerizable molecule 3 is bound to one or both of a part of the double-strand formation site 5 in the first nucleic acid fragment 2 and a part of the double-strand formation site 5 in the aptamer 1.

A labeling material 6 is bound to each of the end portion of the aptamer 1 and the end portion of the first nucleic acid fragment 2. The double-strand formation site 5 of the aptamer 1 and the double-strand formation site 5 of the first nucleic acid fragment 2 are hybridized through their nucleotide sequences complementary to each other to form double-stranded nucleotides binding (or a double-stranded nucleic acid portion).

"Step for Detection of Target Substance"

Subsequently, the step of detecting the target substance 7 using the complex (hybrid) 11 thus prepared is divided into the following "the first step" to "the fourth step", and the constitution of each step will be explained below.

"The First Step"

In "the first step" of the first embodiment, the double-stranded nucleotides binding is destabilized by the first photoisomerization reaction of the photoisomerizable molecule 3 (FIG. 3(b)). The first photoisomerization reaction of the photoisomerizable molecule 3 proceeds by irradiation with a first irradiation light having a first wavelength ($\lambda_1$). In this context, the term "double-stranded nucleotides binding is destabilized by the first photoisomerization reaction of the photoisomerizable molecule 3" is not limited by the mechanism of this destabilization as long as the first photoisomerization of the photoisomerizable molecule 3 can reduce the intermolecular force for binding between the aptamer 1 and the first nucleic acid fragment 2 at the double-stranded nucleic acid portion in the complex (hybrid) 11. This term means that, for example, the structural change of the photoisomerizable molecule 3 caused by the first photoisomerization reaction of the photoisomerizable molecule 3 causes the steric hindrance between the photoisomerizable molecule 3 and the nucleobases of the double-strand formation site 5 to reduce the intermolecular force for binding. For example, due to the generated steric hindrance, the structure of the double-strand formation site 5 is distorted to weaken hydrogen bonding in the complementary base pairs of the aptamer 1 and the nucleic acid fragment 2. In the case, the hydrogen bonds disappear in association with the destabilization of the double-stranded nucleotides binding. The temperature that permits dissolution of the double strand (melting temperature) becomes the first melting temperature $T_{melting-1}$.

The "destabilized double-stranded nucleotides binding" can assume the state where the double-stranded nucleic acid portion is partially or wholly dissociated according to dissociation equilibrium reaction. The dissociation constant $K_{Dhybrid-1}(T_L)$ of the first photoisomerization-treated complex (hybrid)=[Complementary strand]*[Aptamer]/[Destabilized hybrid] shows the temperature dependence of exp($-k*T_{melting-1}/kT_L$). Provided that the solution temperature $T_L$ is higher than the first melting temperature $T_{melting-1}$ the state can be adopted where the double-stranded nucleic acid portion is partially or wholly dissociated.

"The Second Step"

Subsequently, in "the second step" of the first embodiment, the target substance 7 binds to the aptamer 1 (FIG. 3(c)). In the complex 11, the aptamer 1 is in a single-stranded form except that a part of its nucleotide sequence capable of binding to the target substance is comprised in the double-stranded nucleic acid portion. This means that the structure of the single-stranded site of the aptamer 1 can be deformed freely into any configuration. In other words, the aptamer 1 has a double-strand formation site 5 for the first nucleic acid fragment 2 and also has a binding site capable of binding to the target substance 7. Provided that the solution temperature $T_L$ is higher than the first melting temperature $T_{melting-1}$ in the state where at least a part of the double-stranded nucleic acid portion is dissociated as a result of destabilizing the double-stranded nucleic acid portion by "the first step", the aptamer 1 can easily assume a steric structure capable of binding to the target substance 7. Thus, the aptamer 1 can bind to the target substance 7 in the subject to be assayed.

"The Third Step"

Subsequently, in "the third step" of the first embodiment, the double-stranded nucleotides binding site formed between the aptamer 1 and the first nucleic acid fragment 2 is wholly dissociated. In this state, the first nucleic acid fragment 2 is dissolved from the aptamer 1 bound to the target substance 7. Specifically, as the binding of the aptamer 1 to the target substance 7 proceeds in "the second step", the double-stranded nucleotides binding between the double-strand formation sites 5 is dissolved. This "dissolution of the double-stranded nucleotides binding" occurs when the binding between the target substance 7 and the aptamer 1 in the target substance 7/aptamer 1 complex is stronger than the binding between the aptamer 1 and the first nucleic acid fragment 2 in the first photoisomerization-treated complex (hybrid). Specifically, the "dissolution of the double-stranded nucleotides binding" proceeds rapidly in the case where, when the dissociation constant $K_{Dcomplex}(T_L)$ of the target substance 7/aptamer 1 complex=[Target substance]*[Aptamer]/[Complex] is compared with the dissociation constant $K_{Dhybrid-1}(T_L)$ of the first photoisomerization-treated complex (hybrid), such relationship of $K_{Dcomplex}(T_L) \ll K_{Dhybrid-1}(T_L)$ is satisfied.

When the double-stranded nucleotides binding site formed between the aptamer 1 and the first nucleic acid fragment 2 in the first photoisomerization-treated complex (hybrid) is wholly converted into the dissociated state, the double-stranded nucleic acid portion disappears. As a result, the target substance 7/aptamer 1 complex is separated from the first nucleic acid fragment 2 (FIG. 3(d)). In this context, the nucleotide sequence of which the target substance 7-binding site of the aptamer 1 is composed is corresponding to a part or the whole of the nucleotide sequence of the double-strand formation site 5 in the aptamer 1. Accordingly, the configuration of the double-stranded nucleic acid portion in the aptamer 1 is deformed in the case when the target substance 7/aptamer 1 complex is formed by the binding of the target substance 7 to the aptamer 1. The aptamer 1 complexed with the target substance 7 has a particular steric structure in which the target substance 7-binding site is provided. At the solution temperature $T_L$ in "the third step", the state of the particular steric structure thus formed is thermally more stable than the single-stranded state that does not exhibit a steric structure. For this reason, the reformation of the complex (hybrid) of the first nucleic acid fragment 2 with the aptamer 1 complexed with the target substance 7 is inhibited, so that the dissolved state is maintained.

"The Fourth Step"

Subsequently, in "the fourth step" of the first embodiment, the double-stranded nucleotides binding formed between the aptamer 1 and the first nucleic acid fragment 2 in the first photoisomerization-treated complex (hybrid) is stabilized by the second photoisomerization reaction. In this context, the term "double-stranded nucleotides binding is stabilized by the second photoisomerization reaction" is not limited as long as the second photoisomerization of the photoisomerizable molecule 3 in the first photoisomerization-treated complex (hybrid) can enhance the intermolecular force for binding between the aptamer 1 and the first nucleic acid fragment 2 at the double-stranded nucleic acid portion 5. This term means that, for example, the photoisomerizable molecule 3 isomerized by the first photoisomerization reaction is subjected to the second photoisomerization reaction so as to recover its structure to that before the first photoisomerization, thereby recovering the original intermolecular force for binding between the aptamer 1 and the first nucleic acid fragment 2 at the double-stranded nucleic acid portion 5.

In "the third step", the structure of the photoisomerizable molecule 3 isomerized by the first photoisomerization reaction in the first nucleic acid fragment 2 produced by the dissolution is also recovered to that before the first photoisomerization in association with the second photoisomerization reaction. In this context, when the target substance 7 is present in the sample, the aptamer 1 complexed with the target substance 7 is structurally changed at the double-stranded nucleic acid portion to inhibit the reformation of its complex (hybrid) with the first nucleic acid fragment 2 in which the photoisomerizable molecule 3 is restored in the original structure before the first photoisomerization. Thus, the dissolved state in which the first nucleic acid fragment 2 is separated from the aptamer 1 complexed with the target substance 7 is maintained even if subjected to the second photoisomerization reaction (FIG. 3(e)).

On the other hand, in the case when the target substance 7 is absent in the sample, in the first photoisomerization-treated complex (hybrid), in which the double-stranded nucleotides binding has been destabilized by the first photoisomerization reaction of the photoisomerizable molecule 3 in "the first step", the photoisomerizable molecule 3 isomerized by the first photoisomerization reaction is also recovered to that before the first photoisomerization in association with the second photoisomerization reaction. The resulting double-strand formation sites 5 form stable double-stranded nucleotides binding again. The melting temperature $T_{melting}$ of the double-stranded nucleotides binding stabilized by the second photoisomerization treatment becomes the second melting temperature $T_{melting-2}$. Since the second melting temperature $T_{melting-2}$ is sufficiently higher than the solution temperature $T_L$, the stabilized double-stranded nucleotides binding is prevented from being thermally dissociated.

After the second photoisomerization reaction to stabilize the double-stranded nucleotides binding formed between the aptamer 1 and the first nucleic acid fragment 2, the dissolution of the double-stranded nucleic acid portion located in the complex (hybrid) of the aptamer 1 and the first nucleic acid fragment 2 is detected. The approach for detecting the dissolution of the double-stranded nucleic acid portion is not limited as long as the approach can detect a physical or chemical change caused by the dissolution of the double-stranded nucleotides binding at the double-stranded nucleic acid portion located in the complex (hybrid). For example, change in signals such as optical, electric, or color signals caused by the dissolution of the double-stranded nucleotides binding is detected.

When the substance binding to the aptamer 1 (target substance 7) is present in the subject to be assayed, the double-stranded nucleotides binding in the first photoisomerization-treated complex (hybrid) is dissolved in association with the formation of a target substance 7/aptamer 1 complex in "the third step". On the other hand, when such a substance binding to the aptamer 1 (target substance 7) is absent, the double-stranded nucleotides binding in the first photoisomerization-treated complex (hybrid) is destabilized, but the destabilization can not lead to dissolution thereof.

Thus, in "the fourth step", after the stabilization of the double-stranded nucleotides binding, a double-stranded nucleic acid portion is formed between the aptamer 1 and the first nucleic acid fragment 2 in the first photoisomerization-treated complex (hybrid). Thus, the dissolution of the double-stranded nucleotides binding can be detected to thereby determine the presence or absence of the target substance 7 in the subject to be assayed.

In this context, the "advantages and effects" of the detection mechanism used in the method for detecting a target substance according to the first embodiment will be further described in comparison with the conventional techniques (methods for detecting a target substance) described in Patent Document 1 and Non Patent Documents 1 to 2.

In the method for detecting a target substance disclosed in Patent Document 1, during the step of detecting a target substance by contacting a subject to be assayed with an aptamer/nucleic acid fragment complex (hybrid) that has formed a double-stranded nucleic acid portion, the binding strength (dissociation constant $K_{Dhybrid}(T_L)$) between the aptamer and the nucleic acid fragment composing the complex (hybrid) is kept to constant.

As a result, the double-stranded nucleic acid portion between the aptamer and the nucleic acid fragment composing the complex (hybrid) may inhibit the binding of the aptamer to the target substance. When formed in the complex (hybrid), the double-stranded nucleic acid portion of the aptamer has a double helix structure, which in turn inhibits the formation of a steric structure essential to binding to the target substance. For example, when a longer double-stranded nucleic acid portion (a larger number of nucleobases) is used, a higher melting temperature $T_{melting}$ of the double-stranded nucleic acid portion is resulted. In such a case when the melting temperature $T_{melting}$ of the double-stranded nucleic acid portion is higher than the solution temperature $T_L$, the structural change to a steric structure essential to binding to the target substance may be inhibited, and consequently, it may cause such problem that the binding affinity of the aptamer to the target substance is impaired.

For permitting the structural change of the aptamer 1, it is thus required to excessively reduce the number of complementary nucleobases composing the double-stranded nucleic acid portion in order to lower the melting temperature $T_{melting}$ of the double-stranded nucleic acid portion to below the solution temperature $T_L$. Even if the target substance is absent, when the number of complementary nucleobases, which composes the double-stranded nucleic acid portion, is too small, the double-stranded nucleic acid portion is dissolved according to the dissociation constant $K_{Dhybrid}(T_L)$ to promote the dissolution of the complex (hybrid). Thus, even if the target substance is absent, the dissolution of the double-stranded nucleic acid portion happens to be induced, resulting in the subsequent dissolution of the complex (hybrid). This event may obstacle the detection of the target substance based on the dissolution of the complex (hybrid).

By contrast, in the method for detecting a target substance according to the first embodiment, "the first step" of the "target substance detection step" comprises subjecting the photoisomerizable molecule 3 bound to the double-strand formation site(s) 5 in the aptamer 1/first nucleic acid fragment 2 complex (hybrid) to a first photoisomerization treatment to reduce the intermolecular force of the double-stranded nucleotides binding between the aptamer 1 and the first nucleic acid fragment 2. The first photoisomerization treatment of the photoisomerizable molecule 3 is carried out to weaken the intermolecular force of the double-stranded nucleotides binding between the aptamer 1 and the first nucleic acid fragment 2, and thereby, the melting temperature $T_{melting-1}$ of the double-stranded nucleic acid portion in the destabilized complex (hybrid) can be lowered to below the solution temperature $T_L$. As a result, the process of forming a steric structure essential to the binding of the aptamer 1 to the target substance 7 is promoted in "the second step". When the target substance 7 is allowed to bind to the aptamer 1 having the steric structure thus formed, the dissolution of the double-stranded nucleic acid portion 5 proceeds efficiently in association with the formation of a target substance 7/aptamer 1 complex. Thereafter, in "the third step", the formation of the target substance 7/aptamer 1 complex is completed by the contact of the aptamer 1 with the subject to be assayed. Then, in "the fourth step", the photoisomerizable molecule 3 is subjected to a second photoisomerization treatment to thereby enhance the intermolecular force of the double-stranded nucleotides binding between the aptamer 1 and the first nucleic acid fragment 2. As a result, in the complex (hybrid) of the aptamer 1 and the first nucleic acid fragment 2, to which the target substance 7 is not bound, the undissolved double-strand formation sites 5 form stable double-stranded nucleotides binding again. Thus, as a result of the second photoisomerization treatment of the photoisomerizable molecule 3 in "the fourth step", the dissolution of the double-stranded nucleic acid portion 5 is suppressed in the complex (hybrid) 11 of the target substance 7-unbound aptamer 1 and the first nucleic acid fragment 2. In this context, the target substance 7/aptamer 1 complex, which is composed of the aptamer 1 having the formed steric structure and the target substance 7 is stable. Hence, at the solution temperature $T_L$ used in "the fourth step", the aptamer 1 is folded in the steric structure essential to binding to the target substance 7, while the target substance 7 is kept in such state of bring bound with the binding site composing of a particular partial nucleotide sequence in the aptamer 1 having the steric structure thus formed, and thereby, the stable complex is composed. At the solution temperature $T_L$ used in "the fourth step", the aptamer 1 having the formed steric structure is thermally much more stable than the aptamer 1 (single-stranded state) in which the steric structure is dissolved. Therefore, even in the state of the enhanced intermolecular force of the double-stranded nucleotides binding between the aptamer 1 and the first nucleic acid fragment 2 at their double-strand formation sites 5 in the aptamer 1/first nucleic acid fragment 2 complex (hybrid), when the dissociation constant $K_{Dcomplex}(T_L)$ of the target substance 7/aptamer 1 complex=[Target substance]*[Aptamer]/[Complex] is compared with the dissociation constant $K_{Dhybrid-2}(T_L)$ of the second photoisomerization-treated complex (hybrid), at least the condition of $K_{Dcomplex}(T_L) \leq K_{Dhybrid-2}(T_L)$ is satisfied. Thus, even if the first nucleic acid fragment 2 in a single-stranded form acts on the target substance 7/aptamer 1 complex, such phenomenon that the target substance 7/aptamer 1 complex is dissociated to reform the aptamer 1/first nucleic acid fragment 2 complex (hybrid) is not induced. As a result, the first nucleic acid fragment 2 in a single-stranded form, which is produced by the dissolution of the double-stranded nucleotides binding in "the third step", keeps its dissolved state even after the second photoisomerization treatment is carried out in "the fourth step". In this way, in the method for detecting a target substance according to the first embodiment, both of the high reactivity to the target substance 7 and the ability to maintain double-stranded nucleotides binding in the absence of the target substance 7 can be attained by applying the first photoisomerization treatment to the photoisomerizable molecule 3 bound to any one or both of the double-strand formation sites 5 of the aptamer 1 and the first nucleic acid fragment 2, and thereby, a method for assaying a target substance with excellent detection accuracy can be achieved.

Alternatively, Non Patent Document 1 discloses, as schematically shown in FIG. 1, a method for detecting ATP, in which a mixed solution containing a target substance ATP 107 and a nucleic acid double strand formed by an ATP aptamer 101 and a complementary strand 102 is heated up, and then, the solution is cooled down to form a complex of the target substance ATP 107 and the ATP aptamer 101. According to the method disclosed in Non Patent Document 1, the double strand of the ATP aptamer 101 and the complementary strand 102 is temporarily destabilized by heating to dissociate a part thereof. At this solution temperature $T_L$, the complex of the target substance ATP 107 and the ATP aptamer 101 is formed according to the dissociation constant $K_{Dhybrid}(T_L)$ of the ATP aptamer 101/complementary strand 102 complex (hybrid)=[Complementary strand]*[ATP aptamer]/[Hybrid] and the dissociation constant $K_{Dcomplex}(T_L)$ of the target substance ATP 107/ATP aptamer 101 complex=[ATP]*[ATP aptamer]/[Complex]. In the complex (hybrid) of the ATP aptamer 101 and the complementary strand 102 temporarily destabilized at the solution temperature $T_L$, it is considered that the double strand thereof can be restabilized by cooling down.

The destabilization of the double strand by heating is brought about by the dissociation of the hydrogen bonds between the base pairs resulting from the thermal motions of nucleobases composing the base pairs and by the dissociation of a hydrogen bond with the water molecule of a solvent, which is involved in the solvation to the nucleic acid backbone. Accordingly, this heating destabilizes not only the double-stranded nucleic acid portion containing the hydrogen bonds between the base pairs but also the structure of the single-stranded portion in the ATP aptamer 101. Thus, in the case if a solution temperature $T_L$ is set at unnecessarily high level, the efficiency (ratio) at which the ATP aptamer 101 assumes a steric structure for binding to the target substance ATP 107 is reduced, and consequently, the binding affinity to the target substance ATP 107 will be impaired. For this reason, in the case if the solution temperature $T_L$ is selected within unnecessarily high range during the heating, there are expected anxieties that it would inhibit the detection of the target substance ATP 107 based on the formation of the target substance ATP 107/ATP aptamer 101 complex.

By contrast, in the method for detecting a target substance according to the first embodiment, the destabilization of the double-stranded nucleotides binding is brought about by steric hindrance due to the photoisomerization of the photoisomerizable molecule 3. The extent influenced by this destabilization is limited to nucleobases adjacent to the photoisomerizable molecule 3. Thus, the influence of the photoisomerization of the photoisomerizable molecule 3 on the steric structure of the nucleic acid strands is confined to a part of the double-strand formation sites 5 in the aptamer 1 and the first nucleic acid fragment 2, to which the photoisomerizable molecule 3 is bound. Therefore, in the "target substance detection step", the solution temperature $T_L$ is selected in the range of such a temperature that is higher than the melting temperature $T_{melting-1}$ of the double-stranded nucleic acid portion in the destabilized complex (hybrid) and lower than the melting temperature $T_{melting-2}$ of the double-stranded nucleic acid portion in the restabilized complex (hybrid) ($T_{melting-2} > T_L > T_{melting-1}$). The solution temperature $T_L$ can therefore be selected within a range sufficiently lower than the temperature at which the steric structure (which is composed of the single-stranded nucleic acid portion of the aptamer 1) essential to binding to the target substance 7 is thermally destabilized. Thus, in the method for detecting a target substance according to the first embodiment, such a heat treatment in which the solution temperature $T_L$ is increased to $T_{melting-2}$ is employed in order to temporarily destabilize and dissociate the double-stranded nucleic acid portion by the first photoisomerization treatment of the photoisomerizable molecule 3. Nonetheless, in the method for detecting a target substance according to the first embodiment, the adverse effect on detection sensitivity, which is caused by unnecessarily increase in the solution temperature $T_L$ can be remarkably reduced.

Figure 11:
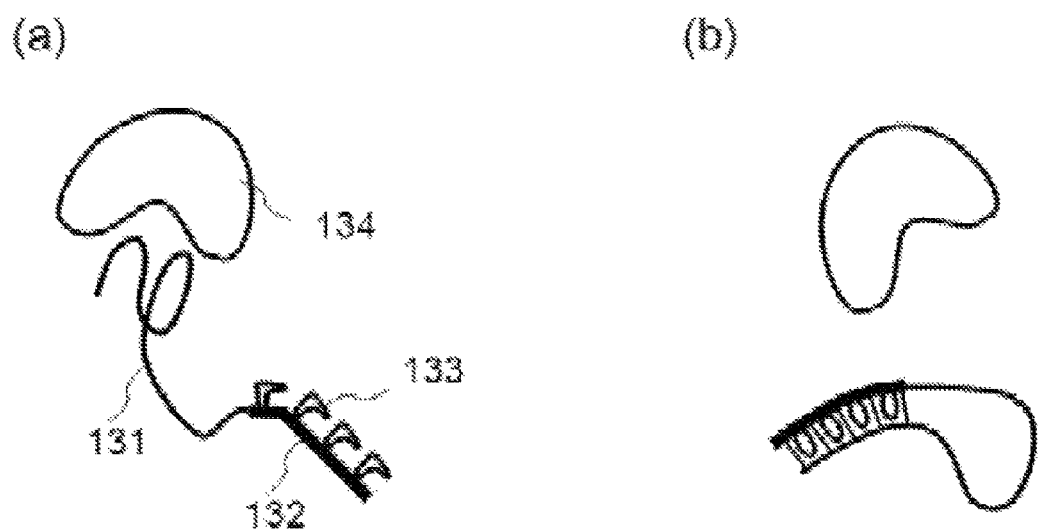
FIG. 11 is a diagram schematically showing the operation of a conventional photoresponsive nucleic acid probe.

Further, Non Patent Document 2 teaches, as schematically shown in FIG. 11, a nucleic acid probe comprising a thrombin aptamer 131 that is capable of binding to a target substance thrombin 134, a complementary strand 132 to a part of the thrombin aptamer 131, and a photoisomerizable molecule 133. The operation and effect of the nucleic acid probe, however, is different from the operation and effect of the complex (hybrid) of the aptamer 1 and the second nucleic acid fragment 2, which is utilized for the first embodiment. In accordance with the method for detecting a target substance according to the first embodiment, in the detection step, the nucleic acid probe disclosed in Non Patent Document 2 cannot be applied, instead of the complex (hybrid) of the aptamer 1 and the second nucleic acid fragment 2, to the detection of the target substance.

In the nucleic acid probe disclosed in Non Patent Document 2, a nucleotide sequence (complementary strand 132) complementary to a part of the thrombin aptamer 131 is added onto an extension of the aptamer, and this complementary strand 132 is modified with azobenzene (photoisomerizable molecule 133) (FIG. 11(a)). Referring to Non Patent Document 2, azobenzene is photoisomerized into a cis form upon irradiation with an ultraviolet light to inhibit the formation of the double-stranded nucleotides binding between the thrombin aptamer 131 and the complementary strand 132. In the case when azobenzene (photoisomerizable molecule 133) is in the trans form, the nucleic acid probe can be maintained in the double-stranded nucleotides binding state ("nucleic acid probe-trans") at a solution temperature $T_L$ lower than the melting temperature $T_{melting-trans}$ of the double-stranded nucleotides binding. In the case when azobenzene (photoisomerizable molecule 133) is in the cis form, however, it causes steric hindrance, and thereby, the double-stranded nucleotides binding is thermally dissolved at the solution temperature $T_L$ to convert the nucleic acid probe to "a single-stranded nucleic acid probe-cis". In such a case, the thrombin aptamer 131, in which the double-stranded nucleotides binding is dissolved, can form a steric structure essential to binding to the thrombin 134 at the solution temperature $T_L$. As the thrombin 134 binds to the binding site located in the steric structure that is formed thereby, a complex of the thrombin 134 and the "single-stranded nucleic acid probe-cis" is constructed. The dissociation constant $K_{Dcomplex-cis}(T_L)$ of the complex of the thrombin 134 and the "single-stranded nucleic acid probe-cis" ("complex-cis"), at the solution temperature $T_L$, is represented by $K_{Dcomplex-cis}(T_L)$=[Thrombin]*[Single-stranded nucleic acid probe-cis]/[Complex-cis].

When the cis form of azobenzene is irradiated with a visible light, the cis form of azobenzene is photoisomerized into the trans form thereof. In the case when azobenzene (photoisomerizable molecule 133) is in the trans form, the formation of the double-stranded nucleotides binding between the thrombin aptamer 131 and the complementary strand 132 is not inhibited. Thus, the "single-stranded nucleic acid probe-trans" present in the solution having the solution temperature $T_L$ is converted to a thermally more stable "nucleic acid probe-trans".

Meanwhile, in the case when the cis form of azobenzene is photoisomerized into the trans form thereof, as a results, the complex of the thrombin 134 and the "single-stranded nucleic acid probe-cis" is also converted to a complex of the thrombin 134 and the "single-stranded nucleic acid probe-trans" (complex-trans). The dissociation constant $K_{Dcomplex-trans}(T_L)$ of the complex of the thrombin 134 and the "single-stranded nucleic acid probe-trans" ("complex-trans"), at the solution temperature $T_L$, is represented by $K_{Dcomplex-trans}(T_L)$=[Thrombin]*[Single-stranded nucleic acid probe-trans]/[Complex-trans].

After such a treatment that the cis form of azobenzene is photoisomerized into the trans form thereof is completed, the "single-stranded nucleic acid probe-trans" concentration [Single-stranded nucleic acid probe-trans] becomes substantially "0" in the solution having the solution temperature $T_L$. As a result, the complex of the thrombin 134 and the "single-stranded nucleic acid probe-trans" ("complex-trans"), which is produced by the photoisomerization treatment, is dissociated according to the dissociation constant $K_{Dcomplex-trans}(T_L)$ to produce a "single-stranded nucleic acid probe-trans" and thrombin. The thus-produced "single-stranded nucleic acid probe-trans" is converted to a thermally more stable "nucleic acid probe-trans" through the formation of double-stranded nucleotides binding between the thrombin aptamer 131 and the complementary strand 132.

Finally, substantially all of the complexes of the thrombin 134 and the "single-stranded nucleic acid probe-trans" ("complex-trans"), which is produced by the photoisomerization treatment, are dissociated, so that only thrombin and the thermally more stable "nucleic acid probe-trans", which is produced by the formation of double-stranded nucleotides binding between the thrombin aptamer 131 and the complementary strand 132 are dissolved in the solution having the solution temperature $T_L$ (FIG. 11(b)).

In the case when, after the binding of the thrombin 134 to the thrombin aptamer 131 is completed by irradiation with an ultraviolet light, the complex is irradiated with a visible light, the complementary strand 132 whose intermolecular force for binding with the thrombin aptamer 131 is restored through the photoisomerization apparently pushes the thrombin 134 aside, and thereby, the formation of the double-stranded nucleotides binding between the aptamer 131 and the complementary strand 132 is initiated. As a result, the thrombin 134 appears to be dissociated from the aptamer 131.

In other words, following effect is reported to be achieved in the nucleic acid probe disclosed in Non Patent Document 2, as the intermolecular force for binding with the aptamer 131 of the complementary strand 132, which is modified with the azobenzene (photoisomerizable molecule 133), is weakened by the photoisomerization of azobenzene into the cis form by irradiation with the ultraviolet light, in association therewith, the binding affinity to the target substance 134 of the aptamer 131 is attained; and as the intermolecular force for binding with the aptamer 131 of the complementary strand 132 is enhanced by the photoisomerization of azobenzene into the trans form by irradiation with the visible light, in association therewith, the binding affinity to the target substance 134 of the aptamer 131 is eliminated. Since all of the complexes of the target substance thrombin 134 and the nucleic acid probe are dissociated by this photoisomerization treatment of the azobenzene into the trans form by irradiation with the visible light, the approach of detecting the double-stranded nucleotides binding between the aptamer 131 and the complementary strand 132 to thereby detect the complex of the target substance thrombin 134 and the nucleic acid probe is inapplicable in principle after the photoisomerization treatment of the azobenzene into the trans form by irradiation with the visible light.

By contrast, the method for detecting a target substance according to the first embodiment is based on the new finding that after carrying out all of the first step to the fourth step, the amount of the aptamer 1/first nucleic acid fragment 2 complex (hybrid) is detected and the target substance 7 can be detected with excellent accuracy on the basis of decrease in the amount of the complex (hybrid) caused by the formation of the target molecule 7/aptamer 1 complex.

In the method for detecting a target substance according to the first embodiment, the dissociation constant $K_{Dcomplex}(T_L)$ of the target substance 7/aptamer 1 complex formed in "the third step"=[Target substance]*[Aptamer having the steric structure]/[Complex] satisfies the condition of $K_{Dcomplex}(T_L) \ll K_{Dhybrid-1}(T_L)$, at the solution temperature $T_L$ used in "the third step" or in "the fourth step", with the dissociation constant $K_{Dhybrid-1}(T_L)$ of the complex (hybrid) destabilized by the first photoisomerization treatment= [Complementary strand after the first photoisomerization treatment]*[Single-stranded aptamer]/[Destabilized hybrid].

Also, the dissociation constant $K_{Dhybrid-2}(T_L)$ of the second photoisomerization-treated complex (hybrid)=[Second photoisomerization-treated complementary strand]*[Single-stranded aptamer]/[Restabilized hybrid] satisfies the condition of the $K_{Dhybrid-2}(T_L) \ll K_{Dhybrid-1}(T_L)$, at the solution temperature $T_L$ used in "the fourth step", in comparison with the dissociation constant $K_{Dhybrid-1}(T_L)$ of the complex (hybrid) destabilized by the first photoisomerization treatment.

At the solution temperature $T_L$ used in "the third step" or in "the fourth step", the "steric structure essential to binding to the target substance 7" carried by the "aptamer having the steric structure" is thermally stable compared with the single-stranded structure of the "single-stranded aptamer" dissociated from the aptamer 1/first nucleic acid fragment 2 complex (hybrid). At the solution temperature $T_L$, the formation of the target substance 7/aptamer 1 complex indicates that the "steric structure essential to binding to the target substance 7" carried by the "aptamer 1 having the steric structure" secures further enhanced thermal stability through the binding to the target substance 7.

In addition, the number of base pairs composing the double-strand formation sites 5 in the aptamer 1/first nucleic acid fragment 2 complex (hybrid) may be adjusted such that at the solution temperature $T_L$ used in "the fourth step", the dissociation constant $K_{Dcomplex}(T_L)$ of the target substance 7/aptamer 1 complex satisfies at least the condition of $K_{Dcomplex}(T_L)$ $K_{Dhybrid-2}(T_L)$, in comparison with the dissociation constant $K_{Dhybrid-2}(T_L)$ of the second photoisomerization-treated complex (hybrid).

On the other hand, in the case if the number of base pairs composing the double-strand formation sites 5 in the aptamer 1/first nucleic acid fragment 2 complex (hybrid) is unnecessarily large, following relationship of $K_{Dhybrid-2}(T_L) < K_{Dcomplex}(T_L) \ll K_{Dhybrid-1}(T_L)$ is given at the solution temperature $T_L$ in "the fourth step". In the case if the relationship of $K_{Dhybrid-2}(T_L) < K_{Dcomplex}(T_L)$ is given, the target substance 7/aptamer 1 complex is inferior in thermal stability to the second photoisomerization-treated complex (hybrid). In a thermal equilibrium produced by keeping the solution temperature $T_L$ in "the fourth step" for a long time, the target substance 7/aptamer 1 complex concentration [Complex] is decreased, while the second photoisomerization-treated complex (hybrid) concentration [Restabilized hybrid] is increased.

Apparently, some of target substances 7 each bound to the aptamer 1 are separated from the aptamer 1 in "the fourth step", as the aptamer 1 and the first nucleic acid fragment 2 restore their intermolecular force for binding with each other. As a result of progressing from "the third step" to "the fourth step", the concentration of the "first nucleic acid fragment 2", which is caused by the "dissolution of the double-stranded nucleotides binding", [Second photoisomerization-treated complementary strand] is predicted to be decreased. The "steric structure" of the aptamer 1 bound to the target substance 7 differs from the "single-stranded structure" suitable for the "formation of double-stranded nucleotides binding" between the "first nucleic acid fragment 2" in the form of the second photoisomerization-treated complementary strand and the aptamer 1. Of course, the formation of double-stranded nucleotides binding between the "aptamer 1 having the steric structure" and the "first nucleic acid fragment 2" by the direct action of the "first nucleic acid fragment 2" on the target substance 7/aptamer 1 complex is inhibited.

Thus, the formation of the second photoisomerization-treated complex (hybrid) requires following three steps: the thermal dissociation of the target substance 7/aptamer 1 complex; the thermal denaturation of the "aptamer 1 having the steric structure" into an aptamer 1 having a single-stranded structure; and the formation of double-stranded nucleotides binding between the aptamer 1 having a single-stranded structure and the "first nucleic acid fragment 2". At the solution temperature $T_L$ used in "the fourth step", following two steps, i.e., the thermal dissociation of the target substance 7/aptamer 1 complex and the thermal denaturation of the "aptamer 1 having the steric structure" into an aptamer 1 having a single-stranded structure, particularly, the thermal dissociation of the target substance 7/aptamer 1 complex, can not be progressed rapidly. A considerable time is therefore required for the "first nucleic acid fragment 2" produced by the "dissolution of the double-stranded nucleotides binding" to complete the reformation of the second photoisomerization-treated complex (hybrid). Thus, some of "first nucleic acid fragments 2" produced by the "dissolution of the double-stranded nucleotides binding" in "the third step" continue to maintain the "dissolved state" during "the fourth step".

When the target substance 7 is absent in the sampled specimen, the target substance 7/aptamer 1 complex is not formed in "the third step". Accordingly, each aptamer 1 produced by the "dissolution of the double-stranded nucleotides binding" exists as a mixture of the "aptamer 1 having the steric structure" and the aptamer 1 having a single-stranded structure in the solution. In this case, the "aptamer 1 having the steric structure" and the aptamer 1 having a single-stranded structure are in thermal equilibrium with each other. In "the fourth step", the aptamer 1 having a single-stranded structure forms double-stranded nucleotides binding with the "first nucleic acid fragment 2" in the form of the second photoisomerization-treated complementary strand to produce a second photoisomerization-treated complex (hybrid). The resulting concentration of the aptamer 1 having a single-stranded structure [Single-stranded aptamer] is decreased in the solution. In this case, the "aptamer 1 having the steric structure" in thermal equilibrium therewith is thermally denatured into an aptamer 1 having a single-stranded structure. Since the rate of formation of the second photoisomerization-treated complex (hybrid) is fast, the conversion of the "aptamer 1 having the steric structure" to the aptamer 1 having a single-stranded structure by thermal denaturation also proceeds rapidly. As a result, when the target substance 7 is absent in the sampled specimen, almost all of aptamers 1 and "first nucleic acid fragments 2", which have been produced by the "dissolution of the double-stranded nucleotides binding" in "the third step", form double-stranded nucleotides binding in "the fourth step" to regenerate the second photoisomerization-treated complex (hybrid). That is, when the target substance 7 is absent in the sampled specimen, most of "first nucleic acid fragments 2", which have been produced by the "dissolution of the double-stranded nucleotides binding", fail to maintain the "dissolved state" during the progress of "the fourth step".

Thus, the "ratio" at which the "dissolved state of the double-stranded nucleotides binding" is maintained after the completion of "the fourth step" clearly differs between in the "presence of the target substance 7 in the sampled specimen" and in the "absence of the target substance 7 in the sampled specimen". Thus, the "ratio" at which the "dissolved state of the double-stranded nucleotides binding" is maintained can be used as a measure to thereby achieve the "method for detecting a target substance" with excellent detection accuracy.

On the other hand, when the nucleic acid probe disclosed in Non Patent Document 2 is subjected to the second photoisomerization treatment by irradiation with a visible light to convert the nucleic acid probe from a "single-stranded nucleic acid probe-cis" to a "single-stranded nucleic acid probe-trans", for effectively eliminating the complex of the target substance thrombin 134 and the "single-stranded nucleic acid probe-trans" ("complex-trans") at the solution temperature $T_L$, it is required to efficiently decrease the "single-stranded nucleic acid probe-trans" concentration [Single-stranded nucleic acid probe-trans] in the liquid phase. It is thus required to efficiently convert the "single-stranded nucleic acid probe-trans" to a "nucleic acid probe-trans".

At the same time, it is required that with decrease in the "single-stranded nucleic acid probe-trans" concentration [Single-stranded nucleic acid probe-trans] in the liquid phase, the dissociation of the complex of the target substance thrombin 134 and the "single-stranded nucleic acid probe-trans" ("complex-trans") should proceed efficiently according to the dissociation constant $K_{Dcomplex\text{-}trans}(T_L)$ of the "complex-trans".

At the solution temperature $T_L$, the thermal equilibrium between the "single-stranded nucleic acid probe-trans" and the "nucleic acid probe-trans" is represented by the equilibrium constant $K_{D\text{-}trans}(T_L)$ of the dissociation reaction of the double-stranded nucleotides binding between the thrombin aptamer 131 and the complementary strand 132=[Single-stranded nucleic acid probe-trans]/[Nucleic acid probe-trans]. The equilibrium constant $K_{D\text{-}trans}(T_L)$ depends on stabilization energy: $\Delta E_{hybrid\text{-}trans}$ associated with the formation of double-stranded nucleotides binding between the thrombin aptamer 131 and the complementary strand 132 in the "nucleic acid probe-trans".

At the solution temperature $T_L$, the dissociation equilibrium of the complex of the target substance thrombin 134 and the "single-stranded nucleic acid probe-trans" ("complex-trans") is represented by the dissociation constant $K_{Dcomplex\text{-}trans}(T_L)$ of the "complex-trans"=[Thrombin]*[Single-stranded nucleic acid probe-trans]/[Complex-trans]. The dissociation constant $K_{Dcomplex\text{-}trans}(T_L)$ of the "complex-trans" depends on stabilization energy: $\Delta E_{complex\text{-}trans}$ associated with the interaction (intermolecular bond) of the "thrombin aptamer 131 having a steric structure" with the thrombin 134 in the "complex-trans".

$\Delta E_{hybrid\text{-}trans} \ll \Delta E_{complex\text{-}trans}$ is considered to be preferable for the solution temperature $T_L$ at which the thermal dissociation of the "complex-trans" can proceed, while the dissociation of the double-stranded nucleotides binding in the "nucleic acid probe-trans" can not proceed.

In the case when the above condition is employed, however, all of the complexes of the target substance thrombin 134 and the "single-stranded nucleic acid probe-cis" ("complex-cis"), which have been formed by the first photoisomerization treatment (FIG. 11(a)), are converted to the target substance thrombin 134 and the "nucleic acid probe-trans" by the second photoisomerization treatment (FIG. 11(b)). Thus, this condition is inconvenient for the detection of the target substance thrombin 134 using the "dissolved state" of the double-stranded nucleotides binding between the thrombin aptamer 131 and the complementary strand 132 as a measure.

Regardless of the presence or absence of the target substance thrombin 134 in the sampled specimen, all nucleic acid probes regenerate double-stranded nucleotides binding between the thrombin aptamer 131 and the complementary strand 132, as shown in FIG. 11b, by the second photoisomerization treatment and are thereby converted to "nucleic acid probes-trans". As a result, the "presence or absence of the target substance" cannot be detected.

In the method for detecting a target substance according to the first embodiment, an unnecessarily large number of base pairs composing the double-strand formation sites 5 in the aptamer 1/first nucleic acid fragment 2 complex (hybrid) produces the relationship of $K_{Dhybrid\text{-}2}(T_L) < K_{Dcomplex}(T_L) \ll K_{Dhybrid\text{-}1}(T_L)$ at the solution temperature $T_L$ in "the fourth step". In the presence of the relationship of $K_{Dhybrid\text{-}2}(T_L) < K_{Dcomplex}(T_L)$, the target substance 7/aptamer 1 complex is inferior in thermal stability to the second photoisomerization-treated complex (hybrid). In a thermal equilibrium produced by keeping the solution temperature $T_L$ in "the fourth step" for a long time, the target substance 7/aptamer 1 complex concentration [Complex] is decreased, while the second photoisomerization-treated complex (hybrid) concentration [Restabilized hybrid] is increased.

In order to avoid the above phenomenon, the number of base pairs composing the double-strand formation sites 5 in the aptamer 1/first nucleic acid fragment 2 complex (hybrid) may be adjusted such that at the solution temperature $T_L$ in "the fourth step", the dissociation constant $K_{Dcomplex}(T_L)$ of the target substance 7/aptamer 1 complex satisfies at least the condition of $K_{Dcomplex}(T_L)$ $K_{Dhybrid\text{-}2}(T_L)$ with the dissociation constant $K_{Dhybrid\text{-}2}(T_L)$ of the second photoisomerization-treated complex (hybrid).

In the method for detecting a target substance according to the first embodiment, the dissociation constant $K_{Dcomplex}(T_L)$ of the target substance 7/aptamer 1 complex at the solution temperature $T_L$ in "the fourth step" is selected at least within the condition of $K_{Dcomplex}(T_L)$ $K_{Dhybrid\text{-}2}(T_L)$, compared with the dissociation constant $K_{Dhybrid\text{-}2}(T_L)$ of the second photoisomerization-treated complex (hybrid). Thereby, the dissociation of the target substance 7/aptamer 1 complex can be prevented at the solution temperature $T_L$ used in "the fourth step". Thus, some of "first nucleic acid fragments 2", which have been produced by the "dissolution of the double-stranded nucleotides binding" in "the third step", continue to maintain the "dissolved state" during "the fourth step".

Accordingly, as described above, the "ratio" at which the "dissolved state of the double-stranded nucleotides binding" is maintained after the completion of "the fourth step" clearly differs between in the "presence of the target substance 7 in the sampled specimen" and in the "absence of the target substance 7 in the sampled specimen". Thus, the "ratio" at which the "dissolved state of the double-stranded nucleotides binding" is maintained can be used as a measure to thereby achieve the "method for detecting a target substance" with excellent detection accuracy.

In the application of the nucleic acid probe disclosed in Non Patent Document 2, the azobenzene (photoisomerizable molecule 133) being attached at the double-strand formation site of a "nucleic acid probe-trans" is photoisomerized into a cis form by the first photoisomerization treatment to convert the "nucleic acid probe-trans" to a thermally unstable "nucleic acid probe-cis". The dissociation of the destabilized double-stranded nucleotides binding in the "nucleic acid probe-cis" produces a "single-stranded nucleic acid probe-cis". The thrombin aptamer 131 incorporated in the "single-stranded nucleic acid probe-cis" is used to form a complex of the target substance thrombin 134 and the "single-stranded nucleic acid probe-cis" ("complex-cis") (FIG. 11(a)). In that stage, the thrombin aptamer 131 incorporated in the "single-stranded nucleic acid probe-cis", which is comprised in the "complex-cis", has a steric structure essential to binding to the thrombin 134. The "single-stranded nucleic acid probe-cis" produced by the dissociation of the destabilized double-stranded nucleotides binding in the "nucleic acid probe-cis" initially has a single-stranded structure at the thrombin aptamer 131 moiety, which is then converted to the thermally stable steric structure.

At the solution temperature $T_L$, the thermal equilibrium between the "single-stranded nucleic acid probe-cis having a single-stranded structure" containing the thrombin aptamer 131 having a single-stranded structure and the "single-stranded nucleic acid probe-cis having a steric structure" containing the thrombin aptamer 131 having a steric structure is represented by the equilibrium constant $K_{denaturing-cis}(T_L)$ of the thermal denaturation reaction of the "steric structure" of the thrombin aptamer 131 moiety into the "single-stranded structure"=[Single-stranded nucleic acid probe-cis having a single-stranded structure]/[Single-stranded nucleic acid probe-cis having a steric structure]. The equilibrium constant $K_{denaturing-cis}(T_L)$ depends on stabilization energy: $\Delta E_{3D\text{-}form\text{-}cis}$ associated with the formation of the steric structure of the thrombin aptamer 131 moiety in the "single-stranded nucleic acid probe-cis".

At the solution temperature $T_L$, the thermal equilibrium between the "single-stranded nucleic acid probe-cis having a single-stranded structure" and the "nucleic acid probe-cis" is represented by the equilibrium constant $K_{D\text{-}cis}(T_L)$ of the dissociation reaction of the destabilized double-stranded nucleotides binding between the thrombin aptamer 131 and the complementary strand 132=[Single-stranded nucleic acid probe-cis having a single-stranded structure]/[Nucleic acid probe-cis]. The equilibrium constant $K_{D\text{-}cis}(T_L)$ depends on stabilization energy: $\Delta E_{hybrid\text{-}cis}$ associated with the presence of the destabilized double-stranded nucleotides binding between the thrombin aptamer 131 and the complementary strand 132 in the "nucleic acid probe-cis".

Since the stabilization energy: $\Delta E_{3D\text{-}form\text{-}cis}$ and the stabilization energy: $\Delta E_{hybrid\text{-}cis}$ are relatively small, the total of concentrations of the complex of the target substance thrombin 134 and the "single-stranded nucleic acid probe-cis" ("complex-cis"), the "single-stranded nucleic acid probe-cis having a steric structure" that is not fixed in the complex, and the "single-stranded nucleic acid probe-cis having a single-stranded structure" varies with slight variation in solution temperature $T_L$. Particularly, the sum of the concentrations of the "single-stranded nucleic acid probe-cis having a steric structure" that is not fixed in the complex and the "single-stranded nucleic acid probe-cis having a single-stranded structure" exhibits variation with slight variation in solution temperature $T_L$.

Another method for detecting a target substance thrombin 134 will be discussed below, wherein, when the target substance thrombin 134 is present in the sampled specimen, the complex of the target substance thrombin 134 and the "single-stranded nucleic acid probe-cis" ("complex-cis") is detected on the basis of the "dissolution" of the destabilized double-stranded nucleotides binding in the "nucleic acid probe-cis" without the second photoisomerization treatment.

The concentration [Complex-cis] of the complex of the target substance thrombin 134 and the "single-stranded nucleic acid probe-cis" ("complex-cis") corresponds to the concentration of the target substance thrombin 134 present in the sampled specimen. On the other hand, the total of the concentration [Single-stranded nucleic acid probe-cis having a steric structure] of the "single-stranded nucleic acid probe-cis having a steric structure" that is not fixed in the complex and the concentration [Single-stranded nucleic acid probe-cis having a single-stranded structure] of the "single-stranded nucleic acid probe-cis having a single-stranded structure" is proportional to the concentration [Nucleic acid probe-cis] of a residual "nucleic acid probe-cis".

In order to detect the concentration [Complex-cis] of the complex of the target substance thrombin 134 and the "single-stranded nucleic acid probe-cis" ("complex-cis") on the basis of the "dissolution" of the destabilized double-stranded nucleotides binding in the "nucleic acid probe-cis", assay conditions are selected so as to satisfy the condition of [Complex-cis]>>([Single-stranded nucleic acid probe-cis having a steric structure]+[Single-stranded nucleic acid probe-cis having a single-stranded structure]).

When the target substance thrombin 134 is absent in the sampled specimen, the total of the concentration [Single-stranded nucleic acid probe-cis having a steric structure] of the "single-stranded nucleic acid probe-cis having a steric structure" that is not fixed in the complex and the concentration [Single-stranded nucleic acid probe-cis having a single-stranded structure] of the "single-stranded nucleic acid probe-cis having a single-stranded structure" is, of course, proportional to the initial concentration [Nucleic acid probe-cis] of the "nucleic acid probe-cis". In this case, ([Single-stranded nucleic acid probe-cis having a steric structure]+[Single-stranded nucleic acid probe-cis having a single-stranded structure]) is increased, as the solution temperature $T_L$ rises to ($T_L+\Delta T$).

In the case if, compared with the melting temperature $T_{melting\text{-}ms}$ of the destabilized double-stranded nucleotides binding in the "nucleic acid probe-cis", a solution temperature $T_L$ set to a temperature slightly lower than the melting temperature $T_{melting\text{-}cis}$ when the solution temperature $T_L$ rises slightly to ($T_L+\Delta T$), such relationship of ($T_L+\Delta T$)>$T_{melting\text{-}cis}$>$T_L$ may be occasionally established. On such occasion, the increased value of ([Single-stranded nucleic acid probe-cis having a steric structure]+[Single-stranded nucleic acid probe-cis having a single-stranded structure]) becomes equal to the total of the concentration [Complex-cis] of the "complex-cis" and ([Single-stranded nucleic acid probe-cis having a steric structure]+[Single-stranded nucleic acid probe-cis having a single-stranded structure]), which will be detected for the case where the target substance thrombin 134 is present at a low concentration in the sampled specimen, which may lead to the "target substance thrombin 134 be present at a low concentration in the sampled specimen".

In the method for detecting a target substance according to the first embodiment, in the case if the target substance 7 is absent in the sampled specimen, when the solution temperature $T_L$ in "the third step" or "the fourth step" may rise slightly to ($T_L+\Delta T$), the amount of the first photoisomerization-treated complex (hybrid) dissociated may be increased in "the third step". Even in such a case, because the melting temperature $T_{melting\text{-}2}$ of the second photoisomerization-treated complex (hybrid) is sufficiently higher than ($T_L+\Delta T$), causes the "formation of double-stranded nucleotides binding" between the "first nucleic acid fragment 2" in the form of the second photoisomerization-treated complementary strand and the aptamer 1 can progress by carrying out the second photoisomerization treatment in "the fourth step". As a result, the concentration of the "first nucleic acid fragment 2" in the form of the second photoisomerization-treated complementary strand, which maintains the "dissolved state", decreases substantially down to "0". Thus, in the method for detecting a target substance according to the first embodiment, in the case if the target substance 7 is absent in the sampled specimen, such "false recognition" that the "target substance 7 be present at a low concentration in the sampled specimen" can never be caused, even if the solution temperature $T_L$ in "the third step" or "the fourth step" slightly varies.

For achieving the "effect of improving target substance detection accuracy" by the method for detecting a target substance according to the first embodiment, it is thus required to consecutively carry out "the second step" to "the fourth step" to satisfy the following conditions (1) to (3):
(1) the photoisomerizable molecule 3 is photoisomerized by the first photoisomerization treatment to destabilize the double-stranded nucleotides binding in the aptamer 1/first nucleic acid fragment 2 complex (hybrid);
(2) the structure of the photoisomerizable molecule 3 is recovered to that before the first photoisomerization treatment by the second photoisomerization treatment to restabilize the destabilized double-stranded nucleotides binding; and
(3) even though the double strand in the binding aptamer 1/first nucleic acid fragment 2 complex (hybrid) is restabilized as a result of recovering the structure of the photoisomerizable molecule 3 to that before the first photoisomerization treatment by the second photoisomerization treatment, in the case when the target substance 7/aptamer 1 complex is formed, the dissociation of the formed target substance 7/aptamer 1 complex, and the reconstruction of the aptamer 1/first nucleic acid fragment 2 complex (hybrid) through the formation of the double-stranded nucleotides binding between the first nucleic acid fragment 2 and the aptamer 1 dissolved are prevented, and thereby, a single-stranded first nucleic acid fragment 2, which is produced in association with the formation of the target substance 7/aptamer 1 complex, is kept in the "dissolved state".

For the nucleic acid probe disclosed in Non Patent Document 2, there is reported the condition required to convert to the state of FIG. 11(b) when azobenzene (photoisomerizable molecule 133) is photoisomerized into a trans form by caring out the second photoisomerization treatment. Nonetheless, Non Patent Document 2 does not disclose, in place of the state of FIG. 11(b), a "condition", which is corresponding to the condition (3), under which, the dissociation of the complex of the target substance thrombin 134 and the "single-stranded nucleic acid probe-trans" ("complex-trans"), and the reconstruction of the "nucleic acid probe-trans (hybrid structure)" through the formation of the double-stranded nucleotides binding between the thrombin aptamer 131 and the complementary strand 132 which compose the "single-stranded nucleic acid probe-trans" dissolved are prevented, and thereby, the complex of the target substance thrombin 134 and the "single-stranded nucleic acid probe-trans" ("complex-trans") is maintained; i.e., the "single-stranded nucleic acid probe-trans" is prevented from being dissociated from the complex of the target substance thrombin 134 and the "single-stranded nucleic acid probe-trans" ("complex-trans") and from forming double-stranded nucleotides binding between its constituent thrombin aptamer 131 and the complementary strand 132 to regenerate the "nucleic acid probe-trans (hybrid structure)" while, i.e., the criteria for selecting the "number of base pairs" composing the double-stranded nucleotides binding site such that stabilization energy: $\Delta E_{hybrid\text{-}trans}$ that is associated with the presence of the restabilized double-stranded nucleotides binding between the thrombin aptamer 131 and the complementary strand 132, which defines the dissociation equilibrium of the double-stranded nucleotides binding in the "complex-trans", and stabilization energy: $\Delta E_{complex\text{-}trans}$ that is associated with the formation of the complex of the thrombin 134 and the "single-stranded nucleic acid probe-trans", which defines the dissociation equilibrium of the complex of the target substance thrombin 134 and the "single-stranded nucleic acid probe-trans" ("complex-trans"), satisfy the condition of $\Delta E_{hybrid\text{-}trans} < \Delta E_{complex\text{-}trans}$; as well as the criteria for setting the solution temperature $T_L$ relative to the melting temperature $T_{melting\text{-}trans}$ of the double-stranded nucleotides binding in the "nucleic acid probe-trans (hybrid structure)". It is thus impossible to detect the target substance (thrombin 134) with excellent accuracy by providing the "second photoisomerization treatment" step that satisfies the condition (3), on the basis of the contents disclosed in Non Patent Document 2.

As explained above, compared with the approach using reversible change in the melting temperature of double-stranded nucleotides binding caused by the reversible photoisomerization of a "photoisomerizable molecule" and the "nucleic acid probe comprising an aptamer linked to its complementary strand" disclosed in Non Patent Document 2, in the method for detecting a target substance according to the first embodiment, a method for detecting a target substance with excellent detection accuracy, in which the "dissolved state" of the double-stranded nucleotides binding in the aptamer 1/first nucleic acid fragment 2 complex (hybrid) largely differs between the presence and absence of the target substance in a sampled specimen, can be achieved. In addition, regarding the selection range for the "number of base pairs and the nucleotide sequence" of the double-stranded nucleic acid portion 5 in the aptamer 1/first nucleic acid fragment 2 complex (hybrid), the "number of base pairs and the nucleotide sequence" can be selected within such wide range in which the melting temperature $T_{melting\text{-}1}$ of the destabilized double-stranded nucleotides binding in the first photoisomerization-treated complex (hybrid) and the melting temperature $T_{melting\text{-}2}$ of the restabilized double-stranded nucleotides binding in the second photoisomerization-treated complex (hybrid) satisfy following relationship of $T_{melting\text{-}1}\ T_L < T_{melting\text{-}2}$, compared with the solution temperature $T_L$ used for the detection process, by use of the reversible photoisomerization of the photoisomerizable molecule 3 being attached at the double-stranded nucleic acid portion 5. This drastically relaxes the restrictions on the sequence design of the double-stranded nucleic acid portion 5. Accordingly, the sequence design of the double-stranded nucleic acid portion 5 that satisfies the above conditions can be easily realized for the nucleotide sequences of a wide variety of aptamers. The method for detecting a target substance according to the first embodiment can thus be applied to the detection of target substances using such a wide variety of aptamers.

As described above, in the method for detecting a target substance according to the first embodiment, the presence or absence of the single-stranded first nucleic acid fragment 2 kept in the "dissolved state" in the solution at the completion of "the second step" to "the fourth step" is detected to thereby detect "whether the target substance is present or absent in the sample solution". Thus, the presence of a "competitor" for the target substance 7, which is capable of being complexed with the aptamer 1, in the sample solution containing no target substance 7 interferes with the detection of "whether the target substance is present or absent in the sample solution". In other words, the aptamer 1 used in the method for detecting a target substance according to the first embodiment is preferably an aptamer free from the "competitor" for the "target substance 7 among "aptamers capable of binding to the target substance". Specifically, the aptamer 1 used in the method for detecting a target substance according to the first embodiment is preferably an aptamer capable of specifically binding to the target substance 7.

Of course, an aptamer capable of binding to the target substance 7 as well as to its "competitor" may be used in such case if no "competitor" for the target substance 7 is contained in the sample solution.

Hereinafter, "detection principles" used in the method for detecting a target substance according to the first embodiment will be explained by taking such specific mode where aptamer capable of specifically binding to the target substance 7 is employed as the aptamer 1 as an example.

In the method for detecting a target substance according to the first embodiment, the aptamer 1 is preferred to be a single-stranded nucleic acid molecule capable of specifically binding to the target substance 7, which has a double-strand formation site 5 capable of forming double-stranded nucleotides binding with the first nucleic acid fragment 2 through their complementary nucleotide sequences, wherein, at the solution temperature $T_L$ used for the detection process, any double-stranded nucleotides binding at the double-strand formation site 5 cannot be formed by the direct action of the first nucleic acid fragment 2 on the target substance 7/aptamer 1 complex. This aptamer 1 in the form of the single-stranded nucleic acid molecule may be, for example, DNA or RNA or may be an artificial nucleic acid such as PNA, as long as the nucleic acid can assume a steric structure essential to specific binding to the target substance 7 at the solution temperature $T_L$ used for the detection process. Also, as long as the nucleic acid can assume a steric structure essential to specific binding to the target substance 7 at the solution temperature $T_L$ used for the detection process, nucleobases in the nucleic acid composing the aptamer 1 in the form of the single-stranded nucleic acid molecule may be, for example, artificially synthesized nucleobases such as fluorinated nucleobases. In addition, as long as the nucleic acid can assume a steric structure essential to specific binding to the target substance 7 at the solution temperature $T_L$ used for the detection process, sugars in the nucleic acid may be, for example, artificially synthesized sugars such as ribose with its 2-hydroxyl group replaced with a fluorine atom. The aptamer 1 assumes the steric structure essential to specific binding to an epitope in the target substance 7 at the solution temperature $T_L$ used for the detection process, and the aptamer 1 may partially have a structural moiety that does not directly participate in the specific binding to an epitope in the target substance 7. The aptamer 1 capable of specifically binding to the target substance 7 may be obtained using, for example, an aptamer screening method known in the art such as SELEX. The aptamer 1 selected by, for example, the SELEX method generally has a steric structure essential to specific binding to an epitope in the target substance 7, and thus the aptamer selected thereby forms an intermolecular bond with the epitope in the target substance 7 through the use of the steric structure to compose a target substance 7/aptamer 1 complex. The aptamer 1 selected by, for example, the SELEX method is the nucleic acid having the steric structure which is generally formed by such process in which the single-stranded nucleic acid molecule is thermally denatured, and then cooled for refolding, and the steric structure is stabilized by the intrachain base pairing between nucleobases at particular sites in the nucleotide sequence of the aptamer 1. If necessary, a desired nucleotide sequence may be added to the nucleic acid sequence obtained by, for example, the SELEX method to synthesize a single-stranded nucleic acid molecule comprising an altered nucleotide sequence. This addition of a nucleotide sequence can adjust the number of base pairs composing the double-stranded nucleic acid portion 5 between the aptamer 1 and its complementary strand (first nucleic acid fragment 2) to thereby adjust the binding strength (melting temperature) of the double-stranded nucleotides binding. As long as, when the aptamer 1 is not forming a complex with the target substance 7, the aptamer 1 having the steric structure can form double-stranded nucleotides binding with the second photoisomerization-treated first nucleic acid fragment 2 at the solution temperature $T_L$ used for the detection process to form a second photoisomerization-treated complex (hybrid), the double-strand formation site 5 in the aptamer 1 may be located at an arbitrary position in the aptamer 1, for example, at the end of the aptamer 1 or in the central part that participates in the formation of the steric structure. Also, As long as, when the aptamer 1 is not forming a complex with the target substance 7, the aptamer 1 having the steric structure can form double-stranded nucleotides binding with the second photoisomerization-treated first nucleic acid fragment 2 at the solution temperature $T_L$ used for the detection process to form a second photoisomerization-treated complex (hybrid), the whole single-stranded nucleic acid sequence of the aptamer 1 may compose the double-strand formation site 5. However, when the target substance 7/aptamer 1 complex is formed at the solution temperature $T_L$ used for the detection process, the phenomenon must be inhibited where the double-stranded nucleotides binding be formed by the direct action of the second photoisomerization-treated first nucleic acid fragment 2 on the double-strand formation site 5 in the aptamer 1 having the steric structure which is used to compose the complex. It is thus preferred that a part of the intermolecular bonding site used for binding the target substance 7 when the target substance 7 and the aptamer 1 is bound with each other should be comprised in the double-strand formation site 5 of the aptamer 1 such that the target substance 7 bound thereto functions as "steric hindrance" against the approaching of the second photoisomerization-treated first nucleic acid fragment 2 to the double-strand formation site 5 of the aptamer 1. At the same time, for easily producing the phenomenon where the dissolution of the destabilized double-stranded nucleotides binding in the first photoisomerization-treated complex (hybrid) is promoted in "the third step" in association with the formation of an intermolecular bond with the aptamer 1 by the action of the target substance 7 on the aptamer 1 when the target substance 7 and the aptamer 1 are bound to from the complex therebetween, it is preferred that a part of the intermolecular bonding site used for binding the target substance 7 when the target substance 7 and the aptamer 1 are bound with each other should be comprised in the double-strand formation site 5 of the aptamer 1. In such a case, when the target substance 7 and the aptamer 1 are bound to form the complex, an intermolecular bond is formed between at least a part of the double-strand formation site 5 in the aptamer 1 and the target substance 7 bound thereto to inhibit the hybridization between the double-strand formation site 5 in the second photoisomerization-treated first nucleic acid fragment 2 and the double-strand formation site 5 in the aptamer 1.

There are reported many cases such that such a target substance 7-binding aptamer selected by the application of the SELEX method exhibits an "RNA switch" in which exchange of the stem involved in the construction of the steric structure is induced in the presence of the target substance 7 to cause structural change to a steric structure suitable for the formation of a more stable complex (e.g., "Endo et al., The Proceedings of The 38$^{th}$ International Symposium on Nucleic Acid Chemistry, 2011, p. 150": the target substance used therefor is theophylline or tetracycline). In the case when such aptamer 1 that exhibits the "RNA switch" during the complex formation with the target substance 7, it is expected to produce the phenomenon where the dissolution of the destabilized double-stranded nucleotides binding in the first photoisomerization-treated complex (hybrid) is promoted in "the third step" in association with the formation of an intermolecular bond by the action of the target substance 7 on the aptamer 1 when the complex is formed by binding the target substance 7 and the aptamer 1.

The optimum number of nucleobases composing the double-strand formation site 5 of the aptamer 1 depends on the binding strength between the aptamer 1 and the target substance 7 used (dissociation constant $K_{Dcomplex}(T_L)$ of the target substance 7/aptamer 1 complex), the binding strength of the destabilized double-stranded nucleotides binding in the first photoisomerization-treated complex (hybrid) (dissociation constant $K_{Dhybrid-1}(T_L)$ of the first photoisomerization-treated complex (hybrid)), and the binding strength of the destabilized double-stranded nucleotides binding in the second photoisomerization-treated complex (hybrid) (dissociation constant $K_{Dhybrid-2}(T_L)$ of the second photoisomerization-treated complex (hybrid)) at the solution temperature $T_L$ used for the detection process. Thus, the optimum value can be appropriately determined and selected for each set of the nucleotide sequence of the aptamer 1 which specifically binds to the target substance 7, the partial nucleotide sequence of a region used as the double-strand formation site 5 in the aptamer 1, and the solution temperature $T_L$ used for the detection process. In the method for detecting a target substance according to the first embodiment, in general, the double-strand formation site 5 in the aptamer 1 is preferably 5 to 20 nucleotides, more preferably 6 to 15 nucleotides, further preferably 7 to 12 nucleotides. "Step 1" requires preparing an "aptamer 1/first nucleic acid fragment 2 complex (hybrid)" with double-stranded nucleotides binding selectively formed between the double-strand formation site 5 in the aptamer 1 and the double-strand formation site 5 in the first nucleic acid fragment 2. It is therefore also necessary that a site comprising the exactly same partial nucleotide sequence as that of the double-strand formation site 5 in the aptamer 1 should be absent in the aptamer 1 itself. An excessively short double-strand formation site 5 in the aptamer 1 increases the possibility that a site comprising the exactly same partial nucleotide sequence as that of the double-strand formation site 5 in the aptamer 1 is present in the aptamer 1 itself. In addition, such an excessively short double-strand formation site 5 in the aptamer 1 causes all of first photoisomerization-treated complexes (hybrids) to be dissolved even in the case when the target substance 7 is absent in the assay sample according to the relationship of $T_{melting-1} \ll T_L$ between the melting temperature $T_{melting-1}$ of the destabilized double-stranded nucleotides binding in the first photoisomerization-treated complex (hybrid) and the solution temperature $T_L$ used for the detection process, and also hinders the reformation of the second photoisomerization-treated complex (hybrid) from being fully completed in "the fourth step" according to the relationship of $T_{melting-2} < T_L$ between the melting temperature $T_{melting-2}$ of the restabilized double-stranded nucleotides binding in the second photoisomerization-treated complex (hybrid) and the solution temperature $T_L$ used for the detection process. On the other hand, an excessively long double-strand formation site 5 in the aptamer 1 hinders a single-stranded aptamer 1 to be produced by the dissolution of the destabilized double-stranded nucleotides binding in the first photoisomerization-treated complex (hybrid) in "the third step" at the solution temperature $T_L$ used for the detection process which is in the relationship of $T_L < T_{melting-1}$ with the melting temperature $T_{melting-1}$ of the destabilized double-stranded nucleotides binding in the first photoisomerization-treated complex (hybrid). Consequently, the folding of the "aptamer 1 having the steric structure", which has the steric structure essential to binding to the target substance 7 is not sufficiently progressed, resulting in a delay in the formation of the target substance 7/aptamer 1 complex, which in turn interferes with the detection of the target substance 7.

Figure 3:
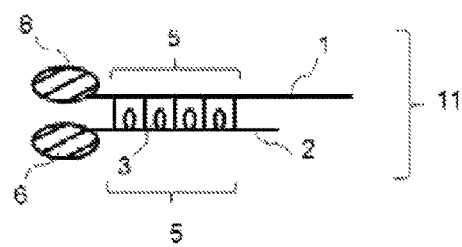
FIG. 3 is a diagram schematically showing the procedures of a method for detecting a target substance using a labeled aptamer according to the first embodiment.
Figure 3:
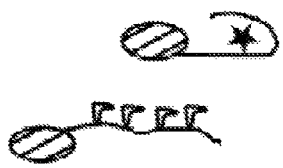
Figure 3:
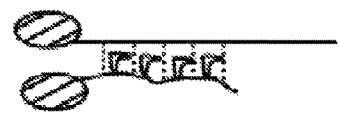
Figure 3:
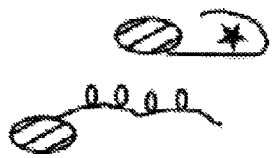
Figure 3:

In the method for detecting a target substance according to the first embodiment, the photoisomerizable molecule 3 is usually bound, as illustrated in FIG. 3, to the double-strand formation site 5 of the first nucleic acid fragment 2, which is complementary to the double-strand formation site 5 in the aptamer 1, when the double-stranded nucleotides binding in the aptamer 1/first nucleic acid fragment 2 complex (hybrid) is modified with the photoisomerizable molecule 3. By the presence of the photoisomerizable molecule 3 only in the first nucleic acid fragment 2, the photoisomerizable molecule 3 is not contained in the single-stranded nucleic acid molecule of the aptamer 1 dissociated by the dissolution of the destabilized double-stranded nucleotides binding in the first photoisomerization-treated complex (hybrid). Thus, the photoisomerizable molecule 3 lacks an interaction, such as steric hindrance, with the aptamer 1 in the "folding process" of forming the steric structure essential to binding to the target substance 7 from the single-stranded nucleic acid molecule of the aptamer 1. This permits sufficient progress of the formation of the aptamer 1 having the steric structure essential to binding to the target substance 7 and thereby facilitates detecting the target substance.

If necessary, for example, for the purpose of adjusting the first melting temperature $T_{melting-1}$ and the second melting temperature $T_{melting-2}$ to desired values, a mode may be selected in which the photoisomerizable molecule 3 is bound to a part of the double-strand formation site 5 in the aptamer 1 instead of the double-strand formation site 5 in the first nucleic acid fragment 2. Alternatively, a mode may be selected in which the photoisomerizable molecules 3 are bound to both of a part of the double-strand formation site 5 in the first nucleic acid fragment 2 and a part of the double-strand formation site 5 in the aptamer 1.

For example, in the case where the photoisomerizable molecule 3 is bound to a part of the double-strand formation site 5 in the aptamer 1, it is preferred that the "folding process" of forming the steric structure essential to binding to the target substance 7 from the single-stranded nucleic acid molecule should also proceed sufficiently in this "aptamer 1 with the photoisomerizable molecule 3 bound to a part thereof".

For example, in the case where the photoisomerizable molecules 3 are bound to all nucleotide residues in the double-strand formation site 5 of the aptamer 1, it is preferred that the "folding process" of forming the steric structure essential to binding to the target substance 7 from the single-stranded nucleic acid molecule should also proceed sufficiently in this "aptamer 1 with the bound photoisomerizable molecules 3".

In order to easily detect the reformation of the second photoisomerization-treated complex (hybrid) having the restabilized double-stranded nucleotides binding in "the fourth step", if necessary, a mode may be selected in which, as illustrated in FIG. 3, the first nucleic acid fragment 2 is modified with a labeling material 6 while the aptamer 1 is also modified with a labeling material 6.

In the method for detecting a target substance according to the first embodiment, as the first nucleic acid fragment 2 forms a double-stranded nucleic acid portion 105 with the aptamer 1 to compose a complex (hybrid), the first nucleic acid fragment 2 has a double-strand formation site 5 comprising a nucleotide sequence complementary to the double-strand formation site 5 in the aptamer 1. The first nucleic acid fragment 2 is a single-stranded nucleic acid molecule capable of forming an aptamer 1/first nucleic acid fragment 2 complex (hybrid). For example, DNA, RNA, or PNA can be used as the first nucleic acid fragment 2. Also, the first nucleic acid fragment 2 may partially comprise a nucleotide sequence that is not complementary to the double-strand formation site 5 in the aptamer 1, in addition to the nucleotide sequence complementary thereto. When the first nucleic acid fragment 2 is modified with a labeling material 6, the labeling material 6 being attached thereon is separated at a distance from the double-strand formation site 5 by addition of such a non-complementary nucleotide sequence, and thereby, the steric hindrance attributed to the labeling material 6 being attached can be reduced, at the stage where the double-stranded nucleotides binding at the double-stranded nucleic acid portion 105 is formed. The double-strand formation site 5 in the first nucleic acid fragment may be located at an arbitrary position in the first nucleic acid fragment 2, for example, at the end of the first nucleic acid fragment 2 or in the central part thereof.

In the method for detecting a target substance according to the first embodiment, in general, the photoisomerizable molecule 3 is bound, as illustrated in FIG. 3, to the double-strand formation site 5 in the first nucleic acid fragment 2. If necessary, such a mode may be selected in which the photoisomerizable molecule 3 is bound to a part of the double-strand formation site 5 in the aptamer 1, instead of the double-strand formation site 5 in the first nucleic acid fragment 2. Also, as illustrated in FIG. 3, the first nucleic acid fragment 2 is modified with a labeling material 6 for use in the detection of the reformation of the second photoisomerization-treated complex (hybrid) having the restabilized double-stranded nucleotides binding in "the fourth step".

In the method for detecting a target substance according to the first embodiment, such molecule which can be reversibly photoisomerized by the first photoisomerization treatment and the second photoisomerization treatment is utilized as the photoisomerizable molecule 3 that is used to modify the double-stranded nucleic acid portion 105. As long as the molecule can reversibly adjust the stability of double-stranded nucleotides binding through the reversible photoisomerization, the scope of the materials used as the photoisomerizable molecule 3 is not limited to any particular group of materials. Preferably used as the photoisomerizable molecule 3 is, for example, such a photoisomerizable molecule that causes steric hindrance against nucleobases composing the double-stranded nucleic acid portion 5 by the first photoisomerization treatment to destabilize the double-stranded nucleotides binding, while dissolving this steric hindrance against the nucleobases composing the double-stranded nucleic acid portion 5 by the second photoisomerization treatment to restabilize the double-stranded nucleotides binding. Specific examples thereof include photoisomerizable molecules that permit reversible cis-trans photoisomerization in association with the first photoisomerization treatment and the second photoisomerization treatment. More specific examples of the photoisomerizable molecules that permit reversible cis-trans photoisomerization in association with the first photoisomerization treatment and the second photoisomerization treatment include azobenzene and its derivatives.

Such a photoisomerizable molecule 3 that can be reversibly photoisomerized by the first photoisomerization treatment and the second photoisomerization treatment is bound to any one or both of the double-strand formation site 5 in the first nucleic acid fragment 2 and the double-strand formation site 5 in the aptamer 1 which compose a double-stranded nucleic acid portion. As a result, the stability of double-stranded nucleotides binding at the double-stranded nucleic acid portion 5 can be adjusted, for example, as described below, by use of the reversible photoisomerization of the photoisomerizable molecule 3. As the steric structure of the photoisomerizable molecule 3 is changed by the reversible photoisomerization, the steric hindrance between the photoisomerizable molecule 3 and nucleobases located in proximity thereto is increased or decreased. In the case when the photoisomerizable molecule 3 is bound to the double-strand formation site 5 of the first nucleic acid fragment 2 and/or the double-strand formation site 5 of the aptamer 1, the first photoisomerization treatment increases the steric hindrance of the photoisomerizable molecule 3 against nucleobases adjacent thereto. As a result, the complementary nucleobases composing the double-stranded nucleic acid portion 5 can no longer maintain orientation having a distance and an angle suitable for base pairing. Thus, the stability of double-stranded nucleotides binding based on the hydrogen bonds between the complementary nucleobases is reduced. The photoisomerizable molecule 3 restores its original steric structure by the second photoisomerization treatment, resulting in reduced (dissolved) steric hindrance against the nucleobases adjacent to the photoisomerizable molecule 3. Thereby, the stability of double-stranded nucleotides binding based on the hydrogen bonds between the complementary nucleobases is regained.

The first nucleic acid fragment 2 or the aptamer 1 with the reversibly photoisomerizable molecule 3 bound to the double-strand formation site 5 can be prepared by the application of a nucleotide synthesis technique known in the art. For the solid-phase synthesis of the single-stranded nucleic acid molecule, for example, a photoisomerizable molecule 3 converted to a phosphoramidite compound or a nucleotide modified with a photoisomerizable molecule 3 is used as a substrate in nucleotide synthesis. In such a case, the substrate molecule modified with the photoisomerizable molecule 3 can be linked to the backbone of the first nucleic acid fragment 2 or the backbone of the aptamer 1 to prepare a single-stranded nucleic acid molecule with the photoisomerizable molecule 3 bound to its double-strand formation site 5. The first nucleic acid fragment 2 or the aptamer 1 thus synthesized has the photoisomerizable molecule 3 inserted between the nucleobases capable of composing the double-stranded nucleic acid portion. Alternatively, after synthesis of a first nucleic acid fragment 2 or an aptamer 1 containing a modified base having a reactive functional group such as an amino group at its double-strand formation site 5, the double-strand formation site 5 may be modified with photoisomerizable molecule 3 through the coupling reaction of the photoisomerizable molecule 3 with the reactive functional group present in the modified base. The number of the photoisomerizable molecule 3 bound to the double-strand formation site 5 of the first nucleic acid fragment 2 or the double-strand formation site 5 of the aptamer 1 is not particularly limited and may be one or more.

A larger number of photoisomerizable molecules 3 bound thereto can further destabilize double-stranded nucleotides binding through the first photoisomerization treatment. Thereby, achieves the melting temperature $T_{melting-1}$ of the destabilized double-stranded nucleotides binding in the first photoisomerization-treated complex (hybrid) is further lowered, and thus, production of a single-stranded aptamer 1 is further progressed in association with the dissolution of the destabilized double-stranded nucleotides binding in the first photoisomerization-treated complex (hybrid) in "the third step" at the solution temperature $T_L$ used for the detection process. Accordingly, the concentration of the aptamer 1 having the steric structure essential to binding to the target substance 7 is further increased. When the target substance 7 is present at a very small content in the sampled specimen, this approach is advantageous in complexing this very small amount of the target substance 7 with the aptamer 1.

In the method for detecting a target substance according to the first embodiment, the photoisomerizable molecule 3 may be bound to any position in the first nucleic acid fragment 2 or the aptamer 1 as long as the photoisomerizable molecule 3 does not interfere with the detection of the "dissolution" of the aptamer 1/first nucleic acid fragment 2 complex (hybrid) in association with the target substance 7/aptamer 1 complex formation. For efficiently adjusting the stability of double-stranded nucleotides binding by the reversible photoisomerization of the photoisomerizable molecule 3, it is preferred that the photoisomerizable molecule 3 should be bound through linkage to nucleotide residue(s) of the double-strand formation site 5 of the first nucleic acid fragment 2 or the double-strand formation site 5 of the aptamer 1, to nucleotide residue(s) adjacent to the double-strand formation site 5, and/or to between any nucleotide residue in the double-strand formation site 5 and a nucleotide residue adjacent thereto. The photoisomerizable molecule 3 can be bound only to any one of the double-strand formation site 5 of the first nucleic acid fragment 2 and the double-strand formation site 5 of the aptamer 1 or, if necessary, to both of the double-strand formation site 5 of the first nucleic acid fragment 2 and the double-strand formation site 5 of the aptamer 1. Preferably, a mode is selected in which the photoisomerizable molecule 3 is bound only to the double-strand formation site 5 of the first nucleic acid fragment 2, whereas the photoisomerizable molecule 3 is not bound to the double-strand formation site 5 of the aptamer 1. In the case of selecting the mode in which the photoisomerizable molecule 3 is not bound to the double-strand formation site 5 of the aptamer 1, the first photoisomerization-treated photoisomerizable molecule 3 has no adverse effect on the steric structure of the aptamer 1 produced in "the third step" in association with the dissociation of the first photoisomerization-treated complex (hybrid) after the first photoisomerization treatment of the photoisomerizable molecule 3. Thus, this aptamer 1 having the steric structure can efficiently form a target substance 7/aptamer 1 complex through binding to the target substance 7 in "the third step". In "the fourth step", the second photoisomerization-treated photoisomerizable molecule 3 after the second photoisomerization treatment of the photoisomerizable molecule 3 has no adverse effect on the steric structure of the aptamer 1 comprised in the target substance 7/aptamer 1 complex. Thus, the detection of the target substance 7 can be carried out with high accuracy on the basis of the detection of the "dissolution" of the aptamer 1/first nucleic acid fragment 2 complex (hybrid) in association with the target substance 7/aptamer 1 complex formation.

A mode may be adopted in which, as illustrated in FIG. 3(b), the destabilized double-stranded nucleotides binding in the first photoisomerization-treated complex (hybrid) after the first photoisomerization treatment maintains the double-stranded nucleotides binding without being completely dissociated at the solution temperature $T_L$ used for the detection process in the case when the target substance 7 is absent in the sampled specimen. Alternatively, a mode may be selected in which the destabilized double-stranded nucleotides binding in the first photoisomerization-treated complex (hybrid) after the first photoisomerization treatment is completely dissociated at the solution temperature $T_L$ used for the detection process even in the case when the target substance 7 is absent in the sampled specimen. In this mode that, following mode may be selected, in which the melting temperature $T_{melting-1}$ of the destabilized double-stranded nucleotides binding in the first photoisomerization-treated complex (hybrid) is set as $T_{melting-1} \ll T_L$, compared with the solution temperature $T_L$ used for the detection process. In "the fourth step", when the second photoisomerization treatment is caned out, the melting temperature $T_{melting-2}$ of the restabilized double-stranded nucleotides binding in the second photoisomerization-treated complex (hybrid) satisfies $T_L < T_{melting-2}$, compared with the solution temperature $T_L$ used for the detection process, and thus, the aptamer 1 and the second photoisomerization-treated first nucleic acid fragment 2 reform double-stranded nucleotides binding to compose a second photoisomerization-treated complex (hybrid). As a result, the "dissolution" of the aptamer 1/first nucleic acid fragment 2 complex (hybrid) is not detected when the target substance 7 is absent in the sampled specimen.

In the method for detecting a target substance according to the first embodiment, the dissociation constant $K_{Dcomplex}(T_L)$ of the target substance 7/aptamer 1 complex and the dissociation constant $K_{Dhybrid-1}(T_L)$ of the first photoisomerization-treated complex (hybrid) at the solution temperature $T_L$ used for the detection process are selected so as to become $K_{Dcomplex}(T_L) \ll K_{Dhybrid-1}(T_L)$. When the target substance 7 is present in the sampled specimen, the destabilized double-stranded nucleotides binding in the first photoisomerization-treated complex (hybrid) is completely dissociated in "the first step". In "the third step", the target substance 7 binds to the resulting aptamer 1 to form a target substance 7/aptamer 1 complex. In "the fourth step", when the second photoisomerization treatment is carried out, the melting temperature $T_{melting-2}$ of the restabilized double-stranded nucleotides binding in the second photoisomerization-treated complex (hybrid) becomes $T_L < T_{melting-2}$, compared with the solution temperature $T_L$ used for the detection process, and therefore, an aptamer 1 that is not comprised in the target substance 7/aptamer 1 complex, and the second photoisomerization-treated first nucleic acid fragment 2 therefore reform double-stranded nucleotides binding to compose a second photoisomerization-treated complex (hybrid). In this case, the aptamer 1 comprised in the target substance 7/aptamer 1 complex neither reforms double-stranded nucleotides binding with the second photoisomerization-treated first nucleic acid fragment 2 nor forms a second photoisomerization-treated complex (hybrid). Some of second photoisomerization-treated first nucleic acid fragments 2 are therefore in the "dissolved" state. Thus, the target substance 7 can be detected on the basis of the detection of the "dissolution" of the aptamer 1/first nucleic acid fragment 2 complex (hybrid). When the first photoisomerization-treated complex (hybrid) is completely dissociated in "the first step", the concentration [Aptamer 1] of the dissociated aptamer 1 is increased. Hence, the formation of the target substance 7/aptamer 1 complex proceeds more rapidly in "the second step" and "the third step". Particularly, when a concentration of the target substance 7 contained in the sampled specimen is low, the ratio at which the target substance 7 forms a target substance 7/aptamer 1 complex according to the dissociation constant $K_{Dcomplex}$ ($T_L$) of the target substance 7/aptamer 1 complex at the solution temperature $T_L$ used for the detection process is improved, and as a result, detection sensitivity for the target substance 7 is improved.

In "the first step", when the first photoisomerization treatment is carried out at the solution temperature $T_L$ used for the detection process, for achieving such condition fit to the complete dissociation of the destabilized double-stranded nucleotides binding in the first photoisomerization-treated complex (hybrid), it is required that the melting temperature $T_{melting-1}$ of the destabilized double-stranded nucleotides binding in the first photoisomerization-treated complex (hybrid) should satisfy the condition of $T_{melting-1} \ll T_L$, compared with the solution temperature $T_L$ used for the detection process. In the case where the number of base pairs forming double-stranded nucleotides binding is not decreased, the melting temperature $T_{melting-1}$ of the destabilized double-stranded nucleotides binding in the first photoisomerization-treated complex (hybrid) can be lowered by increasing the number of the photoisomerizable molecules 3, which are bound to the double-strand formation site 5, and thereby enhancing steric hindrance that is caused by the photoisomerization of the photoisomerizable molecules 3 in association with the first photoisomerization treatment. In the method for detecting a target substance according to the first embodiment, desirably, it is desired that the number of the photoisomerizable molecules 3 that are bound to the double-strand formation site 5 is increased to lower the melting temperature $T_{melting-1}$ of the destabilized double-stranded nucleotides binding in the first photoisomerization-treated complex (hybrid), and thereby, the melting temperature $T_{melting-1}$ of the destabilized double-stranded nucleotides binding in the first photoisomerization-treated complex (hybrid) realizes the condition of $T_{melting-1} \ll T_L$, compared with the solution temperature $T_L$ used for the detection process.

When the aptamer 1/first nucleic acid fragment 2 complex (hybrid) is prepared prior to "the first step", it is preferred that, as illustrated in FIG. 3(a), the photoisomerizable molecule 3 bound to the double-strand formation site 5 should assume a structure that enhances the stability of double-stranded nucleotides binding in the complex (hybrid) 11. In such a case, the complex (hybrid) 11 that maintains double-stranded nucleotides binding can be formed efficiently at the solution temperature $T_L$.

In the method for detecting a target substance according to the first embodiment, as long as the target substance 7 contained in the sampled specimen can be contacted with the first photoisomerization-treated complex (hybrid), the step of adding and mixing a sampled specimen into a solution containing the complex (hybrid) 11 can be performed at any time before carrying out the second photoisomerization treatment so as to restabilize the double-stranded nucleotides binding in the second photoisomerization-treated complex (hybrid) in "the fourth step". For example, the sampled specimen may be added and mixed into a solution containing the complex (hybrid) 11, followed by the first photoisomerization treatment of "the first step" or may be added and mixed thereinto to carry out "the second step" after the completion of "the first step". Alternatively, the addition and mixing of the sampled specimen as well as the first photoisomerization treatment may be carried out in parallel in "the first step".

Specifically, in the method for detecting a target substance according to the first embodiment, as long as the process of forming the target substance 7/aptamer 1 complex with the target substance 7 contained in the sampled specimen is completed before "the fourth step" in which the second photoisomerization treatment is carried out to restabilize the double-stranded nucleotides binding in the second photoisomerization-treated complex (hybrid), the orders of the first photoisomerization treatment and the operation of adding and mixing a sampled specimen can be arbitrarily selected The sampled specimen may be added and mixed into a solution containing the complex (hybrid) 11, followed by the first photoisomerization treatment of "the first step" or may be added and mixed thereinto to carry out "the second step" after the completion of "the first step". Alternatively, the addition and mixing of the sampled specimen as well as the first photoisomerization treatment may be carried out in parallel in "the first step". Further, a complex (hybrid) of the aptamer 1 with the first photoisomerization-treated first nucleic acid fragment 2, which has been in advance to the first photoisomerization treatment, may be prepared, and then by using the complex (hybrid) as the first photoisomerization-treated complex (hybrid), the detection of the target substance 7 may be carried out by adding and mixing a sampled specimen, according to the procedures of "the second step" to "the fourth step". The detection operation is simplified by the adoption of this mode in which the complex (hybrid) of the aptamer 1 with the first photoisomerization-treated first nucleic acid fragment 2, which has been in advance to the first photoisomerization treatment, is prepared, and the complex (hybrid) is used as the first photoisomerization-treated complex (hybrid). In addition, a detection apparatus mentioned later is simplified by employing this mode that eliminates the need of providing a light source for a "first irradiation light having a first wavelength (λ1)", which is used for the first photoisomerization treatment of "the first step" when the detection of the target substance 7 is carried out.

When a first nucleic acid fragment 2 in which a plurality of photoisomerizable molecules 3 are bound to the double-strand formation site 5 and the aptamer 1 are used, and further provided the plurality of photoisomerizable molecules 3 are provided in such a state of being subjected to the first photoisomerization treatment in advance, in the case where the melting temperature $T_{melting-1}$ of the destabilized double-stranded nucleotides binding in the first photoisomerization-treated complex (hybrid) satisfies the condition of $T_{melting-1} \ll T_L$, the aptamer 1 and the first photoisomerization-treated first nucleic acid fragment 2 do not form double-stranded nucleotides binding at the solution temperature $T_L$ used for the detection process. In the method for detecting a target substance according to the first embodiment, a mixture of the aptamer 1 and the first photoisomerization-treated first nucleic acid fragment, which are provided in the "dissolved state" at the solution temperature $T_L$ used for the detection process, can be used in the detection of the target substance 7 in accordance with the operation of "the second step" to "the fourth step". Specifically, the complex 11 used in the method for detecting a target substance according to the first embodiment means the double-strand formation site 5 in the aptamer 1 and the first nucleic acid fragment 2 including a double-strand formation site comprising a nucleotide sequence complementary thereto, which are provided in a following mixture form that is capable of composing a second photoisomerization-treated complex (hybrid), in which, in the case when the target substance 7 is absent in the sampled specimen, the mixture is subjected to the second photoisomerization treatment at the solution temperature $T_L$ used for the detection process, and the double-strand formation site 5 of the resulting second photoisomerization-treated first nucleic acid fragment 2 and the double-strand formation site 5 of an aptamer 1 that is not used to compose the target substance 7/aptamer 1 complex are bound with each other, and thereby, a double-stranded nucleic acid portion is formed. Thus, the scope of the method for detecting a target substance according to the first embodiment also includes the mode using a mixture in which the first photoisomerization-treated first nucleic acid fragment 2 with a plurality of photoisomerizable molecules 3 bounds to its double-strand formation site 5 and the aptamer 1 are mixed in the state of not forming a double-stranded nucleic acid portion. In similar, a following mode in which, at the step of preparation of the complex 11, in the case where the melting temperature $T_{melting-1}$ of the destabilized double-stranded nucleotides binding in the first photoisomerization-treated complex (hybrid) satisfies the condition of $T_{melting-1} \ll T_L$, compared with the solution temperature $T_L$ used for the detection process, instead of preparing the complex (hybrid) 11 of the first nucleic acid fragment 2 and the aptamer 1, a mixture of the first nucleic acid fragment 2 and the aptamer 1, which is in the state of not forming a double-stranded nucleic acid portion, is prepared, and then, the mixture is subjected to the first photoisomerization treatment of "the first step" to convert to such a mixture in which the first photoisomerization-treated first nucleic acid fragment 2 with a plurality of photoisomerizable molecules 3 bounds to its double-strand formation site 5 and the aptamer 1 are mixed in the state of not forming a double-stranded nucleic acid portion, is also included in the scope of the method for detecting a target substance according to the first embodiment.

In the method for detecting a target substance according to the first embodiment, as long as, after the first photoisomerization treatment of "the first step" is carried out, a solution temperature $T_L$, which is used for the detection process of the target substance 7 in "the second step" to "the fourth step", is selected within an appropriate temperature range where the melting temperature $T_{melting-1}$ of the destabilized double-stranded nucleotides binding in the first photoisomerization-treated complex (hybrid) and the melting temperature $T_{melting-2}$ of the restabilized double-stranded nucleotides binding in the second photoisomerization-treated complex (hybrid) satisfy the condition of $T_{melting-1} \ll T_L < T_{melting-2}$, and then, at that temperature, the formation of the target substance 7/aptamer 1 complex is carried out, the complex 11 preparation step may be carried out in combination with heating of a solution for complex 11 preparation. For example, in the step of preparing the complex (hybrid) 11 of the first nucleic acid fragment 2 and the aptamer 1, a mixed solution of the aptamer 1 and the first nucleic acid fragment 2 can be heated to a temperature equal to or higher than the melting temperature $T_{melting}$ that dissolves the double-stranded nucleotides binding in the complex (hybrid) 11, for example, the melting temperature $T_{melting-2}$ of the restabilized double-stranded nucleotides binding in the second photoisomerization-treated complex (hybrid) or higher, and then cooled down to normal temperature (e.g., room temperature: 25° C.), and after that, the photoisomerizable molecule 3 is subjected to the second photoisomerization treatment to prepare a complex (hybrid) of the second photoisomerization-treated first nucleic acid fragment 2 and the aptamer 1, and thereby, the stability of double-stranded nucleotides binding can be increased. When the complex (hybrid) of the second photoisomerization-treated first nucleic acid fragment 2 and the aptamer 1 is used as the complex 11, a "misrecognition" can be avoided in the case when the target substance 7 is absent in the sampled specimen, and consequently, the detection accuracy for the target substance 7 can be improved.

When the melting temperature $T_{melting-1}$ of the destabilized double-stranded nucleotides binding in the first photoisomerization-treated complex (hybrid) is lower than normal temperature (e.g., room temperature: 25° C.) ($T_{melting-1} < 25°$ C.), a solution containing the complex 11 is heated to a temperature equal to or higher than the melting temperature $T_{melting}$, for example, the melting temperature $T_{melting-2}$ of the restabilized double-stranded nucleotides binding in the second photoisomerization-treated complex (hybrid) or higher, in "the first step" of the process for the detection of the target substance 7, to dissociate the double-stranded nucleotides binding in the complex (hybrid) 11 in advance, followed by subjecting to the first photoisomerization treatment. After that, the solution is cooled down to normal temperature (e.g., room temperature: 25° C.), at which a "single-stranded aptamer 1" that is produced by the dissociation of the complex (hybrid) 11, is in turn converted to an "aptamer 1 having the steric structure" essential to binding to the target substance 7. In "the second step", the target substance 7 is contacted with the "aptamer 1 having the steric structure" to form a complex of the target substance 7 and the "aptamer 1 having the steric structure". In the application of this approach, as the double-stranded nucleotides binding in the complex (hybrid) 11 is completely dissociated in advance by heating in "the first step", followed by subjecting the photoisomerizable molecule 3 to the first photoisomerization treatment, the first photoisomerization-treated complex (hybrid) of the first photoisomerization-treated first nucleic acid fragment 2 and the aptamer 1 does not remain at the completion of the first photoisomerization treatment. On the other hand, in the case when the photoisomerizable molecule 3 being attached at the double-stranded nucleotides binding site 5 in the complex (hybrid) 11 is subjected to the first photoisomerization treatment without heating, a moiety, which corresponds to the double-stranded nucleotides binding in the first photoisomerization-treated complex (hybrid), which is converted from the complex (hybrid) 11, remains in an "undissociated state" at the completion of the first photoisomerization treatment. Therefore, by the adoption of the approach in which, the double-stranded nucleotides binding in the complex (hybrid) 11 is dissociated in advance by heating, and then, the first photoisomerization treatment is carried out, the separation of the first photoisomerization-treated first nucleic acid fragment 2 from a "single-stranded aptamer 1" and the subsequent conversion of the "single-stranded aptamer 1" to an "aptamer 1 having the steric structure" essential to binding to the target substance 7 are completed more rapidly, compared with the approach in which the first photoisomerization treatment is carried out without heating. As, by the adoption of this approach, in "the second step", such a process in which the target substance 7 is contacted with the "aptamer 1 having the steric structure" to form a complex of the target substance 7 and the "aptamer 1 having the steric structure" can be more efficiently progressed, and thereby, the detection accuracy for the target substance 7 is improved. Even though the mode in which the double-stranded nucleotides binding in the complex (hybrid) 11 is dissociated in advance by heating, and then the first photoisomerization treatment is carried out is preferred, the conversion of the "single-stranded aptamer 1" to an "aptamer 1 having the steric structure" essential to binding to the target substance 7 is completed more rapidly by the adoption of a mode in which heating as well as the first photoisomerization treatment is carried out in parallel, or a mode in which the first photoisomerization treatment is in advance carried out, and then, feating is performed, compared with the approach in which the first photoisomerization treatment is carried out without heating.

In general, at the solution temperature $T_L$ used for the detection process, the dissociation constant $K_{Dcomplex}(T_L)$ of the complex of the target substance 7 and the "aptamer 1 having the steric structure"=[Target substance]*[Aptamer having the steric structure 1]/[Complex] satisfies the relationship of $K_{Dcomplex}(T_L)<K_{Dhybrid-1}(T_L)$, compared with the dissociation constant $K_{Dhybrid-1}(T_L)$ of the first photoisomerization-treated complex (hybrid)=[Single-stranded aptamer 1]*[First photoisomerization-treated first nucleic acid fragment 2]/[First photoisomerization-treated complex].

In the case when the melting temperature $T_{melting-1}$ of the destabilized double-stranded nucleotides binding in the first photoisomerization-treated complex (hybrid) satisfies the condition of $T_{melting-1}<T_L$, compared with the solution temperature TL used for the detection process, when the first photoisomerization treatment is carried out in "the first step" in parallel with heating to the solution temperature $T_L$ used for the detection process, the aptamer 1 and the first photoisomerization-treated first nucleic acid fragment 2, which have been produced by the dissociation of the first photoisomerization-treated complex (hybrid), are dissolved in the resulting assay solution. At the completion of "the first step", in the assay solution, the aptamer 1 is present in any form of an aptamer 1 comprised in the first photoisomerization-treated complex (hybrid), an "aptamer 1 having the steric structure", and a "single-stranded aptamer 1". Also, the first nucleic acid fragment 2 is present in any form of a first photoisomerization-treated first nucleic acid fragment 2 comprised in the first photoisomerization-treated complex (hybrid) and a "first photoisomerization-treated first nucleic acid fragment 2". By adjusting the ratio [Aptamer 1]/[First nucleic acid fragment 2] of the total concentration [Aptamer 1] of these aptamers 1 to the total concentration [First nucleic acid fragment 2] of these first photoisomerization-treated first nucleic acid fragments 2 contained in the assay solution at the completion of "the first step", the efficiency of formation of the double-stranded nucleic acid portion in the first photoisomerization-treated complex (hybrid) or the ratio of "dissolution" of the double-stranded nucleic acid portion, which is achieved by contacting the target substance 7 therewith in "the second step", can be altered. Thereby, the ratio of "dissolution" of the double-stranded nucleic acid portion in the first photoisomerization-treated complex (hybrid) in association with the target substance 7/aptamer 1 complex formation, i.e., "performance of response" in the method for detecting a target substance according to the first embodiment can be altered.

For example, in the case when the content ratio of the "first nucleic acid fragment 2" to the "aptamer 1" is increased ([Aptamer 1]/[First nucleic acid fragment 2]<1), the concentration [Single-stranded aptamer 1] is decreased according to the dissociation constant $K_{Dhybrid-1}(T_L)$ of the first photoisomerization-treated complex (hybrid)=[Single-stranded aptamer 1]*[First photoisomerization-treated first nucleic acid fragment 2]/[First photoisomerization-treated complex], and the concentration [Aptamer having the steric structure 1] is decreased as well. As the target substance 7/aptamer 1 complex formation proceeds according to the dissociation constant $K_{Dcomplex}(T_L)$ of the complex of the target substance 7 and the "aptamer 1 having the steric structure", the concentration [Single-stranded aptamer 1] drops rapidly, which induces incidentally a rapid decrease in the concentration [Aptamer having the steric structure 1]. As a result, the dissociation of the first photoisomerization-treated complex (hybrid) proceeds efficiently until the completion of the conversion of the target substance 7 to a complex of the target substance 7 and the "aptamer 1 having the steric structure". Therefore, when the target substance 7 is brought into contact with the "aptamer 1 having the steric structure" to form the complex thereof, the "dissolution" of the double-stranded nucleic acid portion in the first photoisomerization-treated complex (hybrid) proceeds rapidly. In such a case, as the concentration [Aptamer having the steric structure 1] originally remains at a low level, the ratio of decrease in the concentration [Aptamer having the steric structure 1] is high in association with the complex formation of the target substance 7 with the "aptamer 1 having the steric structure" even if the concentration [Target substance 7] of the target substance 7 contained in the sampled specimen is set at a low concentration. Thus, as the "dissolution" of the double-stranded nucleic acid portion in the first photoisomerization-treated complex (hybrid) proceeds rapidly, the detection of the target substance 7 can be executed with high detection sensitivity.

On the other hand, in the case when the content ratio of the "first nucleic acid fragment 2" to the "aptamer 1" is decreased ([Aptamer 1]/[First nucleic acid fragment 2]>1), the concentration [First photoisomerization-treated first nucleic acid fragment 2] is decreased according to the dissociation constant $K_{Dhybrid-1}(T_L)$ of the first photoisomerization-treated complex (hybrid)=[Single-stranded aptamer 1]*[First photoisomerization-treated first nucleic acid fragment 2]/[First photoisomerization-treated complex]. Accordingly, among the "first photoisomerization-treated first nucleic acid fragments 2" produced therein, the ratio [First photoisomerization-treated complex]/[First photoisomerization-treated first nucleic acid fragment 2] of the concentration [First photoisomerization-treated complex] of the "first photoisomerization-treated first nucleic acid fragments 2" which is used to compose the "first photoisomerization-treated complex (hybrid)" to the concentration [First photoisomerization-treated first nucleic acid fragment 2] of those being not used to compose the "first photoisomerization-treated complex (hybrid)" gets relatively higher. Due to decrease in concentration [Aptamer having the steric structure 1] in association with the complex formation of the target substance 7 with the "aptamer 1 having the steric structure", the "dissolution" of the double-stranded nucleic acid portion in the first photoisomerization-treated complex (hybrid) proceeds to increase the concentration [First photoisomerization-treated first nucleic acid fragment 2] of the fragment that is not comprised in the "first photoisomerization-treated complex (hybrid)". In such a case, as the concentration [First photoisomerization-treated first nucleic acid fragment 2] of the fragment that is not comprised in the "first photoisomerization-treated complex (hybrid)" is originally set at a relatively low level, the ratio of increase in the concentration [First photoisomerization-treated first nucleic acid fragment 2], in association with the complex formation of the target substance 7 with the "aptamer 1 having the steric structure", gets relatively high. Thus, when this increase in the concentration of the "first nucleic acid fragment 2" that is not comprised in the "complex (hybrid)"

is detected by use of the labeling material 6 being attached in the first nucleic acid fragment 2, the ratio of increase in the concentration of the "first nucleic acid fragment 2" that is not comprised in the "complex (hybrid)", i.e., "S/N ratio", can be improved.

In the method for detecting a target substance according to the first embodiment, the content ratio [Aptamer 1]/[First nucleic acid fragment 2] of the "aptamer 1" to the "first nucleic acid fragment 2" in the assay solution is not particularly limited and can be appropriately set according to the dissociation constant $K_{Dcomplex}(T_L)$ of the complex of the target substance 7 and the "aptamer 1 having the steric structure"=[Target substance]*[Aptamer having the steric structure 1]/[Complex], which is depending on the nucleotide sequence of the "aptamer 1", the ionic strength of the assay solution, the solution temperature $T_L$ used for the detection process, etc. However, in the case of utilizing the efficient progression of the "dissolution" of the double-stranded nucleic acid portion in the "first photoisomerization-treated complex (hybrid)" that is accompanied with the complex formation of the target substance 7 and the "aptamer 1 having the steric structure", too low level of the content of the double-stranded nucleic acid portion in the "first photoisomerization-treated complex (hybrid)" should be avoided. In light of this, the content ratio [Aptamer 1]/[First nucleic acid fragment 2] of the "aptamer 1" to the "first nucleic acid fragment 2" in the assay solution is preferably selected within the range of 0.05 to 20 (i.e., 1/20 to 20/1) in terms of molar ratio.

In the method for detecting a target substance according to the first embodiment, the subject to be assayed, i.e., the sampled specimen containing the target substance, is usually in the form of a solution containing the target substance. In "the first step" to "the fourth step" of the process for detection of the target substance, the solution used can be any solution available in general "hybridization" reaction. Also, when each of "the first step" to "the fourth step" of the process for detection of the target substance is carried out, conditions such as the temperature ($T_L$), pH, and metal ion concentration of the solution used therefor are appropriately set. However, as, in "the second step" to "the fourth step", the target substance 7/aptamer 1 complex is to be formed, or the target substance 7/aptamer 1 complex is to be maintained, desirably, the temperature ($T_L$) and pH of the solution are selected within ranges that can maintain the binding affinity of the aptamer 1 to the target substance 7 (steric structure of the aptamer 1). Also, for detecting the "dissolved" state of the double-stranded nucleic acid portion in "the fourth step", desirably, the temperature ($T_L$) and pH of the solution are selected within ranges that can maintain the double-stranded nucleic acid portion in the "second photoisomerization-treated complex (hybrid)". Therefore, in "the fourth step", desirably, the temperature ($T_L$) and pH of the solution are selected within ranges that can maintain the double-stranded nucleic acid portion in the "second photoisomerization-treated complex (hybrid)", and can maintain the binding affinity of the aptamer 1 to the target substance 7 (steric structure of the aptamer 1) as well.

In the method for detecting a target substance according to the first embodiment, the method that is employed for detection of the "dissolved" state of the double-stranded nucleotides binding that can be formed by the double-strand formation site 5 of the aptamer 1 and the double-strand formation site 5 of the second photoisomerization-treated first nucleic acid fragment 2 is not limited to any specific techniques; and techniques for detecting physical or chemical change in the single-stranded nucleic acid molecule itself or in the labeling material 6 attached to the single-stranded nucleic acid molecule, which change results from the "dissolution" of the double-stranded nucleic acid portion, are applicable thereto. Examples of the physical or chemical change induced in the single-stranded nucleic acid molecule itself or in the labeling material 6, which is usable for the detection, include, but not particularly limited to, color change, fluorescence change, permittivity change, change in electron transfer efficiency, mass change, viscosity change, and thermal change. For example, "increase in the distance" between a fluorescent material and a quencher, which is associated with the "dissolution" of the double-stranded nucleic acid portion, can be detected by means of fluorescence resonance energy transfer (FRET) measurement using an aptamer 1 labeled with the fluorescent material and a first nucleic acid fragment 2 labeled with the quencher. Alternatively, for example, such a method can be used in which the "dissolution" of the double-stranded nucleotides binding is "indirectly detected" "through reduction in double-stranded nucleotides binding" by using a nucleic acid double strand indicator, such as SYBR® Green I, which emits fluorescence when intercalated in a double-stranded nucleic acid portion.

In the method for detecting a target substance according to the first embodiment, the labeling material 6 for use in the detection of the "dissolution" of the double-stranded nucleic acid portion is not limited, as long as the labeling material 6 is "capable of amplifying the physical or chemical change" resulting from the "dissolution" of the double-stranded nucleotides binding between the double-strand formation sites 5, may include fluorescent materials, quenchers, dielectrics, nucleic acids, electrochemically reactive materials, polar molecules, enzymes, catalysts, radioactive materials, proteins, peptides, glycans, dyes, beads, magnetic materials, electromagnetic wave absorbers, electromagnetic wave emitters, electromagnetic wave reflectors, and electromagnetic wave-interfering materials.

These labeling materials may be omitted in the case when use of labeling material is not required for detection, such as a case where a single-stranded nucleic acid that is provided by the dissolution of the double-stranded nucleic acid portion is amplified by means of polymerase chain reaction (PCR) to detect the product thereof.

Particularly preferably, only the first nucleic acid fragment 2 is modified with the labeling material 6 as long as the target substance 7 can be detected. This can reduce the adverse effect of the labeling material 6 being attached on the formation of the steric structure for the binding of the aptamer 1 to the target substance 7 to thereby improve detection sensitivity. Also preferably, the aptamer 1 or the first nucleic acid fragment 2 is modified with the labeling material 6 via a linker, a non-complementary nucleotide sequence, or the like. When modified with the labeling material 6 via a linker or a non-complementary nucleotide sequence, the possibility that steric hindrance resulting from the labeling material 6 inhibits the target substance 7/aptamer 1 complex formation or the formation of double-stranded nucleotides binding between the double-strand formation site 5 of the aptamer 1 and the double-strand formation site 5 of the second photoisomerization-treated first nucleic acid fragment 2 can be lowered. The linker is not particularly limited as long as its nucleic acid strand does not form an intermolecular bond with the aptamer 1 or the second photoisomerization-treated first nucleic acid fragment 2. A linker generally available in the modification of a single-stranded nucleic acid molecule, such as a glycan, a polypeptide, a hydrocarbon chain, or oligoethylene glycol, can be used.

Hereinafter, the approach of detection using the labeling materials 6 will be described again with reference to FIG. 3 by taking, as an example, a mode using azobenzene as the photoisomerizable molecule 3 and a quencher and a fluorescent molecule as the labeling materials 6.

In FIG. 3(a), the double-strand formation site 5 in the first nucleic acid fragment 2 is modified with azobenzene as the photoisomerizable molecule 3. A trans form of azobenzene is bound to the modification site. The double-strand formation site 5 of the first nucleic acid fragment 2 comprising a nucleotide sequence complementary to the double-strand formation site 5 of the aptamer 1 is capable of forming double-stranded nucleotides binding in a "complex (hybrid)" of the aptamer 1 and the first nucleic acid fragment 2. A quencher is linked as the labeling material 6 to the end of the first nucleic acid fragment 2. A fluorescent dye is linked as the labeling material 6 to the end of the aptamer 1. The aptamer 1 and the first nucleic acid fragment 2 are hybridized through their double-strand formation sites 5 comprising nucleotide sequences complementary to each other to form a complex (hybrid) 11. Azobenzene, which is bound as the photoisomerizable molecule 3 to the double-strand formation site 5 in the first nucleic acid fragment 2, assumes a trans-structure in advance by irradiation with a visible violet/blue light (e.g., H-line (404.7 nm) or G-line (435.8 nm) of a high-pressure mercury vapor lamp) having a wavelength of 400 nm or more. Thus, the trans-azobenzene is intercalated between the adjacent hybridized base pairs to thereby stably maintain the double-stranded nucleotides binding.

Before being contacted with a solution of the subject to be assayed, an assay solution containing the "complex (hybrid) 11" of the aptamer 1 with the labeling material 6 linked to its end and the first nucleic acid fragment 2 with the labeling material 6 linked to its end is first subjected to fluorometry (FIG. 3(a)). In this state, the "complex (hybrid) 11" has the double-stranded nucleotides binding formed between the aptamer 1 and the first nucleic acid fragment 2 such that the fluorescent material at the end of the aptamer and the quencher at the end of the first nucleic acid fragment 2 are located in proximity to each other. The fluorescence emitted by the fluorescent material being attached as the labeling material 6 in the aptamer 1 is therefore absorbed by the quencher being attached as the labeling material 6 in the first nucleic acid fragment 2 to cause FRET. Thus, the great portion of the fluorescence emitted by the fluorescent material upon irradiation with a light at an excitation wavelength for the fluorescent material is absorbed by the quencher through FRET. As a result, the fluorescence is observed at a low level.

Next, the assay solution is irradiated with a light for promoting the first photoisomerization reaction to photoisomerize the trans-form of azobenzene into the cis-form of azobenzene, and then, the subject to be assayed (sampled specimen solution) is added to the assay solution. The first irradiation light (wavelength λ1) to cause the first photoisomerization reaction of the trans-azobenzene into cis-azobenzene is an ultraviolet light (e.g., I-line (365.4 nm) of a high-pressure mercury vapor lamp). The trans-form of azobenzene thus irradiated with the ultraviolet light is photoisomerized into a cis form, which produces steric hindrance against base pairs at the double strand site. This steric hindrance reduces the stability of the double-stranded nucleotides binding in the "first photoisomerization-treated complex (hybrid)" of the aptamer 1 and the first photoisomerization-treated first nucleic acid fragment 2 (FIG. 3(b)). When the target substance 7 is present in the subject to be assayed (sampled specimen solution), the target substance 7 subsequently binds to the aptamer 1 (FIG. 3(c)) to form a complex of the target substance 7 and the aptamer 1. Decrease in the concentration of the aptamer 1 in the solution, in association with the complex formation, induces the dissociation of the "first photoisomerization-treated complex (hybrid)" according to the dissociation constant $K_{Dhybrid-1}(T_L)$ of the first photoisomerization-treated complex (hybrid), and thereby, the "dissolution" of the double-stranded nucleotides binding between the aptamer 1 and the first photoisomerization-treated first nucleic acid fragment 2 progresses (FIG. 3(d)).

Next, the assay solution is irradiated with a light for promoting the second photoisomerization reaction to photoisomerize the cis-form of azobenzene back to the trans-form of azobenzene, by which the first photoisomerization-treated first nucleic acid fragment 2 is in turn converted to a second photoisomerization-treated first nucleic acid fragment 2, and then, fluorometry is carried out. The second irradiation light (wavelength $\lambda_2$) to cause the second photoisomerization reaction of the cis-form of azobenzene is a visible violet/blue light (e.g., H-line (404.7 nm) or G-line (435.8 nm) of a high-pressure mercury vapor lamp) having a wavelength of 400 nm or more. The cis-form of azobenzene thus irradiated with the visible light is photoisomerized back to the trans-form, which reduces its steric hindrance against adjacent nucleobase. In this context, when the target substance 7 is present in the sampled specimen, the target substance 7 binds to the aptamer 1 to form a complex. Since the target substance 7 is proximately bound to the nucleobases of the aptamer 1, the rebinding of the complexed aptamer 1 to the second photoisomerization-treated first nucleic acid fragment 2 is inhibited while the "dissolved state" of the second photoisomerization-treated first nucleic acid fragment 2 is maintained (FIG. 3(e)). In such a case, the irradiation of the assay solution with a light at an excitation wavelength for the fluorescent material causes no FRET, because the fluorescent material and the quencher are located at a distance. As a result, fluorescence with a high intensity is observed. On the other hand, when the target substance is absent in the sampled specimen, the double-strand formation site 5 of the aptamer 1 and the double-strand formation site 5 of the second photoisomerization-treated first nucleic acid fragment 2, which have been destabilized in "the first step" and partially dissolved, form a stable double strand state again. The fluorescent material and the quencher are therefore located in proximity to each other in the "second photoisomerization-treated complex (hybrid)". Thus, FRET occurs upon irradiation of the assay solution with a light at an excitation wavelength for the fluorescent material. As a result, fluorescence is observed at a low level.

By using the above detection method, the fluorescence intensity of the assay solution measured before the addition of the subject to be assayed (sampled specimen solution) can be compared with the fluorescence intensity measured in "the fourth step" to examine the presence or absence of the target substance 7 in the sampled specimen.

According to circumstances, for example, if the fluorescence intensity of the assay solution to be measured before the addition of the subject to be assayed (sampled specimen solution) is known or is negligibly small, the measurement of the fluorescence intensity of the assay solution before the addition of the subject to be assayed (sampled specimen solution) can be omitted.

The assay kit of the first embodiment is an assay kit comprising the complex 11 and can be used in the detection of the target substance 7 on the basis of the method for detecting a target substance according to the first embodiment.

Specifically, the complex 11 comprised in the assay kit of the first embodiment includes an aptamer 1 which specifically binds to the target substance 7, a first nucleic acid fragment 2 comprising a nucleotide sequence complementary to the aptamer 1, and a photoisomerizable molecule 3. The aptamer 1 has a double-strand formation site 5 capable of forming double-stranded nucleotides binding with the first nucleic acid fragment 2. The first nucleic acid fragment 2 has a double-strand formation site 5 capable of forming double-stranded nucleotides binding with the aptamer 1. The photoisomerizable molecule 3 is bound to at least any one or both of a part of the double-strand formation site 5 in the first nucleic acid fragment 2 and a part of the double-strand formation site 5 in the aptamer 1.

In the complex 11, the photoisomerizable molecule 3, which is bound to the double-strand formation site 5, is reversibly photoisomerized when subjected to the first photoisomerization treatment and the second photoisomerization treatment used in the method for detecting a target substance according to the first embodiment. When the first photoisomerization treatment is carried out, as the double-stranded nucleotides binding in the first photoisomerization-treated complex (hybrid) is modified with the first photoisomerization-treated photoisomerizable molecule 3, the first photoisomerization-treated photoisomerizable molecule 3 induces steric hindrance to destabilize the double-stranded nucleotides binding. Thereafter, when the second photoisomerization treatment is carried out, the double-stranded nucleotides binding in the second photoisomerization-treated complex (hybrid) is modified with the second photoisomerization-treated photoisomerizable molecule 3, and the second photoisomerization-treated photoisomerizable molecule 3 is reversely photoisomerized to be restored to its steric structure before the first photoisomerization treatment. As a result, the steric hindrance that has been induced by the first photoisomerization-treated photoisomerizable molecule 3 is removed to restabilize the double-stranded nucleotides binding in the second photoisomerization-treated complex (hybrid). Thus, the melting temperature $T_{melting-2}$ of the restabilized double-stranded nucleotides binding in the second photoisomerization-treated complex (hybrid) and the melting temperature $T_{melting-1}$ of the destabilized double-stranded nucleotides binding in the first photoisomerization-treated complex (hybrid) satisfy the relationship of $T_{melting-1} \ll T_{melting-2}$. In the application of the method for detecting a target substance according to the first embodiment, the solution temperature $T_L$ used for the detection process can be selected so as to satisfy the relationship of $T_{melting-1} < T_L < T_{melting-2}$. In such a case, at this solution temperature $T_L$ used for the detection process, the dissociation constant $K_{Dhybrid-1}(T_L)$ of the first photoisomerization-treated complex (hybrid) is in $K_{Dhybrid-2}(T_L) \ll K_{Dhybrid-1}(T_L)$, compared with the dissociation constant $K_{Dhybrid-2}(T_L)$ of the second photoisomerization-treated complex (hybrid); and simultaneously is in $K_{Dcomplex}(T_L) \ll K_{Dhybrid-1}(T_L)$, compared with the dissociation constant $K_{Dcomplex}(T_L)$ of the target substance 7/aptamer 1 complex.

The assay kit of the first embodiment comprises the complex (hybrid) 11 as mentioned above. When applied to the method for detecting a target substance according to the first embodiment, as, in "the first step", the first photoisomerization treatment is carried out, and then, in "the second step", the formation of an intermolecular bond between the target substance 7 contained in the sampled specimen and the aptamer 1 proceeds at the solution temperature $T_L$ used for the detection process, the "dissolution" of the destabilized double-stranded nucleotides binding in the first photoisomerization-treated complex (hybrid) is promoted in association with the target substance 7/aptamer 1 complex formation. After the completion of the target substance 7/aptamer 1 complex formation, when the second photoisomerization treatment is carried out in "the fourth step", an aptamer 1 that is not used to compose the target substance 7/aptamer 1 complex efficiently forms a second photoisomerization-treated complex (hybrid). Thereby, such an effect of the first embodiment that the target substance 7 contained in the sampled specimen can be detected on the basis of the detection of the "dissolved" state of the double-stranded nucleotides binding in the complex (hybrid) can be achieved.

Alternatively, in the assay kit of the first embodiment, the photoisomerizable molecule 3, which is to be comprised in the complex (hybrid) 11, may be subjected in advance to the first photoisomerization treatment to convert into a first photoisomerization-treated photoisomerizable molecule. As the photoisomerizable molecule 3 is subjected to the first photoisomerization treatment in advance, "the first step" of the method for detecting a target substance according to the first embodiment may be omitted, and only "the second step" to "the fourth step" are carried out; and thereby, the assay process for detection of the target substance can be simplified, and thus, the assay therefor can be conducted easily.

The apparatus for detecting a target substance according to the first embodiment, which is suitable for the operation of the method for detecting a target substance according to the first embodiment, comprises: a first light source (wavelength $\lambda_1$) for use in the first light irradiation to subject the photoisomerizable molecule 3 to the first photoisomerization treatment; a second light source (wavelength $\lambda_2$) for use in the second light irradiation to subject the photoisomerizable molecule 3 to the second photoisomerization treatment; a region for binding on which the target substance 7 is allowed to bind to the aptamer 1; and a region for detection on which the dissolution of the double-stranded nucleotides binding in the complex (hybrid) 11 is detected. On the region for binding, the target substance 7 is allowed to bind to the aptamer 1 by bringing the subject to be assayed (sampled specimen) containing the target substance 7 into contact with a solution containing the first photoisomerization-treated complex (hybrid). In other words, on the region for binding, the subject to be assayed (sampled specimen) containing the target substance 7 may be brought into contact with the assay kit of the first embodiment after subjected to the first photoisomerization treatment. The region for detection which is used for detecting the "dissolution" of the double-stranded nucleotides binding in the complex (hybrid) 11 is not limited as long as the region for detection is capable of detecting the physical or chemical change resulting from the "dissolution" of the double-stranded nucleotides binding in the complex (hybrid) 11. Examples of such detection include the detection of optical signals, electric signals, magnetic signals, weight change, and change in signals such as color signal. Specifically, in the apparatus for detecting a target substance according to the first embodiment, which is based on the detection of change in signals resulting from the "dissolution" of the double-stranded nucleotides binding, even if the target substance is contained at a low concentration in the subject to be assayed (sampled specimen), by applying the method for detecting a target substance according to the first embodiment, as explained above, large change in signal is caused to attain high assay sensitivity. In addition, by using such an assay kit in which the aptamer which specifically binds to the target substance is appropriately replaced according to the target substance to be detected, the apparatus can be used in the detection of various target substances. When a plurality of assay kits for detection of different target substances are used to detect the plurality of target substances contained in the sampled specimen, the apparatus may be utilized for the componential analysis of the sampled specimen. In the case where the photoisomerizable molecule 3 to be comprised in the complex (hybrid) 11, which is used for the assay kit of the first embodiment, is subjected to the first photoisomerization treatment to convert into a first photoisomerization-treated photoisomerizable molecule in advance, the apparatus for detecting a target substance according to the first embodiment which employs such assay kit can omit the first light source (wavelength $\lambda_1$) for use in first light irradiation to subject the photoisomerizable molecule 3 to the first photoisomerization treatment.

Second Embodiment

In the method for detecting a target substance according to the second embodiment, a complex (hybrid) 11 for use in the detection of a target substance 7 comprises a linking portion via which a part of the aptamer 1 is linked to a part of a first nucleic acid fragment 2. For example, the aptamer 1 and the first nucleic acid fragment 2 are linked to each other by chemical bond or chemisorption via a spacer 9.

In the method for detecting a target substance according to the second embodiment, as the aptamer 1 and the first nucleic acid fragment 2 are linked to each other via the linking portion, the binding state of the aptamer 1 and the first nucleic acid fragment 2 can be precisely controlled at the step where it is converted to a first photoisomerization-treated complex (hybrid) or to a second photoisomerization-treated complex (hybrid). When the "dissolution" of the double-stranded nucleotides binding is detected in "the fourth step", the background against measurement value is reduced by the "precise control of the binding state of the aptamer 1 and the first nucleic acid fragment 2", and thereby, reliability or detection sensitivity of the measurement are improved.

Figure 4:
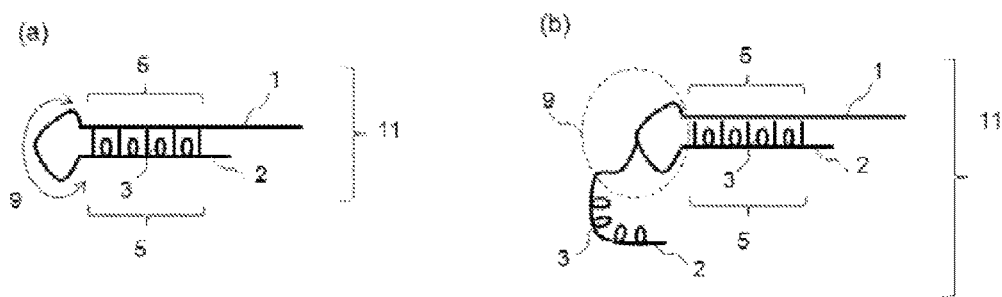
FIG. 4 is a diagram schematically showing the structure of a complex (hybrid) formed by a first nucleic acid fragment and an aptamer linked via a spacer for use in the detection of a target substance according to the second embodiment.

Hereinafter, the "advantages and effects" of the method for detecting a target substance according to the second embodiment will be specifically explained with reference to FIG. 4.

The method for detecting a target substance according to the second embodiment is based on the application of the "detection principles" used in the method for detecting a target substance according to the first embodiment, so that the description of the same or similar points as those in the method for detecting a target substance according to the first embodiment will be omitted.

FIG. 4(a) is a diagram schematically showing one example of the structure of the complex (hybrid) 11, which is used for the detection of the target substance 7 in the method for detecting a target substance according to the second embodiment. FIG. 4(b) is a diagram schematically showing another example of the structure of the complex (hybrid) 11, which is used for the detection of the target substance 7 in the method for detecting a target substance according to the second embodiment.

In the method for detecting a target substance according to the second embodiment, the complex (hybrid) 11 in the structure illustrated in FIG. 4(a) for use in the detection of the target substance 7 comprises an aptamer 1 and one first nucleic acid fragment 2 linked by chemical bond or chemisorption via a spacer 9. The complex (hybrid) 11 in the structure illustrated in FIG. 4(b) comprises an aptamer 1 and two first nucleic acid fragments 2 linked by chemical bond or chemisorption via a triply branched spacer 9.

In similar to the complex (hybrid) 11 illustrated in FIG. 3 for use in the method for detecting a target substance according to the first embodiment, a photoisomerizable molecule 3 is bound to a part of the first nucleic acid fragment 2 or a part of the aptamer 1, or both, in the complex (hybrid) 11 illustrated in FIG. 4(a) for use in the method for detecting a target substance according to the second embodiment. The aptamer 1 and the first nucleic acid fragment 2 linked via the spacer 9 have their respective double-strand formation sites 5 comprising nucleotide sequences complementary to each other and compose the complex (hybrid) 11 by the formation of double-stranded nucleotides binding.

The complex 11 (hybrid) in which the photoisomerizable molecule 3 is bound to the double-strand formation site 5 in the first nucleic acid fragment 2 having the double-stranded nucleotides binding formed with the aptamer 1 linked thereto via the spacer 9, as illustrated in FIG. 4(a) or 4(b), can be used in the detection of the "presence or absence of the target substance 7 in a sampled specimen" using, as a measure, the presence or absence of the "dissolution" of the double-stranded nucleotides binding in the complex 11 (hybrid) in association with the target substance 7/aptamer 1 complex formation, in similar to the complex (hybrid) 11 illustrated in FIG. 3 for use in the method for detecting a target substance according to the first embodiment.

As the complex (hybrid) 11 illustrated in FIG. 4(a) or 4(b), which is utilized in the method for detecting a target substance according to the second embodiment, is a "conjugate molecule" in which the aptamer 1 and the first nucleic acid fragment 2 are linked via the linker 9, even while the double-stranded nucleotides binding in the complex 11 (hybrid) is "dissolved", the aptamer 1 and the first nucleic acid fragment 2 incorporated in the "conjugate molecule" are kept in proximity to each other.

In the process for detection of the target substance 7, in the case when, in "the fourth step", after the second photoisomerization treatment is carried out, double-stranded nucleotides binding is regenerated between an aptamer 1 that is not used for the formation of the target substance 7/aptamer 1 complex and a second photoisomerization-treated first nucleic acid fragment 2, when the frequency of the contact between the aptamer 1 and the second photoisomerization-treated first nucleic acid fragment 2, which are linked via the linker 9 in the "conjugate molecule", (intramolecular contact frequency) is compared with the frequency of the contact between an aptamer 1 and a second photoisomerization-treated first nucleic acid fragment 2, which are comprised in different "conjugate molecules", (intermolecular contact frequency), the "intramolecular contact frequency" is much higher than the "intermolecular contact frequency". Thus, in the case when the aptamer 1 in the "conjugate molecule" is not used for the formation of the target substance 7/aptamer 1 complex, when subjected to the second photoisomerization treatment in "the fourth step" the second photoisomerization treatment in "the fourth step", the aptamer 1 and the second photoisomerization-treated first nucleic acid fragment 2 in the "conjugate molecule" efficiently forms double-stranded nucleotides binding so as to compose a second photoisomerization-treated complex (hybrid) in the "conjugate molecule". Accordingly, in the method for detecting a target substance according to the second embodiment, in the case when the target substance 7 is absent in the sampled specimen, background resulting from a "conjugate molecule" that remains in the "dissolved" state without composing the second photoisomerization-treated complex (hybrid) is reduced, and thereby, assay accuracy for the "absence of the target substance 7 in the sampled specimen" is improved.

Also, when the photoisomerizable molecule 3 bound to the double-strand formation site 5 in the first nucleic acid fragment 2 is subjected to the first photoisomerization treatment, the complex (hybrid) 11 illustrated in FIG. 4(a) or 4(b) is converted to a first photoisomerization-treated complex (hybrid). On the other hand, when the photoisomerizable molecule 3 bound to the double-strand formation site 5 in the first nucleic acid fragment 2 is subjected to the second photoisomerization treatment, the complex (hybrid) is converted to a second photoisomerization-treated complex (hybrid). In such a case, the melting temperature $T_{melting-2}$ of the restabilized double-stranded nucleotides binding in the second photoisomerization treated complex (hybrid) and the melting temperature $T_{melting-1}$ of the destabilized double-stranded nucleotides binding in the first photoisomerization-treated complex (hybrid) satisfy the relationship of $T_{melting-1} \ll T_{melting-2}$. when the method for detecting a target substance according to the second embodiment is applied, the solution temperature $T_L$ used for the detection process is usually selected so as to satisfy the relationship of $T_{melting-1} < T_L < T_{melting-2}$. Even in the "state where the target substance 7 is absent in the sampled specimen", therefore, the "dissolution" of the destabilized double-stranded nucleotides binding in the first photoisomerization-treated complex (hybrid) proceeds in "the second step" while the solution is maintained at the solution temperature $T_L$ used for the detection process. As the aptamer 1 and the second photoisomerization-treated first nucleic acid fragment 2 in the "conjugate molecule" are linked to each other via the linker 9, when subjected to the second photoisomerization treatment in "the fourth step", the aptamer 1 and the second photoisomerization-treated first nucleic acid fragment 2 in the "conjugate molecule" is immediately converted to a second photoisomerization-treated complex (hybrid). In the case when the aptamer 1 is not bound with the target substance 7, the restabilized double-stranded nucleotides binding in the second photoisomerization-treated complex (hybrid) can be rapidly formed by carrying out the second photoisomerization treatment, and thereby, background resulting from a "conjugate molecule" that remains in the-"dissolved" state without composing the second photoisomerization-treated complex (hybrid) can be reduced.

In the complex 11, the photoisomerizable molecule 3, which is bound to the double-strand formation site 5 is reversibly photoisomerized when subjected to the first photoisomerization treatment and the second photoisomerization treatment, which are utilized in the method for detecting a target substance according to the second embodiment. When the first photoisomerization treatment is carried out, as the double-stranded nucleotides binding in the first photoisomerization-treated complex (hybrid) is modified with the first photoisomerization-treated photoisomerizable molecule 3, the first photoisomerization-treated photoisomerizable molecule 3 induces steric hindrance to destabilize the double-stranded nucleotides binding. Thereafter, when the second photoisomerization treatment is carried out, as the double-stranded nucleotides binding in the second photoisomerization-treated complex (hybrid) is modified with the second photoisomerization-treated photoisomerizable molecule 3, the second photoisomerization-treated photoisomerizable molecule 3 is reversely photoisomerized to be restored to its steric structure before the first photoisomerization treatment. As a result, the steric hindrance that has been induced by the first photoisomerization-treated photoisomerizable molecule 3 is removed to restabilize the double-stranded nucleotides binding in the second photoisomerization-treated complex (hybrid). Thus, the melting temperature $T_{melting-2}$ of the restabilized double-stranded nucleotides binding in the second photoisomerization-treated complex (hybrid) and the melting temperature $T_{melting-1}$ of the destabilized double-stranded nucleotides binding in the first photoisomerization-treated complex (hybrid) satisfy the relationship of $T_{melting-1} \ll T_{melting-2}$. When the method for detecting a target substance according to the second embodiment is applied, the solution temperature $T_L$ used for the detection process can be selected so as to satisfy the relationship of $T_{melting-1} < T_L < T_{melting-2}$.

Also, the content ratio of the aptamer 1 to the first nucleic acid fragment 2 in the assay solution can be accurately controlled in consideration of production conditions for the "conjugate molecule". For example, as in the structure illustrated in FIG. 4(a), the "conjugate molecule" is composed of the aptamer 1 and the first nucleic acid fragment 2, which are linked to both ends, respectively, of the spacer 9, the content ratio of the aptamer 1 to the first nucleic acid fragment 2 in the assay solution can be accurately set to 1:1. On the other hand, as, in the structure illustrated in FIG. 4(b), the triply branched spacer 9 is used, the content ratio of the aptamer 1 to the first nucleic acid fragment 2 can be set to 1:2.

The dissociation of the complex (hybrid) refers to the dissociation of the intramolecular double-stranded nucleotides binding in the "conjugate molecule". At the solution temperature $T_L$ used for the detection process, the dissociation constant $K_{Dhybrid-2}(T_L)$ of the double-stranded nucleotides binding in the second photoisomerization-treated complex (hybrid) depends on the concentration [Second photoisomerization-treated conjugate molecule] of the second photoisomerization-treated "conjugate molecule" in which the aptamer 1 is not bound with the target substance 7, and becomes $K_{Dhybrid-2}(T_L)$=[Second photoisomerization-treated conjugate molecule]/[Second photoisomerization-treated complex (hybrid)]. The stability of the second photoisomerization-treated complex (hybrid) depends on stabilization energy: $\Delta_{Ehybrid-2}$ which is associated with the formation of double-stranded nucleotides binding between the double-strand formation site 5 of the aptamer 1 and the double-strand formation site 5 in the first nucleic acid fragment 2, which is bound with the second photoisomerization-treated photoisomerizable molecule 3. The stabilization energy: $\Delta_{Ehybrid-2}$ is essentially unchanged even if the intramolecular content ratio of the aptamer 1 to the first nucleic acid fragment 2 in the "conjugate molecule" is changed from 1:1 to 1:2. Thus, the melting temperature $T_{melting-2}$ of the restabilized double-stranded nucleotides binding in the second photoisomerization-treated complex (hybrid) is essentially identical in both of the "conjugate molecule" in the structure illustrated in FIG. 4(a) and the "conjugate molecule" in the structure illustrated in FIG. 4(b). The dissociation constant $K_{Dhybrid-2}(T_L)$ of the double-stranded nucleotides binding in the second photoisomerization-treated complex (hybrid) is substantially equal between the "conjugate molecule" in the structure illustrated in FIG. 4(a) and the "conjugate molecule" in the structure illustrated in FIG. 4(b).

At the solution temperature $T_L$ used for the detection process, the dissociation constant $K_{Dhybrid-1}(T_L)$ of the double-stranded nucleotides binding in the first photoisomerization-treated complex (hybrid) depends of the concentration [First photoisomerization-treated conjugate molecule] of the first photoisomerization-treated "conjugate molecule", in which the aptamer 1 is not bound with the target substance 7, and becomes $K_{Dhybrid-1}(T_L)$=[First photoisomerization-treated conjugate molecule]/[First photoisomerization-treated complex (hybrid)]. The stability of the first photoisomerization-treated complex (hybrid) depends on stabilization energy: $\Delta_{Ehybrid-1}$ which is associated with the formation of double-stranded nucleotides binding between the double-strand formation site 5 of the aptamer 1 and the double-strand formation site 5 in the first nucleic acid fragment 2, which is bound with the first photoisomerization-treated photoisomerizable molecule 3. The stabilization energy: $\Delta_{Ehybrid-1}$ is essentially unchanged even if the intramolecular content ratio of the aptamer 1 to the first nucleic acid fragment 2 in the "conjugate molecule" is changed from 1:1 to 1:2. Thus, the melting temperature $T_{melting-1}$ of the destabilized double-stranded nucleotides binding in the first photoisomerization-treated complex (hybrid) is essentially identical in both of the "conjugate molecule" in the structure illustrated in FIG. 4(a) and the "conjugate molecule" in the structure illustrated in FIG. 4(b). The dissociation constant $K_{Dhybrid-1}(T_L)$ of the double-stranded nucleotides binding in the first photoisomerization-treated complex (hybrid) is substantially equal between the "conjugate molecule" in the structure illustrated in FIG. 4(a) and the "conjugate molecule" in the structure illustrated in FIG. 4(b).

The adoption of the "conjugate molecule" in the method for detecting a target substance according to the second embodiment can facilitate adjusting the stability (melting temperature) of the double-stranded nucleotides binding and the formation ratio (dissociation constant) of the double-stranded nucleotides binding at the solution temperature $T_L$ used for the detection process, and thereby, detection sensitivity for the "dissolved" state of the double-stranded nucleotides binding can be improved.

In the method for detecting a target substance according to the second embodiment, as the aptamer 1 and the "photoisomerizable molecule 3-bound first nucleic acid fragment 2" that are used to compose the "conjugate molecule", those comprise the same nucleotide sequences as those of the aptamer 1 and the "photoisomerizable molecule 3-bound first nucleic acid fragment 2" used in the method for detecting a target substance according to the first embodiment can be used. An aptamer 1 and a "photoisomerizable molecule 3-bound first nucleic acid fragment 2" each having a functional group capable of forming a bond with the spacer 9 are appropriately used for forming the "conjugate molecule". The functional group to be added to each of the aptamer 1 and the "photoisomerizable molecule 3-bound first nucleic acid fragment 2" is not limited as long as the functional group is capable of forming a bond that is not dissociated from the spacer 9 under the condition used in detection, such as solvent or pH. A popular functional group can be used, such as a carboxyl group, an amino group, a thiol group, a disulfide group, a succinimidyl group, a maleimide group, or biotin. The functional group to be added to each of the aptamer 1 and the "photoisomerizable molecule 3-bound first nucleic acid fragment 2" can be added to the end thereof during the step of preparation of the aptamer 1 and the "photoisomerizable molecule 3-bound first nucleic acid fragment 2" by a typical nucleotide synthesis method. Alternatively, such a conjugate molecule that is formed by modifying a nucleic acid molecule which is used as a starting material in the nucleotide synthesis of the aptamer 1 and the "photoisomerizable molecule 3-bound first nucleic acid fragment 2" with a commercially available linker or the like may be employed as the "conjugate molecule". The functional group to be added to the aptamer 1 may be added to modify an arbitrary site as long as impairing the specific binding of the aptamer 1 to the target substance 7 is not induced thereby. For example, the site modified with the functional group may be located at the end of each of the aptamer 1 and the "photoisomerizable molecule 3-bound first nucleic acid fragment 2" or in the central part thereof. Further, the linkage with the spacer 9 between the aptamer 1 or the "photoisomerizable molecule 3-bound first nucleic acid fragment 2" can be formed by any general cross-coupling method without particular limitations. Alternatively, such a conjugate molecule in which the spacer 9 is inserted between the aptamer 1 and the "photoisomerizable molecule 3-bound first nucleic acid fragment 2" may be synthesized by a typical nucleotide synthesis method using, for example, a commercially available linker in a phosphoramidite form. Preferably, after synthesis of such a "conjugate molecule" that is comprised of the aptamer 1 and the "photoisomerizable molecule 3-bound first nucleic acid fragment 2", which are linked via the spacer 9, unnecessary compounds such as unreacted monomers are removed by HPLC purification or the like, and intramolecular double-stranded nucleotides binding in the "conjugate molecule" is then formed, and thereafter, the resulted conjugate molecule is used as the complex (hybrid) 11.

In the method for detecting a target substance according to the second embodiment, the spacer 9 that is used for construction of the "conjugate molecule" is not particularly limited as long as the spacer neither adsorbs thereon the aptamer 1 or the "photoisomerizable molecule 3-bound first nucleic acid fragment 2" nor forms a specific intermolecular bond with the aptamer 1 or the "photoisomerizable molecule 3-bound first nucleic acid fragment 2". For example, a popular linker available in the linkage between single-stranded nucleic acid molecules, such as a nucleic acid strand having a non-complementary nucleotide sequence, a glycan, a polypeptide, a hydrocarbon chain, or oligoethylene glycol can be used. The spacer 9 is also required not to cause, for example, "steric hindrance" that inhibits the orientations of the double-strand formation site 5 of the aptamer 1 and the double-strand formation site 5 of the "photoisomerizable molecule 3-bound first nucleic acid fragment 2" during the formation of double-stranded nucleotides binding between these double-strand formation sites 5. Thus, the length of the spacer 9 that is used in the "conjugate molecule" in the structure illustrated in FIG. 4(a) is preferably selected within the range of at least 3 Å or longer. On the other hand, in the case if an unnecessarily long spacer 9 is used, there will be increased possibility that double-stranded nucleotides binding is formed between the double-strand formation site 5 in the aptamer 1 of one "conjugate molecule" and the double-strand formation site 5 in the "photoisomerizable molecule 3-bound first nucleic acid fragment 2" of another "conjugate molecule" to form a dimeric complex (hybrid) due to the intermolecular double-stranded nucleotides binding of these two "conjugate molecules". For the purpose of avoiding this increase in the probability of forming a dimeric complex (hybrid) due to the intermolecular double-stranded nucleotides binding, it is preferred that the length of the spacer 9 that is used in the "conjugate molecule" in the structure illustrated in FIG. 4(a) should be selected within the range of at least 200 Å or shorter.

In general, the length of the spacer 9 that is used in the "conjugate molecule" in the structure illustrated in FIG. 4(a) is more preferably selected within the range of 10 Å or longer and 50 Å or shorter.

The complex (hybrid) 11 composed of the "conjugate molecule" that is used in the method for detecting a target substance according to the second embodiment is meant to be in the state where, when the target substance 7 is absent in the sampled specimen, the complex (hybrid) 11 can be wholly converted to a second photoisomerization-treated complex (hybrid) through the intramolecular double-stranded nucleotides binding formed between the respective double-strand formation sites 5 of the aptamer 1 and "photoisomerizable molecule 3-bound first nucleic acid fragment 2" composing the "conjugate molecule", when the photoisomerizable molecule 3 is subjected to the second photoisomerization treatment in "the fourth step" at the solution temperature $T_L$ used for the detection process. Thus, in the case when such a state of "absence of the target substance 7 in the sampled specimen" is detected, such a conjugate molecule in which intramolecular double-stranded nucleotides binding between the double-strand formation site 5 of the aptamer 1 and the double-strand formation site 5 of the first photoisomerization-treated "photoisomerizable molecule 3-bound first nucleic acid fragment 2" is not formed can be used as the the first photoisomerization-treated "conjugate molecule" of which the photoisomerizable molecule 3 is subjected to the first photoisomerization treatment in advance. Even in the case when the target substance 7 is present in the sampled specimen, such a "first photoisomerization-treated conjugate molecule of which the photoisomerizable molecule 3 is subjected to the first photoisomerization treatment in advance" in which intramolecular double-stranded nucleotides binding therebetween is not formed can be used to progress the formation of a complex of the aptamer 1 that is included in the "first photoisomerization-treated conjugate molecule" with the target substance 7. When all of target substances 7 contained in the sampled specimen form target substance 7/aptamer 1 complexes, such a state where a target substance 7 that is not fixed in the complex is substantially absent in the assay solution is given. When the photoisomerizable molecule 3 is subjected to the subsequent second photoisomerization treatment in "the fourth step" at the solution temperature $T_L$ used for the detection process, intramolecular double-stranded nucleotides binding is formed between the respective double-strand formation sites 5 of the aptamer 1 and of the second photoisomerization-treated "photoisomerizable molecule 3-bound first nucleic acid fragment 2", which compose the second photoisomerization-treated "conjugate molecule", so that all of residual "first photoisomerization-treated conjugate molecules" can be converted to second photoisomerization-treated complexes (hybrids).

In other words, in the method for detecting a target substance according to the second embodiment, instead of the complex (hybrid) 11 that is composed of the "conjugate molecule" in the structure illustrated in FIG. 4(a) or 4(b), i.e., the complex (hybrid) 11 that is composed of the "conjugate molecule" having the form of a second photoisomerization-treated complex (hybrid) at the solution temperature $T_L$ used for the detection process, such a mode using a first photoisomerization-treated "conjugate molecule" in which intramolecular double-stranded nucleotides binding is not formed between the double-strand formation site 5 of the aptamer 1 and the double-strand formation site 5 of the first photoisomerization-treated "photoisomerizable molecule 3-bound first nucleic acid fragment 2" at the solution temperature $T_L$ used for the detection process can be employed. In such a case, a mode can be selected which employs the step of preparing the first photoisomerization-treated "conjugate molecule", in which intramolecular double-stranded nucleotides binding is not formed between the aptamer 1 and the first photoisomerization-treated "photoisomerizable molecule 3-bound first nucleic acid fragment 2" linked via the spacer 9, instead of the step of preparing the complex (hybrid) 11 composed of the "conjugate molecule".

Third Embodiment

The method for detecting a target substance according to the third embodiment is also an approach based on the application of the "detection principles" used in the method for detecting a target substance according to the first embodiment or the "detection principles" used in the method for detecting a target substance according to the second embodiment, so that the description of the same or similar points as those in the method for detecting a target substance according to the first embodiment or the method for detecting a target substance according to the second embodiment will be omitted.

Figure 5:
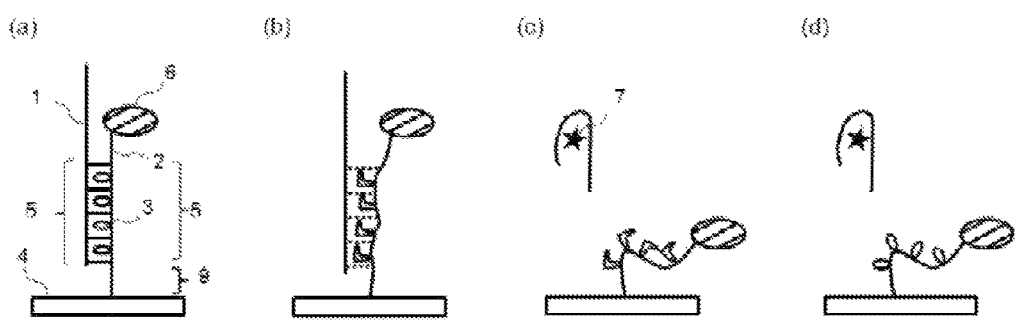
FIG. 5 is a diagram schematically showing the procedures of a method for detecting a target substance using an aptamer according to the third embodiment.

FIG. 5 is a diagram schematically showing the forms of a complex (hybrid) 11 and procedures corresponding to "the first step" to "the fourth step" in the "detection of the target substance 7", which are used in the method for detecting a target substance according to the third embodiment.

In the complex (hybrid) 11 that is used in the method for detecting a target substance according to the third embodiment, one end of a "photoisomerizable molecule 3-bound first nucleic acid fragment 2" in the form where the double-strand formation site 5 of the "photoisomerizable molecule 3-bound first nucleic acid fragment 2" and a double-strand formation site 5 in an aptamer 1 form double-stranded nucleotides binding is immobilized on a basal material for immobilization 4 by chemical bond or chemisorption via a spacer 9. In addition, the "photoisomerizable molecule 3-bound first nucleic acid fragment 2" is modified at the other end with a labeling material 6.

In the method for detecting a target substance according to the third embodiment, has only the "photoisomerizable molecule 3-bound first nucleic acid fragment 2", which is included in the complex (hybrid) 11 comprised of the aptamer 1 and the "photoisomerizable molecule 3-bound first nucleic acid fragment 2", is immobilized on the surface of the basal material for immobilization 4 via the spacer 9. This constitution facilitates a series of operations necessary for carrying out "the first step" to "the fourth step", for example, a series of operations for treating the complex (hybrid) 11, involving a heating treatment, a first photoisomerization treatment, a treatment of contacting with a target substance 7 contained in a sampled specimen, and a second photoisomerization treatment.

For the detection of the "dissolved" state of the double-stranded nucleotides binding in the complex (hybrid) 11, such a device that is applicable to the detection of the "dissolved" state of the "photoisomerizable molecule 3-bound first nucleic acid fragment 2" immobilized on the surface of the basal material for immobilization 4 via the spacer 9 can be used. Thus, a sensor for detection of a target substance can be constructed by the application of the method for detecting a target substance according to the third embodiment using the device and the complex (hybrid) 11 immobilized on the surface of the basal material for immobilization 4.

The method for detecting a target substance according to the third embodiment will be explained with reference to FIG. 5.

First, the step of preparing the complex (hybrid) 11 immobilized on the basal material for immobilization 4 as illustrated in FIG. 5(a) will be described. The complex (hybrid) 11 immobilized on the basal material for immobilization 4 comprises an aptamer 1, a first nucleic acid fragment 2, a photoisomerizable molecule 3, a labeling material 6, a spacer 9, and the basal material for immobilization 4. The photoisomerizable molecule 3 is bound to a double-strand formation site 5 in the first nucleic acid fragment 2. One end of the "photoisomerizable molecule 3-bound first nucleic acid fragment 2" is linked to the spacer 9, and the other end thereof is modified with the labeling material 6. The photoisomerizable molecule 3 is reversibly photoisomerized by subjecting to the first photoisomerization treatment and the second photoisomerization treatment, in similar manner with the photoisomerizable molecule 3 that is used in the method for detecting a target substance according to the first embodiment or the method for detecting a target substance according to the second embodiment.

In the structure illustrated in FIG. 5(a), the "photoisomerizable molecule 3-bound first nucleic acid fragment 2" is immobilized on the surface of the basal material for immobilization 4 by chemical bond or chemisorption via the spacer 9 linked to one end thereof. The double-stranded nucleotides binding is formed between the double-strand formation sites 5 of the "photoisomerizable molecule 3-bound first nucleic acid fragment 2" immobilized on the surface of the basal material for immobilization 4 and the double-strand formation sites 5 of the aptamer 1 to compose the complex (hybrid) 11 immobilized on the basal material for immobilization 4.

When the photoisomerizable molecule 3 is subjected to the first photoisomerization treatment, the stability of the double-stranded nucleotides binding formed between the double-strand formation site 5 of the first photoisomerization-treated "photoisomerizable molecule 3-bound first nucleic acid fragment 2" and the double-strand formation site 5 of the aptamer 1 is reduced. That is, the melting temperature $T_{melting-1}$ of the destabilized double-stranded nucleotides binding in the "first photoisomerization-treated complex (hybrid)", which is composed of the first photoisomerization-treated "photoisomerizable molecule 3-bound first nucleic acid fragment 2" and the aptamer 1, satisfies the relationship of $T_{melting-1} \ll T_{melting}$, compared with the melting temperature $T_{melting}$ of the double-stranded nucleotides binding in the original complex (hybrid) 11. When subjected to the second photoisomerization treatment, the first photoisomerization-treated "photoisomerizable molecule 3-bound first nucleic acid fragment 2" is converted to a second photoisomerization-treated "photoisomerizable molecule 3-bound first nucleic acid fragment 2". Since the photoisomerizable molecule 3 is reversibly photoisomerized by subjecting to the first photoisomerization treatment and the second photoisomerization treatment, the double-stranded nucleotides binding which is formed between the double-strand formation site 5 of the second photoisomerization-treated "photoisomerizable molecule 3-bound first nucleic acid fragment 2" and the double-strand formation site 5 of the aptamer 1 is restabilized to the same level as the stability of the double-stranded nucleotides binding in the original complex (hybrid) 11. That is, the melting temperature $T_{melting-2}$ of the restabilized double-stranded nucleotides binding in the "second photoisomerization-treated complex (hybrid)", which is composed of the second photoisomerization-treated "photoisomerizable molecule 3-bound first nucleic acid fragment 2" and the aptamer 1, is equal to the melting temperature $T_{melting}$ of the double-stranded nucleotides binding in the original complex (hybrid) 11.

Therefore, the melting temperature $T_{melting-1}$ of the destabilized double-stranded nucleotides binding in the "first photoisomerization-treated complex (hybrid)", the melting temperature $T_{melting-2}$ of the restabilized double-stranded nucleotides binding in the "second photoisomerization-treated complex (hybrid)", and the melting temperature $T_{melting}$ of the double-stranded nucleotides binding in the original complex (hybrid) 11 satisfy the relationship of $T_{melting-1} \ll T_{melting} = T_{melting-2}$. In the case where the relationship of $T_L < T_{melting-1}$ is satisfied, compared with the solution temperature $T_L$, the thermal dissociation of the destabilized double-stranded nucleotides binding in the "first photoisomerization-treated complex (hybrid)" does not proceed. In such a case, as illustrated in FIG. 5(b), the "first photoisomerization-treated complex (hybrid)", in which the destabilized double-stranded nucleotides binding is maintained, is immobilized on the surface of the basal material for immobilization 4.

As compared, the dissociation constant $K_{Dhybrid-1}(T_L)$ of the first photoisomerization-treated complex (hybrid)=[Single-stranded aptamer 1]*[First photoisomerization-treated first nucleic acid fragment 2]/[First photoisomerization-treated complex], the dissociation constant $K_{Dhybrid-2}(T_L)$ of the second photoisomerization-treated complex (hybrid)=[Single-stranded aptamer 1]*[Second photoisomerization-treated first nucleic acid fragment 2]/[Second photoisomerization-treated complex], and the dissociation constant $K_{Dcomplex}(T_L)$ of the target substance 7/aptamer 1 complex=[Aptamer having the steric structure 1]*[Target substance 7]/[Complex] satisfy the relationship of $K_{Dhybrid-2}(T_L) < K_{Dcomplex}(T_L) \ll K_{Dhybrid-1}(T_L)$ at the solution temperature $T_L$ used for the detection process. Furthermore, the temperature $T_{aptamer-defolding}$ at which the steric structure of the "aptamer 1 having the steric structure" is thermally dissolved is higher than room temperature (25° C.) and sufficiently lower than $T_{melting-2}$ (25° C. $< T_{aptamer-defolding} \ll T_{melting-2}$). When the solution temperature $T_L$ used for the detection process is selected within the range of 25° C.$< T_L < T_{aptamer-defolding}$, the equilibrium constant $K_{aptamer-defolding}(T_L)$ of the structural change between the "single-stranded aptamer 1" and the "aptamer 1 having the steric structure"=[Single-stranded aptamer 1]/[Aptamer having the steric structure 1] is in at least the relationship of $K_{aptamer-defolding}(T_L) < 1$.

For example, in the case when the solution temperature $T_L$ used for the detection process is set to very slightly lower than the melting temperature $T_{melting-1}$ of the destabilized double-stranded nucleotides binding in the "first photoisomerization-treated complex (hybrid)" ($T_L = T_{melting-1} - \delta T$), when the target substance 7 is contacted with the aptamer 1, which is comprised in the "first photoisomerization-treated complex (hybrid)", to induce the partial structural change of the aptamer 1, stabilization energy: $\Delta E_{hybrid-1}$ attributed to "the destabilized double-stranded nucleotides binding" is slightly decreased. As a result, the melting temperature $T_{melting-1}$ is lowered to some extent ($\delta T$) to become ($T_{melting-1} - \delta T$). Even at this solution temperature $T_L$ used for the detection process, the dissociation of the "first photoisomerization-treated complex (hybrid)" that is accompanied with the contact of the target substance 7 (perturbation: δE) is induced.

Since the solution temperature $T_L$ used for the detection process is very slightly lower than the melting temperature $T_{melting-1}$ of the destabilized double-stranded nucleotides binding in the "first photoisomerization-treated complex (hybrid)", a considerable part of the "first photoisomerization-treated complex (hybrid)" maintains the destabilized double-stranded nucleotides binding without being dissociated if having no contact with the target substance 7.

When the solution temperature $T_L$ used for the detection process is selected within a range where the relationship of $T_{melting-1} < T_L \ll T_{melting-2}$ is satisfied, at this solution temperature $T_L$, the thermal dissociation of the destabilized double-stranded nucleotides binding in the "first photoisomerization-treated complex (hybrid)" proceeds. The "single-stranded aptamer 1" resulting from the thermal dissociation is converted to an "aptamer 1 having the steric structure", which is folded in the steric structure essential to specific binding to the target substance 7. The target substance 7 binds to the "aptamer 1 having the steric structure" to form a target substance 7/aptamer 1 complex. As a result, in the case when the solution temperature $T_L$ used for the detection process is selected within a range where the relationship of $T_{melting-1} < T_L \ll T_{melting-2}$ is satisfied, the destabilized double-stranded nucleotides binding in the "first photoisomerization-treated complex (hybrid)" is completely dissociated, and thereby, all of target substances 7 bind to "aptamers 1 having the steric structure" to form target substance 7/aptamer 1 complexes. An "aptamer 1 having the steric structure" and a "single-stranded aptamer 1" that have not formed the target substance 7/aptamer 1 complex are dissolved in the assay solution. As illustrated in FIG. 5(c), the "first photoisomerization-treated first nucleic acid fragment 2" is immobilized on the surface of the basal material for immobilization 4.

Subsequently, as illustrated in FIG. 5(d), when the second photoisomerization treatment is carried out in "the fourth step", all of "first photoisomerization-treated first nucleic acid fragments 2" immobilized on the surface of the basal material for immobilization 4 are converted to "second photoisomerization-treated first nucleic acid fragments 2". The "single-stranded aptamer 1" dissolved in the assay solution, which has not formed the target substance 7/aptamer 1 complex, forms a "second photoisomerization-treated complex (hybrid)" with the "second photoisomerization-treated first nucleic acid fragment 2", which is immobilized on the surface of the basal material for immobilization 4. Consequently, as the concentration of the "single-stranded aptamer 1" dissolved in the assay solution is decreased thereby, the structural change from the "aptamer 1 having the steric structure" to the "single-stranded aptamer 1" progresses according to the equilibrium constant $K_{aptamer-folding}$ of the structural change between the "single-stranded aptamer 1" and the "aptamer 1 having the steric structure".

When the solution temperature $T_L$ used for the detection process is selected within a range where the relationship of $T_{melting-1} \le T_L \ll T_{melting-2}$ is satisfied, the "aptamer 1 having the steric structure", which has not formed the target substance 7/aptamer 1 complex, is also converted to a "single-stranded aptamer 1", which in turn forms a "second photoisomerization-treated complex (hybrid)" with the "second photoisomerization-treated first nucleic acid fragment 2" which is immobilized on the surface of the basal material for immobilization 4. As a result, as illustrated in FIG. 5(d), the "second photoisomerization-treated first nucleic acid fragment 2" in an amount equal to that of the target substance 7/aptamer 1 complex remains in the "dissolved" state on the surface of the basal material for immobilization 4. This "second photoisomerization-treated first nucleic acid fragment 2" remaining in the "dissolved" state is detected to thereby detect the amount of the target substance 7/aptamer 1 complex, i.e., the amount of the target substance 7 contained in the sampled specimen.

Of course, as, in the case when the target substance 7 is absent in the sampled specimen, no target substance 7/aptamer 1 complex is formed, the "second photoisomerization-treated first nucleic acid fragment 2" remaining in the "dissolved" state is essentially "zero".

At the solution temperature $T_L$ used for the detection process, in the case when the dissociation constant $K_{Dcomplex}(T_L)$ of the target substance 7/aptamer 1 complex is sufficiently small, the dissociation of the target substance 7/aptamer 1 complex is prevented. Thus, in the case when the target substance 7 is present in the sampled specimen, the progress of the dissociation of the target substance 7/aptamer 1 complex, which is formed in "the third step", is also prevented in "the fourth step", as illustrated in FIG. 5(d). Thus, there exists the "second photoisomerization-treated first nucleic acid fragment 2" which is not used to form the "second photoisomerization-treated complex (hybrid)", and thereby, which remains in the "dissolved" state. In the case when the target substance 7 is absent in the sampled specimen, the target substance 7/aptamer 1 complex is also absent. Hence, in "the fourth step", there exists substantially no "second photoisomerization-treated first nucleic acid fragment 2" which is not used to form the "second photoisomerization-treated complex (hybrid)", and thereby, which remains in the "dissolved" state. Thus, whether or not the target substance 7 is present in the subject to be assayed (sampled specimen) can be determined based on the detection of the presence or absence of the "second photoisomerization-treated first nucleic acid fragment 2", which remains in the "dissolved" state.

As the complex (hybrid) 11 used in the method for detecting a target substance according to the third embodiment is immobilized on the basal material for immobilization 4, the complex (hybrid) 11 can be easily recovered from the reaction solution in the "preparation step". In addition, a solid-liquid separation method can be applied to the operation of separating the complex (hybrid) 11 and the first nucleic acid fragment 2 immobilized on the basal material for immobilization 4 from the liquid phase, and thus, the operation for separation can be performed easily, for instance, the "second photoisomerization-treated first nucleic acid fragment 2" remaining in the "dissolved" state can be easily separated from the target substance 7/aptamer 1 complex that is present in the liquid phase after "the fourth step".

Plural types of "complexes (hybrids) 11" that are composed of "aptamers 1", which are respectively capable of binding specifically to plural types of target substances 7 to form complexes therewith, and their complementary "first nucleic acid fragments 2" can be immobilized on the same basal material for immobilization 4. In such a case, identical operations and conditions can be employed for the plural types of "complexes (hybrids) 11" in each step of the first photoisomerization treatment and the second photoisomerization treatment to which the photoisomerizable molecule 3 used for the composition thereof is subjected, the formation of the target substance 7/aptamer 1 complex, and the formation of double-stranded nucleotides binding in each "second photoisomerization-treated complex (hybrid)". If the "dissolved" state of the "first nucleic acid fragment 2" that is complementary to each of "aptamers 1" can be detected independently, the plurality of components (target substances 7) which are contained in the sampled specimen can be detected in parallel. In the case if the plurality of components (target substances 7) that are contained in the sampled specimen can be detected in parallel, the throughput of the assay can be improved.

The complex (hybrid) 11 that is immobilized on the basal material for immobilization 4, as illustrated in FIG. 5(a), can be used as an assay kit for detection of a target substance 7 by the application of the method for detecting a target substance according to the third embodiment.

A detection device which is capable of detecting the "dissolution" of the double-stranded nucleotides binding in the complex (hybrid) 11 can be used as the basal material for immobilization 4 for the immobilization of the complex (hybrid) 11. The detection device having the above structure can be used as a sensor for target substance detection with the aim of detecting the presence or absence of the target substance 7 in a sampled specimen, as mentioned later. The above-mentioned mode wherein the plural types of "complexes (hybrids) 11" that are composed of "aptamers 1", which are respectively capable of binding specifically to the plurality of components (target substances 7) to form complexes therewith, and their complementary "first nucleic acid fragments 2", which can be used for in parallel detection of the plurality of components (target substances 7) contained in the sampled specimen when immobilized on the same basal material for immobilization 4, are immobilized on the surface of the detection device, which is capable of independently detecting the "dissolution" of the double-stranded nucleotides binding in the plurality of the complex (hybrid) 11 can be employed. The detection device having the above structure can be used as a sensor for analysis of components contained in a sampled specimen with the aim of detecting the presence or absence of each component (target substance 7) in parallel, regarding the plural types of target substances 7, in the sampled specimen.

In the complex (hybrid) 11 used in the method for detecting a target substance according to the third embodiment, as the "first nucleic acid fragment 2" that is complementary to the "aptamer 1", similar nucleotide to that used as the "first nucleic acid fragment 2" that is complementary to the "aptamer 1", which is comprised in the complex (hybrid) 11 used in the detection method of the first embodiment, can be used. In the structure illustrated in FIG. 5(a), the photoisomerizable molecule 5 is bound to the double-strand formation site 5 in the "first nucleic acid fragment 2", and the "first nucleic acid fragment 2" is linked at one end to the spacer 9 and is immobilized on the surface of the basal material for immobilization 4 via this spacer 9. The other end of the "first nucleic acid fragment 2" is modified with the labeling material 6.

A functional group that is used in linkage with the spacer 9 is added to the end of the "first nucleic acid fragment 2", which is to be linked to the spacer 9. The functional group for use in linkage with the spacer 9 is not limited as long as the functional group is capable of forming a bond that is not dissociated from the spacer 9 under the condition used in detection, such as solvent or pH. A functional group which is generally employed for linking to the spacer 9, such as a carboxyl group, an amino group, a thiol group, a disulfide group, a succinimidyl group, a maleimide group, or biotin, can be used.

The functional group to be added to the "photoisomerizable molecule 3-bound first nucleic acid fragment 2" can be added to the end thereof during the step of preparation of the "photoisomerizable molecule 3-bound first nucleic acid fragment 2" by a general nucleotide synthesis method. Alternatively, such a nucleotide that is formed by modifying a nucleic acid molecule which is used as a starting material in the nucleotide synthesis of the "photoisomerizable molecule 3-bound first nucleic acid fragment 2" with a commercially available linker or the like may be employed.

The functional group to be added to the "photoisomerizable molecule 3-bound first nucleic acid fragment 2" may be added to modify an arbitrary site as long as impairing the formation of double-stranded nucleotides binding between the double-strand formation site 5 of the aptamer 1 and the double-strand formation site 5 of the "photoisomerizable molecule 3-bound first nucleic acid fragment 2" is not induced thereby. For example, the site modified with the functional group may be located at the end of the "photoisomerizable molecule 3-bound first nucleic acid fragment 2" or in the central part thereof.

The spacer 9 is linked to the end on the side where the double-strand formation site 5 of the "photoisomerizable molecule 3-bound first nucleic acid fragment 2" is positioned. The length of the spacer 9 is preferably 3 Å or longer, more preferably 10 Å or longer. This linkage of the spacer 9 avoids reduction in the formation efficiency of double-stranded nucleotides binding, which results from the steric hindrance that is induced between the basal material for immobilization 4 and the "photoisomerizable molecule 3-bound first nucleic acid fragment 2" in the process of forming the double-stranded nucleotides binding between the double-strand formation site 5 of the "photoisomerizable molecule 3-bound first nucleic acid fragment 2" and the double-strand formation site 5 of the aptamer 1, particularly, forming the double-stranded nucleotides binding between the double-strand formation site 5 of the second photoisomerization-treated "photoisomerizable molecule 3-bound first nucleic acid fragment 2" and the double-strand formation site 5 of the aptamer 1, i.e., forming the double-stranded nucleotides binding in the "second photoisomerization-treated complex (hybrid)".

In the case when the detection device capable of detecting the "dissolution" of the double-stranded nucleotides binding in the complex (hybrid) 11 is employed as the basal material for immobilization 4 for the immobilization of the complex (hybrid) 11, a longer distance between the detection device and the double-strand formation site 5 of the second photoisomerization-treated "photoisomerizable molecule 3-bound first nucleic acid fragment 2" impairs detection sensitivity for the "dissolution" of the double-stranded nucleotides binding. For the purpose of maintaining detection sensitivity for the "dissolution" of the double-stranded nucleotides binding, the length of the spacer 9 is preferably 200 Å or shorter. More preferably, the length of the spacer 9 is selected within the range of 10 Å or longer and 50 Å or shorter. The spacer 9 is not particularly limited as long as the spacer 9 does not form an intermolecular bond with the nucleic acid strand of the aptamer 1 or the nucleic acid strand of the "photoisomerizable molecule 3-bound first nucleic acid fragment 2". For example, a popular linker such as a nucleic acid having a non-complementary nucleotide sequence, a glycan, a polypeptide, a hydrocarbon chain, or oligoethylene glycol can be used.

As to the basal material for immobilization 4 for use in the immobilization of the complex (hybrid) 11, which is used in the method for detecting a target substance according to the third embodiment, a material from which the basal material for immobilization 4 itself is formed is not particularly limited by its material as long as the material enables the "photoisomerizable molecule 3-bound first nucleic acid fragment 2" to be immobilized via the spacer 9 or the material can be subjected to a treatment available in the immobilization via the spacer 9. A method for directly immobilizing a nucleic acid strand onto the surface of the basal material for immobilization 4 includes, for example, a method for forming a peptide bond (—CO—NH—) by use of a functional group (—COOH) introduced to the nucleic acid strand and a functional group (—NH$_2$) introduced to the surface of the basal material for immobilization 4, a method for chemisorbing a thiol group (—SH), which is in advance introduced to the end of the nucleic acid strand, onto the surface of a coating which is in advance provided on the surface of the basal material for immobilization 4 by using gold, platinum, silver, palladium, or the like, and a method for forming a biotin-avidin bond in which avidin is immobilized onto the surface of the basal material for immobilization 4 and then a biotin being attached at the end of the nucleic acid strand is reacted with the avidin. One of approaches widely used for preparation of DNA chips, etc. is a method in which a nucleic acid strand comprised of the nucleotide sequence of interest is sequentially synthesized by using, as a base, a functional group provided on the surface of the basal material for immobilization 4 by means of solid-phase synthesis, and thereby, the resulted nucleic acid strand is immobilized on the surface of the basal material for immobilization 4. In the case when the surface of the basal material for immobilization 4 lacks a functional group available in the immobilization via the spacer 9, a desired functional group may be introduced by subjecting the surface of the basal material for immobilization 4 to surface-treatment with thiol, a silane coupling agent, or the like. A substrate, particles such as beads, or a substrate used for preparation of microarray chips may be used as the basal material for immobilization 4. The shape of the basal material for immobilization 4 is not particularly limited, for example, may be shaped in any form, such as a plate, a sphere, or a rod. When the "photoisomerizable molecule 3-bound first nucleic acid fragment 2" is immobilized in advance on the basal material for immobilization 4, and "hybridization reaction" is then carried out by contacting a solution containing the aptamer 1 therewith, the double-strand formation site 5 of the aptamer 1 and the double-strand formation site 5 of the "photoisomerizable molecule 3-bound first nucleic acid fragment 2", which comprise nucleotide sequences complementary to each other, form double-stranded nucleotides binding to compose a complex (hybrid) 11. In the case when the "photoisomerizable molecule 3-bound first nucleic acid fragment 2" is subjected to the second photoisomerization treatment to convert to a second photoisomerization-treated "photoisomerizable molecule 3-bound first nucleic acid fragment 2", and then, the aptamer 1 and the second photoisomerization-treated "photoisomerizable molecule 3-bound first nucleic acid fragment 2" are subjected to annealing treatment to defold into single-stranded nucleic acid strands thereof, in which the steric structured are dissolved, and after that, "hybridization reaction" is carried out, the resulted the "second photoisomerization-treated complex (hybrid)" can be immobilized onto the basal material for immobilization 4. Alternatively, the "photoisomerizable molecule 3-bound first nucleic acid fragment 2", the end of which is linked to the spacer 9, and the aptamer 1 may be mixed with each other in a solution, and then, "hybridization reaction" may be carried out to form a complex (hybrid) 11, and after that, the resulted complex (hybrid) 11 may be immobilized onto the basal material for immobilization 4 via the spacer 9. Preferably, in such a case, the "hybridization reaction" is performed after completion of the annealing treatment and the second photoisomerization treatment.

As illustrated in FIG. 5(b), the "first photoisomerization-treated complex (hybrid)", in which the photoisomerizable molecule 3 is subjected to the first photoisomerization treatment in advance, may be immobilized onto the basal material for immobilization 4 via the spacer 9 in the temperature range where the "first photoisomerization-treated complex (hybrid)" is not dissociated, and thereby, is immobilized on the basal material for immobilization 4. In the temperature range where the "first photoisomerization-treated complex (hybrid)" is not dissociated, and thereby, is immobilized on the basal material for immobilization 4, the "second photoisomerization-treated complex (hybrid)" may be immobilized onto the basal material for immobilization 4 via the spacer 9 and then converted, by subjecting the photoisomerizable molecule 3 to the first photoisomerization treatment in advance, to the state that the "first photoisomerization-treated complex (hybrid)" is immobilized on the basal material for immobilization 4 via the spacer 9.

In the case when an assay kit in which the "first photoisomerization-treated complex (hybrid)" is still kept in the state of being immobilized on the basal material for immobilization 4 via the spacer 9, "the first step" of subjecting the photoisomerizable molecule 3 to the first photoisomerization treatment can be omitted. Thus, the presence or absence of the target substance 7 in the sampled specimen can be conveniently assayed by carrying out "the second step" to "the fourth step" with "the first step" omitted.

After the first nucleic acid fragment 2 is immobilized thereon, the basal material for immobilization 4 may be subjected to a blocking treatment. The blocking treatment can inhibit the nonspecific adsorption of the target substance 7 onto the surface of the basal material for immobilization 4. The blocking can avoid reduction in target substance 7/aptamer 1 complex formation efficiency caused by the nonspecific adsorption of the target substance 7 and consequently improve S/N. In addition, when the blocking avoids such phenomenon in which a "single-stranded aptamer 1" resulting from the dissociation of the "first photoisomerization-treated complex (hybrid)" happens to bind nonspecifically on the surface of the basal material for immobilization 4, and thereby, the formation of the steric structure essential to binding to the target substance 7 is inhibited, reduction in the efficiency of binding of the target substance 7 to the aptamer 1 can be avoided. The blocking can also prevent the nonspecific binding of the target substance 7/aptamer 1 complex to the surface of the solid member 4. In the blocking treatment, a general blocking agent, such as a hydrophilic polymer (e.g., polyethylene glycol or acrylamide), a protein (e.g., bovine serum albumin), a glycan (e.g., dextrin), a lipid (e.g., phosphatidylcholine), or hydrophilic thiol (e.g., mercaptohexanol), can be used.

In the method for detecting a target substance according to the third embodiment, the method for detection of the "dissolved" state of the double-stranded nucleotides binding which is formed between the double-strand formation site 5 of the aptamer 1 and the double-strand formation site 5 of the second photoisomerization-treated "photoisomerizable molecule 3-bound first nucleic acid fragment 2", i.e., the second photoisomerization-treated "photoisomerizable molecule 3-bound first nucleic acid fragment 2" which is immobilized on the surface of the basal material for immobilization 4, as illustrated in FIG. 5(d), is not particularly limited, and therefore, in similar to the method for detecting a target substance according to the first embodiment, a technique of detecting physical or chemical change in the nucleic acid strand itself as well as the labeling material 6 attached thereto of the second photoisomerization-treated "photoisomerizable molecule 3-bound first nucleic acid fragment 2", which results from the "dissolution" of the double-stranded nucleotides binding in the "second photoisomerization-treated complex (hybrid)". In addition, as only the "second photoisomerization-treated complex (hybrid)" and the second photoisomerization-treated "photoisomerizable molecule 3-bound first nucleic acid fragment 2", which is corresponding to the "dissolved" state of the double-stranded nucleotides binding, are immobilized on the surface of the basal material for immobilization 4, an approach of detecting physical or chemical change in the surface of the basal material for immobilization 4, which is caused by the "dissolved" state of the double-stranded nucleotides binding, may be employed. For example, "permittivity change" in the basal material for immobilization 4, which is induced by the "dissolved" state of the double-stranded nucleotides binding in the "second photoisomerization-treated complex (hybrid)", may be detected by means of surface plasmon resonance, or composition change in the "second photoisomerization-treated complex (hybrid)" and the second photoisomerization-treated "photoisomerizable molecule 3-bound first nucleic acid fragment 2", which are immobilized on the surface of the basal material for immobilization 4, may be detected by means of surface-enhanced Raman scattering. Alternatively, following technique may be employed in which, the target substance 7/aptamer 1 complex dissolved in the liquid phase is isolated, and then the isolated target substance 7/aptamer 1 complex is dissociated to liberate the aptamer 1, and thereafter, the liberated aptamer 1 is detected by DNA detection method, such as technique of DNA chip or PCR.

When a device capable of detecting the physical or chemical change in the second photoisomerization-treated "photoisomerizable molecule 3-bound first nucleic acid fragment 2", its labeling material 6, or the surface of the basal material for immobilization 4, which are induced by the "dissolution" of the double-stranded nucleotides binding, is used as the basal material for immobilization 4, such device, on the surface of which the complex (hybrid) 11 is immobilized, can be used, for example, as a sensor for detection of a target substance 7 with the aim of detecting the presence or absence of the target substance 7 in a sampled specimen. By using such a sensor for detection of a target substance 7, in which the complex (hybrid) 11 is immobilized on its surface to be integrated within the detection device, in site detection, for example, detection of the presence or absence of the target substance 7 in a sampled specimen can be carried out with ease.

The device for use in the sensor for detection of a target substance 7 is not limited as long as the device is capable of detecting the physical or chemical change in the second photoisomerization-treated "photoisomerizable molecule 3-bound first nucleic acid fragment 2", its labeling material 6, or the surface of the basal material for immobilization 4, which result from the "dissolution" of the double-stranded nucleotides binding, for instance, including: devices available in the detection of permittivity change, such as surface plasmon resonance (SPR), surface acoustic wave (SAW) and field-effect transistor (FET); devices available in the detection of dynamic change (mass change), such as quartz crystal microbalance (QCM) and cantilever; photodetection devices, such as photomultipliers and photodiodes, available in the detection of change in optical signal originating from the labeling material 6; and electrochemical detection devices, such as electrodes for electrochemical assay, available in the detection of electrode reaction induced by the labeling material 6.

In the method for detecting a target substance according to the third embodiment, the labeling material 6 which is used to modify the "photoisomerizable molecule 3-bound first nucleic acid fragment 2" is not limited as long as the labeling material 6 is "capable of amplifying" the physical or chemical change resulting from the "dissolution" of the double-stranded nucleotides binding. Any of various substances which are listed as example of substances that are available for the labeling material 6 in the method for detecting a target substance according to the first embodiment is usable. In addition, in the case when the detection device used in the structure of the sensor for detection of a target substance 7, is a device capable of detecting "mass change" or "permittivity change" that is caused by the composition change in the "second photoisomerization-treated complex (hybrid)" and the second photoisomerization-treated "photoisomerizable molecule 3-bound first nucleic acid fragment 2", which are immobilized on the surface of the basal material for immobilization 4, in association with the "dissolution" of the double-stranded nucleotides binding, for example, a QCM, FET device, or SPR device, the modification with the labeling material 6 may be omitted, In the case when an active material for electrode reaction is employed as the labeling material 6 in the application of the method for detecting a target substance according to the third embodiment, a typical example of detection of the "dissolved" state of the double-stranded nucleotides binding "second photoisomerization-treated complex (hybrid)" will be explained again with reference to FIG. 5 again.

In the structure as illustrated in FIG. 5(a), the working electrode of a three electrode-type electrochemical cell, which is used in electrochemical assay, is employed as the basal material for immobilization 4. The "photoisomerizable molecule 3-bound first nucleic acid fragment 2", which is comprised in the complex (hybrid) 11, is immobilized on the surface of the working electrode via the spacer 9. The end of the "photoisomerizable molecule 3-bound first nucleic acid fragment 2" is modified with an active material for electrode reaction, which is used as the labeling material 6.

The working electrode, which is used as the basal material for immobilization 4, as well as a counter electrode and a reference electrode, which are not shown in the figure, are connected to an electrochemical assay apparatus. When a predetermined electric potential is applied to the three electrode-type electrochemical cell, an electron is transferred from the active material for electrode reaction used as the labeling material 6 to the working electrode to oxidize the active material for electrode reaction (electrode oxidation reaction). On the contrary, an electron is transferred from the working electrode to the active material for electrode reaction to reduce the active material for electrode reaction (electrode reduction reaction). The type (electrode oxidation reaction or electrode reduction reaction) of the electrode reaction (electrochemical reaction) in the working electrode is selected according to the active material for electrode reaction used. Electric potentials suitable for the electrode reaction in the working electrode are applied to the working electrode, the counter electrode, or the reference electrode.

The efficiency of the electron transfer process between the working electrode and the active material for electrode reaction being attached being attached as the labeling material 6 at the end of the "photoisomerizable molecule 3-bound first nucleic acid fragment 2" differs depending on the state of being attached to the "second photoisomerization-treated complex (hybrid)" as illustrated in FIG. 5(*a*), the state of being attached to the "first photoisomerization-treated complex (hybrid)" as illustrated in FIG. 5(*b*), the state of being attached to the first photoisomerization-treated "photoisomerizable molecule 3-bound first nucleic acid fragment 2" as illustrated in FIG. 5(*c*), and the state of being attached to the second photoisomerization-treated "photoisomerizable molecule 3-bound first nucleic acid fragment 2" as illustrated in FIG. 5(*d*).

In the case where the target substance 7 is present in the sampled specimen, when the active material for electrode reaction being attached at the end of the "photoisomerizable molecule 3-bound first nucleic acid fragment 2" is subjected to the second photoisomerization treatment in "the fourth step", it is converted into any of the state of being attached to the "second photoisomerization-treated complex (hybrid)" and the state of being attached to the second photoisomerization-treated "photoisomerizable molecule 3-bound first nucleic acid fragment 2".

In the case where the target substance 7 is absent in the sampled specimen, when the active material for electrode reaction being attached at the end of the "photoisomerizable molecule 3-bound first nucleic acid fragment 2" is subjected to the second photoisomerization treatment in "the fourth step", it is inevitably converted to the state of being attached to the "second photoisomerization-treated complex (hybrid)". Before the active material for electrode reaction being attached at the end of the "photoisomerizable molecule 3-bound first nucleic acid fragment 2" is subjected to the first photoisomerization treatment in "the first step", it is inevitably kept in the state of being the "second photoisomerization-treated complex (hybrid)".

Thus, in the case when the target substance 7 is absent in the sampled specimen, a current value which results from the electrode reaction of the active material for electrode reaction being attached at the end of the "photoisomerizable molecule 3-bound first nucleic acid fragment 2" is essentially unchanged between before subjected to the first photoisomerization treatment in "the first step" and after subjected to the second photoisomerization treatment in "the fourth step".

In the case where the target substance 7 is present in the sampled specimen, the state of being attached to the "second photoisomerization-treated complex (hybrid)" is changed to the state of being attached to the second photoisomerization-treated "photoisomerizable molecule 3-bound first nucleic acid fragment 2" in response to the "dissolved" state of the double-stranded nucleotides binding. Therefore, the current value which results from the electrode reaction of the active material for electrode reaction being attached at the end of the "photoisomerizable molecule 3-bound first nucleic acid fragment 2" is changed between before subjected to the first photoisomerization treatment in "the first step" and after subjected to the second photoisomerization treatment in "the fourth step".

Hence, the "dissolved" state of the double-stranded nucleotides binding can be detected on the basis of the "change in current value", which are measured using the electrochemical cell between before subjected to the first photoisomerization treatment in "the first step" and after subjected to the second photoisomerization treatment in "the fourth step", regarding the current value which results from the electrode reaction of the active material for electrode reaction being attached at the end of the "photoisomerizable molecule 3-bound first nucleic acid fragment 2".

In the case when the active material for electrode reaction which is attached as the labeling material 6 at the end of the "photoisomerizable molecule 3-bound first nucleic acid fragment 2" is in the state of being attached to the "second photoisomerization-treated complex (hybrid)", as illustrated in FIG. 5(*a*), the double-stranded nucleotides binding in the "second photoisomerization-treated complex (hybrid)" has a poorly flexible "double helix structure". Though the spacer 9 possesses flexibility, when the length of the spacer 9 is selected within the aforementioned range, the probability that the active material for electrode reaction being attached at the end of the "photoisomerizable molecule 3-bound first nucleic acid fragment 2" takes a position close to the surface of the basal material for immobilization 4, which functions as a working electrode, is low. Therefore, the efficiency of the electron transfer process between the active material for electrode reaction being attached at the end of the "photoisomerizable molecule 3-bound first nucleic acid fragment 2" and the working electrode is kept at a low level.

In the case when the active material for electrode reaction being attached as the labeling material 6 at the end of the "photoisomerizable molecule 3-bound first nucleic acid fragment 2" is in the state of being attached to the second photoisomerization-treated "photoisomerizable molecule 3-bound first nucleic acid fragment 2", as illustrated in FIG. 5(*d*), the double-strand formation site 5 in the second photoisomerization-treated "photoisomerizable molecule 3-bound first nucleic acid fragment 2" has a flexible "single-stranded structure". As the spacer 9 also possesses flexibility, when the length of the spacer 9 is selected within the aforementioned range, the probability that the active material for electrode reaction being attached at the end of the second photoisomerization-treated "photoisomerizable molecule 3-bound first nucleic acid fragment 2" takes a position close to the surface of the basal material for immobilization 4, which functions as a working electrode, is relatively high. Therefore, the efficiency of the electron transfer process between the active material for electrode reaction being attached at the end of the second photoisomerization-treated "photoisomerizable molecule 3-bound first nucleic acid fragment 2" and the working electrode is retained at a relatively high level.

In the method for detecting a target substance according to the third embodiment, in the case when such a mode in which an active material for electrode reaction is employed as the labeling material 6 to modify the end of the "photoisomerizable molecule 3-bound first nucleic acid fragment 2", and the working electrode of a three electrode-type electrochemical cell, which is usable in electrochemical assay, is utilized as the basal material for immobilization 4 to immobilize the complex (hybrid) 11, particularly, the "second photoisomerization-treated complex (hybrid)" is employed, the "dissolved" state of the double-stranded nucleotides binding in the "second photoisomerization-treated complex (hybrid)" can be detected on the basis of the "change in current value" between before subjected to the first photoisomerization treatment in "the first step" and after subjected to the second photoisomerization treatment in "the fourth step". Specifically, whether or not the target substance 7 is present in the subject to be assayed (sampled specimen) can be detected on the basis of the presence or absence of the "change in current value" between before the first photoisomerization treatment in "the first step" and after the second photoisomerization treatment in "the fourth step". In the case if the current value that originates from the electrode reaction for the active material for electrode reaction being attached at the end of the "photoisomerizable molecule 3-bound first nucleic acid fragment 2, which is measured using the electrochemical cell before subjected to the first photoisomerization treatment in "the first step", is negligibly low or its level has been identified in advance, the measurement of the current value before subjected to the first photoisomerization treatment in "the first step" can be omitted.

After the step of preparing the complex (hybrid) 11, particularly, the "second photoisomerization-treated complex (hybrid)", which is immobilized on the surface of the working electrode, the surface of the basal material for immobilization 4 (working electrode) may be washed, if necessary, in order to remove unimmobilized "photoisomerizable molecule 3-bound first nucleic acid fragments 2". Alternatively, after the second photoisomerization treatment is carried out in "the fourth step", the surface of the basal material for immobilization 4 (working electrode) may be washed, if necessary, in order to remove target substance 7/aptamer 1 complexes.

Plural types of "complexes (hybrids) 11" that are plural types of target substances 7 composed of "aptamers 1", which are capable of binding specifically to plural types of target substances 7 to form complexes therewith, and their complementary "first nucleic acid fragments 2" can be respectively on the working electrodes of a plurality of three electrode-type electrochemical cells, which are arranged in array shape. In such a case, identical operations and conditions can be employed in each step of the first photoisomerization treatment and the second photoisomerization treatment of photoisomerizable molecules 3, which is used for the construction of the plural types of "complexes (hybrids) 11", the target substance 7/aptamer 1 complex formation, and the formation of double-stranded nucleotides binding in each "second photoisomerization-treated complex (hybrid)". In the case when the "dissolved" state between each "aptamer 1" and its complementary "first nucleic acid fragment 2" can be detected independently using the plurality of three electrode-type electrochemical cells, which are arranged in array shape, a plurality of components (target substances 7) contained in a sampled specimen can be detected in parallel. The "plurality of three electrode-type electrochemical cells arranged in array shape", which are usable for detecting in parallel, can be used as a "multi-component sensor" suitable with the aim of in parallel assaying the presence or absence of a plurality of components (target substances 7) in a sampled specimen. By using the "multi-component sensor", in site detection of the presence or absence of the target substance 7 in a sampled specimen can be carried out with ease.

The complex (hybrid) 11 composed of the "conjugate molecule" that is used in the method for detecting a target substance according to the second embodiment is meant to be in the state where, when the target substance 7 is absent in the sampled specimen, the complex (hybrid) 11 can be wholly converted to a second photoisomerization-treated complex (hybrid) through the intramolecular double-stranded nucleotides binding formed between the respective double-strand formation sites 5 of the aptamer 1 and "photoisomerizable molecule 3-bound first nucleic acid fragment 2" composing the "conjugate molecule", when the photoisomerizable molecule 3 is subjected to the second photoisomerization treatment in "the fourth step" at the solution temperature $T_L$ used for the detection process.

The complex (hybrid) 11 immobilized on the surface of the basal material for immobilization 4 that is used in the method for detecting a target substance according to the third embodiment is meant to be in the state where: the "photoisomerizable molecule 3-bound first nucleic acid fragment 2" is modified at its end with the labeling material 6 and immobilized on the surface of the basal material for immobilization 4 via the spacer 9; and in the case when the target substance 7 is absent in the sampled specimen, after the photoisomerizable molecule 3 is subjected to the second photoisomerization treatment in "the fourth step", double-stranded nucleotides binding can be formed between the double-strand formation site 5 of the aptamer 1 and the double-strand formation site 5 of the second photoisomerization-treated "photoisomerizable molecule 3-bound first nucleic acid fragment 2" at the solution temperature $T_L$ used for the detection process; and thereby, a "second photoisomerization-treated complex (hybrid)" can be formed on the surface of the basal material for immobilization 4. For example, it may be in such state in which, when the photoisomerizable molecule 3 is subjected to the first photoisomerization treatment at the solution temperature $T_L$ used for the detection process double-stranded nucleotides binding is not be formed between the double-strand formation site 5 of the aptamer 1 and the double-strand formation site 5 of the first photoisomerization-treated "photoisomerizable molecule 3-bound first nucleic acid fragment 2". Therefore, the method for detecting a target substance according to the third embodiment also includes such a mode using following form where: the first photoisomerization-treated "photoisomerizable molecule 3-bound first nucleic acid fragment 2", which is subjected to the first photoisomerization treatment in advance, is immobilized on the surface of the basal material for immobilization 4 via the spacer 9; and the aptamer 1 is mixed therewith in the state of not forming the double-stranded nucleotides binding with the first photoisomerization-treated "photoisomerizable molecule 3-bound first nucleic acid fragment 2". Thus, the method for detecting a target substance according to the third embodiment also includes following mode where: in the "complex (hybrid) 11 preparation step", such mixture is prepared in which the first photoisomerization-treated "photoisomerizable molecule 3-bound first nucleic acid fragment 2", which is subjected to the first photoisomerization treatment in advance, is immobilized on the surface of the basal material for immobilization 4 via the spacer 9; and the aptamer 1 is in the state of not forming the double-stranded nucleotides binding with the first photoisomerization-treated "photoisomerizable molecule 3-bound first nucleic acid fragment 2".

Fourth Embodiment

The method for detecting a target substance according to the fourth embodiment is also an approach based on the application of the "detection principles" used in the method for detecting a target substance according to the first embodiment to the method for detecting a target substance according to the third embodiment, so that the description of the same or similar points as those in the method for detecting a target substance according to the first embodiment to the method for detecting a target substance according to the third embodiment will be omitted.

Figure 6:
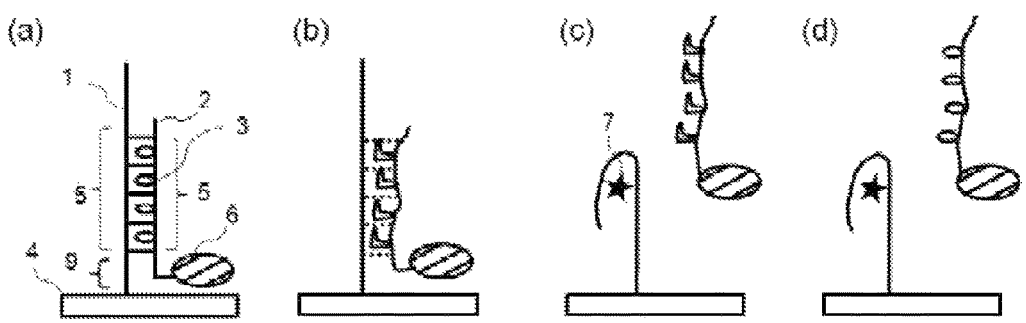
FIG. 6 is a diagram schematically showing the procedures of a method for detecting a target substance using an aptamer immobilized on a basal material for immobilization according to the fourth embodiment.

FIG. 6 is a diagram schematically showing the forms of a complex (hybrid) 11 and procedures corresponding to "the first step" to "the fourth step" in the "detection of the target substance 7", which are used in the method for detecting a target substance according to the fourth embodiment.

The method for detecting a target substance according to the fourth embodiment will be explained with reference to FIG. 6.

In the complex (hybrid) 11 in the structure illustrated in FIG. 6(a) for use in the method for detecting a target substance according to the fourth embodiment, a double-strand formation site 5 in an aptamer 1 and a double-strand formation site 5 in a "photoisomerizable molecule 3-bound first nucleic acid fragment 2" form double-stranded nucleotides binding, and the end of the double-strand formation site 5 in the aptamer 1 is immobilized on a basal material for immobilization 4 by chemical bond or chemisorption via a spacer 9. In addition, the end of the double-strand formation site 5 in the "photoisomerizable molecule 3-bound first nucleic acid fragment 2" is modified with a labeling material 6. As a result, when the complex (hybrid) 11 is comprised thereof, the labeling material 6 being attached at the end of the double-strand formation site 5 in the "photoisomerizable molecule 3-bound first nucleic acid fragment 2" can take a position close to the surface of the basal material for immobilization 4.

When the photoisomerizable molecule 3 is subjected to the first photoisomerization treatment, the stability of the double-stranded nucleotides binding, which is formed between the double-strand formation site 5 of the first photoisomerization-treated "photoisomerizable molecule 3-bound first nucleic acid fragment 2" and the double-strand formation site 5 of the aptamer 1, is reduced. That is, the melting temperature $T_{melting-1}$ of the destabilized double-stranded nucleotides binding in the "first photoisomerization-treated complex (hybrid)", which is composed of the first photoisomerization-treated "photoisomerizable molecule 3-bound first nucleic acid fragment 2" and the aptamer 1, is in the state of $T_{melting-1} \ll T_{melting}$, compared with the melting temperature $T_{melting}$ of the double-stranded nucleotides binding in the original complex (hybrid) 11. When subjected to the second photoisomerization treatment, the first photoisomerization-treated "photoisomerizable molecule 3-bound first nucleic acid fragment 2" is converted to a second photoisomerization-treated "photoisomerizable molecule 3-bound first nucleic acid fragment 2". Since the photoisomerizable molecule 3 is reversibly photoisomerized by being subjected to the first photoisomerization treatment and to the second photoisomerization treatment, the double-stranded nucleotides binding that is formed between the double-strand formation site 5 of the second photoisomerization-treated "photoisomerizable molecule 3-bound first nucleic acid fragment 2" and the double-strand formation site 5 of the aptamer 1 is restabilized to the same level as the stability of the double-stranded nucleotides binding in the original complex (hybrid) 11. That is, the melting temperature $T_{melting-2}$ of the restabilized double-stranded nucleotides binding in the "second photoisomerization-treated complex (hybrid)", which is composed of the second photoisomerization-treated "photoisomerizable molecule 3-bound first nucleic acid fragment 2" and the aptamer 1, is equal to the melting temperature $T_{melting}$ of the double-stranded nucleotides binding in the original complex (hybrid) 11.

Thus, the melting temperature $T_{melting-1}$ of the destabilized double-stranded nucleotides binding in the "first photoisomerization-treated complex (hybrid)", the melting temperature $T_{melting-2}$ of the restabilized double-stranded nucleotides binding in the "second photoisomerization-treated complex (hybrid)", and the melting temperature $T_{melting}$ of the double-stranded nucleotides binding in the original complex (hybrid) 11 satisfy the relationship of $T_{melting-1} \ll T_{melting} = T_{melting-2}$. In the case when the relationship of $T_L < T_{melting-1}$ is satisfied, compared with the solution temperature $T_L$, the thermal dissociation of the destabilized double-stranded nucleotides binding in the "first photoisomerization-treated complex (hybrid)" does not proceed. In such a case, as illustrated in FIG. 6(b), the "first photoisomerization-treated complex (hybrid)" possessing the destabilized double-stranded nucleotides binding is immobilized on the surface of the basal material for immobilization 4.

When comparing the dissociation constant $K_{Dhybrid-1}(T_L)$ of the first photoisomerization-treated complex (hybrid)=[Single-stranded aptamer 1]*[First photoisomerization-treated first nucleic acid fragment 2]/[First photoisomerization-treated complex], the dissociation constant $K_{Dhybrid-2}(T_L)$ of the second photoisomerization-treated complex (hybrid)=[Single-stranded aptamer 1]*[Second photoisomerization-treated first nucleic acid fragment 2]/[Second photoisomerization-treated complex] and the dissociation constant $K_{Dcomplex}(T_L)$ of the target substance 7/aptamer 1 complex=[Aptamer having the steric structure 1]*[Target substance 7]/[Complex], such state of $K_{Dhybrid-2}(T_L) < K_{Dcomplex}(T_L) \ll K_{Dhybrid-1}(T_L)$ is attained at the solution temperature $T_L$ used for the detection process. Furthermore, the temperature $T_{aptamer-defolding}$ at which the steric structure of the "aptamer 1 having the steric structure" is thermally dissolved is higher than room temperature (25° C.) and sufficiently lower than $T_{melting-2}$ (25° C. $< T_{aptamer-defolding} \ll T_{melting-2}$). In the case when the solution temperature $T_L$ used for the detection process is selected within the range of 25° C. $< T_L < T_{aptamer-defolding}$, the equilibrium constant $K_{aptamer-defolding}(T_L)$ of the structural change between the "single-stranded aptamer 1" and the "aptamer 1 having the steric structure"=[Single-stranded aptamer 1]/[Aptamer having the steric structure 1] is in at least the relationship of $K_{aptamer-defolding}(T_L) < 1$.

For example, in the case where the solution temperature $T_L$ used for the detection process is set to very slightly lower than the melting temperature $T_{melting-1}$ of the destabilized double-stranded nucleotides binding in the "first photoisomerization-treated complex (hybrid)" ($T_L = T_{melting-1} - \delta T$), when the target substance 7 is contacted with the aptamer 1 which is comprised in the "first photoisomerization-treated complex (hybrid)" to induce the partial structural change of the aptamer 1, stabilization energy: $\Delta E_{hybrid-1}$ resulting from "the destabilized double-stranded nucleotides binding" is slightly reduced. As a result, as the melting temperature $T_{melting-1}$ is lowered to some extent ($\delta T$) to become ($T_{melting-1} - \delta T$), even at this solution temperature $T_L$ used for the detection process, the dissociation of the "first photoisomerization-treated complex (hybrid)" that is accompanied with the contact of the target substance 7 (perturbation: $\delta E$) is induced.

In such a case, since the solution temperature $T_L$ used for the detection process is very slightly lower than the melting temperature $T_{melting-1}$ of the destabilized double-stranded nucleotides binding in the "first photoisomerization-treated complex (hybrid)", when the target substance 7 is not contacted therewith, a considerable part of the "first photoisomerization-treated complex (hybrid)" maintains the destabilized double-stranded nucleotides binding.

In the case when the solution temperature $T_L$ used for the detection process is selected within a range where the relationship of $T_{melting-1} < T_L \ll T_{melting-2}$ is satisfied, at the solution temperature $T_L$, the thermal dissociation of the destabilized double-stranded nucleotides binding in the "first photoisomerization-treated complex (hybrid)" proceeds. The "single-stranded aptamer 1" resulting from the thermal dissociation is converted to an "aptamer 1 having the steric structure" which has the steric structure essential to specific binding to the target substance 7. The target substance 7 binds to the "aptamer 1 having the steric structure" to form a target substance 7/aptamer 1 complex. As a result, in the case when the solution temperature $T_L$ used for the detection process is selected within a range where the relationship of $T_{melting-1} < T_L \ll T_{melting-2}$ is satisfied, the destabilized double-stranded nucleotides binding in the "first photoisomerization-treated complex (hybrid)" is completely dissociated, and thereby, all of target substances 7 bind to "aptamers 1 having the steric structure" to form target substance 7/aptamer 1 complexes.

Since the end of the double-strand formation site of the aptamer 1 is immobilized on the surface of the basal material for immobilization 4 via the spacer 9, in addition to the target substance 7/aptamer 1 complexm, an "aptamer 1 having the steric structure" and a "single-stranded aptamer 1" that have not formed the target substance 7/aptamer 1 complex are also immobilized on the surface of the basal material for immobilization 4, as illustrated in FIG. 6(c). On the other hand, a first photoisomerization-treated "photoisomerizable molecule 3-bound first nucleic acid fragment 2", which is produced in association with the thermal dissociation of the destabilized double-stranded nucleotides binding in the "first photoisomerization-treated complex (hybrid)", is dissolved in the liquid phase.

Subsequently, when subjected to the second photoisomerization treatment in "the fourth step", as illustrated in FIG. 6(d), all of "first photoisomerization-treated first nucleic acid fragments 2" dissolved in the assay solution are converted to "second photoisomerization-treated first nucleic acid fragments 2". The "second photoisomerization-treated first nucleic acid fragment 2" dissolved in the assay solution forms a "second photoisomerization-treated complex (hybrid)" with the "single-stranded aptamer 1", which has not formed the target substance 7/aptamer 1 complexed. In such a case, since the "single-stranded aptamer 1" is immobilized on the surface of the basal material for immobilization 4, the "second photoisomerization-treated complex (hybrid)" thus formed has the same structure as that of the original "complex (hybrid)", as illustrated in FIG. 6(a). Consequently, as the concentration of the "single-stranded aptamer 1", which is immobilized on the surface of the basal material for immobilization 4, is decreased, the structural change from the "aptamer 1 having the steric structure", which is immobilized on the surface of the basal material for immobilization 4, to the "single-stranded aptamer 1", which is immobilized on the surface of the basal material for immobilization 4, is progressed according to the equilibrium constant $K_{aptamer\text{-}folding}$ of the structural change between the "single-stranded aptamer 1" and the "aptamer 1 having the steric structure".

In the case when the solution temperature $T_L$ used for the detection process is selected within a range where the relationship of $T_{melting-1} < T_L \ll T_{melting-2}$ is satisfied, the "aptamer 1 having the steric structure", which has not formed the target substance 7/aptamer 1 complex, is also converted to a "single-stranded aptamer 1", which in turn forms a "second photoisomerization-treated complex (hybrid)" with the "second photoisomerization-treated first nucleic acid fragment 2", which is dissolved in the assay solution. As a result, as illustrated in FIG. 6(d), the "second photoisomerization-treated first nucleic acid fragment 2" in an amount equal to that of the "target substance 7/aptamer 1 complex" which is immobilized on the surface of the basal material for immobilization 4 remains in the "dissolved" state. This "second photoisomerization-treated first nucleic acid fragment 2" remaining in the "dissolved" state is detected to thereby detect the amount of the target substance 7/aptamer 1 complex, i.e., the amount of the target substance 7 contained in the sampled specimen.

Of course, in the case when the target substance 7 is absent in the sampled specimen, no target substance 7/aptamer 1 complex is formed, and thus, the "second photoisomerization-treated first nucleic acid fragment 2" remaining in the "dissolved" state is essentially "zero".

In the case where, at the solution temperature $T_L$ used for the detection process, the dissociation constant $K_{Dcomplex}$ ($T_L$) of the target substance 7/aptamer 1 complex is sufficiently small, the progress of the dissociation of the "target substance 7/aptamer 1 complex" is suppressed. Therefore, in the case when the target substance 7 is present in the sampled specimen, the progress of the dissociation of the target substance 7/aptamer 1 complex that has been formed in "the third step" is also suppressed in "the fourth step", as illustrated in FIG. 6(d), so that the "second photoisomerization-treated first nucleic acid fragment 2", which is not used to form the "second photoisomerization-treated complex (hybrid)" and thus is retained in the "dissolved" state, is present. In the case when the target substance 7 is absent in the sampled specimen, the "target substance 7/aptamer 1 complex" is also absent. Hence, in "the fourth step", there exists substantially no "second photoisomerization-treated first nucleic acid fragment 2", which is not used to form the "second photoisomerization-treated complex (hybrid)" and thus is retained in the "dissolved" state. Thus, the presence or absence of the "second photoisomerization-treated first nucleic acid fragment 2" remaining in the "dissolved" state can be detected to thereby determine the presence or absence of the target substance 7 in the subject to be assayed (sampled specimen).

In the method for detecting a target substance according to the fourth embodiment, in the complex (hybrid) 11 which is composed of the aptamer 1 and the "photoisomerizable molecule 3-bound first nucleic acid fragment 2", the aptamer 1 is immobilized on the surface of the basal material for immobilization 4 via the spacer 9. Therefore, a series of operations necessary for carrying out "the first step" to "the fourth step", for example, a series of treatment operations for the complex (hybrid) 11. including a heating treatment, a first photoisomerization treatment, a treatment of contacting with a target substance 7 that is contained in a sampled specimen and a second photoisomerization treatment, can be carried out easily.

Particularly, the complex (hybrid) 11, as illustrated in FIG. 6(a), which is used in the method for detecting a target substance according to the fourth embodiment is a "second photoisomerization-treated complex (hybrid)" which is immobilized on the basal material for immobilization 4 and is modified with the labeling material 6, in similar manner to the complex (hybrid) 11, as illustrated in FIG. 5(a), which is used in the method for detecting a target substance according to the third embodiment. Thus, in similar to the complex (hybrid) 11, as illustrated in FIG. 5(a), which can be used as an assay kit for a target substance and a sensor for detection of a target substance by the application of the method for detecting a target substance according to the third embodiment, the complex (hybrid) 11, as illustrated in FIG. 6(a), can also be used as an assay kit for a target substance and a sensor for detection of a target substance by the application of the method for detecting a target substance according to the fourth embodiment.

In the complex (hybrid) 11 that is used in the method for detecting a target substance according to the fourth embodiment, a nucleotide similar to the "aptamer 1" that is comprised in the complex (hybrid) 11 which is used in the method for detecting a target substance according to the first embodiment may be used as the "aptamer 1 thereof. In the structure illustrated in FIG. 6(a), the end of the double-strand formation site 5 in the "aptamer 1" is linked to the spacer 9 and is immobilized on the surface of the basal material for immobilization 4 via the spacer 9.

The photoisomerizable molecule 5 is bound to the double-strand formation site 5 in the "first nucleic acid fragment 2", and the end of the double-strand formation site 5 is modified with the labeling material 6.

A functional group for use in linkage with the spacer 9 is added to the end of the double-strand formation site 5 in the "aptamer 1" to be linked to the spacer 9. The functional group which is used in linkage with the spacer 9 is not limited as long as the functional group is capable of forming a bond that is not dissociated from the spacer 9 by, for example, the solvent or the pH condition used for detection. A functional group generally available in linkage with the spacer 9 can be used, such as a carboxyl group, an amino group, a thiol group, a disulfide group, a succinimidyl group, a maleimide group, or biotin.

The functional group to be added to the end of the double-strand formation site 5 in the "aptamer 1" can be added to the end thereof during the preparation of a single-stranded nucleic acid molecule including the nucleotide sequence of the "aptamer 1" and the nucleotide sequence of its double-strand formation site 5 by a general nucleotide synthesis method. Alternatively, a starting material nucleic acid molecule that is used in the nucleic acid strand synthesis of the "aptamer 1" may be modified with a commercially available linker or the like, and the resulting nucleotide can be used as such an aptamer 1.

Desirably, the functional group to be added to the "aptamer 1" does not impair the formation of double-stranded nucleotides binding between the double-strand formation site 5 of the aptamer 1 and the double-strand formation site 5 of the "photoisomerizable molecule 3-bound first nucleic acid fragment 2". The functional group may be added to modify an arbitrary site as long as impairing the specific binding between the the "aptamer 1" and the target substance 7 is not induced thereby. For example, the site modified with the functional group may be located at the end of the "aptamer 1" or in the central part thereof.

The functional group that may be used for the purpose of immobilizing the single-stranded nucleic acid molecule onto the basal material for immobilization 4 by chemical bond or chemisorption is not limited as long as the functional group is capable of forming a bond that is not dissociated from the surface of the basal material for immobilization 4 by, for example, the solvent or the pH condition used. A general functional group can be used, such as a carboxyl group, an amino group, a thiol group, a disulfide group, a succinimidyl group, a maleimide group, or biotin. These functional groups can be built in by using a general nucleotide synthesis method, or such functional groups that are built in by modifying the nucleic acid with a commercially available linker or the like may be also used.

The end of the double-strand formation site 5 of the aptamer 1, which is used in the formation of double-stranded nucleotides binding with the double-strand formation site 5 of the "photoisomerizable molecule 3-bound first nucleic acid fragment 2", is linked to the spacer 9, and is immobilized on the surface of the basal material for immobilization 4 via the spacer 9. The length of the spacer 9 is preferably 3 Å or longer, more preferably 10 Å or longer. By selecting the length of the spacer 9 within such a range, reduction in the efficiency of the formation of double-stranded nucleotides binding between the double-strand formation site 5 of the "photoisomerizable molecule 3-bound first nucleic acid fragment 2" and the double-strand formation site 5 of the aptamer 1, which is caused by the steric hindrance between the aptamer 1 and the basal material for immobilization 4, can be prevented.

On the other hand, in the case when the length of the spacer 9 is excessively long, in a sensor for detection of a target substance mentioned later, there is increased distance between a region for detection on the basal material for immobilization 4 and the double-stranded nucleotides binding in the complex (hybrid) 11, and thereby, the detection sensitivity for the "dissolution" of the double-stranded nucleotides binding is affected. In consideration of the influence, the length of the spacer 9 is preferably 200 Å or shorter.

More preferably, the length of the spacer 9 is selected within the range of 10 Å or longer and 50 Å or shorter. The spacer 9 is not particularly limited as long as the spacer 9 does not form an intermolecular bond with the aptamer 1 or the "photoisomerizable molecule 3-bound first nucleic acid fragment 2". A general linker such as a nucleic acid having a non-complementary nucleotide sequence, a glycan, a polypeptide, a hydrocarbon chain, or oligoethylene glycol can be used.

In the method for detecting a target substance according to the fourth embodiment, similar basal material to the basal material for immobilization 4 that is used in the method for detecting a target substance according to the third embodiment is usable for the basal material for immobilization 4. Regarding the method for immobilizing the aptamer 1 onto the basal material for immobilization 4 via the spacer 9, such a technique that is utilized in the method for detecting a target substance according to the third embodiment for the process for immobilizing the "photoisomerizable molecule 3-bound first nucleic acid fragment 2" onto the basal material for immobilization 4 via the spacer 9, can be applied to the aptamer 1, in place of the "photoisomerizable molecule 3-bound first nucleic acid fragment 2".

In the method for detecting a target substance according to the fourth embodiment, quite similar technique to the technique that is used in the method for detecting a target substance according to the third embodiment for detecting the "dissolution" of the double-stranded nucleotides binding between the aptamer 1 and the "photoisomerizable molecule 3-bound first nucleic acid fragment 2" can be used as the method for detecting the "dissolution" of the double-stranded nucleotides binding between the aptamer 1 and the "photoisomerizable molecule 3-bound first nucleic acid fragment 2". Thus, such a technique for detection of the physical or chemical change of the surface of the basal material for immobilization 4, the labeling material 6 being attached in the "photoisomerizable molecule 3-bound first nucleic acid fragment 2", the target substance 7/aptamer 1 complex, which are caused by the "dissolution" of the double-stranded nucleotides binding, can be used. Alternatively, a second photoisomerization-treated "photoisomerizable molecule 3-bound first nucleic acid fragment 2" liberated in the liquid phase that is accompanied with the target substance 7/aptamer 1 complex formation may be detected by means of a DNA detection method, such as a DNA chip or PCR.

In the case when the basal material for immobilization 4 is a device capable of detecting the physical or chemical change in the basal material for immobilization 4, the target substance 7/aptamer 1 complex formation, the labeling material 6 being attached in the "photoisomerizable molecule 3-bound first nucleic acid fragment 2", which are caused by the "dissolution" of the double-stranded nucleotides binding, the complex (hybrid) 11 which is immobilized on the surface of this device can be used as a sensor for detection of a target substance 7 with the aim of detecting whether or not the target substance 7 is present in a sampled specimen.

As to the method for detecting a target substance according to the fourth embodiment, is described above as a method for detecting the "dissolved" state of the double-stranded nucleotides binding in association with the target substance 7/aptamer 1 complex formation is explained above by referring to the case where the aptamer 1 is immobilized on the basal material for immobilization 4. As explained above, in the case where the complex (hybrid) 11 is immobilized onto the basal material for immobilization 4, not only the immobilization of the "photoisomerizable molecule 3-bound first nucleic acid fragment 2" that is used in the method for detecting a target substance according to the third embodiment, but also the immobilization of the aptamer 1 that is used in the method for detecting a target substance according to the fourth embodiment may be suitable.

In the method for detecting a target substance according to the third embodiment and the method for detecting a target substance according to the fourth embodiment, the complex (hybrid) 11 is formed in a form in which only one of the aptamer 1 and the "photoisomerizable molecule 3-bound first nucleic acid fragment 2" is immobilized on the basal material for immobilization 4 while the other member is not immobilized on the basal material for immobilization 4. In the method for detecting a target substance according to the present invention, the complex (hybrid) 11 that is immobilized on the basal material for immobilization is not limited to said structure, and following mode may be usable is in which the "photoisomerizable molecule 3-bound first nucleic acid fragment 2" immobilized on one basal material for immobilization, which is used in the method for detecting a target substance according to the third embodiment, and the aptamer 1 immobilized on another basal material for immobilization, which is used in the method for detecting a target substance according to the fourth embodiment form that the complex (hybrid) 11, and thereby, the immobilization of the complex (hybrid) 11 is attained by using the two basal materials for immobilizations. In such a case, detection of the target substance 7 can be carried out by means of the detection of the "dissolved" state of the double-stranded nucleotides binding in association with the target substance 7/aptamer 1 complex formation, in similar manner to the method for detecting a target substance according to the third embodiment and the method for detecting a target substance according to the fourth embodiment.

The complex (hybrid) 11 immobilized on the surface of the basal material for immobilization 4 that is used in the method for detecting a target substance according to the fourth embodiment is meant to be in the state where: the "photoisomerizable molecule 3-bound first nucleic acid fragment 2" is modified at its end with the labeling material 6; on the other hand, the aptamer 1 is immobilized on the surface of the basal material for immobilization 4 via the spacer 9; and in the case when the target substance 7 is absent in the sampled specimen, after the photoisomerizable molecule 3 is subjected to the second photoisomerization treatment in "the fourth step", double-stranded nucleotides binding can be formed between the double-strand formation site 5 of the aptamer 1 and the double-strand formation site 5 of the second photoisomerization-treated "photoisomerizable molecule 3-bound first nucleic acid fragment 2" at the solution temperature $T_L$ used for the detection process, and thereby, a "second photoisomerization-treated complex (hybrid)" can be formed on the surface of the basal material for immobilization 4. For example, it may be in such a state in which, when the photoisomerizable molecule 3 is subjected to the first photoisomerization treatment at the solution temperature $T_L$ used for the detection process double-stranded nucleotides binding may not be formed between the double-strand formation site 5 of the aptamer 1 and the double-strand formation site 5 of the first photoisomerization-treated "photoisomerizable molecule 3-bound first nucleic acid fragment 2". The complex (hybrid) 11 used in the method for detecting a target substance according to the fourth embodiment also includes a complex (hybrid) 11 in a form in which the aptamer 1 is immobilized on the surface of the basal material for immobilization 4 via the spacer 9 and mixed with the first photoisomerization-treated "photoisomerizable molecule 3-bound first nucleic acid fragment 2" after the preliminary first photoisomerization treatment without forming the double-stranded nucleotides binding between the aptamer 1 and the first photoisomerization-treated "photoisomerizable molecule 3-bound first nucleic acid fragment 2". Therefore, the method for detecting a target substance according to the fourth embodiment includes following mode that employees such form where: the aptamer 1 is immobilized on the surface of the basal material for immobilization 4 via the spacer 9; on the other hand, the first photoisomerization-treated "photoisomerizable molecule 3-bound first nucleic acid fragment 2", which has been subjected to the first photoisomerization treatment in advance, is mixed with the aptamer 1, which is in the state of not forming the double-stranded nucleotides binding. For instance, the method for detecting a target substance according to the fourth embodiment includes following mode where: in the "complex (hybrid) 11 preparation step", such mixture is prepared in which, the aptamer 1 is immobilized on the surface of the basal material for immobilization 4 via the spacer 9; on the other hand, the first photoisomerization-treated "photoisomerizable molecule 3-bound first nucleic acid fragment 2", which has been subjected to the first photoisomerization treatment in advance, is in the state of not forming the double-stranded nucleotides binding with the aptamer 1.

Fifth Embodiment

The method for detecting a target substance according to the fifth embodiment is also an approach based on the application of the "detection principles" used in the method for detecting a target substance according to the first embodiment to the method for detecting a target substance according to the fourth embodiment, so that the description of the same or similar points as those in the method for detecting a target substance according to the first embodiment to the method for detecting a target substance according to the fourth embodiment will be omitted.

Figure 7:
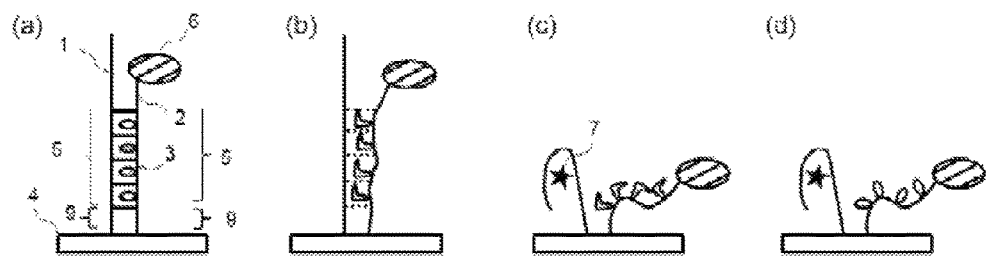
FIG. 7 is a diagram schematically showing the procedures of a method for detecting a target substance using an aptamer immobilized on a basal material for immobilization according to the fifth embodiment. This diagram shows a structure in which a pair of the aptamer and a first nucleic acid fragment is immobilized on the basal material for immobilization.

FIG. 7 is a diagram schematically showing the forms of a complex (hybrid) 11 and procedures corresponding to "the first step" to "the fourth step" in the "detection of the target substance 7", which are used in the method for detecting a target substance according to the fifth embodiment.

The method for detecting a target substance according to the fifth embodiment will be explained with reference to FIG. 7.

In the complex (hybrid) 11 in the structure, as illustrated in FIG. 7(a), which is used in the method for detecting a target substance according to the fifth embodiment, a double-strand formation site 5 in an aptamer 1 and a double-strand formation site 5 in a "photoisomerizable molecule 3-bound first nucleic acid fragment 2" form double-stranded nucleotides binding; and the end of the double-strand formation site 5 in the aptamer 1 is immobilized on a basal material for immobilization 4 by chemical bond or chemisorption via a spacer 9. In addition, the end of the double-strand formation site 5 in the "photoisomerizable molecule 3-bound first nucleic acid fragment 2" is also immobilized on the basal material for immobilization 4 by chemical bond or chemisorption via a spacer 9. The other end of the "photoisomerizable molecule 3-bound first nucleic acid fragment 2" is modified with a labeling material 6. As a result, when the "photoisomerizable molecule 3-bound first nucleic acid fragment 2" is comprised in the complex (hybrid) 11, it is impossible for the labeling material 6 being attached at the other end of the double-strand formation site 5 in the "photoisomerizable molecule 3-bound first nucleic acid fragment 2" to take a position close to the surface of the basal material for immobilization 4, whereas, when the "dissolved" state of the double-stranded nucleotides binding in the complex (hybrid) 11 is attained, it is possible for the labeling material 6 to take a position close to the surface of the basal material for immobilization 4.

When the photoisomerizable molecule 3 is subjected to the first photoisomerization treatment, the stability of the double-stranded nucleotides binding that is formed between the double-strand formation site 5 of the first photoisomerization-treated "photoisomerizable molecule 3-bound first nucleic acid fragment 2" and the double-strand formation site 5 of the aptamer 1 is reduced. That is, the melting temperature $T_{melting-1}$ of the destabilized double-stranded nucleotides binding in the "first photoisomerization-treated complex (hybrid)" which is composed of the first photoisomerization-treated "photoisomerizable molecule 3-bound first nucleic acid fragment 2" and the aptamer 1 is in the state of $T_{melting-1} \ll T_{melting}$, compared with the melting temperature $T_{melting}$ of the double-stranded nucleotides binding in the original complex (hybrid) 11. When subjected to the second photoisomerization treatment, the first photoisomerization-treated "photoisomerizable molecule 3-bound first nucleic acid fragment 2" is converted to a second photoisomerization-treated "photoisomerizable molecule 3-bound first nucleic acid fragment 2". Since the photoisomerizable molecule 3 is reversibly photoisomerized by subjecting to the first photoisomerization treatment and to the second photoisomerization treatment, the double-stranded nucleotides binding which is formed between the double-strand formation site 5 of the second photoisomerization-treated "photoisomerizable molecule 3-bound first nucleic acid fragment 2" and the double-strand formation site 5 of the aptamer 1 is restabilized to the same level as the stability of the double-stranded nucleotides binding in the original complex (hybrid) 11. That is, the melting temperature $T_{melting-2}$ of the restabilized double-stranded nucleotides binding in the "second photoisomerization-treated complex (hybrid)" of the second photoisomerization-treated "photoisomerizable molecule 3-bound first nucleic acid fragment 2" and the aptamer 1 is equal to the melting temperature $T_{melting}$ of the double-stranded nucleotides binding in the original complex (hybrid) 11.

Thus, the melting temperature $T_{melting-1}$ of the destabilized double-stranded nucleotides binding in the "first photoisomerization-treated complex (hybrid)", the melting temperature $T_{melting-2}$ of the restabilized double-stranded nucleotides binding in the "second photoisomerization-treated complex (hybrid)", and the melting temperature $T_{melting-1}$ of the double-stranded nucleotides binding in the original complex (hybrid) 11 satisfy the relationship of $T_{melting-1} \ll T_{melting} = T_{melting-2}$. In the case when the relationship of $T_L < T_{melting-1}$ is satisfied, compared with the solution temperature $T_L$, the thermal dissociation of the destabilized double-stranded nucleotides binding in the "first photoisomerization-treated complex (hybrid)" does not proceed. In such a case, as illustrated in FIG. 7(b), the "first photoisomerization-treated complex (hybrid)" possessing the destabilized double-stranded nucleotides binding is immobilized on the surface of the basal material for immobilization 4.

As compared, the dissociation constant $K_{Dhybrid-1}(T_L)$ of the first photoisomerization-treated complex (hybrid)= [Single-stranded aptamer 1]*[First photoisomerization-treated first nucleic acid fragment 2]/[First photoisomerization-treated complex] and the dissociation constant $K_{Dhybrid-2}(T_L)$ of the second photoisomerization-treated complex (hybrid)=[Single-stranded aptamer 1]*[Second photoisomerization-treated first nucleic acid fragment 2]/ [Second photoisomerization-treated complex] at the solution temperature $T_L$ used for the detection process, they are in the state of $K_{Dhybrid-2}(T_L) \ll K_{Dhybrid-1}(T_L)$. Furthermore, the temperature $T_{aptamer-defolding}$ at which the steric structure of the "aptamer 1 having the steric structure" is thermally dissolved is higher than room temperature (25° C.) and sufficiently lower than $T_{melting-2}$ (25° C. $< T_{aptamer-defolding} \ll T_{melting-2}$). In the case when the solution temperature $T_L$ used for the detection process is selected within the range of 25° C.$< T_L < T_{aptamer-defolding}$, the equilibrium constant $K_{aptamer-defolding}(T_L)$ of the structural change between the "single-stranded aptamer 1" and the "aptamer 1 having the steric structure"=[Single-stranded aptamer 1]/[Aptamer having the steric structure 1] is in at least the relationship of $K_{aptamer-defolding}(T_L) < 1$.

For example, in the case when the solution temperature $T_L$ used for the detection process is set to very slightly lower than the melting temperature $T_{melting-1}$ of the destabilized double-stranded nucleotides binding in the "first photoisomerization-treated complex (hybrid)" ($T_L = T_{melting-1} - \delta T$), when the target substance 7 is contacted with the aptamer 1, which comprised in the "first photoisomerization-treated complex (hybrid)", to induce the partial structural change of the aptamer 1, stabilization energy: $\Delta E_{hybrid-1}$, which originates from "the destabilized double-stranded nucleotides binding", is slightly decreased. As a result, the melting temperature $T_{melting-1}$ is lowered to some extent ($\delta T$) to become ($T_{melting-1} - \delta T$), and thereby, even at the solution temperature $T_L$ used for the detection process, the dissociation of the "first photoisomerization-treated complex (hybrid)" that is accompanied with the contact of the target substance 7 (perturbation: $\delta E$) is induced.

As the solution temperature $T_L$ used for the detection process is very slightly lower than the melting temperature $T_{melting-1}$ of the destabilized double-stranded nucleotides binding in the "first photoisomerization-treated complex (hybrid)", in the case if the target substance 7 is not in contacted therewith, a considerable part of the "first photoisomerization-treated complex (hybrid)" maintains the destabilized double-stranded nucleotides binding without being dissociated.

In the case when the solution temperature $T_L$ used for the detection process is selected within a range where the relationship of $T_{melting-1} < T_L \ll T_{melting-2}$ is satisfied. at the solution temperature $T_L$, the thermal dissociation of the destabilized double-stranded nucleotides binding in the "first photoisomerization-treated complex (hybrid)" proceeds. The "single-stranded aptamer 1" resulting from the thermal dissociation is converted to an "aptamer 1 having the steric structure" which possesses a steric structure essential to specific binding to the target substance 7. The target substance 7 binds to the "aptamer 1 having the steric structure" to form a target substance 7/aptamer 1 complex. As a result, in the case when the solution temperature $T_L$ used for the detection process is selected within a range where the relationship of $T_{melting-1} < T_L \ll T_{melting-2}$ is satisfied, the destabilized double-stranded nucleotides binding in the "first photoisomerization-treated complex (hybrid)" is completely dissociated, and all of target substances 7 bind to "aptamers 1 having the steric structure" to form target substance 7/aptamer 1 complexes.

Since the end of the double-strand formation site 5 of the aptamer 1 is immobilized on the surface of the basal material for immobilization 4 via the spacer 9, in addition to the target substance 7/aptamer 1 complex as illustrated in FIG. 7(c), an "aptamer 1 having the steric structure" and a "single-stranded aptamer 1" that are not used to form the target substance 7/aptamer 1 complex are also immobilized on the surface of the basal material for immobilization 4.

Also, the end of the double-strand formation site 5 of the "photoisomerizable molecule 3-bound first nucleic acid fragment 2" is immobilized on the surface of the basal material for immobilization 4 via the spacer 9. Thus, a first photoisomerization-treated "photoisomerizable molecule 3-bound first nucleic acid fragment 2" resulting from the thermal dissociation of the destabilized double-stranded nucleotides binding in the "first photoisomerization-treated complex (hybrid)" is also immobilized on the surface of the basal material for immobilization 4 via the spacer 9.

In addition, in the case when the dissociation constant $K_{Dcomplex}(T_L)$ of the target substance 7/aptamer 1 complex= [Aptamer having the steric structure 1]*[Target substance 7]/[Complex] satisfies the relationship of $K_{Dcomplex}(T_L) \ll 1$ at the solution temperature $T_L$ used for the detection process, once forming the target substance 7/aptamer 1 complex, as illustrated in FIG. 7(c), the "aptamer 1 having the steric structure" is kept still in the state of the target substance 7/aptamer 1 complex.

When subjected to the second photoisomerization treatment in "the fourth step", the photoisomerizable molecule 3 is photoisomerized, and thereby, the first photoisomerization-treated "photoisomerizable molecule 3-bound first nucleic acid fragment 2" is converted to a second photoisomerization-treated "photoisomerizable molecule 3-bound first nucleic acid fragment 2". The second photoisomerization-treated "photoisomerizable molecule 3-bound first nucleic acid fragment 2" is also immobilized on the surface of the basal material for immobilization 4 via the spacer 9. In such a case, the "aptamer 1 having the steric structure", which is immobilized on the surface of the basal material for immobilization 4 via the spacer 9, at adjacent position to the second photoisomerization-treated "photoisomerizable molecule 3-bound first nucleic acid fragment 2", which is also immobilized, remains in the state of the target substance 7/aptamer 1 complex.

Thus, once forming the target substance 7/aptamer 1 complex, the "aptamer 1 having the steric structure" is not converted to a "single-stranded aptamer 1". Therefore, the second photoisomerization-treated "photoisomerizable molecule 3-bound first nucleic acid fragment 2", which is immobilized on the surface of the basal material for immobilization 4 via the spacer 9, at adjacent position to the "aptamer 1 having the steric structure" that has formed the target substance 7/aptamer 1 complex, cannot form a "second photoisomerization-treated complex (hybrid)" with the "single-stranded aptamer 1", and thereby, is kept in the "dissolved" state of the double-stranded nucleotides binding, as illustrated in FIG. 7(d).

As the "aptamer 1 having the steric structure" that has not formed the target substance 7/aptamer 1 complex is structurally changed thermally to a "single-stranded aptamer 1" according to the equilibrium constant $K_{aptamer-defolding}(T_L)$ at the solution temperature $T_L$ used for the detection process, the resulted "single-stranded aptamer 1" forms a "second photoisomerization-treated complex (hybrid)" with the second photoisomerization-treated "photoisomerizable molecule 3-bound first nucleic acid fragment 2", which is immobilized at adjacent position thereto.

As a result, the target substance 7 that is contained in the sampled specimen is bound to the "aptamer 1 having the steric structure" immobilized on the surface of the basal material for immobilization 4 via the spacer 9, and thereby is immobilized in the form of the target substance 7/aptamer 1 complex on the surface of the basal material for immobilization 4. At a position close to the target substance 7/aptamer 1 complex, the second photoisomerization-treated "photoisomerizable molecule 3-bound first nucleic acid fragment 2" is immobilized in the "dissolved" state of the double-stranded nucleotides binding on the surface of the basal material for immobilization 4 via the spacer 9.

On the other hand, in the case when the target substance 7 is absent in the sampled specimen, any target substance 7/aptamer 1 complex is not formed. Therefore, a "single-stranded aptamer 1", which is converted from the "aptamer 1 having the steric structure" immobilized on the surface of the basal material for immobilization 4 via the spacer 9, and the second photoisomerization-treated "photoisomerizable molecule 3-bound first nucleic acid fragment 2" that is immobilized at a position close to the aptamer 1 form the restabilized double-stranded nucleotides binding to compose a "second photoisomerization-treated complex (hybrid)". Thus, when subjected to the first photoisomerization treatment in "the first step", the "complex (hybrid) 11" that is originally immobilized on the surface of the basal material for immobilization 4 via the spacers 9 is converted to a "first photoisomerization-treated complex (hybrid)". In such a case, in the case when the solution temperature $T_L$ used for the detection process is selected within a range where the relationship of $T_{melting-1} < T_L \ll T_{melting-2}$ is satisfied, the "first photoisomerization-treated complex (hybrid)" is temporarily dissociated by the "dissolution" of its destabilized double-stranded nucleotides binding. As, after that, when subjected to the second photoisomerization treatment in "the fourth step", the photoisomerizable molecule 3 is reversibly photoisomerized, the second photoisomerization-treated "photoisomerizable molecule 3-bound first nucleic acid fragment 2" and the "single-stranded aptamer 1", which are immobilized at the position close to each other, reconstruct the restabilized double-stranded nucleotides binding according to the dissociation constant $K_{Dhybrid-2}(T_L)$ of the second photoisomerization-treated complex (hybrid).

The presence or absence of the "dissolved" state of the double-stranded nucleotides binding, as illustrated in FIG. 7(d), i.e., the second photoisomerization-treated "photoisomerizable molecule 3-bound first nucleic acid fragment 2" that is immobilized at a position close to the target substance 7/aptamer 1 complex on the surface of the basal material for immobilization 4 via the spacer 9, can be detected to thereby detect whether or not the target substance 7 is present in the sampled specimen.

In the complex (hybrid) 11 assembled in the structure as illustrated in FIG. 7(a) that is used in the method for detecting a target substance according to the fifth embodiment, as the photoisomerizable molecule 3 is reversibly photoisomerized by subjecting to the first photoisomerization treatment and the second photoisomerization treatment, both of the original complex (hybrid) 11 and the second photoisomerization-treated complex (hybrid), in which the aptamer 1 and the second photoisomerization-treated "photoisomerizable molecule 3-bound first nucleic acid fragment 2" form stable double-stranded nucleotides binding, are immobilized on the surface of the basal material for immobilization 4 via their spacers 9.

In the structure as illustrated in FIG. 7(a), the molar ratio [Aptamer 1]/[photoisomerizable molecule 3-bound first nucleic acid fragment 2] of the aptamer 1 to the "photoisomerizable molecule 3-bound first nucleic acid fragment 2" is essentially 1 in the complex (hybrid) 11 that is immobilized on the surface of the basal material for immobilization 4 via the spacers 9.

When double-stranded nucleotides binding is formed again after temporal "dissolution" of the double-stranded nucleotides binding, the aptamer 1 and the "photoisomerizable molecule 3-bound first nucleic acid fragment 2" that initially compose the complex (hybrid) 11 can selectively reform the double-stranded nucleotides binding between the original pair of the aptamer 1 and the "photoisomerizable molecule 3-bound first nucleic acid fragment 2". Accordingly, when the "dissolution" of the double-stranded nucleotides binding between this aptamer 1 and the "photoisomerizable molecule 3-bound first nucleic acid fragment 2" that initially compose the complex (hybrid) 11 takes place, and then the aptamer 1 forms a target substance 7/aptamer 1 complex, there is no probability that, in "the fourth step", the second photoisomerization-treated "photoisomerizable molecule 3-bound first nucleic acid fragment 2" forms double-stranded nucleotides binding with another aptamer 1 to form a second photoisomerization-treated complex (hybrid). Thus, background can be reduces and thereby, the detection of the target substance with excellent accuracy can be achieved.

In the case when the target substance 7 is absent in the sampled specimen, when subjected to the first photoisomerization treatment in "the first step", the complex (hybrid) 11 is converted to a "first photoisomerization-treated complex (hybrid)", and in such a case, when the solution temperature $T_L$ used for the detection process is selected within a range where the relationship of $T_{melting-1} < T_L \ll T_{melting-2}$ is satisfied, the destabilized double-stranded nucleotides binding is temporarily "dissolved". When subjected to the second photoisomerization treatment in "the fourth step", the double-stranded nucleotides binding is selectively formed again between the pair of the aptamer 1 and the second photoisomerization-treated "photoisomerizable molecule 3-bound first nucleic acid fragment 2" that initially composes the complex (hybrid) 11.

The nucleotide length of the double-strand formation site 5 in the aptamer 1 can be shortened as long as the nucleotide length of the double-strand formation site 5 in the aptamer 1 is selected within the range where, compared with the solution temperature $T_L$ used for the detection process, the melting temperature $T_{melting-1}$ of the "first photoisomerization-treated complex (hybrid)" and the melting temperature $T_{melting-2}$ of the "second photoisomerization-treated complex (hybrid)" satisfy the relationship of $T_{melting-1} < T_L \ll T_{melting-2}$.

When the complex (hybrid) is converted to the "first photoisomerization-treated complex (hybrid)", and then "first photoisomerization-treated complex (hybrid)" is thermally dissociated to convert the aptamer 1 into a "single-stranded aptamer 1", the melting temperature $T_{melting-1}$ of the "first photoisomerization-treated complex (hybrid)" can be further lowered by shortening nucleotide length of the double-strand formation site 5. Thereby, the "single-stranded aptamer 1" can be converted more efficiently to an "aptamer 1 having the steric structure" essential to binding to the target substance 7. In the case when the melting temperature $T_{melting-1}$ of the "first photoisomerization-treated complex (hybrid)" is further lowered, when the solution temperature $T_L$ used for the detection process is selected within a range where the relationship of $T_{melting-1} < T_L \ll T_{melting-2}$ is satisfied, the solution temperature $T_L$ used for the detection process may be selected from further lower range. When the solution temperature $T_L$ used for the detection process is selected at further lower level, the dissociation constant $K_{Dcomplex}(T_L)$ of the target substance 7/aptamer 1 complex=[Aptamer having the steric structure 1]*[Target substance 7]/[Complex], at the solution temperature $T_L$ used for the detection process, may be further reduced, and thereby, the binding affinity of the aptamer 1 to the target substance 7 (dissociation constant $K_{Dcomplex}(TO)$ is relatively improved. Thus, detection of the target substance with excellent sensitivity can be attained.

In the method for detecting a target substance according to the fifth embodiment, even though, when the complex (hybrid) is converted to an immobilized "first photoisomerization-treated complex (hybrid)" in "the first step", and the solution temperature $T_L$ used for the detection process is selected within a range where the relationship of $T_{melting-1} < T_L \ll T_{melting-2}$ is satisfied, the destabilized double-stranded nucleotides binding in the immobilized "first photoisomerization-treated complex (hybrid)" is wholly "dissolved", when the second photoisomerization treatment is carried out in "the fourth step", the restabilized double-stranded nucleotides binding can be reconstructed, so that the immobilized "second photoisomerization-treated complex (hybrid)" can be completely reconstituted therefrom, Thereby, background drifts can be suppressed.

In the method for detecting a target substance according to the fifth embodiment, the nucleotide length of the double-strand formation site 5 in the aptamer 1, the nucleotide length of the double-strand formation site 5 in the "photoisomerizable molecule 3-bound first nucleic acid fragment 2", and the number of the photoisomerizable molecule 3 to be bound to the site can be suitably determined, so that the solution temperature $T_L$ used for the detection process is selected within a range where the relationship of $T_{melting-1} < T_L \ll T_{melting}$, is satisfied, and the dissociation constant $K_{Dcomplex}(T_L)$ of the target substance 7/aptamer 1 complex falls within an appropriate range. In this view, "design flexibility" is expanded as to the nucleotide length of the double-strand formation site 5 in the aptamer 1, the nucleotide length of the double-strand formation site 5 in the "photoisomerizable molecule 3-bound first nucleic acid fragment 2", and the number of the photoisomerizable molecule 3 to be bound to the site.

In an "assay kit" comprising the complex (hybrid) 11 immobilized on the basal material for immobilization 4, the complex (hybrid) 11 may also be subjected to the first photoisomerization treatment, so as to convert to a "first photoisomerization-treated complex (hybrid)" immobilized on the basal material for immobilization 4. Furthermore, the "first photoisomerization-treated complex (hybrid)" immobilized on the basal material for immobilization 4 may also be temporarily "dissolved", so that the pair of the aptamer 1 and the first photoisomerization-treated "photoisomerizable molecule 3-bound first nucleic acid fragment 2" is immobilized on the basal material for immobilization 4.

When the second photoisomerization treatment is carried out in "the fourth step", the aptamer 1 that has not formed the target substance 7/aptamer 1 complex reconstitutes a "second photoisomerization-treated complex (hybrid)" with the second photoisomerization-treated "photoisomerizable molecule 3-bound first nucleic acid fragment 2" immobilized at a position close thereto. In the case when the concentration of the target substance 7 dissolved in the assay solution is decreased at this stage, some of target substance 7/aptamer 1 complexes are dissociated according to the dissociation constant $K_{Dcomplex}(T_L)$ of the target substance 7/aptamer 1 complex. The aptamer 1 resulting from the dissociation forms a "second photoisomerization-treated complex (hybrid)" with the second photoisomerization-treated "photoisomerizable molecule 3-bound first nucleic acid fragment 2" immobilized adjacently thereto. As a result, the amount of the "aptamer 1 having the steric structure" that has formed the target substance 7/aptamer 1 complex is decreased in association with decrease in the concentration of the target substance 7 that is still dissolved in the assay solution, and the amount of the second photoisomerization-treated "photoisomerizable molecule 3-bound first nucleic acid fragment 2", which is kept in the "dissolved" state, and is immobilized at a position close thereto is also decreased.

In the case if the concentration of the target substance 7 that is still dissolved in the assay solution rises at the point when the reconstitution of the "second photoisomerization-treated complex (hybrid)" is completed by carrying out "the fourth step", the aptamer 1 which is once comprised in the "second photoisomerization-treated complex (hybrid)" cannot converted to an "aptamer 1 having the steric structure" by "dissolving" the restabilized double-stranded nucleotides binding thereof. Therefore, in the case if, at the stage of "the fourth step", the concentration of the target substance 7 which is still dissolved in the assay solution rises, it is impossible to increase the concentration of the target substance 7/aptamer 1 complex in response to the rise in the concentration of the target substance 7.

On the other hand, when subjected to the first photoisomerization treatment, the "second photoisomerization-treated complex (hybrid)" can be converted to a "first photoisomerization-treated complex (hybrid)", and in such a case, when the solution temperature $T_L$ used for the detection process is selected within a range that satisfies the relationship of $T_{melting-1} < T_L \ll T_{melting-2}$, the "first photoisomerization-treated complex (hybrid)" can be converted to an "aptamer 1 having the steric structure" and a first photoisomerization-treated "photoisomerizable molecule 3-bound first nucleic acid fragment 2" by the "dissolution" of the destabilized double-stranded nucleotides binding. In the case when the concentration of the target substance 7 dissolved in the assay solution rises in this state, the resulted "aptamer 1 having the steric structure" can form a target substance 7/aptamer 1 complex according to the dissociation constant $K_{Dcomplex}(T_L)$ of the target substance 7/aptamer 1 complex.

Therefore, by repeatedly carrying out "the first step" to "the fourth step", as illustrated in FIGS. 7(b) to 7(d), the target substance 7/aptamer 1 complex can be formed in response to the concentration of the target substance 7 that is dissolved in the assay solution, both for the case when the concentration of the target substance 7 that is dissolved in the assay solution is increased, as well as for the case when the concentration of the target substance 7 that is dissolved in the assay solution is decreased. The repetitive detection of the "dissolved" state of the double-stranded nucleotides binding by repeatedly carrying out "the first step" to "the fourth step" enables monitoring of time-dependent change in the concentration of the target substance 7 that is dissolved in the assay solution at "fixed time intervals".

When, after the detection is completed in "the fourth step", "washing" is carried out in order to set the concentration of the target substance 7 that is dissolved in the assay solution to "zero", all the target substance 7/aptamer 1 complexes are dissociated, and thereby, such a state that only the "second photoisomerization-treated complex (hybrid)" is immobilized on the surface of the basal material for immobilization 4, i.e. the state as illustrated in FIG. 7(a), is regained. In other words, when, after the detection is completed, the surface of the "assay kit" is washed out by means of a "washing solution" that contains no target substance 7, the surface of the "assay kit" can be recovered back to the state where only the "second photoisomerization-treated complex (hybrid)" is immobilized on the surface of the basal material for immobilization 4. The recovered assay kit can be "recycled".

In the method for detecting a target substance according to the fifth embodiment, employs the complex (hybrid) 11 that is immobilized on the basal material for immobilization 4 is employed. In such a case, the technique, which is used for immobilizing the aptamer 1 onto the basal material for immobilization 4 via the spacer 9 in the method for detecting a target substance according to the fourth embodiment, may be also applied as a method for immobilizing the aptamer 1 onto the basal material for immobilization 4 via the spacer 9. Typically, the aptamer 1 comprises a nucleotide sequence suitable for forming the steric structure essential to specific binding to the target substance 7, and its double-strand formation site 5 that is used in the formation of stable double-stranded nucleotides binding with the second photoisomerization-treated "photoisomerizable molecule 3-bound first nucleic acid fragment 2" comprises a nucleotide sequence complementary to the double-strand formation site 5 in the "photoisomerizable molecule 3-bound first nucleic acid fragment 2". The double-strand formation site 5 in the aptamer 1 has, at its end, a functional group that is used in linkage with the spacer 9 for immobilizing the aptamer 1 onto the basal material for immobilization 4 by chemical bond or chemisorption via the spacer 9.

In the method for detecting a target substance according to the fifth embodiment, the complex (hybrid) 11 that is immobilized on the basal material for immobilization 4 is utilized. In such a case, the technique, which is used for immobilizing the "photoisomerizable molecule 3-bound first nucleic acid fragment 2" onto the basal material for immobilization 4 via the spacer 9 in the method for detecting a target substance according to the third embodiment, can be used as a method of immobilizing the "photoisomerizable molecule 3-bound first nucleic acid fragment 2" onto the basal material for immobilization 4 via the spacer 9. The double-strand formation site 5 of the aptamer 1 and the double-strand formation site 5 of the "photoisomerizable molecule 3-bound first nucleic acid fragment 2" comprise nucleotide sequences complementary to each other, and the end of thereof has a functional group that is used in linkage with the spacer 9 for immobilizing onto the basal material for immobilization 4 by chemical bond or chemisorption via the spacer 9. The "photoisomerizable molecule 3-bound first nucleic acid fragment 2" is modified at the other end with the labeling material 6.

The photoisomerizable molecule 3 is bound to the double-strand formation site 5 in the "photoisomerizable molecule 3-bound first nucleic acid fragment 2". Such a photoisomerizable molecule that is reversibly photoisomerized by subjecting to the first photoisomerization treatment and to the second photoisomerization treatment is used as the photoisomerizable molecule 3. Therefore, the "photoisomerizable molecule 3-bound first nucleic acid fragment 2" that is comprised in the complex (hybrid) 11 immobilized on the basal material for immobilization 4 is equivalent to the second photoisomerization-treated "photoisomerizable molecule 3-bound first nucleic acid fragment 2".

In the complex (hybrid) 11 that is immobilized on the basal material for immobilization 4, the aptamer 1 and the "photoisomerizable molecule 3-bound first nucleic acid fragment 2" are immobilized on the basal material for immobilization 4 via their respective spacers 9 in the state of composing the complex (hybrid). The spacer 9 used for the aptamer 1 and the spacer 9 used for the "photoisomerizable molecule 3-bound first nucleic acid fragment 2" may not have equal lengths as long as the double-strand formation site 5 of the aptamer 1 and the double-strand formation site 5 of the second photoisomerization-treated "photoisomerizable molecule 3-bound first nucleic acid fragment 2" can efficiently form double-stranded nucleotides binding when a "second photoisomerization-treated complex (hybrid)" is formed again therefrom after the dissociation of the "first photoisomerization-treated complex (hybrid)". In general, when both of the lengths of their spacers 9 is equal to each other, efficient formation of double-stranded nucleotides binding can be achieved.

In the method for detecting a target substance according to the fifth embodiment, the target molecule 7 is detected by means of the complex (hybrid) 11 that is immobilized on the basal material for immobilization 4. In such a case, An aptamer 1 or a "photoisomerizable molecule 3-bound first nucleic acid fragment 2", which is not comprised in the complex (hybrid) 11, may be further immobilized on the basal material for immobilization 4 where the complex (hybrid) 11 is immobilized. Thus, the ratio of the aptamer 1 to the "photoisomerizable molecule 3-bound first nucleic acid fragment 2", which are immobilized on the basal material for immobilization 4, are not particularly limited as long as the amount of the complex (hybrid) 11 that is immobilized on the basal material for immobilization 4 is set to a predetermined area density. The ratio can be appropriately set according to the nucleotide sequence of the aptamer 1, the ionic strength of the assay solution, and the solution temperature used for the detection process, etc. The molar ratio of the aptamer 1 to the "photoisomerizable molecule 3-bound first nucleic acid fragment 2, which are immobilized on the basal material for immobilization 4, are preferably between 0.05 and 20 such that the area density of the complex (hybrid) 11 that is immobilized on the basal material for immobilization 4 exceeds the lower limit of the predetermined area density.

The complex (hybrid) 11 immobilized on the surface of the basal material for immobilization 4, which is used in the method for detecting a target substance according to the fifth embodiment, enables detection with excellent detection accuracy and detection sensitivity by using such a structure that the aptamer 1 and the "photoisomerizable molecule 3-bound first nucleic acid fragment 2" is immobilized at a position close to each other on the surface of the basal material for immobilization 4. When detection of the "dissolved" state of the double-stranded nucleotides binding is repeatedly carried out by repeating "the first step" to "the fourth step" at "fixed time intervals", time-dependent change in the concentration of the target substance 7 that is dissolved in the assay solution can be monitored over time. The "assay kit" comprising the complex (hybrid) 11 that is immobilized on the surface of the basal material for immobilization 4 can be easily recovered by "washing" with a "washing solution" that contains no target substance 7 after measurement is completed, and thereby, the "assay kit" can be recycled.

The complex (hybrid) 11 immobilized on the surface of the basal material for immobilization 4, which is used in the method for detecting a target substance according to the fifth embodiment, is meant to be in the state where: in the case when the target substance 7 is absent in the sampled specimen, after the photoisomerizable molecule 3 is subjected to the second photoisomerization treatment in "the fourth step" at the solution temperature $T_L$ used for the detection process, double-stranded nucleotides binding can be formed between the double-strand formation site 5 of the aptamer 1 and the double-strand formation site 5 of the second photoisomerization-treated "photoisomerizable molecule 3-bound first nucleic acid fragment 2", and thereby, a "second photoisomerization-treated complex (hybrid)" can be formed on the surface of the basal material for immobilization 4. For example, it may be in such a state in which, when the photoisomerizable molecule 3 is subjected to the first photoisomerization treatment at the solution temperature $T_L$ used for the detection process, double-stranded nucleotides binding is not be formed between the double-strand formation site 5 of the aptamer 1 and the double-strand formation site 5 of the first photoisomerization-treated "photoisomerizable molecule 3-bound first nucleic acid fragment 2". Therefore, the method for detecting a target substance according to the fifth embodiment includes following mode where: in the "complex (hybrid) 11 preparation step", the aptamer 1 is immobilized on the surface of the basal material for immobilization 4 via the spacer 9; and on the other hand, the first photoisomerization-treated "photoisomerizable molecule 3-bound first nucleic acid fragment 2", which has been subjected to the first photoisomerization treatment in advance, is immobilized at a position close thereto on the surface of the basal material for immobilization 4 via the spacer 9, in the form of not forming the double-stranded nucleotides binding with the aptamer 1.

Sixth Embodiment

The method for detecting a target substance according to the sixth embodiment is also an approach based on the application of the "detection principles" used in the method for detecting a target substance according to the first embodiment to the method for detecting a target substance according to the fifth embodiment, so that the description of the same or similar points as those in the method for detecting a target substance according to the first embodiment to the method for detecting a target substance according to the fifth embodiment will be omitted.

Figure 8:
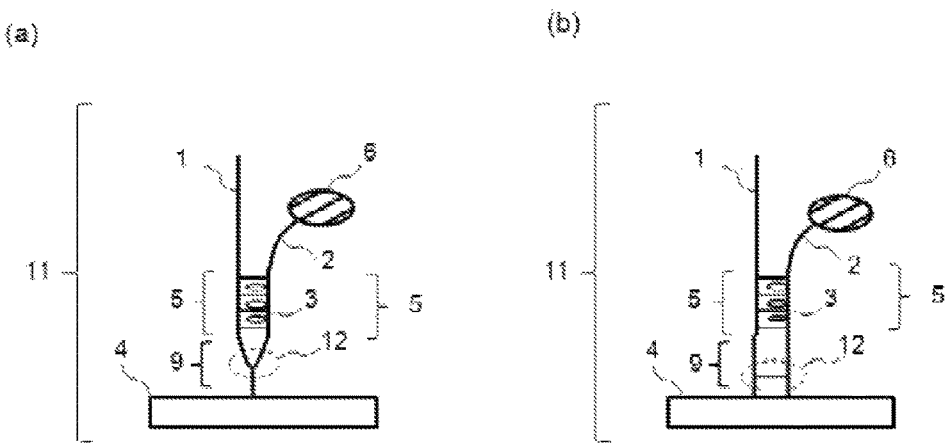
FIG. 8 is a diagram schematically showing the structure of a complex (hybrid) formed by a first nucleic acid fragment and an aptamer linked via a linking portion attached to a spacer for use in the detection of a target substance according to the sixth embodiment. This diagram shows a structure in which the complex (hybrid) is immobilized on a basal material for immobilization by use of the spacer.

FIG. 8 is a diagram schematically showing typical two structures as for the form of a complex (hybrid) 11 that is used in the method for detecting a target substance according to the sixth embodiment.

The method for detecting a target substance according to the sixth embodiment will be explained with reference to FIG. 8.

In the method for detecting a target substance according to the sixth embodiment, the complex (hybrid) 11, as illustrated in FIG. 8(a), has following structure in which: the end of an aptamer 1 and the end of a "photoisomerizable molecule 3-bound first nucleic acid fragment 2" are linked to two branches, respectively, of a spacer 9 having a triply branched linking portion 12; and another branch of the spacer 9 having the branched linking portion 12 is immobilized on a basal material for immobilization 4 by chemical bond or chemisorption. The complex (hybrid) 11, as illustrated in FIG. 8(b), has following structure in which: the end of an aptamer 1 and the end of a "photoisomerizable molecule 3-bound first nucleic acid fragment 2" are linked to two branches, respectively, of a spacer 9 having a ladder-shaped linking portion 12, and two other branches of the spacer 9 having the ladder-shaped linking portion 12 are immobilized on a basal material for immobilization 4 by chemical bond or chemisorption.

In the structure as illustrated in FIG. 8(a), a "conjugate" in which the end of the double-strand formation site 5 in the aptamer 1 and the end of the double-strand formation site 5 in the "photoisomerizable molecule 3-bound first nucleic acid fragment 2" are linked to each other via the spacer 9 having the triply branched linking portion 12 is composed. In the structure as illustrated in FIG. 8(b), a "conjugate" in which the end of the double-strand formation site 5 in the aptamer 1 and the end of the double-strand formation site 5 in the "photoisomerizable molecule 3-bound first nucleic acid fragment 2" are linked to each other via the spacer 9 having the ladder-shaped linking portion 12 is composed.

The double-strand formation site 5 of the aptamer 1 and the double-strand formation site 5 of the "photoisomerizable molecule 3-bound first nucleic acid fragment 2", which compose the "conjugate", possess nucleotide sequences complementary to each other, and thereby, double-stranded nucleotides binding is formed in the "conjugate" to compose the complex (hybrid) 11. Thus, in the case when double-stranded nucleotides binding is formed again after the double-stranded nucleotides binding in the complex (hybrid) 11 is temporally "dissolved", the double-stranded nucleotides binding is selectively formed between the aptamer 1 and the "photoisomerizable molecule 3-bound first nucleic acid fragment 2", which are comprised of the "conjugate", and thereby, the complex (hybrid) 11 is formed in the "conjugate".

The other end of the "photoisomerizable molecule 3-bound first nucleic acid fragment 2" which is comprised in the "conjugate" is modified with a labeling material 6. The photoisomerizable molecule 3 is bound to the double-strand formation site 5 in the "photoisomerizable molecule 3-bound first nucleic acid fragment 2". Such a photoisomerizable molecule which is reversibly photoisomerized when subjected to the first photoisomerization treatment in "the first step" and to the second photoisomerization treatment in "the fourth step" is used as the photoisomerizable molecule 3.

When subjected to the first photoisomerization treatment in "the first step", the photoisomerization of the photoisomerizable molecule 3 in the "photoisomerizable molecule 3-bound first nucleic acid fragment 2" takes place, which is converted thereby to a first photoisomerization-treated "photoisomerizable molecule 3-bound first nucleic acid fragment 2". When the complex (hybrid) 11 composed in the "conjugate" is subjected to the first photoisomerization treatment, the double-stranded nucleotides binding formed between the double-strand formation site 5 of the aptamer 1 and the double-strand formation site 5 of the first photoisomerization-treated "photoisomerizable molecule 3-bound first nucleic acid fragment 2" is destabilized. Thus, the double-stranded nucleotides binding in the "first photoisomerization-treated complex (hybrid)", which is composed of the aptamer 1 and the first photoisomerization-treated "photoisomerizable molecule 3-bound first nucleic acid fragment 2" comprised in the "conjugate", is destabilized.

When subjected to the second photoisomerization treatment, the photoisomerizable molecule 3 in the first photoisomerization-treated "photoisomerizable molecule 3-bound first nucleic acid fragment 2" comprised in the "conjugate" is reversibly photoisomerized, and thereby, the first nucleic acid fragment is in turn converted to a second photoisomerization-treated "photoisomerizable molecule 3-bound first nucleic acid fragment 2". The photoisomerizable molecule 3 in the second photoisomerization-treated "photoisomerizable molecule 3-bound first nucleic acid fragment 2" has the same configuration as that of the photoisomerizable molecule 3 in the original "photoisomerizable molecule 3-bound first nucleic acid fragment 2". Thus, the double-stranded nucleotides binding in the "second photoisomerization-treated complex (hybrid)" which is composed of the aptamer 1 and the second photoisomerization-treated "photoisomerizable molecule 3-bound first nucleic acid fragment 2" that are comprised in the "conjugate" is as stable as the double-stranded nucleotides binding in the original intra-"conjugate" complex (hybrid) 11.

Accordingly, the melting temperature $T_{melting-1}$ of the destabilized double-stranded nucleotides binding in the "first photoisomerization-treated complex (hybrid)" comprised in the "conjugate", the melting temperature $T_{melting-2}$ of the restabilized double-stranded nucleotides binding in the "second photoisomerization-treated complex (hybrid)" comprised in the "conjugate", and the melting temperature $T_{melting}$ of the double-stranded nucleotides binding in the original intra-"conjugate" complex (hybrid) 11 satisfy the relationship of $T_{melting-1} \ll T_{melting} = T_{melting-2}$.

In the method for detecting a target substance according to the sixth embodiment, for example, in the complex (hybrid) 11 that is formed in the "conjugate" as illustrated in FIG. 8(a), the end of the aptamer 1 and the end of the "photoisomerizable molecule 3-bound first nucleic acid fragment 2" are linked by chemical bond to the ends of two branches, respectively, of the spacer 9 having the triply branched linking portion 12. For example, in the complex (hybrid) 11 that is formed in the "conjugate" as illustrated in FIG. 8(b), the end of the aptamer 1 and the end of the "photoisomerizable molecule 3-bound first nucleic acid fragment 2" are linked by chemical bond to the ends of two branches, respectively, of the spacer 9 having the ladder-shaped linking portion 12.

Preferably, the distance between the ends of two branches of the spacer 9 having the triply branched or ladder-shaped linking portion 12, which is used to link the end of the aptamer 1 and the end of the "photoisomerizable molecule 3-bound first nucleic acid fragment 2", is selected on the basis of criteria similar to those for the length of the spacer 9 in the "conjugate", as illustrated in FIG. 4(a), which is used in the method for detecting a target substance according to the second embodiment. Also preferably, such a technique similar to that employed in the method for detecting a target substance according to the second embodiment for linking the end of the aptamer 1 and the end of the "photoisomerizable molecule 3-bound first nucleic acid fragment 2" to the spacer 9 in the "conjugate", as illustrated in FIG. 4(a), is used as the method for linking the end of the aptamer 1 and the end of the "photoisomerizable molecule 3-bound first nucleic acid fragment 2" respectively to the ends of the branches of the spacer 9 having the linking portion 12.

In the complex (hybrid) 11 that is formed in the "conjugate" as illustrated in FIG. 8(a), preferably, such a technique similar to those employed for immobilizing the end of the spacer 9 onto the basal material for immobilization 4 by chemical bond or chemisorption in the complex (hybrid) 11, as illustrated in FIG. 5(a), in the method for detecting a target substance according to the third embodiment or in the complex (hybrid) 11, as illustrated in FIG. 6(a), in the method for detecting a target substance according to the fourth embodiment is used as the method for immobilizing the end of one branch of the spacer 9 having the triply branched linking portion 12 onto the basal material for immobilization 4 by chemical bond or chemisorption.

In the complex (hybrid) 11 that is formed in the "conjugate" as illustrated in FIG. 8(b), preferably, such a technique similar to those employed in the complex (hybrid) 11, as illustrated in FIG. 7(a), which is used in the method for detecting a target substance according to the fifth embodiment, for immobilizing the end of the spacer 9 in the aptamer 1 and the end of the spacer 9 in the "photoisomerizable molecule 3-bound first nucleic acid fragment 2" at positions close to each other onto the basal material for immobilization 4 by chemical bond or chemisorption is used as the method for immobilizing the ends of two branches of the spacer 9 having the ladder-shaped linking portion 12 onto the basal material for immobilization 4 by chemical bond or chemisorption.

In the method for detecting a target substance according to the sixth embodiment, the complex (hybrid) 11 that is formed in the "conjugate" is immobilized on the basal material for immobilization 4 via the spacer 9 having the triply branched linking portion 12 or the spacer 9 having the ladder-shaped linking portion 12, and thus, in similar to the complex (hybrid) 11, as illustrated in FIG. 7(a), which is uses in the method for detecting a target substance according to the fifth embodiment, the aptamer 1 and the "photoisomerizable molecule 3-bound first nucleic acid fragment 2" that compose the complex (hybrid) 11 are kept in the "relative configuration" suitable for the selective reconstruction of double-stranded nucleotides binding between their double-strand formation sites 5. Therefore, in the method for detecting a target substance according to the sixth embodiment, use of the intra-"conjugate" formed complex (hybrid) 11 that is immobilized on the basal material for immobilization 4 exerts effects similar to those brought about by use of the complex (hybrid) 11 that is immobilized on the basal material for immobilization 4 via two spacers 9 in the method for detecting a target substance according to the fifth embodiment. In similar to the method for detecting a target substance according to the fifth embodiment, in the method for detecting a target substance according to the sixth embodiment, background in the detection of the "dissolved" state of the double-stranded nucleotides binding in the complex (hybrid) 11 can be reduced, and thereby, detection of the target substance with excellent accuracy can be achieved. The detection of the target substance with excellent sensitivity can be achieved.

When the method for detecting a target substance according to the sixth embodiment is applied to an "assay kit", the complex (hybrid) 11 that is formed in the "conjugate" is immobilized on the basal material for immobilization 4 via the spacer 9 having the linking portion 12. In such a case, the ratio of the aptamer 1 to the "photoisomerizable molecule 3-bound first nucleic acid fragment 2", which comprise the "conjugate", are accurately controlled by the shape of the spacer 9 having the linking portion 12 to be used. Thus, variation in the ratio of the aptamer 1 to the "photoisomerizable molecule 3-bound first nucleic acid fragment 2" that are immobilized on the basal material for immobilization 4, which are comprised in the "assay kit", is reduced. In a "sensor chip" that employs a device for use in detection as the basal material for immobilization 4, the variation in the ratio of the aptamer 1 to the "photoisomerizable molecule 3-bound first nucleic acid fragment 2", which are immobilized on the surface of the device, is reduced, and thereby, the variation in the production of the "sensor chip" can be reduced to improve yield thereof.

In the "conjugate" in the structure illustrated in FIG. 8(a) or illustrated in FIG. 8(b), which is used in the method for detecting a target substance according to the sixth embodiment, one aptamer 1 and one "photoisomerizable molecule 3-bound first nucleic acid fragment 2" are linked with the spacer 9 having the linking portion 12. In similar to the structure illustrated in FIG. 4(b) for use in the method for detecting a target substance according to the second embodiment, another structure of the "conjugate" may be employed in which one aptamer 1 is linked to a plurality of "photoisomerizable molecule 3-bound first nucleic acid fragments 2" via the spacer 9 having the linking portion 12; and any of these "photoisomerizable molecule 3-bound first nucleic acid fragments 2" and the aptamer 1 compose a complex (hybrid) 11, which is immobilized on the basal material for immobilization 4 via the spacer 9 having the linking portion 12.

In the structure as illustrated in FIG. 8(a), which is used in the method for detecting a target substance according to the sixth embodiment, the complex (hybrid) 11 is immobilized on the basal material for immobilization 4 via the end of one branch of the spacer 9 having the triply branched linking portion 12. In place of the spacer 9 having the triply branched linking portion 12, a spacer 9 having a multi-branched linking portion 12 may be employed to immobilize the complex (hybrid) 11 on the basal material for immobilization 4 via the ends of a plurality of branches thereof.

In the method for detecting a target substance according to the sixth embodiment, a basal material similar to the basal material for immobilization 4 that is used for immobilizing the end of the spacer 9 in the method for detecting a target substance according to the third embodiment to the method for detecting a target substance according to the fifth embodiment may be used as the basal material for immobilization 4, onto whose surface the end(s) of the branch(es) of the spacer 9 having the linking portion 12 is immobilized. If necessary, a functional group which is used for the immobilization of the end(s) of the spacer(s) 9 may be introduced on the surface of the basal material for immobilization 4.

In the process for immobilizing the end(s) of the branch(es) of the spacer 9 having the linking portion 12 onto the surface of the basal material for immobilization 4, a linker having such a functional group, which is used for the immobilization to the surface of the basal material for immobilization 4, is not particularly limited, and various commercially available reagents for the immobilization may be used. For example, Dithiol Phosphoramidite (manufactured by Glen Research Corp.) may be used as the reagent for the immobilization.

The length of the spacer 9 having the linking portion 12 is not particularly limited and is preferably 3 Å or longer for preventing steric hindrance from being induced during the formation of double-stranded nucleotides binding between the aptamer 1 and the "photoisomerizable molecule 3-bound first nucleic acid fragment 2". On the other hand, the length of the spacer 9 having the linking portion 12 is preferably selected within the range of 200 Å or shorter in order to prevent loss of "enrichment effects" which is attained by the orientation to position the aptamer 1 close to "photoisomerizable molecule 3-bound first nucleic acid fragment 2" which compose the "conjugate".

The intra-"conjugate" complex (hybrid) 11 immobilized on the surface of the basal material for immobilization 4 that is used in the method for detecting a target substance according to the sixth embodiment is meant to be in the state where: in the case when the target substance 7 is absent in the sampled specimen, after the photoisomerizable molecule 3 is subjected to the second photoisomerization treatment in "the fourth step" at the solution temperature $T_L$ used for the detection process, double-stranded nucleotides binding is formed between the double-strand formation site 5 of the aptamer 1 and the double-strand formation site 5 of the second photoisomerization-treated "photoisomerizable molecule 3-bound first nucleic acid fragment 2", and thereby, an intra-"conjugate" "second photoisomerization-treated complex (hybrid)" can be formed on the surface of the basal material for immobilization 4. For example, it may be in such a state in which, when the photoisomerizable molecule 3 is the first photoisomerization treatment at the solution temperature $T_L$ used for the detection process, double-stranded nucleotides binding is not formed between the double-strand formation site 5 of the aptamer 1 and the double-strand formation site 5 of the first photoisomerization-treated "photoisomerizable molecule 3-bound first nucleic acid fragment 2", which are comprised in the "conjugate". Therefore, the method for detecting a target substance according to the sixth embodiment includes following mode where: in the "complex (hybrid) 11 preparation step", the aptamer 1 and first photoisomerization-treated "photoisomerizable molecule 3-bound first nucleic acid fragment 2", which has been subjected to the first photoisomerization treatment in advance, are immobilized on the surface of the basal material for immobilization 4 via the spacer 9 having the linking portion 12, in the state of not forming the double-stranded nucleotides binding.

Seventh Embodiment

The method for detecting a target substance according to the seventh embodiment is also an approach based on the application of the "detection principles" used in the method for detecting a target substance according to the first embodiment to the method for detecting a target substance according to the sixth embodiment, so that the description of the same or similar points as those in the method for detecting a target substance according to the first embodiment to the method for detecting a target substance according to the sixth embodiment will be omitted.

Figure 9:
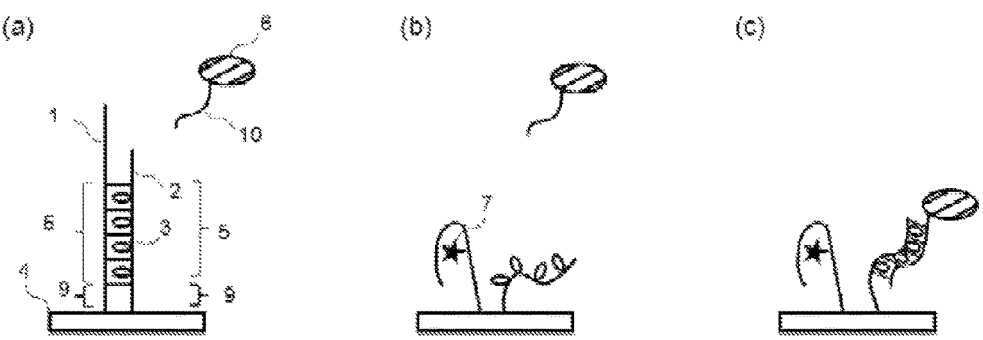
FIG. 9 is a diagram schematically showing the procedures of a method for detecting a target substance using an aptamer immobilized on a basal material for immobilization according to the seventh embodiment. This diagram shows procedures of immobilizing a pair of the aptamer and a first nucleic acid fragment onto a basal material for immobilization and detecting a first nucleic acid fragment not forming a complex (unhybridized) with the aptamer by use of a probe hybridization method using a second nucleic acid fragment.

FIG. 9 is a diagram schematically showing the forms of a complex (hybrid) 11, procedures corresponding to "the first step" to "the fourth step" in the "detection of the target substance 7", and an approach of detecting a second photoisomerization-treated "photoisomerizable molecule 3-bound first nucleic acid fragment 2" by means of a second nucleic acid fragment 10, which are used in the method for detecting a target substance according to the seventh embodiment.

The method for detecting a target substance according to the seventh embodiment will be explained with reference to FIG. 9.

In the complex (hybrid) 11 in the structure illustrated in FIG. 9(a) that is used in the method for detecting a target substance according to the seventh embodiment, a double-strand formation site 5 in an aptamer 1 and a double-strand formation site 5 in a "photoisomerizable molecule 3-bound first nucleic acid fragment 2" form double-stranded nucleotides binding; and the end of the double-strand formation site 5 in the aptamer 1 is immobilized on a basal material for immobilization 4 by chemical bond or chemisorption via a spacer 9. In addition, the end of the double-strand formation site 5 in the "photoisomerizable molecule 3-bound first nucleic acid fragment 2" is also immobilized on the basal material for immobilization 4 by chemical bond or chemisorption via a spacer 9.

The photoisomerizable molecule 3 is bound to the double-strand formation site 5 in the "photoisomerizable molecule 3-bound first nucleic acid fragment 2". Such a photoisomerizable molecule that is reversibly photoisomerized when subjected to the first photoisomerization treatment in "the first step" and to the second photoisomerization treatment in "the fourth step" is used as the photoisomerizable molecule 3.

When the photoisomerizable molecule 3 is subjected to the first photoisomerization treatment, the stability of the double-stranded nucleotides binding which are formed between the double-strand formation site 5 of the first photoisomerization-treated "photoisomerizable molecule 3-bound first nucleic acid fragment 2" and the double-strand formation site 5 of the aptamer 1 is reduced. That is, the melting temperature $T_{melting-1}$ of the destabilized double-stranded nucleotides binding in the "first photoisomerization-treated complex (hybrid)" which is composed of the first photoisomerization-treated "photoisomerizable molecule 3-bound first nucleic acid fragment 2" and the aptamer 1 is in the state of $T_{melting-1} \ll T_{melting}$, compared with the melting temperature $T_{melting}$ of the double-stranded nucleotides binding in the original complex (hybrid) 11. When subjected to the second photoisomerization treatment, the first photoisomerization-treated "photoisomerizable molecule 3-bound first nucleic acid fragment 2" is converted to a second photoisomerization-treated "photoisomerizable molecule 3-bound first nucleic acid fragment 2". Since the photoisomerizable molecule 3 is reversibly photoisomerized by subjecting to the first photoisomerization treatment and to the second photoisomerization treatment, the double-stranded nucleotides binding that is formed between the double-strand formation site 5 of the second photoisomerization-treated "photoisomerizable molecule 3-bound first nucleic acid fragment 2" and the double-strand formation site 5 of the aptamer 1 is restabilized to the same level as the stability of the double-stranded nucleotides binding in the original complex (hybrid) 11. Thus, the melting temperature $T_{melting-2}$ of the restabilized double-stranded nucleotides binding in the "second photoisomerization-treated complex (hybrid)" that is of the second photoisomerization-treated "photoisomerizable molecule 3-bound first nucleic acid fragment 2" and the aptamer 1 is equal to the melting temperature $T_{melting}$ of the double-stranded nucleotides binding in the original complex (hybrid) 11.

Accordingly, the melting temperature $T_{melting-1}$ of the destabilized double-stranded nucleotides binding in the "first photoisomerization-treated complex (hybrid)", the melting temperature $T_{melting-2}$ of the restabilized double-stranded nucleotides binding in the "second photoisomerization-treated complex (hybrid)", and the melting temperature $T_{melting}$ the double-stranded nucleotides binding in the original complex (hybrid) 11 satisfy the relationship of $T_{melting-1} \ll T_{melting} = T_{melting-2}$.

In similar to the complex (hybrid) 11 immobilized on the basal material for immobilization 4, as illustrated in FIG. 7(a), that is used in the method for detecting a target substance according to the fifth embodiment, in the complex (hybrid) 11 immobilized on the basal material for immobilization 4 that is used in the method for detecting a target substance according to the seventh embodiment, when a solution temperature $T_L$ used for the detection process is selected within a range that satisfies the relationship of $T_{melting-1} < T_L \ll T_{melting-2}$, and "the first step" to "the fourth step" are carried out, in the case when the target substance 7 is present in the sample for detection, a target substance 7/aptamer 1 complex is formed, and, in association with the formation, as illustrated in FIG. 9(b), a second photoisomerization-treated "photoisomerizable molecule 3-bound first nucleic acid fragment 2" that is in the "dissolved" state of the double-stranded nucleotides binding, which is immobilized on the basal material for immobilization 4, results therefrom.

In the method for detecting a target substance according to the seventh embodiment, the second photoisomerization-treated "photoisomerizable molecule 3-bound first nucleic acid fragment 2" is detected by means of a second nucleic acid fragment 10. The second nucleic acid fragment 10 comprises a nucleotide sequence complementary to the double-strand formation site 5 of the "photoisomerizable molecule 3-bound first nucleic acid fragment 2"; and the end thereof is modified with a labeling material 6. Thus, as the second nucleic acid fragment 10 comprises the same nucleotide sequence as that of the double-strand formation site 5 of the aptamer 1, the second nucleic acid fragment 10 can form stable double-stranded nucleotides binding, as illustrated in FIG. 9(c), with the double-strand formation site 5 of the second photoisomerization-treated "photoisomerizable molecule 3-bound first nucleic acid fragment 2". The melting temperature $T_{melting-3}$ of the double-stranded nucleotides binding in this complex (hybrid) that is composed of the second photoisomerization-treated "photoisomerizable molecule 3-bound first nucleic acid fragment 2" and the second nucleic acid fragment 10 is equal to the melting temperature $T_{melting}$ of the double-stranded nucleotides binding in the original complex (hybrid) 11. Also, double-stranded nucleotides binding that is formed between the second nucleic acid fragment 10 and the double-strand formation site 5 of the first photoisomerization-treated "photoisomerizable molecule 3-bound first nucleic acid fragment 2" is destabilized, in similar to the double-stranded nucleotides binding in the "first photoisomerization-treated complex (hybrid)". Thus, the melting temperature $T_{melting-4}$ of the destabilized double-stranded nucleotides binding in the complex (hybrid) that is composed of the first photoisomerization-treated "photoisomerizable molecule 3-bound first nucleic acid fragment 2" and the second nucleic acid fragment 10 is equal to the melting temperature $T_{melting-1}$ of the destabilized double-stranded nucleotides binding in the "first photoisomerization-treated complex (hybrid)". Hence, the relationship of $T_{melting-1} = T_{melting-4} \ll T_{melting} = T_{melting-3} = T_{melting-2}$ is satisfied.

When comparing the dissociation constant $K_{Dhybrid-1}(T_L)$ of the first photoisomerization-treated complex (hybrid)=[Single-stranded aptamer 1]*[First photoisomerization-treated first nucleic acid fragment 2]/[First photoisomerization-treated complex] and the dissociation constant $K_{Dhybrid-2}(T_L)$ of the second photoisomerization-treated complex (hybrid)=[Single-stranded aptamer 1]*[Second photoisomerization-treated first nucleic acid fragment 2]/[Second photoisomerization-treated complex], such a state of $K_{Dhybrid-2}(T_L) \ll K_{Dhybrid-1}(T_L)$ is attained at the solution temperature $T_L$ used for the detection process.

When comparing the dissociation constant $K_{Dhybrid-4}(T_L)$ of the complex (hybrid) that is composed of the first photoisomerization-treated "photoisomerizable molecule 3-bound first nucleic acid fragment 2" and the second nucleic acid fragment 10=[Second nucleic acid fragment 10]*[First photoisomerization-treated first nucleic acid fragment 2]/[Complex of the first photoisomerization-treated first nucleic acid fragment 2 and the second nucleic acid fragment 10] and the dissociation constant $K_{Dhybrid-3}(T_L)$ of the complex (hybrid) that is composed of the second photoisomerization-treated "photoisomerizable molecule 3-bound first nucleic acid fragment 2" and the second nucleic acid fragment 10=[Second nucleic acid fragment 10]*[Second photoisomerization-treated first nucleic acid fragment 2]/[Complex of the second photoisomerization-treated first nucleic acid fragment 2 and the second nucleic acid fragment 10], such a state of $K_{Dhybrid-3}(T_L) \ll K_{Dhybrid-4}(T_L)$ is attained at the solution temperature $T_L$ used for the detection process.

In the case when no target substance 7/aptamer 1 complex is formed at the solution temperature $T_L$ used for the detection process, the respective local area densities, [Second photoisomerization-treated first nucleic acid fragment 2]$_S$ and [Single-stranded aptamer 1]$_S$, of the "second photoisomerization-treated first nucleic acid fragment 2" and the "single-stranded aptamer 1" which are immobilized at positions close to each other on the surface of the basal material for immobilization 4 are substantially equal.

As, at the solution temperature $T_L$ used for the detection process, second nucleic acid fragments 10 are uniformly dissolved in the liquid phase, the local area density [Second nucleic acid fragment 10]$_S$ of the "second nucleic acid fragment 10" which is close to the "second photoisomerization-treated first nucleic acid fragment 2" that is immobilized on the surface of the basal material for immobilization 4 is in such a state of [Second nucleic acid fragment 10]$_S \ll$ [Single-stranded aptamer 1]$_S$, compared with the local area density [Single-stranded aptamer 1]$_S$ of the "single-stranded aptamer 1".

In a region where the target substance 7/aptamer 1 complex is formed at the solution temperature $T_L$ used for the detection process, the local area density of the "single-stranded aptamer 1" capable of reconstructing a complex (hybrid) with the "second photoisomerization-treated first nucleic acid fragment 2" that is immobilized at a position close thereto on the surface of the basal material for immobilization 4 is [Single-stranded aptamer 1]$_S$=0. Thus, in the region where the target substance 7/aptamer 1 complex is formed, the local area density [Second nucleic acid fragment 10]$_S$ of the "second nucleic acid fragment 10" is in such a stage of 0=[Single-stranded aptamer 1]$_S \ll$ [Second nucleic acid fragment 10]$_S$, compared with the local area density [Single-stranded aptamer 1]$_S$ of the "single-stranded aptamer 1".

Thus, when no target substance 7/aptamer 1 complex is formed at the solution temperature $T_L$ used for the detection process, double-stranded nucleotides binding is reconstructed between the "second photoisomerization-treated first nucleic acid fragment 2" and the "single-stranded aptamer 1" which are immobilized at positions close to each other on the surface of the basal material for immobilization 4 to form a "second photoisomerization-treated complex (hybrid)", and thereby, the formation of double-stranded nucleotides binding between the "second photoisomerization-treated first nucleic acid fragment 2" and the "second nucleic acid fragment 10" is competitively inhibited.

On the other hand, as in the region where the target substance 7/aptamer 1 complex is formed at the solution temperature $T_L$ used for the detection process, the local area density of the "single-stranded aptamer 1" capable of reconstructing a complex (hybrid) with the "second photoisomerization-treated first nucleic acid fragment 2" is [Single-stranded aptamer 1]$_S$=0, and thus, no competitive inhibition is induced, the formation of double-stranded nucleotides binding between the "second photoisomerization-treated first nucleic acid fragment 2" and the "second nucleic acid fragment 10" proceeds selectively.

As a result, the complex (hybrid) that is composed of the second photoisomerization-treated "photoisomerizable molecule 3-bound first nucleic acid fragment 2" and the second nucleic acid fragment 10 is selectively formed only in the region where the target substance 7/aptamer 1 complex is formed, whereas only the "second photoisomerization-treated complex (hybrid)" is formed in the region where no target substance 7/aptamer 1 complex is formed.

In the method for detecting a target substance according to the seventh embodiment, though the aptamer 1 is immobilized on the basal material for immobilization 4, the target substance 7 forms a target substance 7/aptamer 1 complex, as illustrated in FIG. 9(b). Thus, the dissociation constant $K_{Dcomplex-S}(T_L)$ of the target substance 7/aptamer 1 complex=[Aptamer having the steric structure 1]$_S$*[Target substance 7]/[Complex]$_S$ satisfies the condition of $K_{Dcomplex-S}(T_L)$<<[Target substance 7] at the solution temperature $T_L$ used for the detection process. Hence, there is substantially no probability that an "aptamer 1 having the steric structure" is formed in association with the thermal dissociation of the target substance 7/aptamer 1 complex at the solution temperature $T_L$ used for the detection process, and thereafter, the "aptamer 1 having the steric structure" is further converted to a "single-stranded aptamer 1".

Therefore, in the method for detecting a target substance according to the seventh embodiment, after the complex (hybrid) that is composed of the second photoisomerization-treated "photoisomerizable molecule 3-bound first nucleic acid fragment 2" and the second nucleic acid fragment 10 is formed, as illustrated in FIG. 9(c), detection of the "dissolved" state of the double-stranded nucleotides binding in association with the target substance 7/aptamer 1 complex formation is carried out by means of the labeling material 6 being attached at the end of the second nucleic acid fragment 10, which is comprised in the complex (hybrid).

In the case when the solution temperature $T_L$ used for the detection process is selected within a range that satisfies the relationship of $T_{melting-1}=T_{melting-4}<<T_L<<T_{melting}=T_{melting-3}=T_{melting-2}$ and the relationship of 25° C.<$T_L$<$T_{aptamer-defolding}$. At this solution temperature $T_L$ used for the detection process, the destabilized double-stranded nucleotides binding in the "first photoisomerization-treated complex (hybrid)", which is provided as a result of subjecting the complex (hybrid) to the first photoisomerization treatment in "the first step", is thermally "dissolved". Thus, the complex (hybrid) is temporarily converted to a single-stranded aptamer 1" and a first photoisomerization-treated "photoisomerizable molecule 3-bound first nucleic acid fragment 2" which are immobilized at positions close to each other on the surface of the basal material for immobilization 4. The "single-stranded aptamer 1" that is immobilized on the surface of the basal material for immobilization 4 is converted (folded) to an "aptamer 1 having the steric structure" that is immobilized on the surface of the basal material for immobilization 4. At the solution temperature $T_L$ used for the detection process, the destabilized double-stranded nucleotides binding in the complex (hybrid) that is composed of the first photoisomerization-treated "photoisomerizable molecule 3-bound first nucleic acid fragment 2" that is immobilized on the surface of the basal material for immobilization 4 and the second nucleic acid fragment 10 is also thermally "dissolved".

When subjected to the second photoisomerization treatment in "the fourth step", the first photoisomerization-treated "photoisomerizable molecule 3-bound first nucleic acid fragment 2" immobilized on the surface of the basal material for immobilization 4 is converted to a second photoisomerization-treated "photoisomerizable molecule 3-bound first nucleic acid fragment 2". At the solution temperature $T_L$ used for the detection process, only when the process progresses to this stage, the complex (hybrid) of the second photoisomerization-treated "photoisomerizable molecule 3-bound first nucleic acid fragment 2" and the second nucleic acid fragment 10 can be formed.

In other words, the second nucleic acid fragment 10 may be added to the assay solution at the following point where: after the second photoisomerization treatment is carried out in "the fourth step", the "aptamer 1 having the steric structure" that has not formed the target substance 7/aptamer 1 complex is converted to a "single-stranded aptamer 1", and then, the "single-stranded aptamer 1" reconstructs a "second photoisomerization-treated complex (hybrid)" with the second photoisomerization-treated "photoisomerizable molecule 3-bound first nucleic acid fragment 2". Of course, as mentioned above, as the second nucleic acid fragment 10 does not competitively inhibit the process of reconstructing the "second photoisomerization-treated complex (hybrid)", the second nucleic acid fragment 10 may be added to the assay solution prior to "the first step".

The second nucleic acid fragment 10 used in the method for detecting a target substance according to the seventh embodiment is required not to form a complex (hybrid) with the first photoisomerization-treated "photoisomerizable molecule 3-bound first nucleic acid fragment 2", as illustrated in FIG. 9(b), at the solution temperature $T_L$ used for the detection process, but required to be able to form a complex (hybrid) with the second photoisomerization-treated "photoisomerizable molecule 3-bound first nucleic acid fragment 2".

Therefore, the second nucleic acid fragment 10 comprises a nucleotide sequence complementary to the nucleotide sequence of the double-strand formation site 5 bound with the first photoisomerization-treated "photoisomerizable molecule 3" in the first photoisomerization-treated "photoisomerizable molecule 3-bound first nucleic acid fragment 2". Accordingly, the second nucleic acid fragment 10 comprises a nucleotide sequence complementary to the nucleotide sequence of the double-strand formation site 5 bound with the second photoisomerization-treated "photoisomerizable molecule 3" in the second photoisomerization-treated "photoisomerizable molecule 3-bound first nucleic acid fragment 2".

In the case if a complex (hybrid) is formed between the first photoisomerization-treated "photoisomerizable molecule 3-bound first nucleic acid fragment 2" and the second nucleic acid fragment 10, the double-stranded nucleotides binding that is formed by use of the double-strand formation site 5 of the first photoisomerization-treated "photoisomerizable molecule 3-bound first nucleic acid fragment 2" in the complex (hybrid) is destabilized by the first photoisomerization-treated "photoisomerizable molecule 3" bound to this double-strand formation site 5 of the "photoisomerizable molecule 3-bound first nucleic acid fragment 2"; and thus, the melting temperature $T_{melting\text{-}4}$ of the destabilized double-stranded nucleotides binding is equal to the melting temperature $T_{melting\text{-}1}$ of the destabilized double-stranded nucleotides binding in the "first photoisomerization-treated complex (hybrid)" ($T_{melting\text{-}1}=T_{melting\text{-}4}$). Accordingly, in the case when the solution temperature $T_L$ used for the detection process is selected within a range that satisfies the relationship of $T_{melting\text{-}1}=T_{melting\text{-}4}\ll T_L\ll T_{melting\text{-}3}=T_{melting\text{-}2}$ and the relationship of 25° C.$<T_L<T_{aptamer\text{-}defolding}$, the formation of double-stranded nucleotides binding between the double-strand formation site 5 of the first photoisomerization-treated "photoisomerizable molecule 3-bound first nucleic acid fragment 2" and the second nucleic acid fragment 10 does not proceed, as illustrated in FIG. 9(b).

As, in the case when a complex (hybrid) is formed between the second photoisomerization-treated "photoisomerizable molecule 3-bound first nucleic acid fragment 2" and the second nucleic acid fragment 10, the double-stranded nucleotides binding in the complex (hybrid) that is formed by use of the double-strand formation site 5 of the second photoisomerization-treated "photoisomerizable molecule 3-bound first nucleic acid fragment 2" is restabilized, the melting temperature $T_{melting\text{-}3}$ of this restabilized double-stranded nucleotides binding is equal to the melting temperature $T_{melting\text{-}2}$ of the restabilized double-stranded nucleotides binding in the "second photoisomerization-treated complex (hybrid)" ($T_{melting\text{-}2}=T_{melting\text{-}3}$). Therefore, in the case when the solution temperature $T_L$ used for the detection process is selected within a range that satisfies the relationship of $T_{melting\text{-}1}=T_{melting\text{-}4}\ll T_L\ll T_{melting\text{-}3}=T_{melting\text{-}2}$ and the relationship of 25° C.$<T_L<T_{aptamer\text{-}defolding}$, the formation of double-stranded nucleotides binding between the double-strand formation site 5 of the second photoisomerization-treated "photoisomerizable molecule 3-bound first nucleic acid fragment 2", which is immobilized at a position close to the "aptamer 1 having the steric structure" that is comprised in the target substance 7/aptamer 1 complex, on the surface of the basal material for immobilization 4, and the second nucleic acid fragment 10 proceeds.

As illustrated in FIG. 9(c), the complex (hybrid) that is composed of the second photoisomerization-treated "photoisomerizable molecule 3-bound first nucleic acid fragment 2" and the second nucleic acid fragment 10 is immobilized at a position close to the target substance 7/aptamer 1 complex on the surface of the basal material for immobilization 4. The "dissolved" state of the double-stranded nucleotides binding between the aptamer 1 and the second photoisomerization-treated "photoisomerizable molecule 3-bound first nucleic acid fragment 2" is detected by means of detection of the complex (hybrid) that is composed of the second photoisomerization-treated "photoisomerizable molecule 3-bound first nucleic acid fragment 2" and the second nucleic acid fragment 10. In the method for detecting a target substance according to the seventh embodiment, the labeling material 6 which is added in advance to modify the end of the second nucleic acid fragment 10 is used to detect the complex (hybrid) that is of the second photoisomerization-treated "photoisomerizable molecule 3-bound first nucleic acid fragment 2" immobilized on the surface of the basal material for immobilization 4 and the second nucleic acid fragment 10. In such a case, the method for detection using the labeling material 6 is not limited as long as the method is usable to detect physical or chemical change resulting from the labeling material 6 attached to the second nucleic acid fragment 10 that is immobilized on the surface of the basal material for immobilization 4 via the second photoisomerization-treated "photoisomerizable molecule 3-bound first nucleic acid fragment 2". For example, the detection means detection of change in signals such as optical signal, electric signal, or color signal. Thus, the end of the second nucleic acid fragment 10 is modified with the labeling material 6, for example, a fluorescent material, a quencher, an electrochemically reactive material, a polar substance, an enzyme, or a catalyst.

In the method for detecting a target substance according to the seventh embodiment, such a technique similar to the technique that is used to modify the end of the second nucleic acid fragment 10 in advance with the labeling material 6 in the method for detecting a target substance according to the first embodiment to the method for detecting a target substance according to the sixth embodiment can be employed as the technique for modifying the end of the second nucleic acid fragment 10 in advance with the labeling material 6. Thus, in the method for detecting a target substance according to the seventh embodiment, the labeling material 6, with which the end of the first nucleic acid fragment 2 is in advance modified, in the method for detecting a target substance according to the first embodiment to the method for detecting a target substance according to the sixth embodiment, can be attached to the end of the second nucleic acid fragment 10 by means of similar procedures for modification.

In the method for detecting a target substance according to the third embodiment to the method for detecting a target substance according to the sixth embodiment, when the second photoisomerization-treated "photoisomerizable molecule 3-bound first nucleic acid fragment 2" is in a "single-stranded form" rather than forming a complex (hybrid), it is detected by use of the labeling material 6 being attached at the end thereof. In the method for detecting a target substance according to the seventh embodiment, the labeling material 6 is not particularly limited as long as physical or chemical change resulting from the labeling material 6 being attached at the end of the complex (hybrid) can be detected in such a state where the second photoisomerization-treated "photoisomerizable molecule 3-bound first nucleic acid fragment 2" and the second nucleic acid fragment 10 form the complex (hybrid). Thus, as long as the physical or chemical change resulting from the labeling material 6 being attached at the end of the complex (hybrid) can be detected, such a material similar to the labeling material 6, which is used to detect the second photoisomerization-treated "photoisomerizable molecule 3-bound first nucleic acid fragment 2" in a "single-stranded form" in the method for detecting a target substance according to the third embodiment to the method for detecting a target substance according to the sixth embodiment, for example, a chromogenic substance, an electrochemically reactive material, or a catalytic material can be used.

In the case when a chromogenic substance is used as the labeling material 6 to modify in advance the end of the second nucleic acid fragment 10, the chromogenic substance is immobilized on the surface of the basal material for immobilization 4 via the complex (hybrid) that is composed of the second photoisomerization-treated "photoisomerizable molecule 3-bound first nucleic acid fragment 2" and the second nucleic acid fragment 10. As a result, only the surface of the basal material for immobilization 4, on which the chromogenic substance is immobilized, exhibits color change caused by the chromogenic substance. The color change that is caused by the chromogenic substance on the surface of the basal material for immobilization 4 can be easily identified by visual observation or by a simple check using an image sensor. Examples of the chromogenic substance capable of modifying the end of the single-stranded nucleic acid molecule include dyes, colored beads, and fine metal particles, such as gold nanoparticles, on which surface plasmon is generated.

In the case when an electrochemically reactive material is used as the labeling material 6 to modify in advance the end of the second nucleic acid fragment 10, the electrochemically reactive material is immobilized on the surface of the basal material for immobilization 4 via the complex (hybrid) that is composed of the second photoisomerization-treated "photoisomerizable molecule 3-bound first nucleic acid fragment 2" and the second nucleic acid fragment 10. A conductive substance is placed on the basal material for immobilization 4 or in proximity thereto and used as a working electrode to construct an electrochemical cell. In the case where an electric potential is applied between the electrodes in the electrochemical cell, when the electrochemically reactive material immobilized on the surface of the basal material for immobilization 4 via the complex (hybrid) causes electrochemical reaction at the working electrode, the electrochemical reaction can be detected as "current change". The detected "current change" can be converted to the electric signal of "voltage change" using a simple device. Examples of the electrochemically reactive material capable of modifying the end of the single-stranded nucleic acid molecule include metals, metal complexes, quinones and their derivatives, methylene blue and its derivatives, and heterocyclic compounds such as pyrroles, pyridine, and viologen.

In the case when a catalytic material is used as the labeling material 6 to modify in advance the end of the second nucleic acid fragment 10, the catalytic material is immobilized on the surface of the basal material for immobilization 4 via the complex (hybrid) that is composed of the second photoisomerization-treated "photoisomerizable molecule 3-bound first nucleic acid fragment 2" and the second nucleic acid fragment 10. Examples of the catalytic material capable of modifying the end of the single-stranded nucleic acid molecule include: oxidases such as glucose oxidase and bilirubin oxidase; dehydrogenases such as glucose dehydrogenase; coenzyme oxidases such as diaphorase; peroxide reductases such as horseradish peroxidase and catalase; metal catalysts such as Pt and titanium oxide; catalytic nucleic acids such as ribozyme and deoxyribozyme; and aptamers capable of binding to catalytically active substances, such as hemin aptamers. The detection of the catalytic material immobilized on the surface of the basal material for immobilization 4 via the complex (hybrid) is carried out based on the detection of the catalytic activity of the catalytic material, in which, a substrate or an electron transfer mediator for use in the exhibition of the catalytic activity is added at a predetermined concentration to a solution, and the amount of a reaction product resulting from the catalytic activity is detected. When the reaction product resulting from the catalytic activity exhibits light or color, or electrochemical reaction activity, change in the light or color, or in the electrochemical reaction activity is detected.

In the case when a catalytic material is used, when reaction product is "continuously" produced by means of its catalytic activity, so-called "amplification" is attained thereby; and thus, even if the catalytic material is present in very small amount, more highly sensitive detection can be attained by use of the detection of the reaction products.

In the case when the catalytic material is used as the labeling material 6 to modify the end of the second nucleic acid fragment 10, the catalytic material is quantitatively attached to the second nucleic acid fragment 10. In such a case, the catalytic material can be quantitatively attached to the end of the second nucleic acid fragment 10 by means of popular reaction such as amine coupling, gold-thiol reaction, or nucleic acid elongation/synthesis reaction.

In the case when the complex (hybrid) that is composed of the second photoisomerization-treated "photoisomerizable molecule 3-bound first nucleic acid fragment 2" immobilized on the surface of the basal material for immobilization 4 and the second nucleic acid fragment 10 is detected by use of the labeling material 6 being attached at the end of the second nucleic acid fragment 10, the detection should be carried out in such a state that the solution is free from a dissolved second nucleic acid fragment 10 that is modified at its end with the labeling material 6, as illustrated in FIG. 9(c). For example, after the formation of the complex (hybrid) of the second photoisomerization-treated "photoisomerizable molecule 3-bound first nucleic acid fragment 2" and the second nucleic acid fragment 10 is completed, the surface of the basal material for immobilization 4 is washed out such that the concentration of the labeling material 6-modified second nucleic acid fragment 10 remaining in the solution becomes "zero". In addition, the labeling material 6-modified second nucleic acid fragment 10 is prevented from nonselectively adhering onto the surface of the basal material for immobilization 4 without being mediated by the complex (hybrid) that is composed of the second photoisomerization-treated "photoisomerizable molecule 3-bound first nucleic acid fragment 2" and the second nucleic acid fragment 10. Such nonspecific adhesion of the labeling material 6-labeled second nucleic acid fragment 10 is prevented, for example, by subjecting the surface of the basal material for immobilization 4 to the blocking treatment.

Of course, the nucleotide sequence of the second nucleic acid fragment 10 and the type of the labeling material 6 are selected so as to prevent the labeling material 6, as illustrated in FIG. 9(a), from being immobilized onto the surface of the basal material for immobilization 4 through linking with the "second photoisomerization-treated complex (hybrid)", which results from the binding of the labeling material 6-modified second nucleic acid fragment 10 to the "second photoisomerization-treated complex (hybrid)" that is immobilized on the surface of the basal material for immobilization 4 at the solution temperature $T_L$ used for the detection process. Thus, the nucleotide sequence of the second nucleic acid fragment 10 is selected such that the nucleotide sequence of the second nucleic acid fragment 10 is free from a complementary nucleotide sequence capable of forming stable double-stranded nucleotides binding at the solution temperature $T_L$ used for the detection process with a partial nucleotide sequence of a region other than the double-strand formation site 5 of the "single-stranded aptamer 1" that is comprised in the "second photoisomerization-treated complex (hybrid)". Further, the nucleotide sequence of the second nucleic acid fragment 10 is selected so as to prevent the second nucleic acid fragment 10 itself from serving as an aptamer capable of forming any complex with the "second photoisomerization-treated complex (hybrid)" at the solution temperature $T_L$ used for the detection process. Also, employed as the labeling material 6 is such a labeling material that is prevented from forming a complex through a stable intermolecular bond with the "second photoisomerization-treated complex (hybrid)" at the solution temperature $T_L$ used for the detection process. Employed as the labeling material 6 is such a labeling material that is prevented from being immobilized by chemical bond or chemisorption to the end of the "single-stranded aptamer 1" or the second photoisomerization-treated "photoisomerizable molecule 3-bound first nucleic acid fragment 2" which are comprised in the "second photoisomerization-treated complex (hybrid)" at the solution temperature $T_L$ used for the detection process. Furthermore, employed as the labeling material 6 is such a labeling material that is prevented from causing intermolecular binding through the intercalation to the double-stranded nucleotides binding site in the "second photoisomerization-treated complex (hybrid)" at the solution temperature $T_L$ used for the detection process. In addition, some nucleic acid molecules might exceptionally form three-stranded helix in some cases. Thus, employed is such a second nucleic acid fragment 10 that the nucleotide sequence of the second nucleic acid fragment 10 itself is free from a partial nucleotide sequence that forms three-stranded helix with the double-stranded nucleotides binding site in the "second photoisomerization-treated complex (hybrid)" at the solution temperature $T_L$ used for the detection process.

Of course, the nucleotide sequence of the second nucleic acid fragment 10 and the type of the labeling material 6 are selected so as to prevent the labeling material 6-modified second nucleic acid fragment 10 from being dimerized through the partial binding of the nucleic acid strand of the second nucleic acid fragment 10 itself to the labeling material 6 at the solution temperature $T_L$ used for the detection process. Furthermore, the nucleotide sequence of the second nucleic acid fragment 10 is selected so as to prevent the labeling material 6-modified second nucleic acid fragment 10 from being dimerized through intramolecular double-stranded nucleotides binding that is formed between sites functioning as partial sequences complementary to each other, which is accidentally carried by the nucleic acid strand of the second nucleic acid fragment 10 itself, at the solution temperature $T_L$ used for the detection process. In addition, the nucleotide sequence of the second nucleic acid fragment 10 is selected so as to prevent the nucleic acid strand of the second nucleic acid fragment 10 itself from partially forming a steric structure (causing folding), which inhibits the formation of the complex (hybrid) that is composed of the second photoisomerization-treated "photoisomerizable molecule 3-bound first nucleic acid fragment 2" and the second nucleic acid fragment 10 at the solution temperature $T_L$ used for the detection process.

For example, in the case when a catalytic material is used as the labeling material 6, the type of the catalytic material used is selected such that the catalytic reaction for the "second photoisomerization-treated complex (hybrid)" is not induced by the catalytic activity of the catalytic material at the solution temperature $T_L$ used for the detection process.

The nucleotide sequence of the second nucleic acid fragment 10 and the type of the labeling material 6 are selected so as to prevent the labeling material 6, as illustrated in FIG. 9(*b*), from being immobilized onto the surface of the basal material for immobilization 4 through linking with the "target substance 7/aptamer 1 complex", which results from the binding of the labeling material 6-modified second nucleic acid fragment 10 to the "target substance 7/aptamer 1 complex", that is immobilized on the surface of the basal material for immobilization 4 at the solution temperature $T_L$ used for the detection process. Therefore, employed as the labeling material 6 is such a labeling material that is prevented from forming a complex through a stable intermolecular bond with the target substance 7/aptamer 1 complex at the solution temperature $T_L$ used for the detection process. Employed as the labeling material 6 is such a labeling material that is prevented from causing a binding with an "aptamer 1 having the steric structure" by use of a site differing from the target substance 7-binding site in the "aptamer 1 having the steric structure" that is comprised in the target substance 7/aptamer 1 complex at the solution temperature $T_L$ used for the detection process.

Of course, employed as the labeling material 6 is such a labeling material that is prevented from inducing the competitive inhibition against the target substance 7 at the solution temperature $T_L$ used for the detection process, which inhibition is caused by such a phenomenon that the labeling material can also bind, by use of the target substance 7-binding site, to the "aptamer 1 having the steric structure" essential to binding to the target substance 7. Employed as the labeling material 6 is such a labeling material that is prevented from inhibiting the target substance 7/aptamer 1 complex formation, which inhibition is caused by formation of an intermolecular bond between the labeling material 6 and the target substance 7 that is contained in the solution at the solution temperature $T_L$ used for the detection process. In addition, the nucleotide sequence of the second nucleic acid fragment 10 is selected so as to prevent the nucleic acid strand of the second nucleic acid fragment 10 itself from partially forming a steric structure (causing folding), which inhibits the target substance 7/aptamer 1 complex formation at the solution temperature $T_L$ used for the detection process as a result of forming an intermolecular bond between this "second nucleic acid fragment 10 having a steric structure" and the target substance 7 that is contained in the solution.

In addition, the nucleotide sequence of the second nucleic acid fragment 10 and the type of the labeling material 6 are selected so as to prevent the "labeling material 6-modified second nucleic acid fragment 10", as illustrated in FIG. 9(*b*), from forming a complex with the target substance 7 through binding to the target substance 7 at the solution temperature $T_L$ used for the detection process when the target substance 7 is present in the solution.

Furthermore, the nucleotide sequence of the second nucleic acid fragment 10 and the type of the labeling material 6 are selected so as to prevent the "labeling material 6-modified second nucleic acid fragment 10", as illustrated in FIG. 9(*b*), from immobilizing the labeling material 6 onto the surface of the basal material for immobilization 4 through the binding of the "labeling material 6-modified second nucleic acid fragment 10" to a "single-stranded aptamer 1" or an "aptamer 1 having the steric structure" that is provided in association with the "dissolution" of the double-stranded nucleotides binding in the "first photoisomerization-treated complex (hybrid)" at the solution temperature $T_L$ used for the detection process.

In the method for detecting a target substance according to the seventh embodiment, detection of the "dissolved" state of the double-stranded nucleotides binding is carried out, for example, in such a state where the second photoisomerization-treated "photoisomerizable molecule 3-bound first nucleic acid fragment 2" and the second nucleic acid fragment 10 form a complex (hybrid), as illustrated in FIG. 9(c), by use of the labeling material 6 being attached at the end of the complex (hybrid). The second nucleic acid fragment 10 comprises a partial nucleotide sequence complementary to a partial nucleotide sequence of the double-strand formation site 5 in the second photoisomerization-treated "photoisomerizable molecule 3-bound first nucleic acid fragment 2"; and for example, DNA, RNA, or PNA can be used therefor. The nucleotide sequence of the second nucleic acid fragment 10 in general comprises a "non-complementary nucleotide sequence", in addition to the "nucleotide sequence complementary to a partial nucleotide sequence of the double-strand formation site 5". In the nucleotide sequence of the second nucleic acid fragment 10, the "nucleotide sequence complementary to a partial nucleotide sequence of the double-strand formation site 5" may be located at an arbitrary position of the second nucleic acid fragment 10, for example, at the end of the second nucleic acid fragment 10 or in the central part thereof. In the complex (hybrid) that is composed of the second photoisomerization-treated "photoisomerizable molecule 3-bound first nucleic acid fragment 2" and the second nucleic acid fragment 10, as illustrated in FIG. 9(c), the double-strand formation site 5 in the "first nucleic acid fragment 2" is linked to the spacer 9, while the second nucleic acid fragment 10 is provided at one end with the "complementary nucleotide sequence" and modified at the other end with the labeling material 6.

By contrast, a structure may be employed in which the "complementary nucleotide sequence" in the second nucleic acid fragment 10 is placed at the end thereof that is further modified with the labeling material 6. In this structure, the labeling material 6 is retained at a position close to the surface of the basal material for immobilization 4 in the state where the second photoisomerization-treated "photoisomerizable molecule 3-bound first nucleic acid fragment 2" and the second nucleic acid fragment 10 compose the complex (hybrid).

In the method for detecting a target substance according to the seventh embodiment, the second nucleic acid fragment 10 is added, as illustrated in FIG. 9(a), after "the first step" and before "the second step" is carried out. The formation of a complex (hybrid) between the "single-stranded first nucleic acid fragment 2" in the "dissolved" state and the second nucleic acid fragment 10 is therefore required not to proceed essentially when subjected to the first photoisomerization treatment and required to proceed when subjected to the second photoisomerization treatment. For example, in the case if the photoisomerizable molecule 3 is not bound to the "first nucleic acid fragment 2" and is bound only to the "aptamer 1", the "single-stranded first nucleic acid fragment 2" in the "dissolved" state is already capable of forming a complex (hybrid) with the second nucleic acid fragment 10 when subjected to the first photoisomerization treatment, even if the second photoisomerization treatment is not carried out yet. Thus, in the method for detecting a target substance according to the seventh embodiment, employment of such a form is avoided in which the photoisomerizable molecule 3 is not bound to the "first nucleic acid fragment 2" and is bound only to the "aptamer 1". In the case when such a form where some photoisomerizable molecules 3 are bound to the "aptamer 1", while remaining photoisomerizable molecules 3 are bound to the "first nucleic acid fragment 2", at least, the melting temperature $T_{melting\text{-}partial\text{-}4}$ of the destabilized double-stranded nucleotides binding in the complex (hybrid) of the second photoisomerization-treated "photoisomerizable molecule 3-partially bound first nucleic acid fragment 2" and the second nucleic acid fragment 10 must satisfy the condition of $T_{melting\text{-}partial\text{-}4} < T_L$, compared with the solution temperature $T_L$ used for the detection process. It is thus required to select the number of the bound photoisomerizable molecules 3 in the "photoisomerizable molecule 3-partially bound first nucleic acid fragment 2" and the sites modified with the photoisomerizable molecules 3 in the double-strand formation site 5 of the "first nucleic acid fragment 2" so as to satisfy the above condition of $T_{melting\text{-}partial\text{-}4} < T_L$. Of course, the structure illustrated in FIG. 9(a), i.e., the structure in which the photoisomerizable molecule 3 is not bound to the "aptamer 1" and is bound only to the "first nucleic acid fragment 2", is more preferably employed.

In the method for detecting a target substance according to the seventh embodiment, in the case when the target substance 7 is absent in the subject to be assayed (sampled specimen), as no target substance 7/aptamer 1 complex is formed, no complex (hybrid) is formed between a second photoisomerization-treated "photoisomerizable molecule 3-bound first nucleic acid fragment 2", which is immobilized at a position close to a target substance 7/aptamer 1 complex, and the second nucleic acid fragment 10. Thus, whether or not the target substance 7 is present in the subject to be assayed (sampled specimen) can be detected based on the detection of the presence or absence of the complex (hybrid) of the second photoisomerization-treated "photoisomerizable molecule 3-bound first nucleic acid fragment 2" and the second nucleic acid fragment 10.

Therefore, in the method for detecting a target substance according to the seventh embodiment, in the case when the target substance 7 is absent in the subject to be assayed (sampled specimen), as such a phenomenon where the labeling material 6 is immobilized onto the surface of the basal material for immobilization 4 via the complex (hybrid) that is composed of the second photoisomerization-treated "photoisomerizable molecule 3-bound first nucleic acid fragment 2" and the second nucleic acid fragment 10 is excluded, low background levels and high S/N is achieved. As a result, in the method for detecting a target substance according to the seventh embodiment, whether or not the target substance 7 is present in the subject to be assayed (sampled specimen) can be detected with high sensitivity.

Specifically, in the case when the target substance 7 is absent in the subject to be assayed (sampled specimen), when the solution temperature $T_L$ used for the detection process is selected within a range that satisfies the relationship of $T_{melting\text{-}1} = T_{melting\text{-}4} \ll T_L \ll T_{melting} = T_{melting\text{-}3} = T_{melting\text{-}2}$ and the relationship of $25° C. < T_L < T_{aptamer\text{-}defolding}$, the formation of the complex (hybrid) that is composed of the second photoisomerization-treated "photoisomerizable molecule 3-bound first nucleic acid fragment 2" and the second nucleic acid fragment 10 is efficiently inhibited through the competitive reaction of the second nucleic acid fragment 10 with the aptamer 1 that is immobilized on the surface of the basal material for immobilization 4, As the solution temperature $T_L$ used for the detection process is set within the range of $T_{melting\text{-}1} = T_{melting\text{-}4} \ll T_L$ relative to the melting temperature $T_{melting\text{-}1}$ of the destabilized double-stranded nucleotides binding in the complex (hybrid) of the first photoisomerization-treated "photoisomerizable molecule 3-bound first nucleic acid fragment 2" and the aptamer 1 and the melting temperature $T_{melting-4}$ of the destabilized double-stranded nucleotides binding in the complex (hybrid) of the first photoisomerization-treated "photoisomerizable molecule 3-bound first nucleic acid fragment 2" and the second nucleic acid fragment 10, at the solution temperature $T_L$ used for the detection process, both of the complex (hybrid) that is composed of the first photoisomerization-treated "photoisomerizable molecule 3-bound first nucleic acid fragment 2" and the aptamer 1 and the complex (hybrid) that is composed of the first photoisomerization-treated "photoisomerizable molecule 3-bound first nucleic acid fragment 2" and the second nucleic acid fragment 10 are kept in the state of being thermally "dissolved". Thus, the area density of the first photoisomerization-treated "photoisomerizable molecule 3-bound first nucleic acid fragment 2" is much higher (by order of magnitude) than the effective area density of the second nucleic acid fragment 10 on the surface of the basal material for immobilization 4. After that, when subjected to the second photoisomerization treatment, the aptamer 1 that is immobilized on the surface of the basal material for immobilization 4 preferentially forms a complex (hybrid) with the second photoisomerization-treated "photoisomerizable molecule 3-bound first nucleic acid fragment 2" is immobilized at a position close thereto. On the other hand, in the case when the target substance 7 is absent in the subject to be assayed (sampled specimen), as for the second photoisomerization-treated "photoisomerizable molecule 3-bound first nucleic acid fragment 2", which is dissolved in the liquid phase fails to form a complex (hybrid), as a result of the competitively inhibition by the aptamer 1 that is immobilized on the surface of the basal material for immobilization 4, formation of a complex (hybrid) that is composed of the second photoisomerization-treated "photoisomerizable molecule 3-bound first nucleic acid fragment 2 and the" second nucleic acid fragment 10 is not progressed at all.

In the case where the number of base pairs composing the double-stranded nucleotides binding in the complex (hybrid) that is composed of the second photoisomerization-treated "photoisomerizable molecule 3-bound first nucleic acid fragment 2" and the second nucleic acid fragment 10 is larger than the number of base pairs composing the double-stranded nucleotides binding in the "second photoisomerization-treated complex (hybrid)", the melting temperature $T_{melting-3}$ of the double-stranded nucleotides binding in the complex (hybrid) that is composed of the second photoisomerization-treated "photoisomerizable molecule 3-bound first nucleic acid fragment 2" and the second nucleic acid fragment 10 is significantly higher than the melting temperature $T_{melting-2}$ of the double-stranded nucleotides binding in the "second photoisomerization-treated complex (hybrid)" ($T_{melting-2}<T_{melting-3}$). In similar, in the case where the number of base pairs composing the double-stranded nucleotides binding in the complex (hybrid) that is composed of the first photoisomerization-treated "photoisomerizable molecule 3-bound first nucleic acid fragment 2" and the second nucleic acid fragment 10 is larger than the number of base pairs composing the double-stranded nucleotides binding in the "first photoisomerization-treated complex (hybrid)", the melting temperature $T_{melting-4}$ of the double-stranded nucleotides binding in the complex (hybrid) that is composed of the first photoisomerization-treated "photoisomerizable molecule 3-bound first nucleic acid fragment 2" and the second nucleic acid fragment 10 is significantly higher than the melting temperature $T_{melting-1}$ of the double-stranded nucleotides binding in the "first photoisomerization-treated complex (hybrid)" ($T_{melting-1}<T_{melting-4}$). As a result, the order of $T_{melting-1}<T_{melting-4}<T_{melting-2}<T_{melting-3}$ is established.

In the case then the solution temperature $T_L$ used for the detection process is set within the relationship of $T_{melting-1}<T_L<T_{melting-4}<T_{melting-2}<T_{melting-3}$, at the solution temperature $T_L$ used for the detection process, the destabilized double-stranded nucleotides binding in the complex (hybrid) that is composed of the first photoisomerization-treated "photoisomerizable molecule 3-bound first nucleic acid fragment 2" and the aptamer 1 is thermally "dissolved", but the complex (hybrid) that is composed of the first photoisomerization-treated "photoisomerizable molecule 3-bound first nucleic acid fragment 2" and the second nucleic acid fragment 10 is in the state of not being thermally "dissolved". when this state is subjected to the second photoisomerization treatment, the complex (hybrid) that is composed of the first photoisomerization-treated "photoisomerizable molecule 3-bound first nucleic acid fragment 2" and the second nucleic acid fragment 10, which is not thermally "dissolved", is converted to a complex (hybrid) that is composed of the second photoisomerization-treated "photoisomerizable molecule 3-bound first nucleic acid fragment 2" and the second nucleic acid fragment 10. Therefore, in the case if the target substance 7 is absent in the subject to be assayed (sampled specimen), there occurs such a phenomenon where the labeling material 6 is immobilized onto the surface of the basal material for immobilization 4 via the complex (hybrid) that is composed of the second photoisomerization-treated "photoisomerizable molecule 3-bound first nucleic acid fragment 2" and the second nucleic acid fragment 10.

In the method for detecting a target substance according to the seventh embodiment, following approach is selected to prevent the phenomenon where the labeling material 6 is immobilized onto the surface of the basal material for immobilization 4 via the complex (hybrid) that is composed of the second photoisomerization-treated "photoisomerizable molecule 3-bound first nucleic acid fragment 2" and the second nucleic acid fragment 10, even when the target substance 7 is absent in the subject to be assayed (sampled specimen). For this purpose, in the case where the number of base pairs composing the double-stranded nucleotides binding in the complex (hybrid) that is composed of the second photoisomerization-treated "photoisomerizable molecule 3-bound first nucleic acid fragment 2" and the second nucleic acid fragment 10 is equal to the number of base pairs composing the double-stranded nucleotides binding in the "second photoisomerization-treated complex (hybrid)", the melting temperature $T_{melting-3}$ of the double-stranded nucleotides binding in the complex (hybrid) that is composed of the second photoisomerization-treated "photoisomerizable molecule 3-bound first nucleic acid fragment 2" and the second nucleic acid fragment 10 may be set to be equal to the melting temperature $T_{melting-2}$ of the double-stranded nucleotides binding in the "second photoisomerization-treated complex (hybrid)" ($T_{melting-2}=T_{melting-3}$). The number of base pairs composing the double-stranded nucleotides binding in the complex (hybrid) that is composed of the first photoisomerization-treated "photoisomerizable molecule 3-bound first nucleic acid fragment 2" and the second nucleic acid fragment 10 is set to be equal to the number of base pairs composing the double-stranded nucleotides binding in the "first photoisomerization-treated complex (hybrid)", and thereby, the melting temperature $T_{melting-4}$ of the double-stranded nucleotides binding in the complex (hybrid) that is composed of the first photoisomerization-treated "photoisomerizable molecule 3-bound first nucleic acid fragment 2" and the second nucleic acid fragment 10 may be set to be equal to the melting temperature $T_{melting-1}$ of the double-stranded nucleotides binding in the "first photoisomerization-treated complex (hybrid)" ($T_{melting-4}=T_{melting-1}$). As a result, the order of $T_{melting-4}=T_{melting-1}<T_{melting-3}=T_{melting-2}$ is established.

When the solution temperature $T_L$ used for the detection process is selected within a range that satisfies the relationship of $T_{melting-4}=T_{melting-1}<T_L<T_{melting-3}=T_{melting-2}$, in the case if the target substance 7 is absent in the subject to be assayed (sampled specimen), the occurrence of the phenomenon where the labeling material 6 is immobilized onto the surface of the basal material for immobilization 4 via the complex (hybrid) of the second photoisomerization-treated "photoisomerizable molecule 3-bound first nucleic acid fragment 2" and the second nucleic acid fragment 10, can be reliably prevented.

However, in the case where the number of base pairs composing the double-stranded nucleotides binding in the complex (hybrid) that is composed of the second photoisomerization-treated "photoisomerizable molecule 3-bound first nucleic acid fragment 2" and the second nucleic acid fragment 10 is significantly smaller than the number of base pairs composing the double-stranded nucleotides binding in the "second photoisomerization-treated complex (hybrid)", the melting temperature $T_{melting-3}$ of the double-stranded nucleotides binding in the complex (hybrid) that is composed of the second photoisomerization-treated "photoisomerizable molecule 3-bound first nucleic acid fragment 2" and the second nucleic acid fragment 10 is remarkably lower than the melting temperature $T_{melting-2}$ of the double-stranded nucleotides binding in the "second photoisomerization-treated complex (hybrid)" ($T_{melting-3}<<T_{melting-2}$). In similar, in the case when the number of base pairs composing the double-stranded nucleotides binding in the complex (hybrid) that is composed of the first photoisomerization-treated "photoisomerizable molecule 3-bound first nucleic acid fragment 2" and the second nucleic acid fragment 10 is significantly decreased to below the number of base pairs composing the double-stranded nucleotides binding in the "first photoisomerization-treated complex (hybrid)", the melting temperature $T_{melting-4}$ of the double-stranded nucleotides binding in the complex (hybrid) that is composed of the first photoisomerization-treated "photoisomerizable molecule 3-bound first nucleic acid fragment 2" and the second nucleic acid fragment 10 is remarkably lower than the melting temperature $T_{melting-1}$ of the double-stranded nucleotides binding in the "first photoisomerization-treated complex (hybrid)" ($T_{melting-4}<<T_{melting-1}$). As a result, the order of $T_{melting-4}<<T_{melting-3}<T_{melting-1}<<T_{melting-2}$ may be established in some cases.

In such a case, when the solution temperature $T_L$ used for the detection process is selected within a range that satisfies the relationship of $T_{melting-4}<<T_{melting-3}<T_{melting-1}<T_L<<T_{melting-2}$, at the solution temperature $T_L$ used for the detection process, the double-stranded nucleotides binding in the complex (hybrid) that is composed of the second photoisomerization-treated "photoisomerizable molecule 3-bound first nucleic acid fragment 2" and the second nucleic acid fragment 10 is in the state of being thermally "dissolved".

In consideration of those facts, in the method for detecting a target substance according to the seventh embodiment, the number of base pairs composing the double-stranded nucleotides binding in the complex (hybrid) that is composed of the second photoisomerization-treated "photoisomerizable molecule 3-bound first nucleic acid fragment 2" and the second nucleic acid fragment 10 is preferably selected within a range equal to or very slightly smaller than the number of base pairs composing the double-stranded nucleotides binding in the "second photoisomerization-treated complex (hybrid)", more preferably is set to be equal to each other.

The number of base pairs composing the double-stranded nucleotides binding in the complex (hybrid) that is composed of the second photoisomerization-treated "photoisomerizable molecule 3-bound first nucleic acid fragment 2" and the second nucleic acid fragment 10 may be changed depending on, for example, the nucleotide sequences and salt intensities of the aptamer 1 and the first nucleic acid fragment 2. In general, the number of base pairs (the number of complementary nucleobases) composing the double-stranded nucleotides binding is 8 nucleobases or more, only as a guide for values that enable stable binding in a solution. The number of base pairs composing the double-stranded nucleotides binding is selected such that the melting temperature $T_{melting-1}$ of the double-stranded nucleotides binding in the "first photoisomerization-treated complex (hybrid)", the melting temperature $T_{melting-2}$ of the double-stranded nucleotides binding in the "second photoisomerization-treated complex (hybrid)", and the solution temperature $T_L$ used for the detection process satisfy the relationship of $25°C.<T_{melting-1}<T_L<<T_{melting-2}$.

Eighth Embodiment

The method for detecting a target substance according to the eighth embodiment is also an approach based on the application of the "detection principles" used in the method for detecting a target substance according to the first embodiment to the method for detecting a target substance according to the seventh embodiment, so that the description of the same or similar points as those in the method for detecting a target substance according to the first embodiment to the method for detecting a target substance according to the seventh embodiment will be omitted.

Figure 10:
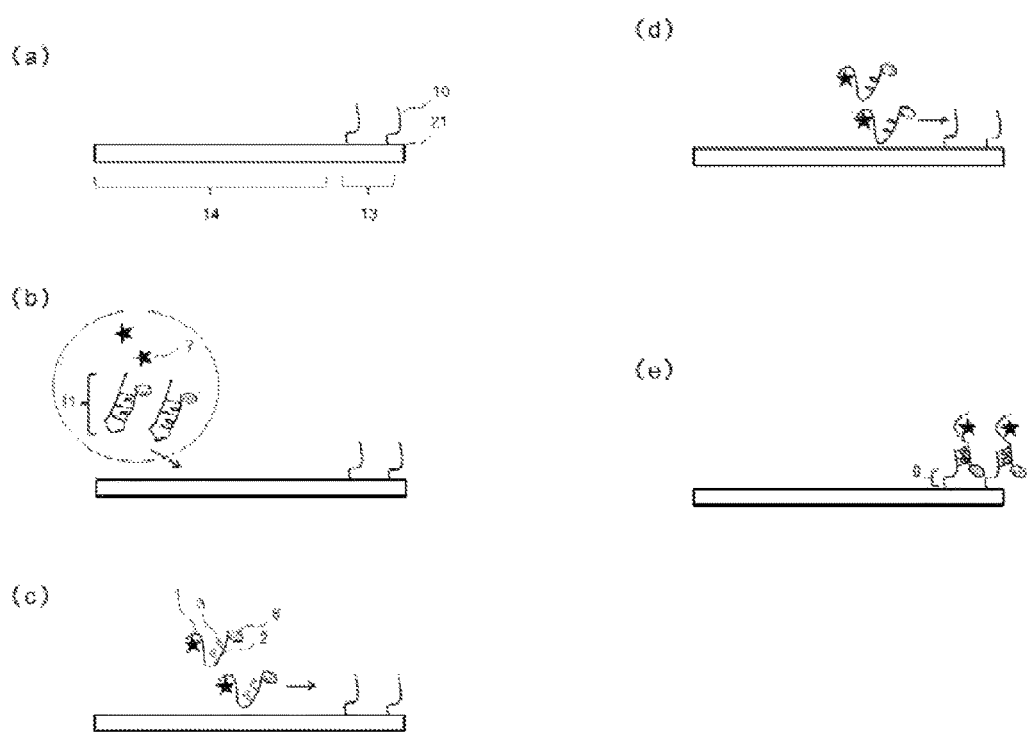
FIG. 10 is a diagram schematically showing the procedures of a method for detecting a target substance using an aptamer linked to a first nucleic acid fragment via a spacer according to the eighth embodiment. This diagram shows procedures of detecting a first nucleic acid fragment not forming a complex (unhybridized) with the aptamer by use of a probe hybridization method using a second nucleic acid fragment immobilized on a region for capture disposed on a solvent-philic substrate.

FIG. 10 is a diagram schematically showing the forms of a complex (hybrid) 11, procedures corresponding to "the first step" to "the fourth step" in the "detection of the target substance 7", and an approach of detecting a second photoisomerization-treated "photoisomerizable molecule 3-bound first nucleic acid fragment 2" by means of a second nucleic acid fragment 10, which are used in the method for detecting a target substance according to the eighth embodiment.

The method for detecting a target substance according to the eighth embodiment will be explained with reference to FIG. 10.

In the method for detecting a target substance according to the eighth embodiment, the second nucleic acid fragment 10 that is use in the detection of the second photoisomerization-treated "photoisomerizable molecule 3-bound first nucleic acid fragment 2" is immobilized on the surface of a solvent-philic basal material for immobilization 4 by chemical bond or chemisorption. The solvent-philic basal material for immobilization 4, as illustrated in FIG. 10(a), is a solvent-philic basal material 21 that is composed of two regions. One of these two regions in the solvent-philic basal material 21 is a region for detection 13. The second nucleic acid fragment 10 is immobilized on the surface of the region for detection 13; and the end of the second nucleic acid fragment 10 is immobilized on the surface of the region for detection 13 via a spacer 9. The other region of the solvent-philic basal material 21 is a region for capture 14. The region for capture 14 has high affinity for a solvent. As illustrated in FIG. 10(*b*), the complex (hybrid) 11 and the target substance 7 that are contained in a liquid droplet is migrated, together with the solvent composing the liquid droplet, along the surface of the region for capture 14 and thereby captured onto the region for capture 14 in the solvent-philic basal material 21. The complex (hybrid) 11 and the target substance 7 thus captured on the region for capture 14, together with the solvent, reach the region for detection 13 as a result of being migrated along the surface of the region for capture 14. After the capture on the region for capture 14, "the first step" to "the fourth step" are carried out by the time when the complex (hybrid) 11 and the target substance 7 reach the region for detection 13 through the migrated along the surface of the region for capture 14. At the time when the complex (hybrid) 11 and the target substance 7 have reached the region for detection 13, the second photoisomerization-treated "photoisomerizable molecule 3-bound first nucleic acid fragment 2" is detected by means of the second nucleic acid fragment 10.

Meanwhile, the complex (hybrid) 11 that is contained in the liquid droplet, as illustrated in FIG. 10(*b*), is in the form of a "conjugate" in which a double-strand formation site 5 in an aptamer 1 and a double-strand formation site 5 in a "photoisomerizable molecule 3-bound first nucleic acid fragment 2" are linked via a spacer 9. The other end of the "photoisomerizable molecule 3-bound first nucleic acid fragment 2" is modified with a labeling material 6. In the "conjugate molecule" composing the complex (hybrid) 11, the photoisomerizable molecule 3 bound to the double-strand formation site 5 in the "photoisomerizable molecule 3-bound first nucleic acid fragment 2" is reversibly photoisomerized when subjected to the first photoisomerization treatment and to the second photoisomerization treatment. Thus, the complex (hybrid) 11 that is contained in the liquid droplet, as illustrated in FIG. 10(*b*), corresponds to a "second photoisomerization-treated complex (hybrid)" having double-stranded nucleotides binding, which is formed by the aptamer 1 and the second photoisomerization-treated "photoisomerizable molecule 3-bound first nucleic acid fragment 2" incorporated in the "conjugate molecule".

The liquid droplet, as illustrated in FIG. 10(*b*), contains the complex (hybrid) 11 mixed with the subject to be assayed (sampled specimen); and thus, the target substance 7 contained in the subject to be assayed (sampled specimen) and the complex (hybrid) 11 are dissolved in the solvent of the liquid droplet. In the case when the target substance 7 is absent in the subject to be assayed (sampled specimen), only the complex (hybrid) 11 is dissolved in the solvent of the liquid droplet free from the target substance 7.

The liquid droplet is spotted (added dropwise) onto the surface of the upstream part of the region for capture 14 in the solvent-philic basal material 21. The complex (hybrid) 11 and the target substance 7 are migrated, together with the solvent, from the spotting (dropwise addition) position toward the downstream part along the surface of the region for capture 14 solvent-philic to the solvent in the liquid droplet.

Immediately after the spotting (dropwise addition) of the liquid droplet onto the surface of the upstream part of the region for capture 14 in the solvent-philic basal material 21, the complex (hybrid) 11 is subjected to the first photoisomerization treatment in "the first step". In addition, the temperature of the solvent-philic basal material 21 is adjusted to a solution temperature ($T_L$) used for the detection process.

Accordingly, the liquid droplet migrated along the surface of the region for capture 14 in the solvent-philic basal material 21 is kept at the solution temperature ($T_L$) used for the detection process. In the method for detecting a target substance according to the eighth embodiment, such a state is selected where the complexes (hybrids) 11 and target substances 7 are uniformly dissolved in the liquid droplet to be spotted (added dropwise). Thus, the concentration [Complex (hybrid)]$_{CAP}$ of the complex (hybrid) 11 and the concentration [Target substance]$_{CAP}$ of the target substance 7, which are contained in the liquid phase to be migrated along the surface of the region for capture 14 are set to be equal to the concentration [Complex (hybrid)] of the complex (hybrid) 11 and the concentration [Target substance] of the target substance 7, respectively, in the liquid droplet.

As the photoisomerizable molecule 3 is subjected to the first photoisomerization treatment to cause first photoisomerization thereof, the "photoisomerizable molecule 3-bound first nucleic acid fragment 2" in the "conjugate molecule" composing the complex (hybrid) 11 is converted to a first photoisomerization-treated "photoisomerizable molecule 3-bound first nucleic acid fragment 2". In such a case, the original complex (hybrid) 11, i.e., the "second photoisomerization-treated complex (hybrid)", is converted to a "first photoisomerization-treated complex (hybrid)" composed of a "conjugate molecule" having double-stranded nucleotides binding, which is formed between the first photoisomerization-treated "photoisomerizable molecule 3-bound first nucleic acid fragment 2" and the aptamer 1 that are linked via the spacer 9. As compared, the melting temperature $T_{melting-1}$ of the destabilized double-stranded nucleotides binding in the "first photoisomerization-treated complex (hybrid)" and the melting temperature $T_{melting}$ of the double-stranded nucleotides binding in the original complex (hybrid) 11, i.e., the melting temperature $T_{melting-2}$ of the stabilized double-stranded nucleotides binding in the "second photoisomerization-treated complex (hybrid)", following relationship of $T_{melting-1} \ll T_{melting} = T_{melting-2}$ is attained.

In the case when the solution temperature ($T_L$) used for the detection process is selected so as to satisfy the relationship of $T_{melting-1} < T_L \ll T_{melting} = T_{melting-2}$, at the solution temperature ($T_L$) used for the detection process, the destabilized double-stranded nucleotides binding in the "first photoisomerization-treated complex (hybrid)" is thermally "dissolved", and thereby, the original complex (hybrid) is temporarily converted into a first photoisomerization-treated "unfolding-type conjugate molecule" comprising a "single-stranded aptamer 1" and the first photoisomerization-treated "photoisomerizable molecule 3-bound first nucleic acid fragment 2", which are linked via the spacer 9. Thus, the equilibrium constant $K_{D\text{-}hybride-1}$ between the "first photoisomerization-treated complex (hybrid)" and the first photoisomerization-treated "unfolding-type conjugate molecule" at the solution temperature ($T_L$) used for the detection process is represented by $K_{D\text{-}hybride-1}=$[First photoisomerization-treated unfolding-type conjugate molecule]$_{CAP}$/[First photoisomerization-treated complex (hybrid)]$_{CAP}$, and is $K_{D\text{-}hybride-1} > 1$.

Then, the "single-stranded aptamer 1" is converted to an "aptamer 1 having the steric structure" through the formation of the steric structure essential to binding to the target substance 7. This structural change (folding) from the "single-stranded aptamer 1" to the "aptamer 1 having the steric structure" causes thermal energy stabilization. Therefore, at the solution temperature ($T_L$) for the detection process, the first photoisomerization-treated "unfolding-type conjugate molecule" is converted to a first photoisomerization-treated "folding-type conjugate molecule", in which the "single-stranded aptamer 1" moiety in the first photoisomerization-treated "unfolding-type conjugate molecule" is converted to an "aptamer 1 moiety having the steric structure". The equilibrium constant $K_{aptamer\text{-}folding\text{-}1}(T_L)$ between the first photoisomerization-treated "unfolding-type conjugate molecule" and the first photoisomerization-treated "folding-type conjugate molecule" at the solution temperature $(T_L)$ used for the detection process is represented by $K_{aptamer\text{-}folding\text{-}1}(T_L)$=[First photoisomerization-treated unfolding-type conjugate molecule]$_{CAP}$/[First photoisomerization-treated folding-type conjugate molecule]$_{CAP}$, and is $K_{aptamer\text{-}folding\text{-}1}(T_L)<1$.

As illustrated in FIG. 10(c), in the case when the target substance 7 is present in the liquid phase, the target substance 7 binds to the "aptamer 1 moiety having the steric structure" in the first photoisomerization-treated "folding-type conjugate molecule" to form a complex that is composed of the first photoisomerization-treated "folding-type conjugate molecule" and the target substance 7. At the solution temperature $(T_L)$ used for the detection process, the dissociation constant $K_{D\text{-}complex\text{-}1}(T_L)$ of the complex that is composed of the first photoisomerization-treated "folding-type conjugate molecule" and the target substance 7, i.e., the first photoisomerization-treated "folding-type conjugate molecule/target substance complex", is represented by $K_{D\text{-}complex\text{-}1}(T_L)$=[Target substance]$_{CAP}$*[First photoisomerization-treated folding-type conjugate molecule]$_{CAP}$/[First photoisomerization-treated folding-type conjugate molecule/target substance complex]$_{CAP}$. As the target substance 7 contained in the liquid droplet forms the complex according to the dissociation constant $K_{D\text{-}complex\text{-}1}(T_L)$ at the solution temperature $(T_L)$ used for the detection process, the concentration [Target substance]$_{CAP}$ of the target substance 7 dissolved in the liquid phase is exponentially decreased, as the migration proceeds. Since the "first photoisomerization-treated folding-type conjugate molecule" is consumed in association with the complex formation, the "first photoisomerization-treated unfolding-type conjugate molecule" is rapidly converted to the "first photoisomerization-treated folding-type conjugate molecule" according to the equilibrium constant $K_{aptamer\text{-}folding\text{-}1}(T_L)$. Finally, such a state that substantially no "first photoisomerization-treated unfolding-type conjugate molecule" remains in the liquid phase is achieved. Thus, as illustrated in FIG. 10(c), substantially all of target substances 7 contained in the liquid droplet added dropwise are used to form the first photoisomerization-treated "folding-type conjugate molecule/target substance complexes", and the resulted complexes are migrated along the surface of the region for capture 14, together with the first photoisomerization-treated "folding-type conjugate molecule" that is not fixed in the complex.

After the completion of the complex formation, when subjected to the second photoisomerization treatment in "the fourth step", the first photoisomerization-treated "photoisomerizable molecule 3-bound first nucleic acid fragment 2" moiety is converted to a second photoisomerization-treated "photoisomerizable molecule 3-bound first nucleic acid fragment 2" moiety. As a result, as illustrated in FIG. 10(d), the first photoisomerization-treated "folding-type conjugate molecule" is converted to a second photoisomerization-treated "folding-type conjugate molecule", and thereby, the first photoisomerization-treated "folding-type conjugate molecule/target substance complex" is converted to a second photoisomerization-treated "folding-type conjugate molecule/target substance complex".

The equilibrium constant $K_{aptamer\text{-}folding\text{-}2}(T_L)$ between the second photoisomerization-treated "unfolding-type conjugate molecule" and the second photoisomerization-treated "folding-type conjugate molecule" at the solution temperature $(T_L)$ used for the detection process is represented by $K_{aptamer\text{-}folding\text{-}2}(T_L)$=[Second photoisomerization-treated unfolding-type conjugate molecule]$_{CAP}$/[Second photoisomerization-treated folding-type conjugate molecule]$_{CAP}$, and is $K_{aptamer\text{-}folding\text{-}2}(T_L)<1$. The equilibrium constant $K_{aptamer\text{-}folding\text{-}2}(T_L)$, which corresponds to the equilibrium constant of the folding/defolding process of the "aptamer 1" moiety, is essentially equal to the equilibrium constant $K_{aptamer\text{-}folding\text{-}1}(T_L)$.

Meanwhile, the second photoisomerization-treated "unfolding-type conjugate molecule" reconstructs a "second photoisomerization-treated complex (hybrid)" through the formation of double-stranded nucleotides binding between the double-strand formation site 5 in the "single-stranded aptamer 1" and the double-strand formation site 5 in the second photoisomerization-treated "photoisomerizable molecule 3-bound first nucleic acid fragment 2". The equilibrium constant $K_{D\text{-}hybride\text{-}2}$ between the "second photoisomerization-treated complex (hybrid)" and the second photoisomerization-treated "unfolding-type conjugate molecule" at the solution temperature $(T_L)$ used for the detection process is represented by $K_{D\text{-}hybride\text{-}2}$=[Second photoisomerization-treated unfolding-type conjugate molecule]$_{CAP}$/[Second photoisomerization-treated complex (hybrid)]$_{CAP}$, and is $K_{D\text{-}hybride\text{-}2} \ll 1$.

Also, the first photoisomerization-treated "folding-type conjugate molecule/target substance complex" is converted to a second photoisomerization-treated "folding-type conjugate molecule/target substance complex". At the solution temperature $(T_L)$ used for the detection process, the dissociation constant $K_{D\text{-}complex\text{-}2}(T_L)$ of the complex that is composed of the second photoisomerization-treated "folding-type conjugate molecule" and the target substance 7, i.e., the second photoisomerization-treated "folding-type conjugate molecule/target substance complex", is represented by $K_{D\text{-}complex\text{-}2}(T_L)$=[Target substance]$_{CAP}$*[Second photoisomerization-treated folding-type conjugate molecule]$_{CAP}$/[Second photoisomerization-treated folding-type conjugate molecule/target substance complex]$_{CAP}$. The dissociation constant $K_{D\text{-}complex\text{-}2}(T_L)$, which corresponds to the equilibrium constant of the dissociation process of the target substance 7 that forms the complex with the "aptamer 1 moiety having the steric structure", is essentially equal to the dissociation constant $K_{D\text{-}complex\text{-}1}(T_L)$.

At the stage where the second photoisomerization treatment is carried out in "the fourth step", as illustrated in FIG. 10(d), the first photoisomerization-treated "folding-type conjugate molecule/target substance complex" and a residual first photoisomerization-treated "folding-type conjugate molecule", together with the solvent, have already reached the downstream part of the region for capture 14 in the solvent-philic basal material 21. When reaching the region for detection 13 in the solvent-philic basal material 21, the second photoisomerization-treated "folding-type conjugate molecule" that is converted from the first photoisomerization-treated "folding-type conjugate molecule" by carrying out the second photoisomerization treatment is further converted to a second photoisomerization-treated "unfolding-type conjugate molecule" according to the equilibrium constant $K_{aptamer\text{-}folding\text{-}2}(T_L)$ at the solution temperature $(T_L)$ used for the detection process. A "second photoisomerization-treated complex (hybrid)" is further formed therefrom, as a result of reconstructing the double-stranded nucleotides binding according to the equilibrium constant $K_{D\text{-}hybride\text{-}2}$. Thus, the second photoisomerization-treated "folding-type conjugate molecule" remaining in the liquid phase is converted to a "second photoisomerization-treated complex (hybrid)".

Meanwhile, the second photoisomerization-treated "folding-type conjugate molecule/target substance complexes" that is converted from the first photoisomerization-treated "folding-type conjugate molecule/target substance complexes" are gradually dissociated according to the dissociation constant $K_{D\text{-}complex\text{-}2}(T_L)$, with decrease in the concentration [Second photoisomerization-treated folding-type conjugate molecule]$_{CAP}$ of the second photoisomerization-treated "folding-type conjugate molecule" remaining in the liquid phase. As this dissociation proceeds, the concentration [Target substance]$_{CAP}$ of the "target substance 7" dissolved in the liquid phase relatively rises at a sharp rate from almost "zero". The dissociation rate is therefore slowed dawn.

As a result, unless an unnecessarily long time is required from the second photoisomerization treatment in "the fourth step" to the arrival at the region for detection 13 in the solvent-philic basal material 21, the total of the concentration [Second photoisomerization-treated folding-type conjugate molecule/target substance complex]$_{CAP}$ of the second photoisomerization-treated "folding-type conjugate molecule/target substance complex" and the concentration [Second photoisomerization-treated folding-type conjugate molecule]$_{CAP}$ of the second photoisomerization-treated "folding-type conjugate molecule", which are contained in the liquid phase at the stage of reaching the region for detection 13 in the solvent-philic basal material 21 can be substantially equivalent to the concentration [Second photoisomerization-treated folding-type conjugate molecule/target substance complex]$_{CAP\text{-}0}$ of the second photoisomerization-treated "folding-type conjugate molecule/target substance complex", which is converted from the first photoisomerization-treated "folding-type conjugate molecule/target substance complex" by carrying out the second photoisomerization treatment, As illustrated in FIG. 10(e), the second nucleic acid fragment 10 that is immobilized on the surface of the region for detection 13 in the solvent-philic basal material 21 is hybridized with the double-strand formation site 5 in the second photoisomerization-treated "photoisomerizable molecule 3-bound first nucleic acid fragment 2" that is comprised in the second photoisomerization-treated "folding-type conjugate molecule/target substance complex" to form double-stranded nucleotides binding. Also, the second nucleic acid fragment 10 can be hybridized with the double-strand formation site 5 in the second photoisomerization-treated "photoisomerizable molecule 3-bound first nucleic acid fragment 2" that is comprised in the second photoisomerization-treated "folding-type conjugate molecule", which is attached with the labeling material 7, to form double-stranded nucleotides binding.

That is, the total of the concentration [Second photoisomerization-treated folding-type conjugate molecule/target substance complex]$_{CAP}$ of the second photoisomerization-treated "folding-type conjugate molecule/target substance complex" and the concentration [Second photoisomerization-treated folding-type conjugate molecule]$_{CAP}$ of the second photoisomerization-treated "folding-type conjugate molecule" contained in the liquid phase at the stage of reaching the region for detection 13 in the solvent-philic basal material 21 can be hybridized with the second nucleic acid fragment 10 that is immobilized on the surface of the region for detection 13 in the solvent-philic basal material 21 to form double-stranded nucleotides binding.

It is hypothesized that the total amount of second photoisomerization-treated "folding-type conjugate molecule/target substance complexes", which is converted from first photoisomerization-treated "folding-type conjugate molecule/target substance complexes" by carrying out the second photoisomerization treatment, is immobilized by the formation of double-stranded nucleotides binding through hybridization with the second nucleic acid fragment 10 that is immobilized on the surface of the region for detection 13 in the solvent-philic basal material 21. At that stage, the area density of the immobilized second photoisomerization-treated "folding-type conjugate molecule/target substance complex" is [Second photoisomerization-treated folding-type conjugate molecule]$_{S\text{-}0}$. The immobilized second photoisomerization-treated "folding-type conjugate molecule/target substance complex" can be dissociated into an immobilized second photoisomerization-treated "folding-type conjugate molecule" and an immobilized "target substance 7", and at the solution temperature $(T_L)$ used for the detection process, the dissociation constant $K_{D\text{-}complex\text{-}2\text{-}S}(T_L)$ thereof is represented by $K_{D\text{-}complex\text{-}2\text{-}S}(T_L)=$[Target substance]$_{CAP}$*[Immobilized second photoisomerization-treated folding-type conjugate molecule]$_S$/[Immobilized second photoisomerization-treated folding-type conjugate molecule/target substance complex]$_S$. The dissociation constant $K_{D\text{-}complex\text{-}2\text{-}S}(T_L)$ also corresponds to the equilibrium constant of the dissociation process of the target substance 7 that forms the complex with the "aptamer 1 moiety having the steric structure", and thus, the dissociation constant $K_{D\text{-}complex\text{-}2\text{-}S}(T_L)$ is essentially equal to the dissociation constant $K_{D\text{-}complex\text{-}2}(T_L)$.

Accordingly, some of immobilized second photoisomerization-treated "folding-type conjugate molecule/target substance complexes" are dissociated into immobilized second photoisomerization-treated "folding-type conjugate molecules" and immobilized "target substances 7" according to the dissociation constant $K_{D\text{-}complex\text{-}2\text{-}S}(T_L)$. As a result, what is detected is the total of the area density [Immobilized second photoisomerization-treated folding-type conjugate molecule/target substance complex]$_S$ of the immobilized second photoisomerization-treated "folding-type conjugate molecule/target substance complex" and the area density [Immobilized second photoisomerization-treated folding-type conjugate molecule]$_S$ of the immobilized second photoisomerization-treated "folding-type conjugate molecule".

The second photoisomerization-treated "folding-type conjugate molecule/target substance complex" that is immobilized by the formation of double-stranded nucleotides binding through hybridization with the second nucleic acid fragment 10 remains immobilized as a second photoisomerization-treated "folding-type conjugate molecule" even if the target substance 7 that forms a complex with its "aptamer 1 moiety having the steric structure" is then dissociated therefrom. This second photoisomerization-treated "folding-type conjugate molecule" remains immobilized as a second photoisomerization-treated "unfolding-type conjugate molecule" even if the "aptamer 1 moiety having the steric structure" is further thermally defolded to convert into a "single-stranded aptamer 1". As the labeling material 6 being attached at the end of the second photoisomerization-treated "photoisomerizable molecule 3-bound first nucleic acid fragment 2" moiety, which is hybridized with the second nucleic acid fragment 10 to form the double-stranded nucleotides binding, is detected, even if the conjugate molecule is present in any of those forms mentioned above, it is detected as a labeling material 6 that is immobilized on the region for detection 13 in the solvent-philic basal material 21.

On the other hand, the recovered "second photoisomerization-treated complex (hybrid)" also reaches the region for detection 13 in the solvent-philic basal material 21 and is dissolved in the liquid phase covering the surface of the region for detection 13. The end of the second photoisomerization-treated "photoisomerizable molecule 3-bound first nucleic acid fragment 2" moiety comprised in the "second photoisomerization-treated complex (hybrid)" unimmobilized on the surface of the region for detection 13 is modified with the labeling material 6. Therefore, after the "second photoisomerization-treated complex (hybrid)" that has reached the region for detection 13 in the solvent-philic basal material 21 is removed by washing off, only the labeling material 6 being attached at the end of the second photoisomerization-treated "photoisomerizable molecule 3-bound first nucleic acid fragment 2" moiety having the double-stranded nucleotides binding formed through hybridization with the second nucleic acid fragment 10 is detected.

When the "second photoisomerization-treated complex (hybrid)" that has reached the region for detection 13 in the solvent-philic basal material 21 is removed by washing off, the target substance 7 dissolved in the liquid phase covering the surface of the region for detection 13 is removed by washing as well. Dissociation of the target substances 7 from the second photoisomerization-treated "folding-type conjugate molecule/target substance complexes" that are immobilized by the formation of double-stranded nucleotides binding through hybridization with the second nucleic acid fragment 10 are gradually progressed according to the dissociation constant $K_{D-complex-2-S}(T_L)$ at the solution temperature ($T_L$) used for the detection process.

Thus, as a predetermined time is required from the end of caning out the second photoisomerization treatment in "the fourth step" to the arrival at the region for detection 13 in the solvent-philic basal material 21, the required time is set to an appropriate range. Within the predetermined duration, the "second photoisomerization-treated complex (hybrid)" is recovered from the first photoisomerization-treated "folding-type conjugate molecule" that remains in the solution. As a result, the generation of "noise" resulting from the event where some of second photoisomerization-treated "folding-type conjugate molecules" that are converted from the first photoisomerization-treated "folding-type conjugate molecules" reach the region for detection 13 in the solvent-philic basal material 21, and hybridize with the second nucleic acid fragment 10 that is immobilized on the surface of the region for detection 13 in the solvent-philic basal material 21 to form double-stranded nucleotides binding can be prevented.

In the method for detecting a target substance according to the eighth embodiment, when the original "complex (hybrid)" that is corresponding to the "second photoisomerization-treated complex (hybrid)" is subjected to the first photoisomerization treatment in "the first step" at the solution temperature ($T_L$) used for the detection process, the double-stranded nucleotides binding in the "complex (hybrid)" is destabilized, and then, is further "dissociated" to convert to a first photoisomerization-treated "unfolding-type conjugate molecule". Subsequently, the "single-stranded aptamer 1" moiety that is comprised in the first photoisomerization-treated "unfolding-type conjugate molecule" is converted to an "aptamer 1 moiety having the steric structure" by help of the "folding/defolding equilibrium process" at the solution temperature ($T_L$) used for the detection process, and thereby, a first photoisomerization-treated "folding-type conjugate molecule" is attained. In such a case, when the target substance 7 is contained in the liquid droplet to be spotted, the target substance 7 binds to the "aptamer 1 moiety having the steric structure" in the first photoisomerization-treated "folding-type conjugate molecule" to quickly form a first photoisomerization-treated "folding-type conjugate molecule/target substance complex".

For example, in the case where, however, the concentration [Complex (hybrid)] of the original "complex (hybrid)" is equal to the concentration [Target substance] of the target substance 7, as schematically shown in FIG. 10(*b*), a certain amount of time is required for completing the formation of almost all the first photoisomerization-treated "folding-type conjugate molecule/target substance complexes", as schematically shown in FIG. 10(*c*), after the first photoisomerization treatment is carried out. Thus, period of a "predetermined time ($t_1$)" must be taken from the end of carrying out the first photoisomerization treatment in "the first step" to the start of carrying out the second photoisomerization treatment in "the fourth step". The process in which the first photoisomerization treatment is carried out in "the first step", and after an interval of the "predetermined time ($t_1$)", the second photoisomerization treatment is carried out in "the fourth step" is schematically shown as the passage of time during which the solution is migrated along the surface of the region for capture 14 in the solvent-philic basal material 21, as illustrated in FIGS. 10(*b*) to 10(*d*).

The equilibrium constant $K_{aptamer-folding-1}(T_L)$=[First photoisomerization-treated unfolding-type conjugate molecule]$_{CAP}$/[First photoisomerization-treated folding-type conjugate molecule]$_{CAP}$ and the equilibrium constant $K_{aptamer-folding-2}(T_L)$=[Second photoisomerization-treated unfolding-type conjugate molecule]$_{CAP}$/[Second photoisomerization-treated folding-type conjugate molecule]$_{CAP}$, which depend on the "folding/defolding equilibrium process" of the aptamer 1 at the solution temperature ($T_L$) used for the detection process, are essentially equal to each other, and are in the relationship of $K_{aptamer-folding-1}(T_L)$=$K_{aptamer-folding-2}(T_L)$<1. The equilibrium constant between the "second photoisomerization-treated unfolding-type conjugate molecule" and the "second photoisomerization-treated complex (hybrid)" at the solution temperature ($T_L$) used for the detection process is represented by the dissociation constant $K_{D-hybride-2}$=[Second photoisomerization-treated unfolding-type conjugate molecule]$_{CAP}$/[Second photoisomerization-treated complex (hybrid)]$_{CAP}$, and is $K_{D-hybride-2}$<<1. A certain amount of time is required for converting the mixture of the "first photoisomerization-treated folding-type conjugate molecules" and "first photoisomerization-treated unfolding-type conjugate molecules", which are in equilibrium at the solution temperature ($T_L$) used for the detection process, to the "second photoisomerization-treated complexes (hybrids)".

Therefore, a "predetermined time ($t_2$)" must be taken from the end of carrying out the second photoisomerization treatment in "the fourth step" to the arrival at the region for detection 13 in the solvent-philic basal material 21. The process in which the second photoisomerization treatment is carried out in "the fourth step", and at the time when an interval of the "predetermined time ($t_2$)" passes, the solution reaches the site at which the second nucleic acid fragment 10 is immobilized on the region for detection 13 in the solvent-philic basal material 21 is schematically shown as the passage of time during which the solution is migrated along the surface of a region from the downstream part of the region for capture 14 to the region for detection 13 in the solvent-philic basal material 21, as illustrated in FIGS. 10(*d*) and 10(*e*).

As explained above, in the method for detecting a target substance according to the eighth embodiment, when "the first step" to "the fourth step" are carried out at the solution temperature ($T_L$) used for the detection process, as the "target substance 7" and the "complex (hybrid) 11" that is composed of a "conjugate molecule" are contained in advance in the liquid droplet to be spotted (added dropwise) onto the surface of the upstream part of the region for capture 14, the "target substance 7" and the "complex (hybrid) 11" that is composed of a "conjugate molecule" are therefore migrated, together with the solvent in the liquid droplet thus spotted (added dropwise), along the surface of the solvent-philic region for capture 14 and thereby captured onto the surface by means of the solvent-philic region (region for capture 14) in the solvent-philic basal material 21. Thus, a technical feature provided thereby is that following time course where, after the spotting (dropwise addition) of the liquid droplet, the "predetermined time ($t_1$)" and the "predetermined time ($t_2$)" are taken between the first photoisomerization treatment and the second photoisomerization treatment and between the second photoisomerization treatment and the arrival at the region for detection 13, respectively, as illustrated in FIGS. 10(*b*) to 10(*e*), can be set (adjusted) with high reproducibility.

In the method for detecting a target substance according to the eighth embodiment, in the case when the target substance 7 is absent in the subject to be assayed (sampled specimen), as no first photoisomerization-treated "folding-type conjugate molecule/target substance complex" is formed, there is no chance for the second photoisomerization-treated "folding-type conjugate molecule/target substance complex" to hybridize with the second nucleic acid fragment 10 on the region for detection 13 in the solvent-philic basal material 21 to form double-stranded nucleotides binding thereby. In the case when the target substance 7 is present in the subject to be assayed (sampled specimen), as the first photoisomerization-treated "folding-type conjugate molecule/target substance complex" is formed and then converted to a second photoisomerization-treated "folding-type conjugate molecule/target substance complex" when subjected to the second photoisomerization treatment, the thus-resulted complex is hybridized with the second nucleic acid fragment 10 on the region for detection 13 in the solvent-philic basal material 21 to form double-stranded nucleotides binding.

Thus, whether or not the target substance 7 is present in the subject to be assayed (sampled specimen) can be detected based on detection of the presence or absence of the labeling material 6 being attached at the end of the second photoisomerization-treated "photoisomerizable molecule 3-bound first nucleic acid fragment 2" moiety in the second photoisomerization-treated "folding-type conjugate molecule/target substance complex", which is immobilized on the surface of the region for detection 13 by the formation of double-stranded nucleotides binding through hybridization with the second nucleic acid fragment 10 on the region for detection 13 in the solvent-philic basal material 21.

In the method for detecting a target substance according to the eighth embodiment, when the presence or absence of the labeling material 6 being attached at the end of the second photoisomerization-treated "photoisomerizable molecule 3-bound first nucleic acid fragment 2" moiety in the second photoisomerization-treated "folding-type conjugate molecule/target substance complex" that is immobilized on the surface of the region for detection 13, which results from the formation of double-stranded nucleotides binding through hybridization with the second nucleic acid fragment 10, is detected, the "second photoisomerization-treated complex (hybrid)" that has reached the region for detection 13 is removed in advance by washing off. Therefore, the "second photoisomerization-treated complex (hybrid)" and the "target substance 7" that is nonselectively adsorbed onto the surface of the region for detection 13 in the solvent-philic basal material 21 is removed by washing of as well. The detection can be carried out with reduction of background that is caused by the labeling material 6 being attached at the end of the second photoisomerization-treated "photoisomerizable molecule 3-bound first nucleic acid fragment 2" moiety in the "second photoisomerization-treated complex (hybrid)" that is nonselectively adsorbed, and as a result, the accuracy of the "detection of the target substance 7" is improved.

After an assay solution is prepared by dissolving a predetermined concentration of the "complex (hybrid) 11" that is composed of a "conjugate molecule" and a predetermined amount of the subject to be assayed (sampled specimen) in a solvent, a liquid droplet of the assay solution is spotted in a predetermined amount onto the upstream part of the solvent-philic region (region for capture 14) in the solvent-philic basal material 21. As, after spotted, the liquid droplet is migrated along the surface of the region for capture 14, a series of operations comprising the first photoisomerization treatment, the second photoisomerization treatment, the arrival at the region for detection 13, and the hybridization reaction with the second nucleic acid fragment 10 that is immobilized on the surface of the region for detection 13, can be carried out at the solution temperature ($T_L$) used for the detection process. Thus, the easy handling of the subject to be assayed (sampled specimen) is achieved, and the detection of the presence or absence of the target substance 7 in the subject to be assayed (sampled specimen) can be carried out with ease.

In the method for detecting a target substance according to the eighth embodiment, as the mode as illustrated in FIG. 10(*a*) utilizes the "complex (hybrid) 11" that is composed of a "conjugate molecule", such structure can be preferably employed in which the end of the "photoisomerizable molecule 3-bound first nucleic acid fragment 2" moiety that is comprised in the "conjugate molecule" is modified with the labeling material 6. Following "advantages" can be attained by modifying of the end of the "photoisomerizable molecule 3-bound first nucleic acid fragment 2" moiety with the labeling material 6. The labeling material has no influence on any of the "folding" process to form the "steric structure" essential to binding to the target substance 7 in the "aptamer 1" moiety that is comprised in the "conjugate molecule" and the "defolding" process to recover a "single-stranded structure" by dissolving the "steric structure". Furthermore, the labeling material has no influence on any of the process of binding the target substance 7 to the "aptamer 1 moiety having the steric structure", and the process of separating the target substance 7 therefrom. The labeling material does not inhibit the hybridization reaction to form a "second photoisomerization-treated complex (hybrid)" from a second photoisomerization-treated "folding-type conjugate molecule". The labeling material does not inhibit the thermal dissociation process to convert a "first photoisomerization-treated complex (hybrid)" to a first photoisomerization-treated "unfolding-type conjugate molecule". The labeling material does not inhibit the hybridization reaction of the second nucleic acid fragment 10 with the second photoisomerization-treated "photoisomerizable molecule 3-bound first nucleic acid fragment 2" that is comprised in the second photoisomerization-treated "folding-type conjugate molecule/target substance complex".

The labeling material 6 may be attached to any site in the "conjugate molecule" as well as the above-listed "advantages" that are provided by the modification of the end of the "photoisomerizable molecule 3-bound first nucleic acid fragment 2" moiety with the labeling material 6 are not impaired. Thus, the aptamer 1 or the spacer 9 that are comprised in the "conjugate molecule" may be modified with the labeling material 6, unless the aforementioned "advantages" are impaired.

In the method for detecting a target substance according to the eighth embodiment, in the structure as illustrated in FIG. 10(a), the spacer 9 that links the double-strand formation site 5 in the aptamer 1 and the double-strand formation site 5 in the second photoisomerization-treated "photoisomerizable molecule 3-bound first nucleic acid fragment 2", which is used in the "complex (hybrid) 11" that is composed of a "conjugate molecule", corresponds to the spacer 9 that is used in the structure as illustrated in FIG. 4(a) in the method for detecting a target substance according to the third embodiment. Thus, the spacer 9 used in the structure as illustrated in FIG. 10(a) can be selected in similar manner to the spacer 9 used in the structure as illustrated in FIG. 4(a), and the linkage is made therewith.

In the method for detecting a target substance according to the eighth embodiment, as for the "complex (hybrid) 11" that is composed of a "conjugate molecule", for example, such a form comprising the basal material for immobilization 4 as illustrated in FIG. 7(a) that is used in the method for detecting a target substance according to the fifth embodiment or such a form comprising the basal material for immobilization 4 as illustrated in FIG. 8(a) or 8(b) that is used in the method for detecting a target substance according to the sixth embodiment can be used, as long as each "conjugate molecule" can be independently dissolved in a solvent and migrated, together with the target substance 7, along the surface of the region for capture 14 in the solvent-philic basal material 21 to reach the region for detection 13 in the solvent-philic basal material 21 from the spotting position on the region for capture 14. As it is required that each "conjugate molecule" comprising the basal material for immobilization 4 should be able to be independently "dispersed" in a solvent and also migrated along the surface of the region for capture 14, a very small basal material for immobilization dispersible in a solvent, for example, a basal material for immobilization in a fine particle form, such as a microsphere or microfiber, can be used as the basal material for immobilization 4 that satisfies the requirement.

In such a case, preferably, one "conjugate molecule" is immobilized on each basal material for immobilization 4, or in the case when a plurality of "conjugate molecules" are immobilized on each basal material for immobilization 4, preferably, such a state in which all of the "conjugate molecules" that are immobilized thereon are always bound with the target molecule 7 can be attained.

In the method for detecting a target substance according to the eighth embodiment, as, in the case when the target substance 7 is absent in the subject to be assayed (sampled specimen), no first photoisomerization-treated "folding-type conjugate molecule/target substance complex" is formed, there is no chance that the second photoisomerization-treated "folding-type conjugate molecule/target substance complex" hybridize to the second nucleic acid fragment 10 to form double-stranded nucleotides binding therebetween on the region for detection 13 in the solvent-philic basal material 21.

Therefore, even if a plurality of "conjugate molecules" are immobilized on each basal material for immobilization 4, whether or not the target substance 7 is present in the subject to be assayed (sampled specimen) can be easily detected by the application of the method for detecting a target substance according to the eighth embodiment.

In the method for detecting a target substance according to the eighth embodiment, in the mode as illustrated in FIG. 10(a), the second nucleic acid fragment 10 is immobilized on the region for detection 13 in the solvent-philic basal material 21. For example, as illustrated in FIG. 10(e), the second nucleic acid fragment 10 is immobilized on the region for detection 13 in the solvent-philic basal material 21 by chemical bond or chemisorption via the spacer 9. In such a case, the functional group which is used in linkage with the spacer 9 is not limited as long as the functional group is capable of forming a bond that is not dissociated from the spacer 9 by, for example, the solvent or the pH condition used for detection. Those functional groups can be built in by means of a popular nucleotide synthesis method or the modification of the nucleic acid with a commercially available linker or the like. In the second nucleic acid fragment 10, the site linked to the spacer 9 is preferably set to the end of the second nucleic acid fragment 10, as illustrated in FIG. 10(e). Alternatively, the site linked to the spacer 9 may be set at an arbitrary position as long as the hybridization reaction of the double-strand formation site 5 in the second photoisomerization-treated "photoisomerizable molecule 3-bound first nucleic acid fragment 2" with the second nucleic acid fragment 10 that has a nucleotide sequence complementary thereto is not inhibited. The spacer 9 may be linked to, for example, the central part of the second nucleic acid fragment 10 instead of the end of the second nucleic acid fragment 10 as long as said requirements are satisfied.

The length of the spacer 9 that is linked to the second nucleic acid fragment 10 is preferably 3 Å or longer, more preferably 10 Å or longer. Such selection prevents reduction in the formation efficiency of double-stranded nucleotides binding between the double-strand formation site 5 of the second photoisomerization-treated "photoisomerizable molecule 3-bound first nucleic acid fragment 2" and the second nucleic acid fragment 10, which is induced by such factors as the steric hindrance of the solvent-philic basal material 21 against the second nucleic acid fragment 10. Further, when the length of the spacer 9 is excessively long, there is excessively increased distance between a region for detection and the labeling material 6, and thereby, the detection sensitivity for the "dissolution" state by using the labeling material 6 may be decreased. Therefore, preferably, the length of the spacer 9 is selected within the range of 200 Å or shorter. More preferably, the length of the spacer 9 is selected within the range of 10 Å or longer and 50 Å or shorter.

The spacer 9 that is linked to the second nucleic acid fragment 10 is not particularly limited as long as the spacer 9 does not form binding with the aptamer 1 or the first nucleic acid fragment 2. A popular linker such as a nucleic acid having a non-complementary nucleotide sequence, a glycan, a polypeptide, a hydrocarbon chain, or oligoethylene glycol can be used.

In the method for detecting a target substance according to the eighth embodiment, preferably, the total amount of the second photoisomerization-treated "folding-type conjugate molecule/target substance complexes" is hybridized with the second nucleic acid fragment 10 to be immobilized on the surface of the region for detection 13 in the solvent-philic basal material 21, as in the mode as illustrated in FIGS. 10(*d*) and 10(*e*). For example, even when the total amount of the "complexes (hybrids) 11", each of which is composed of a "conjugate molecule", contained in the spotted liquid droplet is converted to the second photoisomerization-treated "folding-type conjugate molecule/target substance complexes", as in the mode as illustrated in FIGS. 10(*a*) to 10(*e*), the total amount thereof is preferably hybridized with the second nucleic acid fragment 10 so to be immobilized on the surface of the region for detection 13 in the solvent-philic basal material 21. In such a case, the total number of molecules of second nucleic acid fragments 10 to be immobilized on the surface of the region for detection 13 in the solvent-philic basal material 21 is preferably selected so as to be equal to or larger than the total number of molecules of the "complexes (hybrids) 11", each of which is composed of a "conjugate molecule" that is contained in the liquid droplet to be spotted.

In general, the total number of molecules of the "complexes (hybrids) 11", each of which is composed of a "conjugate molecule" that is contained in the liquid droplet to be spotted is preferably selected so as to be equal to or larger than the total number of molecules of target substances 7 that is contained in the liquid droplet to be spotted.

Typically, at first, the total number of molecules of second nucleic acid fragments 10 to be immobilized on the surface of the region for detection 13 in the solvent-philic basal material 21 is determined; with respect to the number thus determined, the total number of molecules of the "complexes (hybrids) 11", each of which is composed of a "conjugate molecule" that is contained in the liquid droplet to be spotted, is selected appropriately within a range that satisfies the above requirements. After that, the amount of the subject to be assayed (sampled specimen) added is adjusted such that the total number of molecules of target substances 7 that is contained in this liquid droplet falls within a range that does not exceed the total number of molecules of the "complexes (hybrids) 11", each of which is composed of a "conjugate molecule". In the case when the upper limit of the concentration range of the target substance 7 that is contained in the subject to be assayed (sampled specimen) is known, the amount of the subject to be assayed (sampled specimen) added is adjusted to a range that satisfies the above requirements even if applying to the case of upper limit of the concentration.

In the case when the concentration range of the target substance 7 that is contained in the subject to be assayed (sampled specimen) is indeed unknown, the subject to be assayed (sampled specimen) is diluted at a plurality of ratios, for example, 100-fold, 50-fold, 10-fold, and 5-fold ratios, to prepare secondary samples having such dilution levels, and then, the amounts of the secondary samples added are adjusted to a range that satisfies the above requirements.

In the method for detecting a target substance according to the eighth embodiment, in the mode as illustrated in FIG. 10(*a*), the solvent-philic basal material 21 is provided with the region for capture 14 and the region for detection 13. The solvent-philic basal material 21 used therein has a surface solvent-philic to a solvent that is contained in the liquid droplet, in the case when the liquid droplet of an assay solution containing the "complex (hybrid) 11" that is composed of a "conjugate molecule" and the target substance 7 dissolved in a solvent is spotted onto the surface of the upstream part of the region for capture 14, as illustrated in FIG. 10(*b*). The surface solvent-philic to a solvent usually means that the surface has a contact angle less than 90 degrees against the solvent of interest. In such a case, preferably, the material itself which composes the surface has a contact angle less than 90 degrees against the solvent of interest. In the case when the material itself that compose the surface has a contact angle less than 90 degrees against the solvent of interest, when the internal structure of the solvent-philic basal material 21 is rendered porous, the spotted liquid droplet is rapidly migrated along the porous surface of the solvent-philic basal material 21 by help of the capillary action. In the region for detection, as the porous surface has a microscopic actual surface area much larger than the apparent surface area, the area density of the second nucleic acid fragment 10 that is immobilized on the porous surface can be markedly increased. In other words, as the total number of molecules of second nucleic acid fragments 10 that are immobilized on the region for detection 13 can be markedly increased, the total number of molecules of the "complexes (hybrids) 11", each of which is composed of a "conjugate molecule", contained in the liquid droplet to be spotted can be relatively increased. Thus, as the concentration of the "complex (hybrid) 11" composed of a "conjugate molecule" that is contained in the liquid droplet to be spotted can be relatively increased, in general, good result for improving detection accuracy can be obtained. In general, when the area density of the second nucleic acid fragment 10 immobilized on the region for detection 13 is increased, in general, the area density of the labeling material 6 immobilized is relatively increased, and thereby, good result for improving the S/N ratio during the detection of the labeling material 6 is obtained.

The assay solution is a solution using an aqueous solvent. Examples of porous materials solvent-philic to water that is used as the solvent therein include porous filters made of glass fiber, nitrocellulose, cellulose, synthetic fiber, or non-woven fabric.

The region for capture 14 that is provided on the solvent-philic basal material 21 functions as a "flow channel" through which the spotted liquid droplet is migrated along the solvent-philic surface to reach the region for detection 13. Thus, a structure can be employed in which the region with a limited width functioning as a "flow channel" has a solvent-philic surface, while the other region has a non-solvent-philic surface. For example, a groove-like region with a limited width functioning as a "flow channel" is formed on the surface of a base made of a non-solvent-philic material. A solvent-philic porous surface may be formed inside the groove-like region with a limited width by use of a solvent-philic porous material and used as the region for capture 14. The region for detection 13 may be formed in the form of a "pool" having a solvent-philic porous surface, at the end of the groove-like region with a limited width functioning as a "flow channel".

In the method for detecting a target substance according to the eighth embodiment, in the mode as illustrated in FIG. 10(*a*), the second nucleic acid fragment 10 is immobilized via the spacer 9 only on the surface of the region for detection 13 in the solvent-philic basal material 21. The technique that is used for immobilizing the spacer 9 onto the surface of the basal material for immobilization 4 by chemical bond or chemisorption in the method for detecting a target substance according to the third embodiment to the method for detecting a target substance according to the seventh embodiment can be also employed as a method for immobilizing the spacer 9 that is linked to the second nucleic acid fragment 10 onto the solvent-philic surface of the region for detection 13 by chemical bond or chemisorption.

For example, a functional group for use in the immobilization of the spacer 9 is introduced only to the solvent-philic surface of the region for detection 13, and the spacer 9 is immobilized by means of the functional group. In such a case, an approach can be used in which the surface of the region of the solvent-philic basal material 21 other than the solvent-philic surface of the region for detection 13 is subjected to masking, and thereby, the functional group is introduced only to the solvent-philic surface of the region for detection 13. Alternatively, an approach may be used in which the functional group is introduced to the solvent-philic surface of the solvent-philic basal material 21, and then, a reaction solution containing the spacer 9-linked second nucleic acid fragment 10 is spotted only onto the region of the region for detection 13, so that the reaction for immobilizing the spacer 9 is carried out only in the region that has received the selective spotting.

In the mode as illustrated in FIG. 10(b), such procedures are employed in which an assay solution containing the "complex (hybrid) 11" composed of a "conjugate molecule" and the target substance 7 dissolved in a solvent is prepared in advance, and a liquid droplet of the assay solution is spotted onto the upstream part of the region for capture 14 in the solvent-philic basal material 21.

The following procedures may be employed, instead of the procedures which comprise: preparing in advance an assay solution containing the "complex (hybrid) 11" composed of a "conjugate molecule" and the target substance 7 dissolved in a solvent, and spotting a liquid droplet of the assay solution.

First, a solvent-philic basal material is impregnated with a predetermined amount of the "complex (hybrid) 11" that is composed of a "conjugate molecule", and then is subjected to drying-up treatment to prepare a "complex retainer" in advance. A predetermined amount of the subject to be assayed (sampled specimen) is dissolved in a solvent to prepare a diluted solution of the subject to be assayed (sampled specimen). A liquid droplet of the diluted solution of the subject to be assayed (sampled specimen) is spotted onto the surface of the "complex retainer". During the process of migrating the diluted solution of the subject to be assayed (sampled specimen) on the "complex retainer", the "complex (hybrid) 11" composed of a "conjugate molecule" that is included in advance in the "complex retainer" is eluted into the solvent. Finally, the solution migrated on the "complex retainer" becomes an assay solution containing the "complex (hybrid) 11" that is composed of a "conjugate molecule" and the target substance 7, which are dissolved in the solvent.

The "complex retainer" is layered over the surface of the upstream part of the region for capture 14 in the solvent-philic basal material 21. In such a case, the solution that is migrated on the "complex retainer" is migrated along the surface of the upstream part of the region for capture 14 in the solvent-philic basal material 21, which underlies the "complex retainer". As a result, such a state where the assay solution containing the "complex (hybrid) 11" that is composed of a "conjugate molecule" and the target substance 7, which are dissolved in the solvent is migrated along the surface of the upstream part of the region for capture 14 in the solvent-philic basal material 21 is achieved.

For the purpose of achieving such a state where the liquid droplet of the diluted solution of the subject to be assayed (sampled specimen) that is spotted onto the surface of the "complex retainer" is migrated uniformly throughout the surface of the "complex retainer", a "sample introduction portion" capable of sucking up a large amount of the diluted solution of the subject to be assayed (sampled specimen) may be layered over the surface of the "complex retainer". When the liquid droplet of the diluted solution of the subject to be assayed (sampled specimen) is spotted onto the "sample introduction portion", the liquid droplet is temporarily sucked up with the "sample introduction portion", and then starts to be uniformly migrated throughout the surface of the "complex retainer".

Substantially the equivalent operations to the operation of preparing in advance an assay solution containing the "complex (hybrid) 11" that is composed of a "conjugate molecule" and the target substance 7, which are dissolved in a solvent and the operation of spotting a liquid droplet of the assay solution onto the upstream part of the region for capture 14 in the solvent-philic basal material 21 can be carried out more easily by use of the "complex retainer" and, further, the "sample introduction portion".

In the mode as illustrated in FIG. 10(a), such mode in which a region for use as the region for detection 13 is provided contiguously to the region functioning as the region for capture 14 on the solvent-philic basal material 21; and the assay solution migrated through the region for capture 14 is subsequently migrated to the region for detection 13 is employed. Thus, as long as the assay solution migrated through the region for capture 14 is subsequently migrated to the region for detection 13, another mode in which the region functioning as the region for capture 14 and the region for use as the region for detection 13 may be separately prepared and then linked to each other may be employed. In such a structure, in similar to the structure as illustrated in FIG. 10(a), the region functioning as the region for capture 14 and the region for use as the region for detection 13 can be joined to each other at their end faces. Such a structure where the region for use as the region for detection 13 may be layered on the terminal portion of the region functioning as the region for capture 14 may be optionally employed In the mode as illustrated in FIGS. 10(b) and 10(c), such a procedure in which an assay solution containing the "complex (hybrid) 11" that is composed of a "conjugate molecule" and the target substance 7, which are dissolved in a solvent, is prepared in advance; a liquid droplet of the assay solution is spotted onto the upstream part of the region for capture 14 in the solvent-philic basal material 21; and then, the assay solution, which is migrated along the surface of the region for capture 14 in the solvent-philic basal material 21, is subjected to the first photoisomerization treatment at the solution temperature ($T_L$) used for the detection process. As described above, a procedure may be employed in which the temperature of the assay solution is raised to the solution temperature ($T_L$) used for the detection process after the first photoisomerization treatment is carried out.

Therefore, such a procedure may be employed in which: an assay solution containing the "first photoisomerization-treated complex (hybrid) 11" that is composed of a "conjugate molecule" and the target substance 7, which are dissolved in a solvent is prepared in advance; a liquid droplet of the assay solution is spotted onto the upstream part of the region for capture 14 in the solvent-philic basal material 21; and then, the temperature of the assay solution is raised to the solution temperature ($T_L$) used for the detection process.

In the method for detecting a target substance according to the eighth embodiment, as illustrated in FIGS. 10(c) and 10(d), the formation of the first photoisomerization-treated "folding-type conjugate molecule/target substance complex" must be completed before the second photoisomerization treatment is carried out. When the procedure is employed in which: an assay solution containing the "first photoisomerization-treated complex (hybrid) 11" that is composed of a "conjugate molecule" and the target substance 7, which are dissolved in a solvent is prepared in advance; a liquid droplet of the assay solution is spotted onto the upstream part of the region for capture 14 in the solvent-philic basal material 21; and then, the temperature of the assay solution is raised to the solution temperature ($T_L$) used for the detection process, the formation of the first photoisomerization-treated "folding-type conjugate molecule/target substance complex" can be completed more reliably. In such a case, as such a procedure in which the assay solution that is migrated along the surface of the region for capture 14 in the solvent-philic basal material 21 is subjected to only the second photoisomerization treatment is used, the complicated "time adjustment" from the end of the first photoisomerization treatment to the carrying out of the second photoisomerization treatment in the corresponding apparatus configuration can be eliminated.

As illustrated in FIG. 10(c), in order to achieve such a state where all of target substances 7 form first photoisomerization-treated "folding-type conjugate molecule/target substance complexes", it is required that surplus of the first photoisomerization-treated "folding-type conjugate molecules" should be migrated, together with the first photoisomerization-treated "folding-type conjugate molecule/target substance complexes", along the surface of the region for capture 14 in the solvent-philic basal material 21.

In the method for detecting a target substance according to the eighth embodiment, it is required that, in the case when the target substance 7 is absent in the subject to be assayed (sampled specimen), such a process in which all of "complexes (hybrids) 11" that is each composed of a "conjugate molecule", which is originally contained in the assay solution is converted to the "second photoisomerization-treated complex (hybrid) 11" that is composed of a "conjugate molecule" within the period from the end of the second photoisomerization treatment to the arrival at the region for detection 13 should be completed. As long as the aforementioned requirement is satisfied, in place of the "second photoisomerization-treated complex (hybrid) 11" that is composed of a "conjugate molecule", a "first photoisomerization-treated complex (hybrid)" that is composed of a "conjugate molecule", a first photoisomerization-treated "folding-type conjugate molecule", or a first photoisomerization-treated "unfolding-type conjugate molecule" may be used, as the "complex (hybrid) 11" that is composed of a "conjugate molecule", which is originally contained in the assay solution.

Also, at the step of preparing a "complex (hybrid)" that is composed of a "conjugate molecule", instead of preparation of the "second photoisomerization-treated complex (hybrid) 11" that is composed of a "conjugate molecule", such a mode in which a first photoisomerization-treated "folding-type conjugate molecule", or a first photoisomerization-treated "unfolding-type conjugate molecule" is prepared may be selected.

In the method for detecting a target substance according to the eighth embodiment, the assay kit for a target substance comprises: a solvent-philic basal material 21 comprising a region for detection 13 and a region for capture 14; a "complex (hybrid) 11" that is composed of a "conjugate molecule"; and a second nucleic acid fragment 10. The second nucleic acid fragment 10 is immobilized on the region for detection 13 in the solvent-philic basal material 21 by chemical bond or chemisorption via a spacer 9. By means of this assay kit for a target substance, whether or not a target substance 7 is present in a subject to be assayed (sampled specimen) can be easily detected with high accuracy in accordance with the method for detecting a target substance according to the eighth embodiment.

When the region for detection 13 in the solvent-philic basal material 21, which is utilized in the assay kit, is a detection device capable of detecting the hybridization of the second nucleic acid fragment 10 with the second photoisomerization-treated "photoisomerizable molecule 3-bound first nucleic acid fragment 2" by use of the labeling material 6 being attached at the end of the "photoisomerizable molecule 3-bound first nucleic acid fragment 2", the assay kit can be used as a sensor chip for target substance assaying.

The apparatus for detecting a target substance according to the eighth embodiment, which is used to implement the method for detecting a target substance according to the eighth embodiment, comprises: the assay kit; contacting means which brings the sensor chip into contact with an assay solution containing a subject to be assayed; a light source for use to subject the photoisomerizable molecule in the "complex (hybrid) 11" that is composed of a "conjugate molecule" comprised in the assay kit to the second photoisomerization treatment; and a region for detection which is used to detect the dissolution of the double-stranded nucleotides binding in the "complex (hybrid) 11" that is composed of a "conjugate molecule". In other words, the region for detection which is used to detect the dissolution of the double-stranded nucleotides binding in the "complex (hybrid) 11" that is composed of a "conjugate molecule" detects physical or chemical change caused by the hybridization of the second nucleic acid fragment 10 that is immobilized on the region for detection 13 with the second photoisomerization-treated "photoisomerizable molecule 3-bound first nucleic acid fragment 2", by use of the labeling material 6 being attached at the end of the "photoisomerizable molecule 3-bound first nucleic acid fragment 2". The apparatus for detecting a target substance according to the eighth embodiment may optionally comprise a light source for use to subject the photoisomerizable molecule in the "complex (hybrid) 11" that is composed of a "conjugate molecule" to the first photoisomerization treatment.

While the invention of the present application has been explained with reference to the embodiments (and the exemplary embodiments), the scope of the invention disclosed in the present application is not limited to the embodiments (and the exemplary embodiments) described above. Various modifications that may be understood by a person skilled in the art may be made in the constitutions and detailed features of the invention of the present application within the scope of the invention of the present application.

This application claims the priority based on Japanese patent Application No. 2012-73255 filed on Mar. 28, 2012. The disclosure thereof is incorporated herein by reference in their entirety.

INDUSTRIAL APPLICABILITY

The method for detecting a target substance according to the present invention is suitably used in the detection of the target substance with high reliability.

The invention claimed is:

1. A method for detecting a target substance,
characterized in that: the method comprising the steps of:
preparing a complex comprising:

an aptamer which is capable of binding to the target substance in a sampled specimen;

a first nucleic acid fragment comprising a nucleotide sequence complementary to the aptamer; and a photoisomerizable molecule bound to both of or only any one of the aptamer and the first nucleic acid fragment, wherein the photoisomerizable molecule is bound to a part or all of nucleotide residues in a double-strand formation site where the aptamer and the first nucleic acid fragment hybridize with each other, nucleotide residues adjacent to the double-strand formation site, and between nucleotide residues of the double-strand formation site and nucleotide residues adjacent thereto;

subjecting the photoisomerizable molecule in the complex to a first photoisomerization treatment to destabilize double-stranded nucleotides binding in the complex;

allowing the target substance to bind to the aptamer so as to separate the first nucleic acid fragment from the double-strand formation site of the aptamer;

subjecting the photoisomerizable molecule to a second photoisomerization treatment to stabilize double-stranded nucleotides binding in the double-strand formation site; and detecting dissolution of the double-stranded nucleotides binding wherein the first nucleic acid fragment separates from the aptamer.

2. The method for detecting a target substance according to claim 1, wherein the complex comprises a linking portion via which a part of the aptamer and a part of the first nucleic acid fragment are linked to each other.

3. The method for detecting a target substance according to claim 1, wherein a part of both or only any one of the aptamer and the first nucleic acid fragment is immobilized on a basal material for immobilization.

4. The method for detecting a target substance according to claim 1, wherein the step of detecting dissolution of double-stranded nucleotides binding comprises the steps of:

allowing a second nucleic acid fragment to bind to the first nucleic acid fragment separated from the double-strand formation site, wherein the second nucleic acid fragment comprising a nucleotide sequence complementary to the first nucleic acid fragment; and detecting binding of the second nucleic acid fragment to the first nucleic acid fragment to thereby detect the dissolution of double-stranded nucleotides binding.

5. The method for detecting a target substance according to claim 4, wherein the second nucleic acid fragment is immobilized on the basal material for immobilization.

6. The method for detecting a target substance according to claim 4, wherein the basal material for immobilization comprises a solventphilic region.

7. The method for detecting a target substance according to claim 4, wherein at least one of the aptamer, the first nucleic acid fragment, and the second nucleic acid fragment comprises a labeling material.

8. The method for detecting a target substance according to claim 1, wherein the photoisomerizable molecule is bound only to the first nucleic acid fragment.

9. An assay kit for use in the detection of a target substance, characterized in that the kit comprising a complex comprising:

an aptamer which can bind to the target substance in a sampled specimen, a first nucleic acid fragment comprising a nucleotide sequence complementary to the aptamer, and a photoisomerizable molecule bound to both of or only any one of the aptamer and the first nucleic acid fragment, wherein the photoisomerizable molecule is bound to a part or all of nucleotide residues of a double-strand formation site where the aptamer and the first nucleic acid fragment hybridize with each other, nucleotide residues adjacent to the double-strand formation site, and between nucleotide residues of the double-strand formation site and nucleotide residues adjacent thereto, and the aptamer and the first nucleic acid fragment are not linked via a spacer, or the aptamer and the first nucleic acid fragment are linked via a branched spacer.

10. An apparatus for detecting a target substance, characterized in that the apparatus comprising:

an assay kit for use in the detection of a target substance;

a region for binding on which the target substance is bound to the aptamer;

a region for detection on which dissolution of double-stranded nucleotides binding is detected; and a light source for use to subject the photoisomerizable molecule contained in the complex to a second photoisomerization treatment, wherein the assay kit comprising a complex comprising:

an aptamer which can bind to the target substance in a sampled specimen, a first nucleic acid fragment comprising a nucleotide sequence complementary to the aptamer, and a photoisomerizable molecule bound to both of or only any one of the aptamer and the first nucleic acid fragment, wherein the photoisomerizable molecule is bound to a part or all of nucleotide residues of a double-strand formation site where the aptamer and the first nucleic acid fragment hybridize with each other, nucleotide residues adjacent to the double-strand formation site, and between nucleotide residues of the double-strand formation site and nucleotide residues adjacent thereto, and the aptamer and the first nucleic acid fragment are linked via a spacer; and a second nucleic acid fragment that is capable of hybridizing with the first nucleic acid fragment is immobilized on the region for detection.

* * * * *